(12) United States Patent
Suzuki et al.

(10) Patent No.: US 7,476,688 B2
(45) Date of Patent: Jan. 13, 2009

(54) CYCLIC AMIDINE DERIVATIVES

(75) Inventors: Shuichi Suzuki, Ushiku (JP);
Masanobu Shinoda, Ibaraki (JP);
Motoji Kogushi, Moriya (JP); Hiroko Kobayashi, Tsuchiura (JP)

(73) Assignee: EISAI R&D Management Co., Ltd., Tokyo (JP)

( * ) Notice: Subject to any disclaimer, the term of this patent is extended or adjusted under 35 U.S.C. 154(b) by 468 days.

(21) Appl. No.: 10/475,060

(22) PCT Filed: Apr. 19, 2002

(86) PCT No.: PCT/JP02/03949

§ 371 (c)(1),
(2), (4) Date: Jun. 11, 2004

(87) PCT Pub. No.: WO02/085850

PCT Pub. Date: Oct. 31, 2002

(65) Prior Publication Data
US 2004/0254376 A1   Dec. 16, 2004

(30) Foreign Application Priority Data

Apr. 19, 2001 (JP) .............................. 2001-121829
Sep. 5, 2001 (JP) .............................. 2001-269422

(51) Int. Cl.
A61K 31/407 (2006.01)
C07D 209/54 (2006.01)
(52) U.S. Cl. .......................... 514/409; 548/408; 548/409
(58) Field of Classification Search ................. 514/409; 548/408, 409
See application file for complete search history.

(56) References Cited

U.S. PATENT DOCUMENTS

| 3,717,648 | A | 2/1973 | Diana .......................... 546/223 |
| 3,773,788 | A | 11/1973 | Vis ............................. 548/558 |
| 3,859,302 | A | 1/1975 | Dixon .................... 548/331.5 |
| 3,887,577 | A | 6/1975 | Dixon .................... 548/331.5 |
| 3,904,395 | A | 9/1975 | Eilrich et al. ............... 504/277 |
| 3,920,688 | A | 11/1975 | Eilrich et al. ........... 548/331.5 |
| 3,989,709 | A | 11/1976 | White et al. ................ 544/250 |
| 4,004,016 | A | 1/1977 | Yale et al. ................... 514/388 |
| 4,075,342 | A | 2/1978 | Sale et al. ................... 514/292 |
| 4,118,504 | A | 10/1978 | Giraldi et al. ............... 514/416 |
| 4,126,613 | A | 11/1978 | Grisar et al. ................ 540/605 |
| 4,521,793 | A | 6/1985 | Kabashima et al. ......... 346/201 |
| 5,143,912 | A | 9/1992 | Burner et al. ............... 514/210 |
| 5,258,387 | A | 11/1993 | Burner et al. ............... 514/291 |
| 5,362,738 | A | 11/1994 | Burner et al. ............... 514/294 |
| 5,677,322 | A | 10/1997 | Yasumura et al. ........... 514/369 |
| 5,935,952 | A | 8/1999 | Todo et al. ............... 514/230.2 |
| 5,977,134 | A | 11/1999 | Ciccarone et al. ........... 514/307 |
| 6,046,211 | A | 4/2000 | Hansen, Jr. et al. |
| 6,051,718 | A | 4/2000 | Freyne et al. ............. 548/316.1 |
| 6,077,320 | A | 6/2000 | Andrean et al. ................ 8/405 |
| 6,087,380 | A | 7/2000 | Hauel et al. .................. 514/336 |
| 6,114,532 | A | 9/2000 | Ries et al. .................... 546/162 |
| 6,187,799 | B1 | 2/2001 | Wood et al. ................. 514/363 |
| 6,194,447 | B1 | 2/2001 | Jensen et al. ................ 514/388 |
| 6,376,530 | B1 | 4/2002 | Claiborne et al. ........... 514/416 |
| 6,825,220 | B2 * | 11/2004 | Jesudason et al. ........... 514/340 |
| 2004/0004197 | A1 | 1/2004 | Sano |
| 2004/0004204 | A1 | 1/2004 | Wang |
| 2004/0242627 | A1 | 12/2004 | Suzuki et al. |
| 2005/0245592 | A1 | 11/2005 | Susuki et al. |
| 2006/0058370 | A1 | 3/2006 | Shimomura et al. ......... 548/400 |

FOREIGN PATENT DOCUMENTS

DE            2003825         12/1970

(Continued)

OTHER PUBLICATIONS

Poos et al. "Pharmacological . . ." Ca 77:19523 (1972).*

(Continued)

*Primary Examiner*—Celia Chang
(74) *Attorney, Agent, or Firm*—Andrea L. C. Robidoux; Choate, Hall & Stewart, LLP

(57) ABSTRACT

A cyclic amidine derivative represented by the formula:

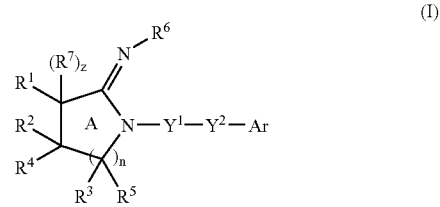

(I)

[wherein $R^1$, $R^2$ and $R^3$ represent hydrogen, $C_{1-6}$ alkyl, aryl-$C_{1-6}$ alkyl, etc.; $R^4$, $R^5$ and $R^7$ represent hydrogen, $C_{1-6}$ alkyl, etc.; Z represents 0 or 1; $R^6$ represents hydrogen, $C_{1-6}$ alkyl, $C_{1-6}$ alkyloxycarbonyl, etc.; n represents 1 or 2; $Y^1$ represents a single bond, —$CH_2$—, etc.; $Y^2$ represents a single bond, —CO—, etc.; Ar represents hydrogen, a group represented by the formula:

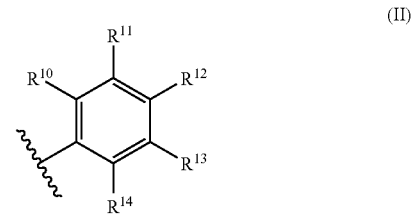

(II)

[wherein $R^{10}$-$R^{14}$ represent hydrogen, $C_{1-6}$ alkyl, hydroxyl, $C_{1-6}$ alkoxy, etc., and $R^{11}$ and $R^{12}$ or $R^{12}$ and $R^{13}$ may bond together to form a 5- to 8-membered heterocycle], etc.] or a salt thereof.

28 Claims, No Drawings

FOREIGN PATENT DOCUMENTS

| | | |
|---|---|---|
| DE | 2154525 | 6/1972 |
| DE | 2551868 | 8/1976 |
| EP | 364204 | 10/1989 |
| EP | 638075 | 2/1994 |
| EP | 842161 | 7/1996 |
| EP | 934280 | 9/1997 |
| EP | 847749 | 11/1997 |
| EP | 1091942 | 7/1999 |
| EP | 1176141 | 3/2000 |
| FR | 8129MM | 8/1968 |
| GB | 1295478 | 11/1972 |
| GB | 1344663 | 1/1974 |
| JP | 48-42875 | 12/1973 |
| JP | S51-22720 | 2/1976 |
| JP | S51-125071 | 11/1976 |
| JP | 53-71063 | 12/1976 |
| JP | 62-22760 | 7/1985 |
| JP | 4-244083 | 8/1990 |
| JP | 3-50555 | 3/1991 |
| JP | 4-504709 | 8/1992 |
| JP | H07-32103 | 2/1995 |
| JP | H08-225753 | 9/1996 |
| JP | 9-40643 | 2/1997 |
| JP | 10-167965 | 6/1998 |
| JP | 10-509150 | 9/1998 |
| JP | 11-509191 | 8/1999 |
| JP | 12-503678 | 3/2000 |
| JP | 2002-155060 | 5/2002 |
| WO | WO 83/02920 | 9/1983 |
| WO | WO 96/05192 | 2/1996 |
| WO | EP 789571 | 5/1996 |
| WO | WO98/00408 | 1/1998 |
| WO | WO 98/37075 | 8/1998 |
| WO | WO 99/26943 | 6/1999 |
| WO | WO 99/40072 | 8/1999 |
| WO | WO00/01676 | 1/2000 |
| WO | WO 00/53582 | 9/2000 |
| WO | EP 1178802 | 11/2000 |
| WO | WO 00/67755 | 11/2000 |

OTHER PUBLICATIONS

Hansen et al. "Preparation of amidino . . ." CA 132:265104 (2000).*
Mehrotra et al. "Discovery of Novel 2,8-diazaspiro . . ." CA 140:385509 (2004).*
Ahn, et al., "Structure-Activity Relationships of Pyrroloquinazolines as Thrombin Receptor Antagonists", *Bioorganic & Medicinal Chemistry Letters*, 9: 2073-2078, 1999.
Bernatowicz, et al., "Development of Potent Thrombin Receptor Antagonist Peptides", *J. Med. Chem.* 39: 4879-4887, 1996.
Cohen, et al., "Enantiospecific Synthesis of Leukotrienes $C_4$, $D_4$, and $E_4$ and [14,15-$^3$H2] Leukotriene $E_4$ Dimethyl Ester", *J. Am. Chem. Soc.* 105: 3661-3672, 1983.
Compernolle, et al., "Synthesis and Preliminary in vitro Metabolic Studies on N,N-Dimethyl-N'-2-Imidazolyl-N'—Benzyl-1,2-Ethanediamine, an Analog of the Carcinogenic Antihistamine Methapyrilene", J. Heterocyclic Chem., 19: 1403-1408, 1982.
Hoekstra, "Thrombin Receptor (PAR-1) Antagonists. Heterocycle-Based Peptidomimetics of the SFLLR Agonist Motif", *Bioorganic & Medicinal Chemistry Letters*, 8: 1649-1654, 1998.
Hung, et al., "Thrombin-Induced Events in Non-Platelet Cells are Mediated by the Unique Proteolytic Mechanisms Established for the Cloned Platelet Thrombin Receptor", *The Journal of Cell Biology*, 116(3): 827-832, 1992.
Hung, et al., "Cloned Platelet Thrombin Receptor is Necessary for Thrombin-Induced Platelet Activation", *J. Clin. Invest.*, 89: 1350-1353, 1992.
Janusz, et al., "New Cyclooxygenase-2/5-Lipoxygenase Inhibitors. 1. 7-tert-Butyl1-2;3-Dihydro-3,3-Dimethylbenzofuran Derivatives as Gastrointestinal Safe Antiinflammatory and Analgesic Agents: Discovery and Variation of the 5-Keto Substituent", *J. Med. Chem.* 41: 1112-1123, 1998.
Lipinski, et al., "Bioisosteric Prototype Design of Biaryl Imidazolyl and Triazolyl Competitive Histamine $H_2$—Receptor Antagonists", *J. Med. Chem.* 29: 2154-2163, 1986.
Liu, et al., "The Mechanisms of Titanium Complex-Catalyzed Reduction of Aryl Halides by Sodium Borohydride is Strongly Solvent Dependent", *J. Org. Chem.* 59: 940-942, 1994.
Mancuso, et al., "Activated Dimethyl Sulfoxide: Useful Reagents for Synthesis", Reviews, pp. 165-185, 1981.
McComsey, et al., "Macrocyclic Hexapeptide Analogues of the Thrombin Receptor (PAR-1) Activation Motif Sfllrn" *Bioorganic & Medicinal Chemistry Letters*, 9: 255-260, 1999.
Ngaiza, et al., "a 14 Amino Acid Peptide Derived from the Amino Terminus of the Cleaved Thrombin Receptor Elevates Intracellular Calcium and Stimulates Prostacyclin Production in Human Endothelial Cells", Biochemical and Biophysical Research Communications, 179(3): 1656-1661, 1991.
Sarembock, et al., "Effectiveness of Recombinant Desulphatohirudin in Reducing Restenosis After Balloon Angioplasty of Atherosclerotic Femoral Arteries in Rabbits", *Circulation*, 84: 232-243, 1991.
Sato, et al., "Organic Solvent—and Halide Free Oxidation of Alcohols with Aqueous Hydrogen Peroxide", *J. Am. Chem. Soc.* 119: 12386-12387, 1997.
Tawada, et al., "Studies on Antidiabetic Agents. IX. A New Aldose Reductase Inhibitor, AD-5467, and Related 1,4-Benzoxazine and 1,4-Benzothiazine Derivatives: Synthesis and Biological Activity", *Chem. Pharm. Bull.*38(5): 1238-1245, 1990.
Vu, et al., "Molecular Cloning of a Functional Thrombin Receptor Reveals a Novel Proteolytic Mechanism of Receptor Activation", *Cell*, 64: 1057-1068, 1991.
Vu. et al., "Domains Specifying Thrombin-Receptor Interaction", *Nature*, 353: 674-677, 1991.
Zhao, et al., "A Novel Chromium Trioxide Catalyzed Oxidation of Primary Alcohols to the Carboxylic Acids", *Tetrahedron Letters*, 39: 5323-5326, 1998.
Klötzer et al., "Acylderivate von 2-Amino-1-pyrrolinen", *Monatshefte Fur Chemie*, 102(2): 627-634, 1971.
Supplementary Partial European Search Report in a corresponding EP application No. EP 02720534.
Alfaia, et al., "Quaternization Reaction of Heterocyclic Imines in Methanol—A Case of Strong Anti-Reactivity Selectivity Principle with Isoselective Temperature", *European Journal of Organic Chemistry*, 3627-3631, 2000.
Caroti, et al., "A Facile Synthesis of 5,7-Dihydro-5-Oxopyrido [3',2':5,6] Pyrimido-[1,2-a] Benzimidazoles. A New Heterocyclic Ring System", *J. Heterocycl. Chem.*, 23(6): 1833-1836, 1986.
DA Settimo, et al., "Synthesis of 2-Methylbenzimidazole Derivatives Tested for Antiinflammatory Activity", *Farmaco*, 49(12): 829-834, 1994.
DA Settimo, et al., "Synthesis and Anti-Inflammatory Properties of 2-Amino-Benzimidazole Derivatives", *Farmaco*, 47(10): 1293-1313, 1992.
Da Settimo, et al., "Syntheis and Antihypertensive Activity of Some 2-Aminobenzimidazole and Indole Derivatives", *Farmaco*, 46(2): 357-367, 1991.
Da Settimo, et al., "Synthesis and Evaluation of Aminoadamantane Derivatives for In Vitro Anti-HIV and Antitumor Activities", *Farmaco*, 50(5): 321-326, 1995.
Dixon, et al., "Bioactive Diversity and Screening Library Selection via Affinity Fingerprinting", *J.Chemical Information and Computer Sciences*, 38(6): 1192-1203, 1998.
North, et al., "A Study of Some 1-Alkyl-2,3-Dihydroimidazo [1,2-a] Benzimidazoles", *Journal of Heterocyclic Chemistry*, 6(5): 655-662, 1969.
Ogura, et al., "Studies on Heterocyclic Compounds, 10. Synthesis of Some Imidazo [1,2-α] Benzimidazoles with Potent Analgetic Activites", Journal of Medicinal Chemistry, 15(9): 923-926, 1972.
Rehse, et al., "New NO-Donors with Antithrombotic and Vasodilating Activities", XI. 2-Nitrosiminobenzimidazoles, *Arch. Pharm.* 328:(1) 77-80, 1995.

Vassallo, et al.. "Structure-Function Relationships in the Activation of Platelet Thrombin Receptors by Receptor-Derived Peptides", *The Journal of Biological Chemistry*, 267(9): 6081-6085, 1992.
Babichev, F.S., et al., "Structure of Reaction Products Of 1-Amino-3H-Isoindole With Benzyl Chloride and .Alpha.-Bromoketones," *Ukrainskii Khimicheskii Zhurnal*, 50(6): 623-626, 1984. (Abstract).
Lessel, J., "Benzodiazepine Und Isoindole Durch Acylierung Von Amidinen Benzodiazepines And Isoindoles By Acylation Of Amidines," *Pharmazie*, 48(11): 812-816, 1993.
May, et al., "Chemie Und Biologische Eigenschaften Substituierter 3-Amino-1H-Isoindole," *Arzneim.-Forsch*, 30(11): 1487-1493, 1980.
O'Sullivan, R.D. and Parkins, A.W., "The Synthesis Of N-Heterocycles Using Ortho-Metallated Primary Benzylamine Complexes Of Palladium And Platinum," *J. Chem. Soc., Chem. Commun.*, 1165-1166, 1984.
"Oxazines And Thiazines," *Chemical Abstracts*, 78: 478, 1973. (Abstract No. 111227).
Toja, E., et al., "Synthesis And Pregnancy Terminating Activity Of 2-Arylimidazo '2, 1-a! Isoquinolines And Isoindoles," *Arzneim.-Forsch*, 33(11): 1222-6, 1983.
Sawanishi, H., et al., "Studies On Diazepines. XXI. Photochemical Synthesis Of 1H-2,4-Benzodiazepines From 4-Azidoisoquinolines," *Chem. Pharm. Bull.*, 33(10): 4564-4571, 1985.
Sawanish, H. and Tsuchiya, T., "Synthesis And Characterization Of 1H-2, 4-Benzodiazepines," *Heterocycles*, 22(12): 2725-2728, 1984.
Ahn, et al., "Inhibition of Cellular Action of Thrombin by N3-Cyclopropyl-7-{[4-(1-methylethyl)phenyl]methyl}-7H-pyrrolo[3,2-f]quinazoline-1,3-diamine (SCH 79797), a Nonpeptide Thrombin Receptor Antagonist," *Biochem. Pharm.*, 60: 1425-1434, 2000.
Andrade-Gordon, et al., "Design, Synthesis, and Biological Characteriation of a Peptide-mimetic Antagonist for a Tethered-ligand Receptor," *PNAS*, 96: 12257-12262, 1999.
Anisimova, et al., "Imidazo [1,2-a] Benzimidazole Derivatives. X. Nitration of 2,9-Disubstituted Imidazo [1,2-a] Benzimidazole," *Khim. Geteroisikl. Soedin*, 2: 258-262, 1975.
Anisimova, et al., "Imidazo [1,2-a] Benzimidazole Derivatives. 22. Synthesis of 2, 3-dihydroimidazo [1, 2-a]benzimidazoles from 3-(2-hydroxyethyl)-2-iminobenzimidazolines," *Khim. Geteroisikl. Soedin*,7: 918-925, 1986.
Anisimova, et al., "Imidazo [1,2-a] Benzimidazole Derivatives. 25. Reaction of 2, 9-disubstituted Imidazo [1,2-a]benzimidazoles With Acrylic Acids and Their Derivatives," *Khim. Geteroisikl. Soedin*, 11: 1496-1502, 1987.
Babchiev et al., "The Structure of the Salts of 2-amino.DELTA.1-pyrroline with Benzyl Chloride and .alpha-halo Ketones," *Ukr. Khim. Zh.*, 52: 398-401, 1986.
Babichev, et al., "Derivatives Of s-Triazolo (5,1-a)isoindole," *Ukr. Khim. Zh.*, 47(3): 291-295, 1981 (original and abstract).
Babichev, et al., "Reaction Of o-Chloromethylbenzonitrile With Acid Hydrazides," *Ukr. Khim. Zh.*, 47(7): 735-738, 1981.
Babichev, et al., "1-imino-2-alkylacylisoindolines," *Ukr. Khim. Zh.*, 50(10): 1105-1110, 1984.
Babichev, et al., "The Structure of Products of the Reaction of 1-Amino-3H-Isoindole with Benzyle Chloride and α-Bromoketones," *Ukrainskii Khimicheskii Zhurnal*, 50: 623-626, 1984 (original and abstract).
Chackalamannil, et al., "Potent, Low Molecular Weight Thrombin Receptor Antagonists," *Bioorg. Med. Chem. Lett.*, 11: 2851-2853, 2001.
*Chemical Abstracts*, 53, abs.No. 15082h-15085d.
*Chemical Abstracts*, 72, abs.No. 132428.
*Chemical Abstracts*, 76, abs.No. 153482.
*Chemical Abstracts*, 102, abs.No. 16106c-16107d.
*Chemical Abstracts*, 102, abs.No. 220805.
*Chemical Abstracts*, 103, abs.No. 104932.
*Chemical Abstracts*, 127, abs.No. 81319.
Clemens, et al., "Untersuchungen zur Chemie von Isoindolen und Isoindoleninen, 3-Hydroximino-1-alkyl(aryl)-isoindoline und 3-Hydroxylamino-1-alkyl(aryl)-1H-isoindoline," *Z.Naturforsch., B:Chemical Sci.*, 51(12): 1791-1810, 1996 (original).

Gorlitzer, "Zur Cyclisierung von Phthaladehyd mit Acetophenonen," *Arch.Pharm.*, 309(5): 356-66, 1976.
Gorlitzer and Buβ, "Zur Reaktion von Phthalaldehyd mit Anthranilsäureestern," *Arch Pharm.*, 318(8): 735-43, 1985.
Kato, et al., "In Vitro Antiplatelet Profile of FR171113, a Novel Non-peptide Thrombin Receptor Antagonist," *Europ. J. Pharm.*, 384: 197-202, 1999.
Kigasawa, et al., "Studies On The Syntheses Of Analgesics," *J. Heterocycl. Chem.*, 15(3): 369-375, 1978.
Korbonits, et al., "4-Aminobutanoic Amidoxime Derivatives. Synthesis of 1-Substituted 2-Hydroximinopyrrolidines, a Novel Type of Lactames," *Acta. Chim. Hung.*, 117: 239-245, 1984.
Koshchienko, et al., "Synthesis and Antibacterial Activity of 3-(alkoxymethyl)-2-amino-1-methylbenzimidazolium Chlorides," *Khim. Farm. Zh.*, 11: 14-17, 1977.
Koshchienko, et al., "New Synthesis of Imidazo [1,2-a] Benzimidazole Derivatives," *Khim. Geterotsikl. Soedin*, 1: 140-141, 1975.
Kovalev, et al., "Synthesis and Pharmacological Properties of Some Disubstituted Imidazo[1,2-a] Benzimidazole Derivates," *Khim. Farm. Zh.*, 13: 57-62, 1979.
Kovtunenko, et al., "Preparation and Reactions of 1R-2-iminopyrrolidines," *Ukr. Khim. Zh.*, 52: 63-70, 1986.
Kovtunenko, et al., "6,7-Dihydro-5H-pyrrolo[1,2-a]imidazole Derivatives," *Ukr. Khim. Zh.*, 52: 647-651, 1986.
Kovtushenko, et al., "Synthesis Of Pyrido (1,2-b) (2,4) Benzodiazepine-6(11H)-imines," *Khim. Geterotsikl. Soedin.*, (9): 1264-1269, 1987 (original and abstract).
Kovtushenko, et al., "1-Amino-2R-3H-isoindolium Salts," *Ukr. Khim. Zh.*, 50(5): 530-534, 1984.
Kovtushenko, et al., "1-imino-2- And 1-imino-2R-3-Phenylisoindolines," *Ukr. Khim. Zh.*, 50(11): 1198-1203, 1984.
Kovtushenko, et al., "Derivatives Of 5H-imidazo (2, 1-a)isoindole," *Ukr. Khim. Zh.*, 51(6): 644-649, 1985.
Kreher and Hennige, "Reaktionen von 1-Alkoxy-isoindoleninen," *Z.Naturforsch., Teil B*, 28(11-12): 801-804, 1973 (original).
Kuz'menk, et al., "Synthesis of 9-aminoimidazo [1,2-a]benzimidazoles and Their Deamination," *Khim. Geterotsikl. Soedin*, 11: 1517-1523, 1990.
Langlois, et al., "Synthesis of New Bicyclic Amidines. 1. Derivatives of Imidazole, 1,3,4-Triazole and Tetrazole," *J. Heterocycl. Chem*, 19: 193-200, 1982.
Latli, et al., "Novel and Potent 6-Chloro-3-pyridinyl Ligands for the α4β2 Neuronal Nicotinic Acetylcholine Receptor," *J. Med. Chem.*, 42: 2227-2234, 1999.
Nannini, et al., "New Analgesic-anti-inflammatory Drugs," *Arzneim.-Forsch.*, 23(8): 1090-1100, 1973.
Nantermet, et al., "Nonpeptidic small-molecule antagonists of the human platelet thrombin receptor (PAR-1)", 221st *ACS National Meeting (San Diego)*/MEDI/Protease-Activated Receptor Antagonists, Paper 341: (Oral), Wed Apr. 4, 2001.
Vanden Eynde, et al., "Novel Synthesis Of Heterocycles With N-(1-Haloalkyl)azinium Halides," *Bulletin Soc.Chim.Belg.*, 101(6): 509-512, 1992.
*Vest. Kiev. Un-ta. Khimiya*, (26): 21-25, 1985.
Yale, et al., "Quaternary Derivatives for 2-Aminobenzimidazole and 2-Phenylethyl-and Phenyloxymethyl Halides", *J. Heterocycl. Chem.*, 15(3): 505-507, 1978.
Yale and Bristol, "1-Aralkyl-2(1H)-Pyridinimines and Their Derivatives," *J Heterocycl. Chem*, 12: 1027-1029, 1975.
Ahn, et al., "Development of proteinase-activated receptor 1 antagonists as therapeutic agents for thrombosis, restenosis and inflammatory diseases", *Current Pharmaceutical Design*, 9: 2349-2365, 2003.
Anisimova et al., "Synthesis and pharmacological activity of some 2,3-dihydroimidazo[1,2-a]benzimidazoles and their intermediates" *Khimiko-Farmatsevticheskii Zhurnal*, 21(3):313-319 1987.
Rehse et al., "New NO-donors with antithrombotic and vasodilating activites. XI. 2-Nitrosiminobenzimidazoles" *Archtv der Pharmazie*, 328(1):77-80 1995.
Kawahara et al., Fifth AFMC International Medicinal Chemistry Symposium, A-100, Oct. 14-17, 2003.
Kawahara et al., 227th ACS National Meeting, MEDI 85, Mar. 28-Apr. 1, 2004.

Chackalamannil et al., 221st ACS National Meeting, MEDI 342, Apr. 1-5, 2001.

Ahn et al., Drugs of the Future, 26(11): pp. 1065-1085, Nov. 2001.

Chemical Abstracts 77:19523, McNeil Laboratories Inc. 1972. (English abstract for FR 8129MM).

"Oxazines and Thiazines," Chemical Abstracts (1973) 78:478 (Abstract No. 111229).

Chemical Abstracts 53, Abstract No. 16106c-16107d.

* cited by examiner

CYCLIC AMIDINE DERIVATIVES

PRIORITY INFORMATION

The present application claims the benefit under 35 U.S.C. § 371 of International Application No.: PCT/JP02/03949 (published PCT application No. WO 02/085850), filed 19 Apr. 2002, which claims priority to Japanese Patent Application Nos.: 2001-121829, filed 19 Apr. 2001, and 2001-269422, filed 5 Sep. 2001, the entire contents of each of these applications are hereby incorporated herein by reference.

BACKGROUND OF THE INVENTION

A recent approach for thrombosis has involved inhibiting thrombin enzyme activity, and compounds used for this purpose have included heparin, low molecular weight heparin, hirudin, argatroban, hirulog and the like. All such compounds inhibit the enzyme activity of thrombin, and work by inhibiting fibrin blood clot formation without specifically inhibiting the effect of thrombin on cells. Bleeding tendency is therefore a common side effect encountered in the clinic. The role of thrombin in thrombosis is not limited to its blood clotting activity, as it is believed to also participate in platelet aggregation at sites of vascular injury occurring as a result of the activation of platelet thrombin receptor.

Another approach for thrombosis has been the use of intravenous injection agents such as Abciximab, Eptifibatide and Tirofiban, as GPIIb/IIIa receptor antagonists. These compounds, while exhibiting powerful anti-thrombotic effects by suppressing platelet aggregation induced by various stimulation such as thrombin, ADP, collagen, PAF or the like, also produce a bleeding tendency as a side effect similarly to thrombin enzyme activity inhibitors. For this reason, no such compounds have yet been marketed, although their development as oral agents continues to progress.

Restenosis is a vascular hyperproliferative response to vascular wall injury induced by invasive treatment such as coronary angioplasty, and this phenomenon may be provoked by the direct or indirect effect of thrombin on cells. Platelets adhere to injured blood vessels, leading to release of growth factors and eliciting proliferation of smooth muscle cells. Smooth muscle cells may also be affected indirectly by the action of thrombin on endothelial cells. Also, platelet adhesion occurs and procoagulant activity increases at sites of vascular injury. Smooth muscle cells can undergo further direct stimulation due to the high local thrombin concentration which is produced at such sites. While recent studies using the powerful thrombin inhibitor hirudin have suggested that thrombin induces cell proliferation during the process of restenosis, it has not yet been determined whether the thrombin effect is direct or indirect (Sarembock et al., Circulation 1992, 84: 232-243). Despite the implication of the cellular effects of thrombin in a variety of pathological symptoms, no therapeutically active substance is known which specifically blocks such effects.

The thrombin receptor (PAR1) has recently been cloned (Vu et al., Cell, 1991, 64: 1057-1068), opening an important door to development of substances which target cellular thrombin receptors. Detailed examination of the amino acid sequence of this thrombin receptor has revealed a thrombin binding site and hydrolysis site located in the 100 residue amino terminal domain of the receptor. Later research by amino acid mutation in the receptor has established that limited hydrolysis of this portion of the thrombin receptor by thrombin is necessary for receptor activation (Vu et al., Nature, 1991, 353: 674-677). A synthetic peptide corresponding to the amino acid sequence newly generated by hydrolysis of the thrombin receptor (the synthetic peptide is known as "thrombin receptor activating peptide", or TRAP) can activate receptors which have not been hydrolyzed by thrombin. This suggests that the cleavage of the receptor, the new amino acid sequence generated at the amino terminal (known as the "tethered ligand peptide") functions as the ligand and interacts with the distal binding site. Further studies of TRAP have confirmed homology of the thrombin receptors present in platelet, endothelial cell, fibroblast and smooth muscle cell (Hung et al., J. Cell. Biol. 1992, 116: 827-832; and Ngaiza, Jaffe, Biochem. Biophys. Res. Commun. 1991, 179: 1656-1661).

Research on the structure activity relationship of TRAP suggests that the pentapeptide Phe-Leu-Leu-Arg-Asn is a weak antagonist for platelet thrombin receptors activated by either thrombin or TRAP (Vassallo. et al., J. Biol. Chem., 1992, 267: 6081-6085 (1992)). Different approaches to receptor antagonism have also been examined by other groups. One of these approaches has been an attempt to prepare antibodies for the thrombin binding domain of the thrombin receptor. Such antibodies specifically and effectively suppress activation of platelets by thrombin, and act as thrombin receptor antagonists (Hung et al., J. Clin. Invest. 1992, 89: 1350-1353). Another approach has been the development of peptide derivatives from TRAP (Steven M. S., J. Med. Chem. 1996, 39: 4879-4887; William J. H., Bioorg. Med. Chem. Lett. 1998, 8: 1649-1654; and David F. M., Bioorg. Med. Chem. Lett. 1999, 9: 255-260). Yet another approach has been the development of low molecular weight compounds discovered by high throughput screening using various assay systems such as receptor binding (Andrew W. S. et al., Bioorg. Med. Chem. Lett. 1999, 9: 2073-2078; Scherig Plough WO99/26943; and Halord S. et al., ACS meeting in October 2001).

DETAILED DESCRIPTION OF CERTAIN PREFERRED EMBODIMENTS OF THE INVENTION

Compounds having antagonistic action on thrombin receptors are expected to exhibit excellent effects for therapy or prevention of diseases associated with thrombin, and therefore offer promise for effective therapy or prevention of, for example, thrombosis, vascular restenosis, deep venous thrombosis, pulmonary embolism, cerebral infarction, heart diseases, disseminated intravascular coagulation, hypertension, inflammatory diseases, rheumatism, asthma, glomerulonephritis, osteoporosis, neurological diseases, malignant tumors, and the like. It has been highly desired to provide thrombin receptor antagonists which are satisfactory in numerous aspects including pharmacological activity, thrombin receptor specificity, safety, dosage and oral efficacy.

However, conventional thrombin receptor antagonists have been inadequate in terms of receptor specificity and oral efficacy.

It is therefore an object of the present invention to search for and discover compounds having excellent thrombin receptor inhibiting activity and being therefore useful as thrombin receptor antagonists.

The inventors have completed thorough research in light of such circumstances, leading to the synthesis of novel cyclic amidine derivatives represented by the following general formula (I), the results of which have unexpectedly revealed that these compounds or salts thereof have excellent thrombin receptor inhibiting activity and are useful as thrombin receptor antagonists, which culminated in the present invention.

<1> In one aspect, the present invention provides a compound represented by the formula:

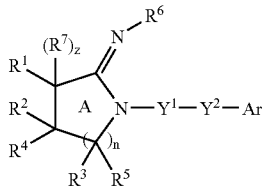

(I)

[wherein $R^1$, $R^2$, $R^3$, $R^4$, $R^5$ and $R^7$ are the same or different and each independently represents (1) hydrogen, (2) cyano, (3) halogen or (4) a group selected from Substituent Group A below, z represents 0 or 1, and $R^2$ and $R^4$ may bond together to form a 5- to 6-membered ring having 1 to 5 atoms selected from C, N and O; $R^4$ and $R^5$ may bond together to form a single bond; $R^6$ represents (1) hydrogen, (2) $C_{1-6}$ alkyl, (3) acyl, (4) carbamoyl, (5) hydroxyl, (6) $C_{1-6}$ alkoxy, (7) $C_{1-6}$ alkyloxycarbonyloxy, (8) $C_{3-8}$ cycloalkyl, (9) $C_{1-6}$ alkyloxycarbonyl optionally substituted with acyloxy or (10) a $C_{6-14}$ aromatic hydrocarbon ring group or a 5- to 14-membered aromatic heterocyclic group (each of the foregoing members being optionally substituted with at least one group selected from Substituent Group E below); n represents an integer of 1 or 2; $Y^1$ represents a single bond, —$(CH_2)_m$—, —$CR^8$—, —$CR^8CR^9$—, —$CH_2CO$—, —$NR^8$—, —$SO$—, —$SO_2$—, —$CO$—, —$CONR^8$— or —$SO_2NR^8$—[wherein m represents an integer of 1 to 3, $R^8$ and $R^9$ are the same or different and each independently represents hydrogen, halogen, $C_{1-6}$ alkyl, carboxyl or $C_{1-6}$ alkoxycarbonyl]; $Y^2$ represents a single bond, O, N, —$(CH_2)_m$—, —$CR^8$—, $CR^8R^9$—, —$CO$—, —$SO$—, —$SO_2$— or —$C(=N-OR^8)$—[wherein m, $R^8$ and $R^9$ have the same definitions given above]; and Ar represents (1) hydrogen, (2) a group represented by the formula:

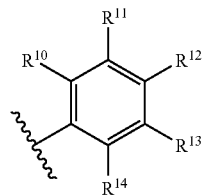

(II)

[wherein $R^{10}$, $R^{11}$, $R^{12}$, $R^{13}$ and $R^{14}$ are the same or different and each independently represents (1) hydrogen, (2) cyano, (3) halogen, (4) nitro or (5) a group selected from Substituent Group B below, and $R^{11}$ and $R^{12}$ or $R^{12}$ and $R^{13}$ may bond together to form a 5- to 8-membered heterocycle optionally having 1 to 4 hetero atoms selected from N, S and O and optionally substituted with at least one group selected from Substituent Group F], or (3) a 5- to 14-membered aromatic heterocyclic group optionally substituted with at least one group selected from Substituent Group G below.

<Substituent Group A> represents moieties selected from the group consisting of $C_{1-6}$ alkyl, alkylidene, $C_{2-6}$ alkenyl, $C_{2-6}$ alkynyl, acyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, amino, $C_{1-6}$ alkylamino, $C_{3-8}$ cycloalkylamino, acylamino, sulfonylamino, sulfonyl, sulfamoyl, $C_{3-8}$ cycloalkyl, a 5- to 14-membered non-aromatic heterocyclic group, a $C_{6-14}$ aromatic hydrocarbon ring group and a 5- to 14-membered aromatic heterocyclic group, each of the foregoing members being optionally substituted with at least one group selected from Substituent Group A' below;

<Substituent Group A'> represents moieties selected from the group consisting of $C_{1-6}$ alkyl, $C_{2-6}$ alkenyl, $C_{2-6}$ alkynyl, cyano, acyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, amino, $C_{1-6}$ alkylamino, $C_{3-8}$ cycloalkylamino, acylamino, ureido, ureylene, sulfonylamino, sulfonyl, sulfamoyl, halogen, $C_{3-8}$ cycloalkyl, a heterocyclic alkyl group, a 5- to 14-membered non-aromatic heterocyclic group, a $C_{6-14}$ aromatic hydrocarbon ring group and a 5- to 14-membered aromatic heterocyclic group, wherein the $C_{6-14}$ aromatic hydrocarbon ring group and the 5- to 14-membered aromatic heterocyclic group may be substituted with at least one group selected from the group consisting of $C_{1-6}$ alkyl, cyano, acyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, nitro, amino, $C_{1-6}$ alkylamino, $C_{3-8}$ cycloalkylamino, acylamino, ureido, ureylene, sulfonylamino, sulfonyl, sulfamoyl, halogen and $C_{3-8}$ cycloalkyl;

<Substituent Group B> represents moieties selected from the group consisting of $C_{1-6}$ alkyl, $C_{2-6}$ alkenyl, $C_{2-6}$ alkynyl, acyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, amino, $C_{1-6}$ aminoalkyl, $C_{1-6}$ alkylamino, $C_{3-8}$ cycloalkylamino, acylamino, ureido, sulfonylamino, sulfonyl, sulfamoyl, $C_{3-8}$ cycloalkyl, a 5- to 14-membered non-aromatic heterocyclic group, a $C_{6-14}$ aromatic hydrocarbon ring group and a 5- to 14-membered aromatic heterocyclic group, each of the foregoing members being optionally substituted with at least one group selected from Substituent Group B' below;

<Substituent Group B'> represents moieties selected from the group consisting of $C_{1-6}$ alkyl, $C_{2-6}$ alkenyl, $C_{2-6}$ alkynyl, oxo, cyano, $C_{1-6}$ cyanoacyl, $C_{2-7}$ acyl, $C_{1-6}$ alkanoyl, benzoyl, aralkanoyl, $C_{1-6}$ alkoxyalkylcarbonyl, $C_{1-6}$ hydroxyalkylcarbonyl, carboxyl, $C_{1-6}$ carboxyalkyl, $C_{1-6}$ carboxyalkyloxy, carbamoyl, carbamoylalkyloxy, $C_{1-6}$ alkoxycarbonyl, $C_{1-10}$ alkoxycarbonyl-$C_{1-6}$ alkyl, $C_{1-10}$ alkoxycarbonyl-$C_{1-6}$ alkyloxy, $C_{1-6}$ monoalkylaminocarbonyl, $C_{2-6}$ dialkylaminocarbonyl, hydroxyl, $C_{1-6}$ alkoxy, $C_{1-10}$ alkoxyalkyl, $C_{1-10}$ aralkyloxyalkyl, $C_{1-6}$ hydroxyalkyl, $C_{3-8}$ cycloalkyloxy, amino, $C_{1-6}$ alkylamino, $C_{3-8}$ cycloalkylamino, acylamino, ureido, ureylene, $C_{1-6}$ alkylsulfonylamino, phenylsulfonylamino, $C_{1-6}$ alkylsulfonyl, phenylsulfonyl, $C_{1-6}$ monoalkylaminosulfonyl, $C_{2-6}$ dialkylaminosulfonyl, sulfamoyl, halogeno, $C_{3-8}$ cycloalkyl, a 5- to 14-membered non-aromatic heterocyclic group, a $C_{6-14}$ aromatic hydrocarbon ring group, a 5- to 14-membered aromatic heterocyclic group, a heterocyclic aminocarbonyl group, a heterocyclic aminosulfonyl group and isoxazolinyl, wherein the 5- to 14-membered non-aromatic heterocyclic group, the $C_{6-14}$ aromatic hydrocarbon ring group, the 5- to 14-membered aromatic heterocyclic group and isoxazolinyl may be independently substituted with at least one group selected from the group consisting of $C_{1-6}$ alkyl, oxo, cyano, acyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, nitro, amino, $C_{1-6}$ aminoalkyl, $C_{1-6}$ alkylamino, $C_{1-6}$ dialkylamino, $C_{3-8}$ cycloalkylamino, acylamino, ureido, ureylene, alkylsulfonylamino, alkylsulfonyl, sulfamoyl, halogeno and $C_{3-8}$ cycloalkyl;

<Substituent Group E> represents moieties selected from the group consisting of $C_{1-6}$ alkyl, cyano, acyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, amino, $C_{1-6}$ alkylamino, $C_{3-8}$ cycloalkylamino, acylamino, ureido, ureylene, sulfonylamino, sulfonyl, sulfamoyl, halogen and $C_{3-8}$ cycloalkyl;

<Substituent Group F> represents moieties selected from the group consisting of (1) hydrogen, (2) cyano, (3) halogen, (4) oxo and (5) $C_{1-6}$ alkyl, alkenyl, alkynyl, acyl, $C_{1-6}$ alkanoyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, amino, imino, $C_{1-6}$ aminoalkyl, $C_{1-6}$ alkylamino, $C_{3-8}$ cycloalkylamino, acylamino, ureido, sulfonylamino, sulfonyl, sulfamoyl, $C_{3-8}$ cycloalkyl, a 5- to 14-membered non-aromatic heterocyclic group, a $C_{6-14}$ aromatic hydrocarbon ring group and a 5- to 14-membered aromatic heterocyclic group (each of the foregoing members being optionally substituted with at least one group selected from Substituent Group F' below);

<Substituent Group F'> represents moieties selected from the group consisting of $C_{1-6}$ alkyl, oxo, cyano, acyl, carboxyl, carbamoyl, $C_{1-6}$ alkoxycarbonyl, benzyloxycarbonyl, $C_{1-6}$ alkylaminocarbonyl, hydroxyl, $C_{1-6}$ alkoxy, $C_{3-8}$ cycloalkyloxy, amino, $C_{1-6}$ alkylamino, $C_{3-8}$ cycloalkylamino, acylamino, ureido, ureylene, $C_{1-6}$ alkylsulfonylamino, $C_{1-6}$ alkylsulfonyl, sulfamoyl, halogeno, $C_{3-8}$ cycloalkyl, a 5- to 14-membered non-aromatic heterocyclic group, a $C_{6-14}$ aromatic hydrocarbon ring group and a 5- to 14-membered aromatic heterocyclic group;

<Substituent Group G> represents moieties selected from the group consisting of $C_{1-6}$ alkyl, cyano, acyl, carboxyl, carbamoyl, $C_{1-6}$ alkoxycarbonyl, $C_{1-6}$ alkylaminocarbonyl, sulfonyl, sulfamoyl, halogeno and $C_{3-8}$ cycloalkyl.] or salt thereof.

<2> In certain embodiments, the invention provides a compound according to <1> or salt thereof, wherein $R^1$, $R^2$ and $R^3$ are the same or different and each independently represents a group selected from the group consisting of hydrogen, $C_{1-6}$ alkyl, $C_{1-6}$ alkoxy, aryl-$C_{1-6}$ alkyl and aryl-$C_{1-6}$ alkylidene, $R^4$, $R^5$ and $R^7$ are the same or different and each independently represents a group selected from the group consisting of hydrogen, $C_{1-6}$ alkyl and hydroxyl, z represents 0 or 1, $R^2$ and $R^4$ may bond together to form a 5- to 6-membered ring optionally having 1 to 5 hetero atoms selected from N, S and O, and $R^4$ and $R^5$ may bond together to form a single bond; $R^6$ represents a group selected from the group consisting of hydrogen, $C_{1-6}$ alkyl and $C_{1-6}$ alkyloxycarbonyl optionally substituted with acyloxy; n represents 1; $Y^1$ represents a single bond or —$(CH_2)_m$— [wherein m represents an integer of 1 to 3]; $Y^2$ represents a single bond or —CO—; and Ar represents hydrogen or a group represented by the formula:

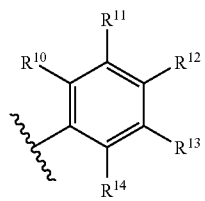

(II)

[wherein $R^{10}$, $R^{11}$, $R^{12}$, $R^{13}$ and $R^{14}$ are the same or different and each independently represents a group selected from the group consisting of hydrogen, $C_{1-6}$ alkyl, hydroxyl, $C_{1-6}$ alkoxy, $C_{1-6}$ alkylamino, $C_{3-8}$ cycloalkylamino, acylamino, a 5- to 14-membered non-aromatic heterocyclic group and $C_{1-6}$ alkyloxycarbonyloxy, and $R^{11}$ and $R^{12}$ or $R^{12}$ and $R^{13}$ may bond together to form a 5- to 8-membered heterocycle (i) optionally having 1 to 4 hetero atoms selected from N, S and O and (ii) optionally substituted with at least one group selected from the group consisting of cyano, oxo, and $C_{1-6}$ alkyl, acyl, $C_{1-6}$ alkanoyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, amino, $C_{1-6}$ alkylamino, sulfonyl and a 5- to 14-membered non-aromatic heterocyclic group, each of the foregoing members being optionally substituted with at least one group selected from Substituent Group F" below:

<Substituent Group F"> represents moieties selected from the group consisting of $C_{1-6}$ alkyl, oxo, cyano, acyl, carboxyl and $C_{1-6}$ alkoxy].

<3> In certain other embodiments, the invention provides a compound according to <1> or salt thereof, wherein $Y^1$ is —$CH_2$—.

<4> In certain other embodiments, the invention provides a compound according to <1> or salt thereof, wherein $Y^2$ is —CO—.

<5> In certain other embodiments, the invention provides a compound according to <1> or salt thereof, wherein $Y^1$ is —$CH_2$— and $Y^2$ is —CO—.

<6> In certain other embodiments, the invention provides a compound according to <1> or salt thereof, wherein $Y^1$ is a single bond, $Y^2$ is a single bond and Ar is hydrogen.

<7> In certain other embodiments, the invention provides a compound according to <1> or salt thereof, wherein Ar is a group represented by the formula:

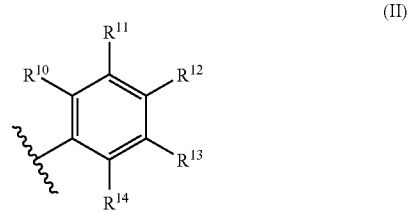

(II)

[wherein $R^{10}$, $R^{11}$, $R^{12}$, $R^{13}$ and $R^{14}$ have the same definitions given below].

<8> In certain other embodiments, the invention provides a compound according to <7> or salt thereof, wherein $R^{10}$ and $R^{14}$ are hydrogen.

<9> In certain other embodiments, the invention provides a compound according to <1> or salt thereof, wherein Ar is (1) a group represented by the formula:

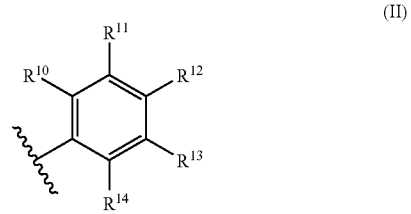

(II)

[wherein $R^{10}$, $R^{11}$, $R^{12}$, $R^{13}$ and $R^{14}$ have the same definitions given above] or (2) a 5- to 14-membered aromatic heterocyclic group optionally substituted with at least one group selected from Substituent Group G above.

<10> In certain other embodiments, the invention provides a compound according to <9> or salt thereof, wherein $R^{10}$ and $R^{14}$ are hydrogen.

<11> In certain other embodiments, the invention provides a compound according to <1> or salt thereof, wherein Ar is (1) a group represented by the formula:

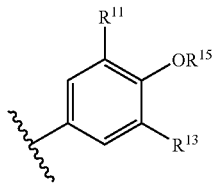

(IV)

[wherein $R^{11}$ and $R^{13}$ have the same definitions given above, and $R^{15}$ represents (1) hydrogen or (2) a group selected from Substituent Group H below, wherein $R^{11}$ and $R^{15}$ may bond together to form a 5- to 8-membered heterocycle optionally substituted with at least one group selected from Substituent Group F above and optionally having 1 or 2 hetero atoms selected from N, S and O.

<Substituent Group H> represents moieties selected from the group consisting of $C_{1-6}$ alkyl, $C_{2-6}$ alkenyl, $C_{2-6}$ alkynyl, acyl, $C_{1-6}$ alkoxycarbonyl, aminocarbonyl, $C_{1-6}$ alkylaminocarbonyl, $C_{3-8}$ cycloalkyl, $C_{1-6}$ aminoalkyl, sulfonyl, $C_{3-8}$ cycloalkylamino, a 5- to 14-membered non-aromatic heterocyclic group, a $C_{6-14}$ aromatic hydrocarbon ring group and a 5- to 14-membered aromatic heterocyclic group, each of the foregoing members being optionally substituted with at least one group selected from Substituent Group H' below;

<Substituent Group H'> represents moieties selected from the group consisting of $C_{1-6}$ alkyl, $C_{2-6}$ alkenyl, $C_{2-6}$ alkynyl, oxo, cyano, $C_{1-6}$ cyanoalkyl, $C_{2-7}$ acyl, $C_{1-6}$ alkanoyl, benzoyl, aralkanoyl, $C_{1-6}$ alkoxyalkylcarbonyl, $C_{1-6}$ hydroxyalkylcarbonyl, carboxyl, $C_{1-6}$ carboxyalkyl, $C_{1-6}$ carboxyalkyloxy, carbamoyl, carbamoylalkyloxy, $C_{1-6}$ alkoxycarbonyl, $C_{1-10}$ alkoxycarbonyl-$C_{1-6}$ alkyl, $C_{1-10}$ alkoxycarbonyl-$C_{1-6}$ alkyloxy, $C_{1-6}$ monoalkylaminocarbonyl, $C_{2-6}$ dialkylaminocarbonyl, hydroxyl, $C_{1-6}$ alkoxy, $C_{1-10}$ alkoxyalkyl, $C_{1-10}$ aralkyloxyalkyl, $C_{1-6}$ hydroxyalkyl, $C_{3-8}$ cycloalkyloxy, amino, $C_{1-6}$ alkylamino, $C_{3-8}$ cycloalkylamino, acylamino, ureido, ureylene, $C_{1-6}$ alkylsulfonylamino, phenylsulfonylamino, $C_{1-6}$ alkylsulfonyl, phenylsulfonyl, $C_{1-6}$ monoalkylaminosulfonyl, $C_{2-6}$ dialkylaminosulfonyl, sulfamoyl, halogeno, $C_{3-8}$ cycloalkyl, a 5- to 14-membered non-aromatic heterocyclic group, a $C_{6-14}$ aromatic hydrocarbon ring group, a 5- to 14-membered aromatic heterocyclic group, a heterocyclic aminocarbonyl group, a heterocyclic aminosulfonyl group and isoxazolinyl, wherein the 5- to 14-membered non-aromatic heterocyclic group, the $C_{6-14}$ aromatic hydrocarbon ring group, the 5- to 14-membered aromatic heterocyclic group and isoxazolinyl may be independently substituted with at least one group selected from the group consisting of $C_{1-6}$ alkyl, oxo, cyano, acyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, nitro, amino, $C_{1-6}$ aminoalkyl, $C_{1-6}$ alkylamino, $C_{1-6}$ dialkylamino, $C_{3-8}$ cycloalkylamino, acylamino, ureido, ureylene, alkylsulfonylamino, alkylsulfonyl, sulfamoyl, halogeno and $C_{3-8}$ cycloalkyl].

<12> In certain other embodiments, the invention provides a compound according to <1> or salt thereof, wherein Ar is a group represented by the formula:

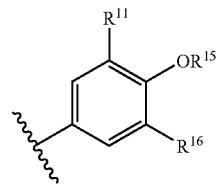

(V)

[wherein $R^{11}$ and $R^{15}$ have the same definitions given above, and $R^{16}$ represents (1) hydrogen or (2) a group selected from Substituent Group H above, and $R^{11}$ and $R^{15}$ or $R^{15}$ and $R^{16}$ may bond together to form a 5- to 6-membered heterocycle optionally substituted with at least one group selected from Substituent Group F above and optionally having 1 or 2 hetero atoms selected from N, S and O].

<13> In certain other embodiments, the invention provides a compound according to <1> or salt thereof, wherein Ar is a group represented by the formula:

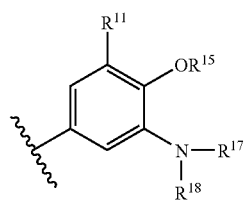

(VI)

[wherein $R^{11}$ and $R^{15}$ have the same definitions given above, and $R^{17}$ and $R^{18}$ are the same or different and each independently represents (1) hydrogen or (2) a group selected from Substituent Group I below, and $R^{11}$ and $R^{15}$, $R^{15}$ and $R^{17}$, $R^{15}$ and $R^{18}$, or $R^{17}$ and $R^{18}$ may bond together to form a 5- to 8-membered heterocycle optionally substituted with at least one group selected from Substituent Group F above and optionally having 1 or 2 hetero atoms selected from N, S and O.

<Substituent Group I> represents moieties selected from the group consisting of $C_{1-6}$ alkyl, $C_{2-6}$ alkenyl, $C_{2-6}$ alkynyl, acyl, carbamoyl, $C_{1-6}$ alkoxycarbonyl, $C_{1-6}$ alkylaminocarbonyl, $C_{1-6}$ aminoalkyl, sulfonyl, sulfamoyl, $C_{3-8}$ cycloalkyl, a 5- to 14-membered non-aromatic heterocyclic group, a $C_{6-14}$ aromatic hydrocarbon ring group and a 5- to 14-membered aromatic heterocyclic group, each of the foregoing members being optionally substituted with at least one group selected from Substituent Group I' below;

<Substituent Group I'> represents moieties selected from the group consisting of $C_{1-6}$ alkyl, $C_{2-6}$ alkenyl, $C_{2-6}$ alkynyl, oxo, cyano, $C_{1-6}$ cyanoalkyl, $C_{2-7}$ acyl, $C_{1-6}$ alkanoyl, benzoyl, aralkanoyl, $C_{1-6}$ alkoxyalkylcarbonyl, $C_{1-6}$ hydroxyalkylcarbonyl, carboxyl, $C_{1-6}$ carboxyalkyl, $C_{1-6}$ carboxyalkyloxy, carbamoyl, carbamoylalkyloxy, $C_{1-6}$ alkoxycarbonyl, $C_{10}$ alkoxycarbonyl-$C_{1-6}$ alkyl, $C_{1-10}$ alkoxycarbonyl-$C_{1-6}$ alkyloxy, $C_{1-6}$ monoalkylaminocarbonyl, $C_{2-6}$ dialkylaminocarbonyl, hydroxyl, $C_{1-6}$ alkoxy, $C_{1-10}$ alkoxyalkyl, $C_{1-10}$ aralkyloxyalkyl, $C_{1-6}$ hydroxyalkyl, $C_{3-8}$ cycloalkyloxy, amino, $C_{1-6}$ alkylamino, $C_{3-8}$ cycloalkylamino, acylamino, ureido, ureylene, $C_{1-6}$ alkylsulfonylamino, phenylsulfonylamino, $C_{1-6}$ alkylsulfonyl, phenylsulfonyl, $C_{1-6}$ monoalkylaminosulfonyl, $C_{2-6}$ dialkylaminosulfonyl, sulfamoyl, halogeno, $C_{3-8}$ cycloalkyl, a 5- to 14-membered non-aromatic heterocyclic group, a $C_{6-14}$ aromatic hydrocarbon ring group, a 5- to 14-membered aromatic heterocyclic group, a heterocyclic aminocarbonyl group, a heterocyclic aminosulfonyl group and isoxazolinyl, wherein the 5- to 14-membered non-aromatic heterocyclic group, the $C_{6-14}$ aromatic hydrocarbon ring group, the 5- to 14-membered aromatic heterocyclic group and isoxazolinyl may be independently substituted with at least one group selected from the group consisting of $C_{1-6}$ alkyl, oxo, cyano, acyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, nitro, amino, $C_{1-6}$ aminoalkyl, $C_{1-6}$ alkylamino, $C_{1-6}$ dialkylamino, $C_{3-8}$ cycloalkylamino, acylamino, ureido, ureylene, alkylsulfonylamino, alkylsulfonyl, sulfamoyl, halogeno and $C_{3-8}$ cycloalkyl].

<14> In another aspect, the invention provides a pharmaceutical composition comprising a compound according to <1> or salt thereof.

<15> In certain embodiments, the invention provides a composition according to <14>, wherein the composition is useful as a thrombin receptor antagonist.

<16> In certain other embodiments, the invention provides a composition according to <14>, wherein the composition is useful as a thrombin receptor PAR1 antagonist.

<17> In certain other embodiments, the invention provides a composition according to <14>, wherein the composition is useful as a platelet aggregation inhibitor.

<18> In certain other embodiments, the invention provides a composition according to <14>, wherein the composition is useful as a proliferation inhibitor for smooth muscle cells.

<19> In certain other embodiments, the invention provides a composition according to <14>, wherein the composition is useful as a proliferation inhibitor for endothelial cells, fibroblasts, nephrocytes, osteosarcoma cells, muscle cells, cancer cells and/or glia cells.

<20> In certain other embodiments, the invention provides a composition according to <14>, wherein the composition is useful as a therapeutic or prophylactic agent for thrombosis, vascular restenosis, deep venous thrombosis, pulmonary embolism, cerebral infarction, heart disease, disseminated intravascular coagulation, hypertension, inflammatory disease, rheumatism, asthma, glomerulonephritis, osteoporosis, neurological disease and/or malignant tumor.

<21> In yet another aspect, the invention provides the use of a compound according to <1> or salt thereof for the manufacture of a thrombin receptor antagonist.

<22> In certain embodiments, the invention provides the use according to <21>, wherein the thrombin receptor antagonist is a PAR1 receptor antagonist.

<23> In certain other embodiments, the invention provides the use of a compound according to <1> or salt thereof for the manufacture of a platelet aggregation inhibitor.

<24> In a further aspect, the invention provides a therapeutic method for treating or preventing a disease associated with thrombin receptors, comprising administering to a patient suffering from the disease, a therapeutically effective dose of a compound according to <1> or salt thereof.

<25> In certain embodiments, the invention provides a therapeutic method for treating or preventing a proliferative disease of endothelial cells, fibroblasts, nephrocytes, osteosarcoma cells, muscle cells, cancer cells and/or glia cells, comprising administering to a patient suffering from the disease, a therapeutically effective dose of a compound according to <1> or thereof.

The present invention will now be explained in greater detail.

Several of the structural formulas given for the compounds of the invention throughout the present specification will represent only a specific isomer for convenience, but the invention is not limited to such specific isomers and encompasses all isomers and isomer mixtures, including geometric isomers, asymmetric carbon-derived optical isomers, stereoisomers and tautomers which are implied by the structures of the compounds, and any isomer or mixture thereof may be used. The compounds of the invention therefore include those having asymmetric carbons in their molecules and existing as optically active forms or racemic forms, and all such compounds are encompassed by the invention without restrictions. There are also no restrictions on any crystalline polymorphism of the compounds, and any crystal forms may be used alone or in mixtures. The compounds of the invention and their salts may also be in the form of anhydrides or solvates such as hydrates, and all such forms are included within the scope of the claims of the present specification. Metabolites of the compounds of the invention produced by degradation in the body, as well as prodrugs of the compounds of the invention and their salts, are also encompassed within the scope of the claims of the present specification.

The symbols and terms used throughout the present specification will now be defined, with a more detailed description of the invention.

The term "and/or" as used throughout the present specification carries the meaning of both "and" and "or".

The term "halogen" used throughout the present specification refers to an atom such as fluorine, chlorine, bromine or iodine, and preferably fluorine, chlorine or bromine.

The term "$C_{1-6}$ alkyl" used throughout the present specification refers to an alkyl group of 1 to 6 carbons, such as, for example, linear or branched alkyl groups such as methyl, ethyl, n-propyl, iso-propyl, n-butyl, iso-butyl, sec-butyl, tert-butyl, n-pentyl, 1,1-dimethylpropyl, 1,2-dimethylpropyl, 2,2-dimethylpropyl, 1-ethylpropyl, 2-ethylpropyl, n-hexyl, 1-methyl-2-ethylpropyl, 1-ethyl-2-methylpropyl, 1,1,2-trimethylpropyl, 1-propylpropyl, 1-methylbutyl, 2-methylbutyl, 1,1-dimethylbutyl, 1,2-dimethylbutyl, 2,2-dimethylbutyl, 1,3-dimethylbutyl, 2,3-dimethylbutyl, 2-ethylbutyl, 2-methylpentyl and 3-methylpentyl, and more preferably methyl, ethyl, n-propyl, iso-propyl, n-butyl, iso-butyl, sec-butyl, tert-butyl and n-pentyl.

The term "$C_{2-6}$ alkenyl" used throughout the present specification refers to an alkenyl group of 2 to 6 carbons, such as, for example, vinyl, allyl, 1-propenyl, 2-propenyl, isopropenyl, 2-methyl-1-propenyl, 3-methyl-1-propenyl, 2-methyl-2-propenyl, 3-methyl-2-propenyl, 1-butenyl, 2-butenyl, 3-butenyl, 1-pentenyl, 1-hexenyl, 1,3-hexanedienyl and 1,6-hexanedienyl.

The term "$C_{2-6}$ alkynyl" used throughout the present specification refers to an alkynyl group of 2 to 6 carbons, such as, for example, ethynyl, 1-propynyl, 2-propynyl, 1-butynyl, 2-butynyl, 3-butynyl, 3-methyl-1-propynyl, 1-ethynyl-2-propynyl, 2-methyl-3-propynyl, 1-pentynyl, 1-hexynyl, 1,3-hexanediynyl and 1,6-hexanediynyl.

The term "$C_{3-8}$ cycloalkyl" used throughout the present specification refers to a cycloalkyl group composed of 3 to 8 carbons, such as, for example, cyclopropyl, cyclobutyl, cyclopentyl, cyclohexyl, cycloheptyl and cyclooctyl.

The term "$C_{3-8}$ cycloalkenyl" used throughout the present specification refers to a $C_{3-8}$ cycloalkenyl group composed of 3 to 8 carbons, such as, for example, cyclopropen-1-yl, cyclopropen-3-yl, cyclobuten-1-yl, cyclobuten-3-yl, 1,3-cyclobutadien-1-yl, cyclopenten-1-yl, cyclopenten-3-yl, cyclopenten-4-yl, 1,3-cyclopentadien-1-yl, 1,3-cyclopentadien-2-yl, 1,3-cyclopentadien-5-yl, cyclohexen-1-yl, cyclohexen-3-yl, cyclohexen-4-yl, 1,3-cyclohexadien-1-yl, 1,3-cyclohexadien-2-yl, 1,3-cyclohexadien-5-yl, 1,4-cyclohexadien-3-yl, 1,4-cyclohexadien-1-yl, cyclohepten-1-yl, cyclohepten-3-yl, cyclohepten-4-yl, cyclohepten-5-yl, 1,3-cyclohepten-2-yl, 1,3-cyclohepten-1-yl, 1,3-cycloheptadien-5-yl, 1,3-cycloheptadien-6-yl, 1,4-cycloheptadien-3-yl, 1,4-cycloheptadien-2-yl, 1,4-cycloheptadien-1-yl, 1,4-cycloheptadien-6-yl, 1,3,5-cycloheptatrien-3-yl, 1,3,5-cycloheptatrien-2-yl, 1,3,5-cycloheptatrien-1-yl, 1,3,5-cycloheptatrien-7-yl, cycloocten-1-yl, cycloocten-3-yl, cycloocten-4-yl, cycloocten-5-yl, 1,3-cyclooctadien-2-yl, 1,3-cyclooctadien-1-yl, 1,3-cyclooctadien-5-yl, 1,3-cyclooctadien-6-yl, 1,4-cyclooctadien-3-yl, 1,4-cyclooctadien-2-yl, 1,4-cyclooctadien-1-yl, 1,4-cyclooctadien-6-yl, 1,4-cyclooctadien-6-yl, 1,5-cyclooctadien-3-yl, 1,5-cyclooctadien-2-yl, 1,3,5-cyclooctatrien-3-yl, 1,3,5-cyclooctatrien-2-yl, 1,3,5-cyclooctatrien-1-yl, 1,3,5-cyclooctatrien-7-yl, 1,3,6-cyclooctatrien-2-yl, 1,3,6-cyclooctatrien-1-yl, 1,3,6-cyclooctatrien-5-yl and 1,3,6-cyclooctatrien-6-yl.

The term "$C_{1-6}$ alkoxy" used throughout the present specification refers to an alkoxy group of 1 to 6 carbons, such as, for example, methoxy, ethoxy, n-propoxy, iso-propoxy, sec-propoxy, n-butoxy, iso-butoxy, sec-butoxy, tert-butoxy, n-pentyloxy, iso-pentyloxy, sec-pentyloxy, n-hexoxy, iso-hexoxy, 1,1-dimethylpropyloxy, 1,2-dimethylpropyloxy, 2,2-dimethylpropyloxy, 2-ethylpropyloxy, 1-methyl-2-ethylpropyloxy, 1-ethyl-2-methylpropyloxy, 1,1,2-trimethylpropyloxy, 1,1,2-trimethylpropyloxy, 1,1-dimethylbutyloxy, 1,2-dimethylbutyloxy, 2,2-dimethylbutyloxy, 2,3-dimethylbutyloxy, 1,3-dimethylbutyloxy, 2-ethylbutyloxy, 1,3-dimethylbutyloxy, 2-methylpentoxy, 3-methylpentoxy and hexyloxy.

The term "$C_{2-6}$ alkenyloxy" used throughout the present specification refers to an alkenyloxy group of 2 to 6 carbons, such as, for example, vinyloxy, allyloxy, 1-propenyloxy, 2-propenyloxy, isopropenyloxy, 2-methyl-1-propenyloxy, 3-methyl-1-propenyloxy, 2-methyl-2-propenyloxy, 3-methyl-2-propenyloxy, 1-butenyloxy, 2-butenyloxy, 3-butenyloxy, 1-pentenyloxy, 1-hexenyloxy, 1,3-hexanedienyloxy and 1,6-hexanedienyloxy.

The term "acyl" used throughout the present specification refers to an atomic group derived by removing the OH group from a carboxyl group of a carboxylic acid, and it is preferably a $C_{2-7}$ acyl group (an atomic group derived by removing the OH group from a carboxyl group of a $C_{2-7}$ carboxylic acid (more preferably fatty acid)), of which examples include acetyl, propionyl, butyroyl and benzoyl.

The term "$C_{6-14}$ aromatic hydrocarbon ring group" used throughout the present specification refers to an aromatic hydrocarbon ring group composed of 6 to 14 carbons, and includes monocyclic groups as well as fused rings such as bicyclic and tricyclic groups. Examples include phenyl, indenyl, 1-naphthyl, 2-naphthyl, azulenyl, heptalenyl, biphenyl, indacenyl, acenaphthyl, fluorenyl, phenalenyl, phenanthrenyl, anthracenyl, cyclopentacyclooctenyl and benzocyclooctenyl.

The term "5- to 14-membered aromatic heterocyclic group" used throughout the present specification refers to a monocyclic, bicyclic or tricyclic 5- to 14-membered aromatic heterocyclic group comprising one or more hetero atoms selected from the group consisting of nitrogen, sulfur and oxygen. Examples include (i) nitrogen-containing aromatic heterocyclic groups such as pyrrolyl, pyridyl, pyridazinyl, pyrimidinyl, pyrazinyl, triazolyl, tetrazolyl, benzotriazolyl, pyrazolyl, imidazolyl, benzimidazolyl, indolyl, isoindolyl, indolidinyl, purinyl, indazolyl, quinolyl, isoquinolyl, quinolidyl, phthalazyl, naphthylidinyl, quinoxalyl, quinazolinyl, cinnolinyl, pteridinyl, imidazotriazinyl, pyrazinopyridazinyl, acridinyl, phenanthridinyl, carbazolyl, carbazolinyl, perimidinyl, phenanthrolinyl, phenacenyl, imidazopyridinyl, imidazopyrimidinyl, pyrazolopyridinyl, pyrazolopyridinyl, etc.; (ii) sulfur-containing aromatic heterocyclic groups such as thienyl, benzothienyl, etc.; (iii) oxygen-containing aromatic heterocyclic groups such as furyl, pyranyl, cyclopentapyranyl, benzofuryl, isobenzofuryl, etc.; and (iv) aromatic heterocyclic groups containing 2 or more different hetero atoms, such as thiazolyl, isothiazolyl, benzothiazolyl, benzothiadiazolyl, phenothiazinyl, isoxazolyl, furazanyl, phenoxazinyl, oxazolyl, isoxazoyl, benzoxazolyl, oxadiazolyl, pyrazoloxazolyl, imidazothiazolyl, thienofuranyl, furopyrrolyl, pyridoxazinyl, etc.

The term "5- to 14-membered non-aromatic heterocyclic group" used throughout the present specification refers to a monocyclic, bicyclic or tricyclic 5- to 14-membered non-aromatic heterocyclic group comprising one or more hetero atoms selected from the group consisting of nitrogen, sulfur and oxygen. Examples include pyrrolidyl, pyrrolyl, piperidyl, piperazyl, imidazolyl, pyrazolidyl, imidazolidyl, morpholyl, tetrahydrofuryl, tetrahydropyranyl, aziridinyl, oxiranyl and oxathiolanyl. Non-aromatic heterocyclic groups also include a pyridone ring-derived group, and a non-aromatic fused ring (for example, a phthalimide ring-derived group and a succinimide ring-derived group).

The term "5- to 8-membered heterocycle" used throughout the present specification refers to a 5- to 8-membered aromatic or non-aromatic heterocycle.

The term "aryl" used throughout the present specification refers to an atomic group remaining after elimination of one hydrogen atom bonded to the ring of the aromatic hydrocarbon. Examples include phenyl, tolyl, xylyl, biphenyl, naphthyl, anthoryl and phenanthoryl.

The term "alkylidene" used throughout the present specification refers to a divalent group derived by the loss of two hydrogen atoms from the same carbon of an aliphatic hydrocarbon (preferably a $C_{1-6}$ alkane). Examples include ethylidene and the like.

The expression "optionally substituted" appearing throughout the present specification has the same meaning as "having one or multiple substituents in any desired combination at substitutable positions".

The term "hetero atom" used throughout the present specification refers specifically to oxygen, sulfur, nitrogen, phosphorus, arsenic, antimony, silicon, germanium, tin, lead, boron, mercury and the like, and preferably oxygen, sulfur and nitrogen.

Throughout the present specification, the prefix "n-" signifies a normal type or primary substituent, "sec-" signifies a secondary substituent, "t-" signifies a tertiary substituent and "i-" signifies an iso type substituent.

The definitions of $R^1, R^2, R^3, R^4, R^5, R^7, z, n, R^6, Y^1, Y^2$ and Ar in the compounds of the invention represented by the general formula (I) above are as explained above. In certain exemplary embodiments, n is 1 and ring A is a pyrrolidine ring.

In certain embodiments, $R^1$, $R^2$ and $R^3$ are each independently a group selected from the group consisting of hydrogen, $C_{1-6}$ alkyl, $C_{1-6}$ alkoxy, aryl-$C_{1-6}$ alkyl and aryl-$C_{1-6}$ alkylidene. In certain other embodiments, $R^4$, $R^5$ and $R^7$ are each independently a group selected from the group consisting of hydrogen, $C_{1-6}$ alkyl and hydroxyl. In certain other embodiments, when $R^1$ is bonded to ring A as a single bond, the number (z) of $R^7$ is preferably 1. In certain other embodiments, when $R^1$ is a double bond and is bonded to ring A, the number (z) of $R^7$ is preferably 0. $R^2$ and $R^4$ may also bond together to form a 5- to 6-membered ring having 1 to 5 atoms selected from C, N and O. $R^4$ and $R^5$ may bond together to form a single bond.

In certain other embodiments, $R^6$ is a group selected from the group consisting of hydrogen, $C_{1-6}$ alkyl and $C_{1-6}$ alkyloxycarbonyl optionally substituted with acyloxy.

In certain other embodiments, $Y^1$ is a single bond or —$(CH_2)_m$— [wherein m represents an integer of 1 to 3] and $Y^2$ is preferably a single bond or —CO—, there being more preferred (i) a combination that $Y^1$ is —$CH_2$— and $Y^2$ is —CO—, and (ii) a combination that $Y^1$ and $Y^2$ are both single bonds.

In certain other embodiments, Ar represents hydrogen or a group represented by the formula:

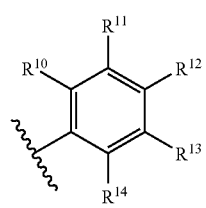

(II)

(wherein $R^{10}$, $R^{11}$, $R^{12}$, $R^{13}$ and $R^{14}$ have the same definitions given above].

In certain other embodiments, when $Y^1$ is —$CH_2$— and $Y^2$ is —CO—, Ar is a group represented by the general formula (II) above. In certain other embodiments, when $Y^1$ and $Y^2$ are each a single bond, Ar is hydrogen.

In certain other embodiments, $R^{10}$, $R^{11}$, $R^{12}$, $R^{13}$ and $R^{14}$ are the same or different and are each independently a group selected from the group consisting of hydrogen, $C_{1-6}$ alkyl, hydroxyl, $C_{1-6}$ alkoxy, $C_{1-6}$ alkylamino, $C_{3-8}$ cycloalkylamino, acylamino, a 5- to 14-membered non-aromatic heterocyclic group and $C_{1-6}$ alkyloxycarbonyloxy. In certain exemplary embodiments, $R^{10}$ and $R^{14}$ are more preferably hydrogen. In certain other embodiments, $R^{11}$ and $R^{12}$ or $R^{12}$ and $R^{13}$ may bond together to form a 5- to 8-membered heterocycle (i) optionally having 1 to 4 hetero atoms selected from N, S and O and (ii) optionally substituted with at least one group selected from the group consisting of cyano, oxo, and $C_{1-6}$ alkyl, acyl, $C_{1-6}$ alkanoyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, amino, $C_{1-6}$ alkylamino, sulfonyl and a 5- to 14-membered non-aromatic heterocyclic group (each of the foregoing members being optionally substituted with at least one group selected from Substituent Group F''' below:

<Substituent Group F'''> represents moieties selected from the group consisting of $C_{1-6}$ alkyl, oxo, cyano, acyl, carboxyl and $C_{1-6}$ alkoxy).

A preferred group for (ii) above is the group consisting of cyano, oxo, $C_{1-6}$ alkyl, cyano-$C_{1-6}$ alkyl, $C_{1-6}$ acyl, carboxyl, $C_{1-6}$ alkoxycarbonyl, $C_{1-6}$ alkylaminocarbonyl, hydroxyl and $C_{1-6}$ alkoxy.

In certain other embodiments, $R^{10}$ and $R^{14}$ are hydrogen and Ar is represented by the formula:

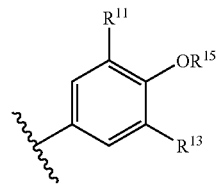

(IV)

[wherein $R^{11}$ and $R^{13}$ have the same definitions given above, $R^{15}$ represents (1) hydrogen or (2) a group selected from Substituent Group H above, and $R^{11}$ and $R^{15}$ may bond together to form a 5- to 8-membered heterocycle optionally substituted with at least one group selected from Substituent Group F above and optionally having 1 or 2 hetero atoms selected from N, S and O]; a group represented by the formula:

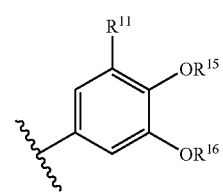

(V)

[wherein $R^{11}$ and $R^{15}$ have the same definitions given above, $R^{16}$ represents (1) hydrogen or (2) a group selected from Substituent Group H above, and $R^{11}$ and $R^{15}$ or $R^{15}$ and $R^{16}$ may bond together to form a 5- to 6-membered heterocycle optionally substituted with at least one group selected from Substituent Group F above and optionally having 1 or 2 hetero atoms selected from N, S and O]; or a group represented by the formula:

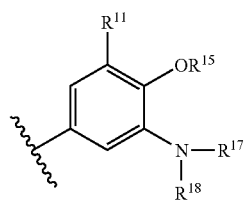

(VI)

[wherein $R^{11}$ and $R^{15}$ have the same definitions given above, $R^{17}$ and $R^{18}$ are the same or different and each independently represents (1) hydrogen or (2) a group selected from Substituent Group I above, and $R^{11}$ and $R^{15}$, $R^{15}$ and $R^{17}$, $R^{15}$ and $R^{18}$, or $R^{17}$ and $R^{18}$ may bond together to form a 5- to 8-membered heterocycle optionally substituted with at least one group selected from Substituent Group F above and optionally having 1 or 2 hetero atoms selected from N, S and O].

The term "salt" used throughout the present specification is not particularly restrictive so long as the salt is formed with a compound of the invention and is pharmacologically acceptable. Examples include hydrogen halide acid salts (for example, hydrofluoride, hydrochloride, hydrobromide and hydroiodide), inorganic acid salts (for example, sulfate, nitrate, perchlorate, phosphate, carbonate and bicarbonate), organic carboxylate (for example, acetate, trifluoroacetate, oxalate, maleate, tartarate, fumarate and citrate), organosulfonate (for example, methanesulfonate, trifluoromethanesulfonate, ethanesulfonate, benzenesulfonate, toluenesulfonate and camphorsulfonate), amino acid salts (for example, aspartate and glutamate), quaternary amine salts, alkali metal salts (for example, sodium salts and potassium salts) or alkaline earth metal salts (for example, magnesium salts and calcium salts). In certain embodiments, salts of the invention are "pharmacologically acceptable salts" such as hydrochloride, oxalate, trifluoroacetate and the like.

Production processes for compounds of the invention and salts thereof will now be described. Various processes are possible for production of the compounds of the invention represented by the general formula (I) above and their salts, and the synthesis may be carried out by ordinary organic synthetic methods. The following representative production processes will now be presented.

[Representative Production Processes]

Exemplary synthetic methods for the preparation of saturated cyclic amidine derivatives are shown in the following production processes I to K.

<Production Process I>

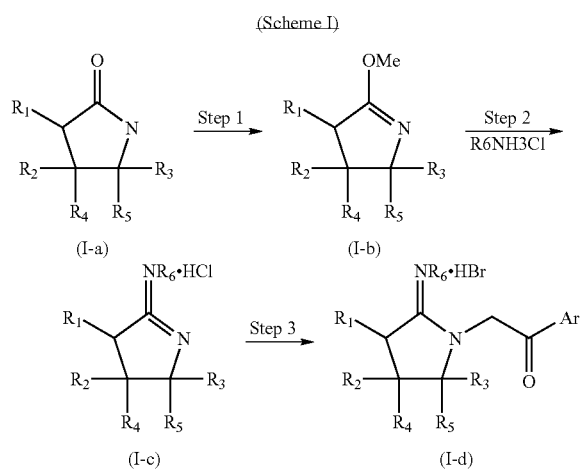

This scheme depicts an exemplary method for the synthesis of a cyclic amidine (I-d) involving an imidate (I-b) as an intermediate. In the formulas, R1-R6 and Ar have the same definitions as those for the compound represented by formula (I) in claim 1.

Step 1 represents a method of converting a lactam to an imidate. Compound (I-b) may be obtained by reaction with trimethyloxonium tetrafluoroborate in dichloromethane at room temperature.

Step 2 represents a substitution reaction by an amino group. Compound (I-c) may be obtained by heating compound (I-b) in an alcohol solvent to reflux in the presence of ammonium chloride or an alkylamine hydrochloride.

Step 3 represents a coupling reaction with phenacyl bromide and can be accomplished by the following two types of methods: (1) After an acetonitrile solution of compound (I-c) is reacted with an equivalent amount of DBU to obtain a salt free form, phenacyl bromide is reacted therewith; alternatively, after compound (I-c) is converted to a salt free form with a basic ion-exchange resin in an alcohol solvent, phenacyl bromide is reacted therewith in a mixed solvent of an alcohol and acetonitrile. Either method enables compound (I-d) to be produced.

A cyclic amidine represented by (I-c) may also be synthesized according to the method shown in Production Process J.

<Production Process J>

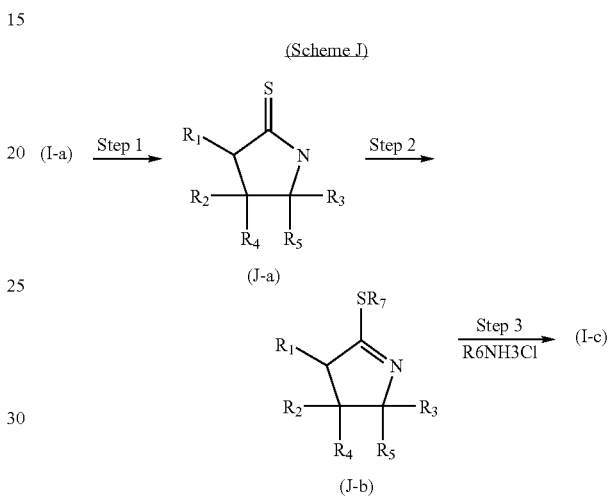

This scheme depicts an exemplary method for synthesis of a cyclic amidine (I-c) involving a thioimidate (J-b) as an intermediate. In the formulas, R1, R2, R3, R4, R5 and R6 have the same definitions as those for the compound represented by formula (I) in claim 1. R7 represents methyl or ethyl.

Step 1 represents a method for synthesis of a thiolactam. Compound (J-a) may be obtained by reaction with Lawesson's reagent in a solvent such as tetrahydrofuran.

Step 2 represents a method of alkylation of the sulfur atom. Compound (J-b) may be obtained by reaction with methyl iodide or ethyl iodide in a solvent such as dimethylformamide in the presence of potassium carbonate.

Step 3 represents a method of substitution into an amino group. Compound (1c) may be obtained similarly to Step 2 of Scheme I.

Here, the synthesis of a lactam (I-a), which serves as the starting material for Production Processes I and J, may be carried out according to the process shown in Scheme I-1 or Scheme I-2 in the method described in Hansen, Donald W. D., Jr., et al. WO96/35677. Alternatively, it may be synthesized using the methods described in the following: pyroglutamic acid derivatives and pyroglutaminol derivatives are utilized in C. Najera et al., Tetrahedron: Asymmetry, 10, p. 2245 (1999); alkoxycarbonyl-substituted derivatives are utilized in T. S. Mansour et al., Bioorg. Med. Chem. Lett., 1, p 757 (1991), K. J. Lindstrom et al., Syn. Commun., 20, P 2335 (1990); aminosubstituted derivatives are utilized in S. Ranganathan et al., Tetrahedron Lett., 29, p 3111 (1988); and the Pauson-Khand reaction is utilized as a synthetic method for bicyclic compounds in M. E. Krafft et al., J. Org. Chem., 57, p 5277 (1992). Further alternatively, a variety of conversions may be carried out on these compounds according to standard techniques to produce compounds, which may also be utilized.

(Scheme I-1)

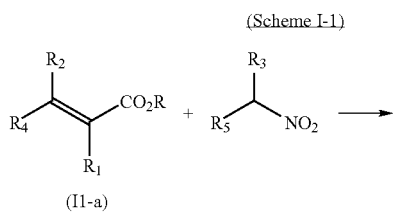

(I1-a)

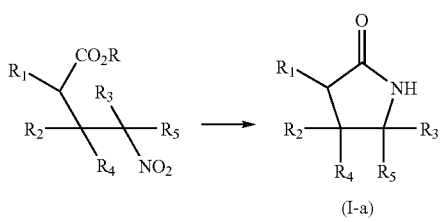

(I-a)

(Scheme I-2)

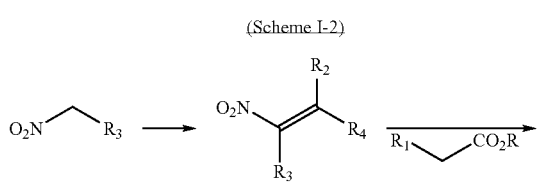

In the formulas, R1, R2, R3 and R4 have the same definitions as those for the compound represented by formula (I) in claim 1. Here, an unsaturated ester derivative represented by (I1-a) may be synthesized from the corresponding carbonyl compound using Wittig reaction, Honer-Emmons reaction or the method described in Y. Ueno et al., Tetrahedron Lett., 39, p 3753 (1978).

Further, the introduction of an alkyl group or an alkylidene group is possible from a lactam represented by (I-a) according to the methods shown in Schemes I-3 and I-4.

(Scheme I-3)

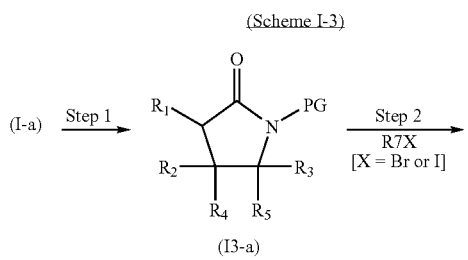

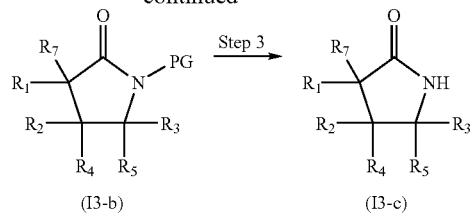

In the formulas, R1, R2, R3, R4 and R7 have the same definitions as those for the compound represented by formula (I) in claim 1.

Step 1 represents a method of protecting the nitrogen atom of a lactam with a Boc group. Compound (I3-a) may be obtained by reaction with di-tert-butyl dicarbonate in dichloromethane in the presence of triethylamine or dimethylaminopyridine.

Step 2 represents a method of alkylation. Compound (I3-b) may be obtained by reaction with an alkyl halide after an anion is generated using lithium hexamethyldisilazane in tetrahydrofuran.

Step 3 represents a method of removing the protecting group. Compound (I3-c) may be obtained by dissolving compound (I3-b) in trifluoroacetic acid diluted with dichloroethane to perform deprotection.

The obtained compound (I3-c) may be converted to the final target compound by the methods shown in Production Processes I and J.

(Scheme I-4)

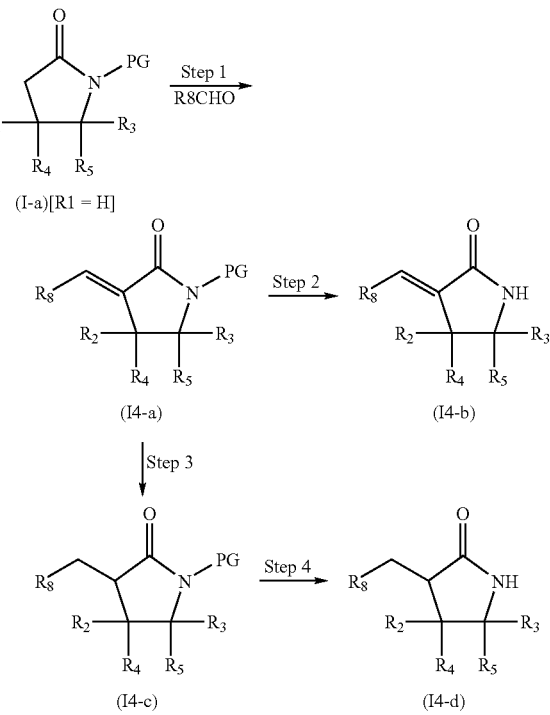

In the formulas, R1, R2, R3, R4 and R5 have the same definitions as those for the compound represented by formula (I) in claim 1. R8 presents optionally substituted alkyl, optionally substituted phenyl or an aromatic heterocyclic group.

Step 1 represents condensation with an aldehyde. After an anion is generated using lithium hexamethyldisilazane in tetrahydrofuran, the aldehyde is reacted with compound (I-a). When an aromatic aldehyde is employed, dehydration proceeds in after-treatment and a compound represented by (I4-a) may be obtained. On the other hand, when a saturated aldehyde is employed, an alcohol is isolated, and thereafter, the following two-step conversion is carried out: (1) a mesylate may be obtained by reaction with mesyl chloride in dichloromethane in the presence of triethylamine; (2) compound (I4-a) may be obtained by treatment with DBU in a solvent such as acetonitrile.

Steps 2 and 4 each represent a method of removing the protecting group and may be carried out in the same manner as Step 2 in Scheme I-3.

Step 3 represents a method of reducing a double bond. Compound (I4-c) may be obtained by conducting hydrogenation in an alcohol solvent in the presence of palladium-carbon.

The obtained compounds (I4-b) and (I4-d) may be converted to the final target compounds by the methods shown in Production Methods I and J. It is also possible to directly obtain an amidine by utilizing a nitrile group.

<Production Method K>

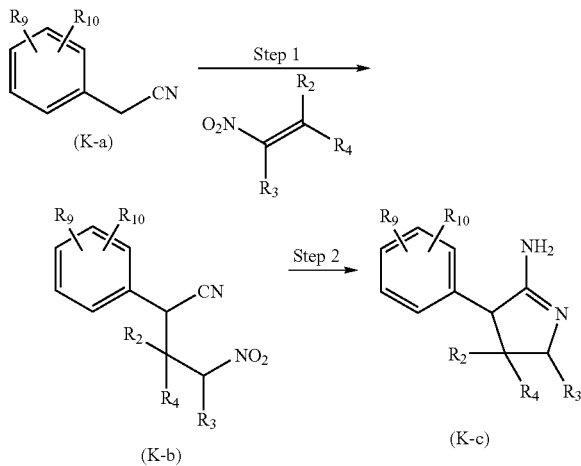

This scheme depicts an exemplary method for synthesis of a cyclic amidine (K-c). In the formulas, R2, R3 and R4 have the same definitions as those for the compound represented by formula (I) in claim 1. R9 represents hydrogen, cyano, halogeno, hydroxyl, allyloxy, alkoxycarbonyl, optionally substituted alkoxy, optionally substituted alkyl, optionally substituted amino, or optionally substituted aminosulfonyl. R10 represents hydrogen, halogeno, optionally substituted alkyl or optionally substituted alkoxy.

The reactions used here may be carried out by employing the techniques similar to those shown in Scheme I-2.

The following are exemplary synthetic methods for the starting materials used in the production processes described above.

<Production Process AP>

This is an exemplary process for synthesis of intermediates (AP1-c), (AP1-d), (AP1-e), (AP2-b), (AP2-c) and (AP2-d) as common starting materials for synthesis of aminophenol derivatives.

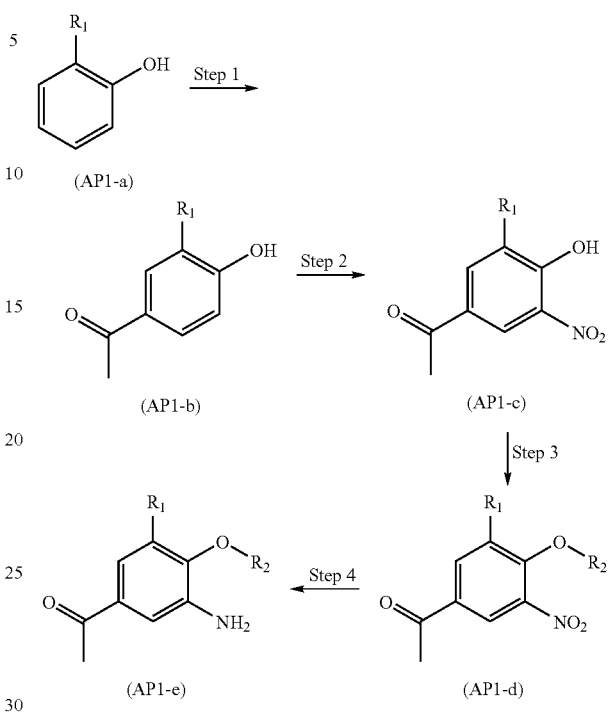

This scheme depicts an exemplary method for synthesis of compound (AP1-e) from compound (AP1-a). In the formulas, R1 represents hydrogen, optionally substituted alkyl, optionally substituted cycloalkyl or optionally substituted alkoxy. R2 has the same definition as R6 and R7 in Production Process MO.

Step 1 represents a step of Friedel-Crafts acylation. Compound (AP1-b) may be obtained by reacting compound (AP1-a) with acetyl chloride in a solvent such as dichloromethane or toluene, in the presence of a Lewis acid such as aluminum chloride, zinc chloride or tin (II) chloride, at −70° C. to room temperature.

Step 2 represents a step of nitration. Compound (AP1-c) may be obtained by reaction with fuming nitric acid or concentrated nitric acid in a solvent such as toluene, hexane, ether or acetic anhydride. Alternatively, the reaction may be conducted by generating nitric acid from sodium nitrate and hydrochloric acid.

Step 3 represents a step of introducing a substituent R2 having any of various structures at the hydroxyl group of compound (AP1-c). Compound (AP1-d) may be obtained by reaction with a halide, mesylate or tosylate in a solvent such as dimethylformamide, acetonitrile, tetrahydrofuran, dichloromethane or acetone, in the presence of a base such as potassium carbonate, cesium carbonate, sodium hydrogencarbonate, trialkylamine, a pyridine derivative or sodium hydride. In the formulas, R2 has the same definition as R6 in Step 1 of Production Process MO.

Step 4 represents a step of reduction of the nitro group. Compound (AP1-e) may be obtained by reaction in a solvent such as tetrahydrofuran, ethyl acetate, methanol or ethanol under a hydrogen atmosphere, in the presence of a catalyst such as palladium-carbon. Alternatively, compound (AP1-e) may be obtained by conducting the reaction in a solvent such as hydrated methanol or hydrated ethanol in the presence of ammonium chloride, with addition of iron at the reflux temperature of the solvent.

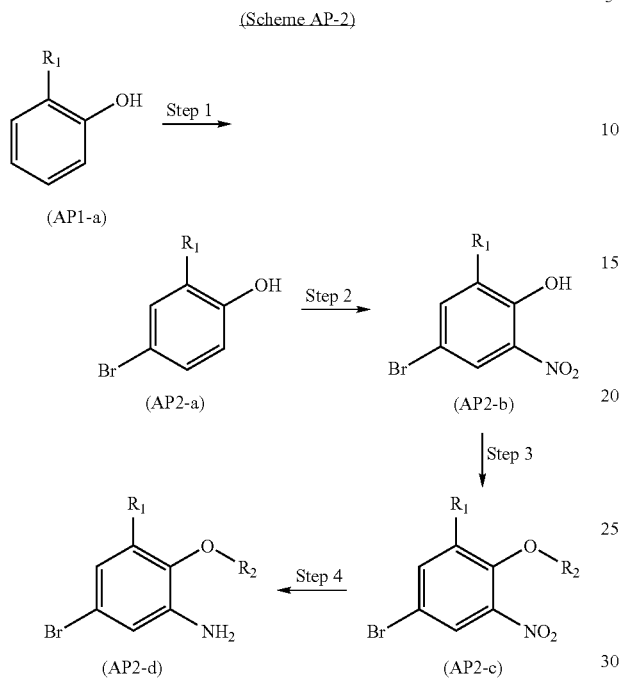

(Scheme AP-2)

This scheme depicts an exemplary method for synthesis of (AP2-d) from (AP1-a). In the formulas, R1 represents hydrogen, optionally substituted alkyl, optionally substituted cycloalkyl or optionally substituted alkoxy.

Step 1 represents a step of bromination of the para-position relative to the phenolic hydroxyl group. Reaction with bromine is conducted in a solvent such as methanol, ethanol or chloroform. Alternatively, compound (AP2-a) may be obtained by reaction with N-bromosuccinimide in a solvent such as acetonitrile or dimethylformamide.

Step 2 represents a step of nitration. Compound (AP2-b) may be obtained by reaction with fuming nitric acid or concentrated nitric acid in a solvent such as toluene, hexane, ether or acetic anhydride. Alternatively, the reaction may be conducted by generating nitric acid from sodium nitrate and hydrochloric acid.

Step 3 represents a step of introducing a substituent R2 with any of various structures at the hydroxyl group of compound (AP2-b). Compound (AP2-c) may be obtained by reaction with a halide, mesylate or tosylate in a solvent such as dimethylformamide, acetonitrile, tetrahydrofuran, dichloromethane or acetone, in the presence of a base such as potassium carbonate, cesium carbonate, sodium hydrogencarbonate, trialkylamine, a pyridine derivative or sodium hydride. In the formulas, R2 has the same definition as R6 in Step 1 of Production Process MO.

Step 4 represents a step of reduction of the nitro group. Compound (AP2-d) may also be obtained by conducting the reaction in a solvent such as hydrated methanol or hydrated ethanol in the presence of ammonium chloride, with addition of iron at the reflux temperature of the solvent.

The following Production Processes PP to BOL are exemplary production processes for aminophenol derivatives using compounds synthesized by Production Process AP as the starting materials.

<Production Process PP>

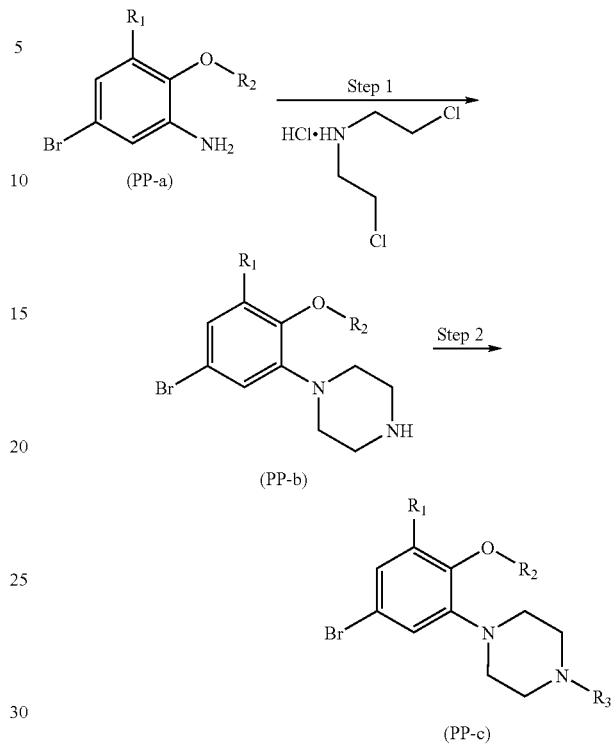

Production Process PP is an exemplary synthetic method for a piperazine derivative.

Step 1 represents a step of treating the amino group of compound (PP-a) with bis(chloroethyl)amine hydrochloride to form a piperazine ring. Preferably, compound (PP-a) is reacted with bis(chloroethyl)amine hydrochloride in 1,2-dichlorobenzene while heating to reflux, and the reaction is conducted while removing the generated hydrogen chloride gas to yield compound (PP-b).

In the formulas, R1 represents hydrogen, optionally substituted alkyl, optionally substituted cycloalkyl, optionally substituted alkoxy, optionally substituted alkylamino, etc. R2 represents hydrogen, optionally substituted alkyl, etc.

The formulas in Production Process PP show only a piperazine group, but any 5- to 8-membered ring containing plural nitrogen atoms may be formed, without any restriction to piperazine.

Step 2 represents a step of introducing substituent R3 at the secondary amine position of the piperazine of compound (PP-b). Compound (PP-b) may be reacted with reagent R3-X1 (X1=halogen) in an appropriate solvent such as dichloromethane or tetrahydrofuran, in the presence of an inorganic base such as potassium carbonate or sodium hydrogencarbonate or in the presence of an organic base such as trialkylamine or a pyridine derivative to yield R3 introduced compound (PP-c). R3 of reagent R3-X1 represents optionally substituted alkyl, optionally substituted alkyl having cyano on the end or a branch, alkyl having protected or substituted carboxylic acid on the end or a branch, alkyl having protected or substituted hydroxyl on the end or a branch, alkyl having protected or substituted amino on the end or a branch, optionally substituted sulfonyl, optionally substituted acyl, or optionally substituted carbamoyl. The reagent used to introduce substituent R3 into compound (PP-b) may be, instead of R3-X1 mentioned above, di-t-butyl dicarbonate or optionally substituted isocyanate. Compound (PP-b) may be subjected to reductive amination using an optionally substituted aldehyde or ketone and sodium triacetoxyborohydride or sodium cyanoborohydride for introduction of substituent R3.

Compound (PP-c) obtained by this Production Process may be converted to the final target compound by Production Process A.

<Production Process MO>

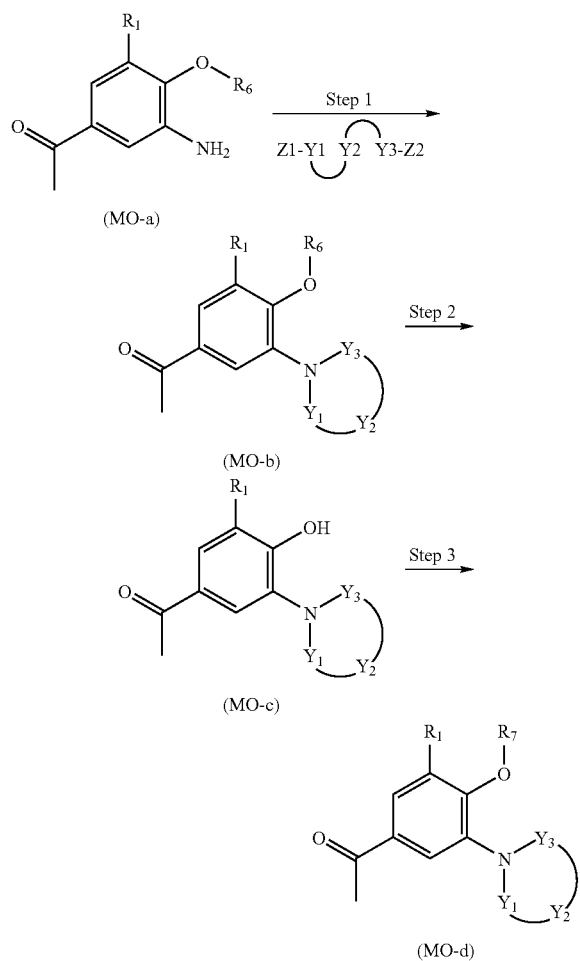

Production Process MO is an exemplary production process for a heterocyclic amino derivative.

Step 1 represents a step of treating the amino group of compound (MO-a) with a reagent represented by Z1-Y1-Y2-Y3-Z2 to form a nitrogen-containing ring.

Compound (MO-b) may be obtained by reacting compound (MO-a) with reagent Z1-Y1-Y2-Y3-Z2 in an appropriate solvent such as dimethylformamide, tetrahydrofuran or dichloromethane, in the presence of an inorganic base such as potassium carbonate, sodium hydrogencarbonate or cesium carbonate or in the presence of an organic base such as trialkylamine or a pyridine derivative.

Z1 and Z2 in the reagent Z1-Y1-Y2-Y3-Z2 represent leaving groups such as halogen or sulfonate. Y1 and Y3 represent methylene optionally substituted with alkyl, alkoxy or the like, carbonyl, carboxyl, sulfonyl or amide. Elements to form the main chain at the portion represented by —Y2- include carbon, oxygen, nitrogen and sulfur, and there are no particular restrictions on the length of the chain. Where possible, the element forming the —Y2- main chain may also have as a substituent optionally substituted alkyl, optionally substituted alkoxy, optionally substituted alkoxyalkyl, optionally substituted hydroxyalkyl, hydroxy, carbonyl, optionally protected or substituted carboxyl, optionally protected or substituted carboxyalkyl, optionally protected or substituted amine, optionally protected or substituted aminoalkyl, etc. An oxo group may also be present on the —Y2- main chain to form carbonyl, sulfonyl or sulfinyl together with carbon or sulfur on the main chain.

In the formulas, R1 has the same definition as R1 in Step 1 of Production Process PP. R6 represents optionally substituted alkyl, a protecting group for hydroxyl, such as methoxymethyl, tetrahydropyranyl or trialkylsilyl, or alternatively alkyl having cyano at the end or a branch, alkyl having protected or substituted carboxylic acid on the end or a branch, arylalkyl having protected or substituted carboxylic acid on the end or a branch, alkyl having protected or substituted hydroxyl on the end or a branch, arylalkyl having protected or substituted hydroxyl on the end or a branch, alkyl having protected or substituted amino on the end or a branch, arylalkyl having protected or substituted amino on the end or a branch, optionally substituted sulfonyl, optionally substituted acyl, optionally substituted carbamoyl, etc.

Step 2 represents a step of deprotection when R6 of compound (MO-b) is a protecting group for the phenolic hydroxyl group. For example, compound (MO-c) wherein R6 is methoxymethyl may be obtained by treating compound (MO-b) with an acidic mixed solvent such as 5 N hydrochloric acid/acetone or 10% aqueous perchloric acid/tetrahydrofuran.

Step 3 represents a step of introducing a new substituent R7 at the phenolic hydroxyl group of compound (MO-c).

R7 has the same definition as R6 in Step 1 of Production Process MO.

Compound (MO-d) wherein X2 of reagent R7-X2 described below is a leaving group such as halogen or sulfonate may be synthesized in the following manner. Compound (MO-d) may be obtained by reacting compound (MO-c) with reagent R7-X2 in an appropriate solvent such as dimethylformamide, acetonitrile, diethyl ether, tetrahydrofuran or dichloromethane, in the presence of an inorganic base such as potassium carbonate, sodium hydrogencarbonate or cesium carbonate or in the presence of an organic base such as trialkylamine or a pyridine derivative, or in the presence of sodium hydride.

Compound (MO-d) wherein R7 is methyl may be obtained at a high yield by reacting compound (MO-c) with diazomethane in diethyl ether or with trimethylsilyldiazomethane in acetonitrile-diisopropylethylamine-methanol.

Compound (MO-d) wherein X2 in reagent R7-X2 is hydroxyl may be obtained by reacting compound (MO-c) with reagent R7-X2 by the publicly known Mitsunobu reaction in an appropriate solvent such as tetrahydrofuran or toluene.

In Production Process MO, R6 and R7 may sometimes undergo conversion to a structure which is not defined herein by a method easily predictable by a person skilled in the art at an appropriate stage after introduction. Likewise, the —N—Y1-Y2-Y3(-N) portion obtained by cyclization in Step 1 may sometimes also undergo conversion to a structure which is not defined herein. (Conversion of the —N—Y1-Y2-Y3(-N) portion is described in some of the following Production Process examples).

Compounds (MO-b), (MO-c) and (MO-d) obtained in this Production Process may be converted to the final target compounds by Production Process A.

<Production Process PR>

Production Process PR is an exemplary synthetic method for pyrrolidine derivatives.

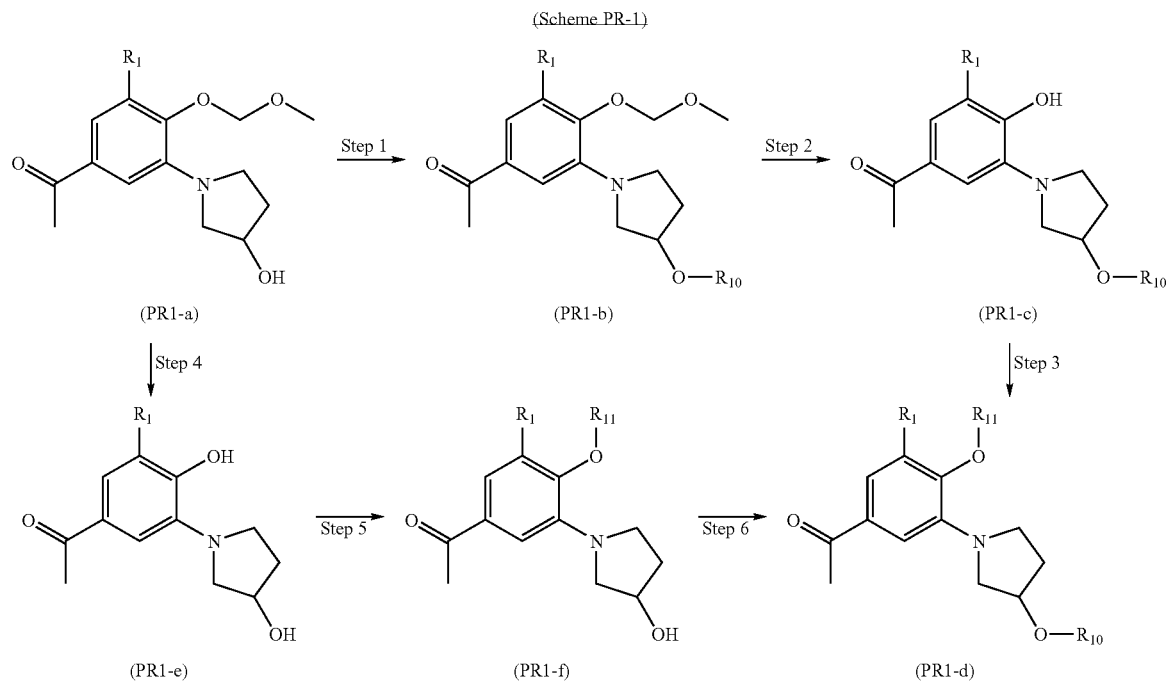

(Scheme PR-1)

Scheme PR-1 depicts an exemplary production scheme whereby the —N—Y1-Y2-Y3(-N) portion obtained by cyclization in Step 1 of Production Process MO may undergo additional structural conversion. In the formulas, R1 has the same definition as R1 in Step 1 of Production Process PP. R10 and R11 have the same definitions as R6 and R7 in Production Process MO. Although only methoxymethyl is mentioned as a protecting group for the phenolic hydroxyl group of compounds (PR1-a) and (PR1-b), there is no limitation to methoxymethyl.

Step 1 represents a step of introducing a substituent R10 at the hydroxyl group of compound (PR1-a). The reaction is conducted using reagent R10-X3 in an appropriate alkaline hydrated organic solvent, in the presence of a phase transfer catalyst. Preferably, compound (PR1-b) is obtained by reaction of reagent R10-X3 with compound (PR1-a) in a mixture of 50% aqueous sodium hydroxide and toluene in the presence of tetrabutylammonium bromide. Here, X3 is a leaving group such as halogen or sulfonate.

Step 2 represents a step of treating compound (PR1-b) in the same manner as Step 2 of Production Process MO to yield compound (PR1-c).

Step 3 represents a step of introducing a new substituent R11 at the phenolic hydroxyl group of compound (PR1-c). Compound (PR1-c) may be treated in the same manner as for introduction of R7 in Step 3 of Production Process MO to yield R11 introduced compound (PR1-d).

Step 4 represents a step of treating compound (PR1-a) in the same manner as Step 2 of Production Process MO to yield compound (PR1-e).

Step 5 represents a step of selectively introducing substituent R11 only at the phenolic hydroxyl group of compound (PR1-e). Utilizing the difference in reactivity between the two hydroxyl groups of compound (PR1-e), treatment may be carried out in the same manner as for introduction of R7 in Step 3 of Production Process MO to yield R11 introduced compound (PR1-f).

Step 6 represents a step of treating compound (PR1-f) in the same manner as Step 1 of this Scheme PR-1 to yield compound (PR1-d).

Compounds (PR1-b) and (PR1-d) obtained in this Scheme PR-1 may be converted to the final target compounds by Production Process A.

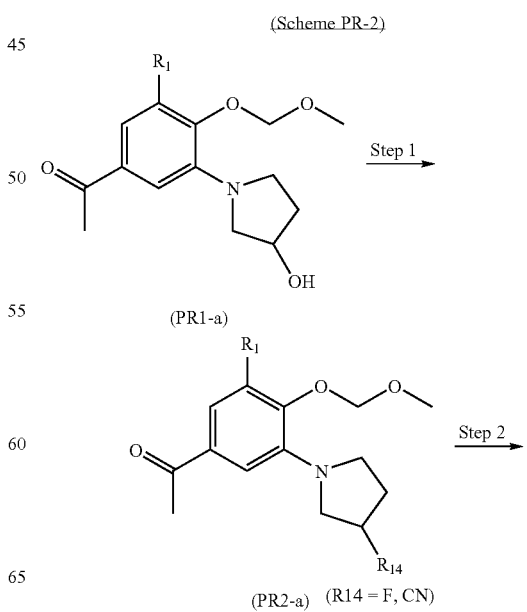

(Scheme PR-2)

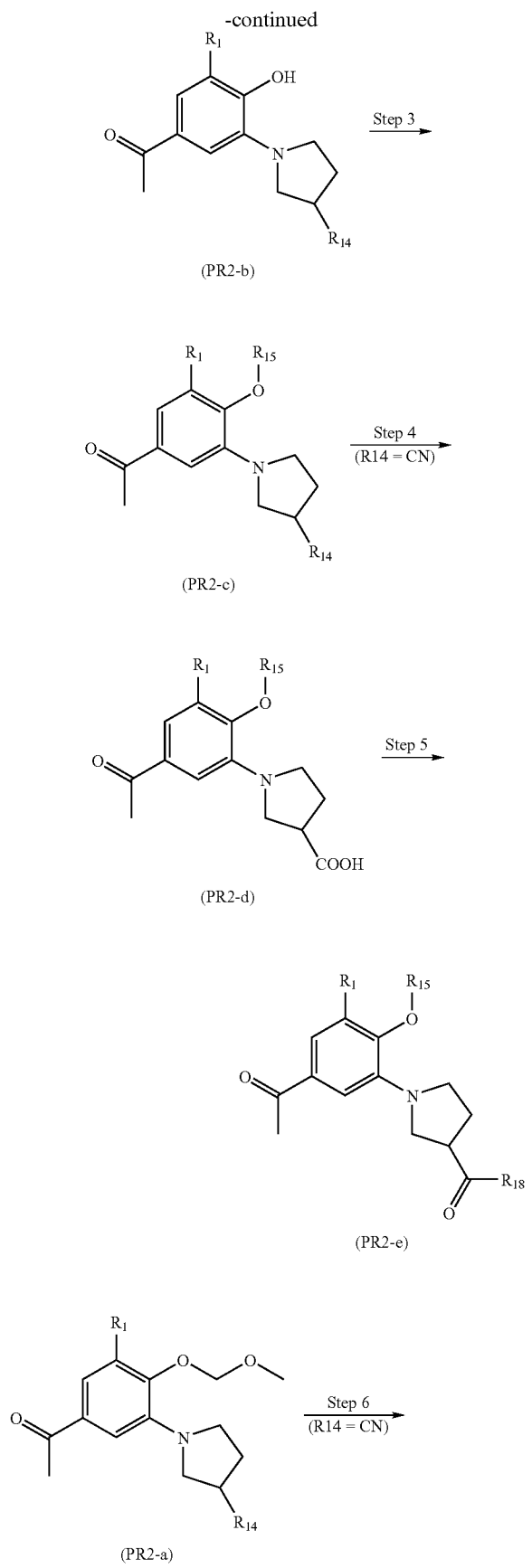

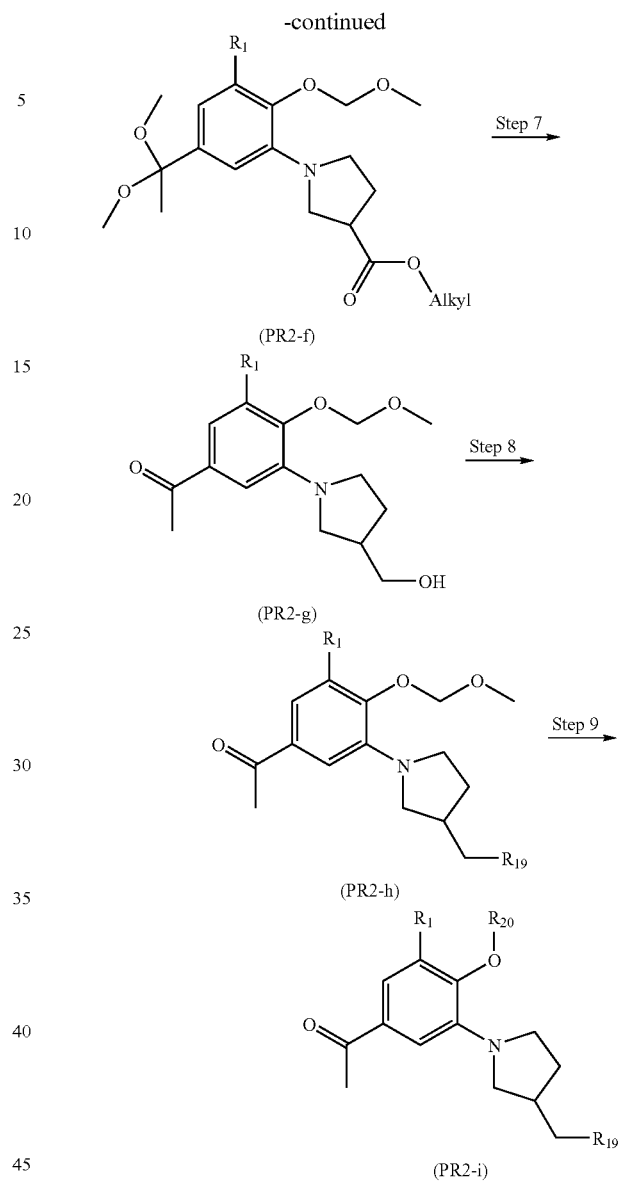

Scheme PR-2 is another exemplary production scheme whereby the —N—Y1-Y2-Y3(-N) portion obtained by cyclization in Step 1 of Production Process MO may undergo additional structural conversion. In the formulas, R1 has the same definition as R1 in Step 1 of Production Process PP. R15 and R20 have the same definitions as R6 and R7 in Production Process MO.

Step 1 represents a step of replacing the hydroxyl group of compound (PR1-a) with a substituent R14 (F or CN). When R14 is fluoro, compound (PR1-a) may be treated with diethylaminosulfur trifluoride (DAST) in dichloromethane to yield compound (PR2-a: R14=F). When R14 is cyano, the hydroxyl group of compound (PR1-a) may first be converted to a leaving group with an acyl chloride reagent such as methanesulfonyl chloride in an appropriate solvent such as dichloromethane, in the presence of a base such as triethylamine. A hydrogen cyanide salt may then be reacted with this intermediate to introduce a cyano group. Preferably, the intermediate is added to dimethylformamide and reacted with sodium cyanide in the presence of tetrabutylammonium iodide to yield compound (PR2-a: R14=CN).

Step 2 represents a step of treating compound (PR2-a) (R14=F or CN) in the same manner as Step 2 of Production Process MO to yield compound (PR2-b) (R14=F or CN).

Step 3 represents a step of introducing substituent R15 at the phenolic hydroxyl group of compound (PR2-b) (R14=F or CN). Compound (PR2-b) may be treated in the same manner as for introduction of R7 in Step 3 of Production Process MO to yield R15 introduced compound (PR2-c) (R14=F or CN).

Step 4 represents a step of converting compound (PR2-c) wherein R14=CN to compound (PR2-d) wherein cyano may be converted to carboxyl by alkali hydrolysis. Preferably, compound (PR2-c) wherein R14=CN may be reacted by heating to reflux in a mixed solvent of aqueous sodium hydroxide and ethanol to yield compound (PR2-d).

Step 5 represents a step of esterifying or amidating the carboxylic acid group of compound (PR2-d) for introduction of a substituent R18 by common methods. The carboxylic acid group of compound (PR2-d) may be converted to an active species by a common method such as an acid mixing method using a chloroformic acid ester or an acid chloride method using oxalyl chloride, and then reacted with an alcohol or amine for conversion to (PR2-e). Alternatively, (PR2-d) may be esterified by reaction with the corresponding alkyl halide reagent in the presence of an appropriate base or by reaction with di-tert-butyl dicarbonate in tert-butyl alcohol in the presence of dimethylaminopyridine. Compound (PR2-d) may also be subjected to dehydration reaction using an alcohol or amine and a peptide-forming condensing agent, for conversion to compound (PR2-e). The synthesis may also be carried out by other suitable known reactions. R18 represents amino or alkoxy.

Step 6 represents a step of subjecting compound (PR2-a: R14=CN) to alkali hydrolysis in the same manner as Step 4 followed by treatment in the same manner as the esterification in Step 5, and then ketal protection of the carbonyl group of the acetophenone. After converting compound (PR2-a: R14=CN) to a carboxylic acid ester, it may be reacted with a ketalizing reagent such as methyl orthoformate under acidic conditions to yield compound (PR2-f). Preferably, the methyl orthoformate is reacted with the carbonyl group in methanol in the presence of an acid catalyst such as camphorsulfonic acid or p-toluenesulfonic acid and Molecular Sieve 3A, to yield compound (PR2-f).

Step 7 represents a step of reducing the ester group of compound (PR2-f) for conversion to a hydroxymethyl group, and then selectively deprotecting only the ketal protection of the carbonyl group of the acetophenone. First, compound (PR2-f) is reacted with an ester-reducing reagent such as lithium aluminum hydride in an appropriate solvent such as tetrahydrofuran or diethyl ether, for conversion to a hydroxymethyl group. Next, under mildly acidic conditions, and preferably under conditions with an acetic acid-tetrahydrofuran-water (4:1:1) mixed acid solvent, the ketal protecting group for the carbonyl group is selectively deprotected while leaving the methoxymethyl group for the phenolic hydroxyl, to yield compound (PR2-g).

Step 8 represents a step of converting the hydroxyl group of compound (PR2-g) to substituent R19 (cyano or various alkoxy).

When R19 is cyano, treatment may be carried out in the same manner as for conversion in Step 1 when R14 is cyano, to yield compound (PR2-h) wherein hydroxymethyl of compound (PR2-g) may be converted to cyanomethyl, in which case R19 represents cyano. When R19 is alkoxy, compound (PR2-g) is treated in the same manner as Step 1 of Scheme PR-1 to yield compound (PR2-h) for conversion to alkoxy, in which case R19 has the same definition as OR10 in Scheme PR-1.

Step 9 represents a step of deprotecting the methoxymethyl group serving as the protecting group for the phenolic hydroxyl group of compound (PR2-h), and then introducing a substituent R20. First, compound (PR2-h) is treated in the same manner as Step 2 of Production Process MO to remove the methoxymethyl group. It is then treated in the same manner as for introduction of R7 in Step 3 of Production Process MO to yield compound R20 introduced (PR2-i).

Compounds (PR2-c), (PR2-e) and (PR2-i) obtained in this Scheme PR-2 may be converted to the final target compounds by Production Process A.

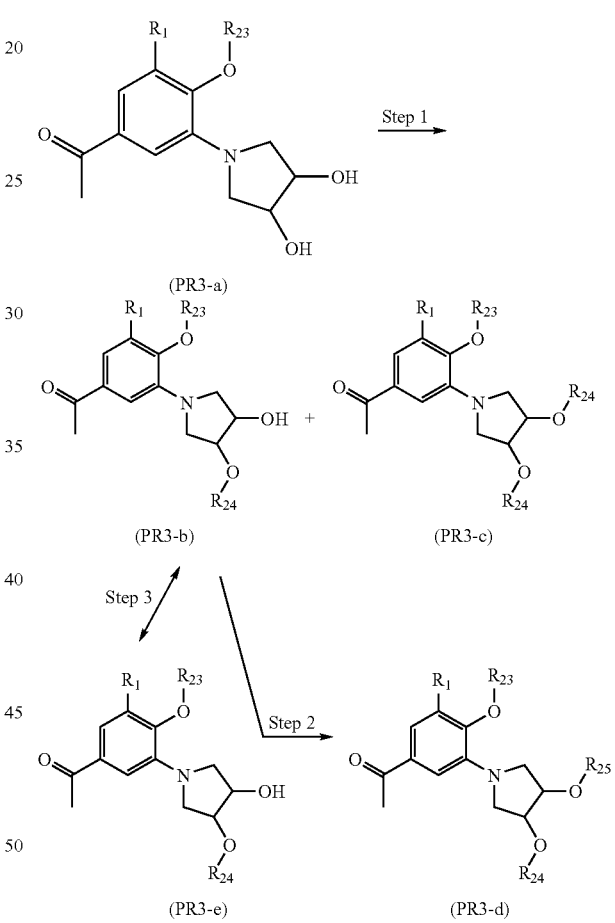

Scheme PR-3 is an exemplary production scheme whereby the —N—Y1-Y2-Y3(-N) portion obtained by cyclization in Step 1 of Production Process MO may undergo additional structural conversion. In the formulas, R1 has the same definition as R1 in Step 1 of Production Process PP. R23, R24 and R25 have the same definitions as R6 and R7 in Production Process MO.

Step 1 represents a step of treating compound (PR3-a) in the same manner as Step 1 of Scheme PR-1 to yield compound (PR3-b) having one substituent R24 introduced therein and compound (PR3-c) having two substituents R24 introduced therein. Alternatively, when R24 is methoxymethyl or the like, an excess of methoxymethyl chloride may be reacted with compound (PR3-a) in the presence of diisopropylethylamine to yield compounds (PR3-b) and (PR3-c). Compounds (PR3-b) and (PR3-c) may be separated by silica gel column chromatography.

Step 2 represents a step of treating compound (PR3-b) in the same manner as Step 1 to yield compound (PR3-d) having a newly introduced substituent R25.

Step 3 represents a step of stereoinversion of the hydroxyl group of compound (PR3-b) to yield compound (PR3-e). Compound (PR3-b) is reacted with m-nitrobenzenesulfonyl chloride in dichloromethane in the presence of triethylamine and dimethylaminopyridine. It is then treated with cesium acetate while heating in dimethylsulfoxide to yield a hydroxyl-inverted acetate. This is treated with potassium carbonate in methanol to yield hydroxyl-inverted compound (PR3-e).

Compounds (PR3-b), (PR3-c) and (PR3-d) obtained in Scheme PR-3 may be converted to the final target compounds by Production Process A. Compound (PR3-e) may also be treated in the same manner as Step 2 of this scheme and then converted to the final target compound by Production Process A.

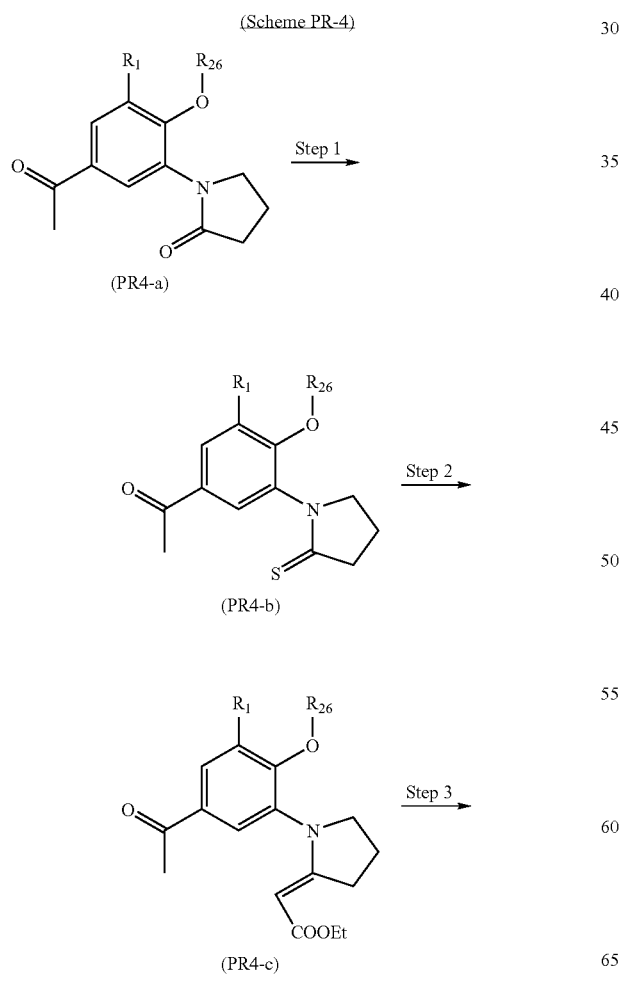

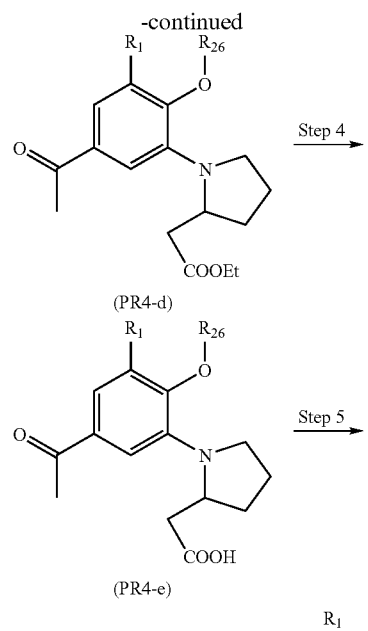

Scheme PR-4 is an exemplary production scheme whereby the —N—Y1-Y2-Y3(-N) portion obtained by cyclization in Step 1 of Production Process MO may undergo additional structural conversion. In the formulas, R1 has the same definition as R1 in Step 1 of Production Process PP. R26 has the same definition as R6 and R7 in Production Process MO.

Step 1 represents a step of treating compound (PR4-a) with Lawesson's reagent while heating in 1,4-dioxane to yield a thioamide (PR4-b).

Step 2 represents a step of treating compound (PR4-b) with ethyl O-trifluoromethanesulfonylhydroxyacetate, triphenylphosphine and triethylamine to yield compound (PR4-c).

Step 3 represents a step of reacting compound (PR4-c) with sodium triacetoxyborohydride in 1,2-dichloroethane in the presence of acetic acid for reduction of the enamine to yield compound (PR4-d).

Step 4 represents a step of converting compound (PR4-d) to a carboxylic acid derivative (PR4-e) under appropriate conditions such that substituent R26 is not affected. Generally, it is treated with aqueous sodium hydroxide or aqueous lithium hydroxide in an alcohol or an alcohol-tetrahydrofuran mixed solvent for alkali hydrolysis to yield compound (PR4-e).

Step 5 represents a step of treating compound (PR4-e) with di-tert-butyl dicarbonate in tert-butanol in the presence of dimethylaminopyridine to yield the tert-butylesterified compound (PR4-f).

Compounds (PR4-c), (PR4-d) and (PR4-f) obtained in this Scheme (PR-4) may be converted to the final target compounds by Production Process A.

(Scheme PR-5)

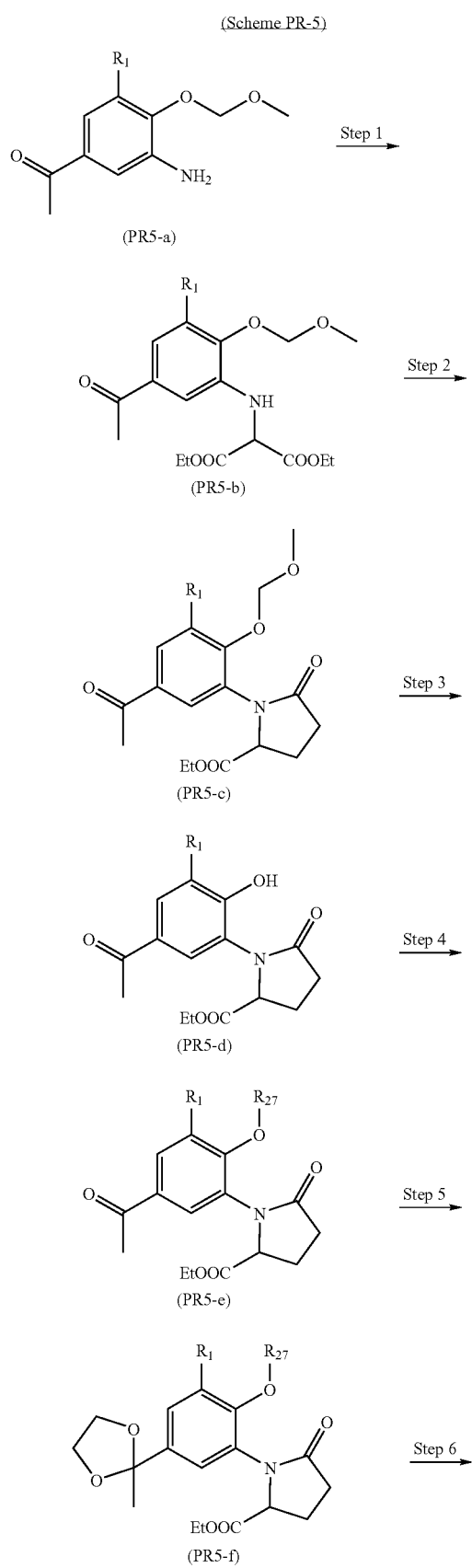

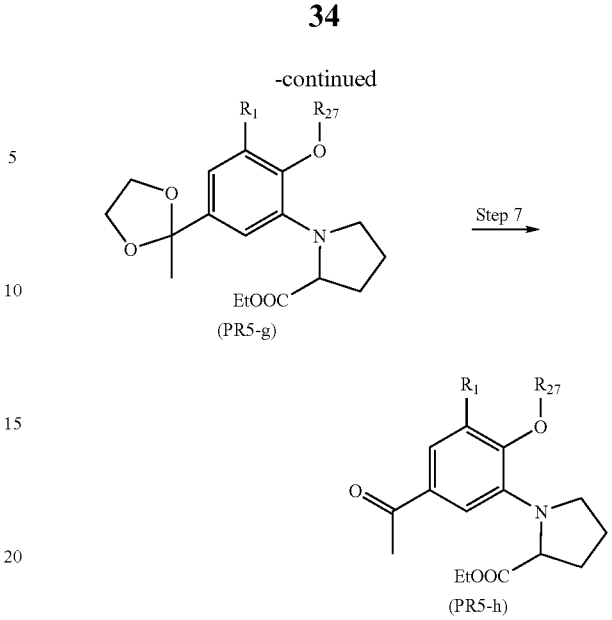

Scheme PR-5 is an exemplary production scheme whereby the —N—Y1-Y2-Y3(-N) portion obtained by cyclization in Step 1 of Production Process MO may undergo additional structural conversion. In the formulas, R1 has the same definition as R1 in Step 1 of Production Process PP. R27 has the same definition as R6 and R7 in Production Process MO.

Step 1 represents a step of treating compound (PR5-a) with a catalytic amount of rhodium (II) acetate dimer and the known reagent diethyl diazomalonate while heating in toluene, to yield compound (PR5-b).

Step 2 represents a step of treating compound (PR5-b) with equivalents of sodium ethoxide and ethyl acrylate while heating in ethanol to yield the cyclized compound (PR5-c).

Step 3 represents a step of treating compound (PR5-c) with 5 N hydrochloric acid while heating in ethanol to yield compound (PR5-d) having the methoxymethyl protecting group removed.

Step 4 represents a step of converting compound (PR5-d) to compound (PR5-e) having a newly introduced substituent R27. Compound (PR5-e) may be obtained by treatment in the same manner as for introduction of R7 in Step 3 of Production Process MO.

Step 5 represents a step of treating compound (PR5-e) with 1,2-bis(trimethylsiloxy)ethane and triethylsilyltriflate in dichloromethane to yield compound (PR5-f), wherein the acetyl carbonyl of compound (PR5-e) is ketal-protected.

Step 6 represents a step of reducing the lactam carbonyl of compound (PR5-f) for conversion to methylene. Compound (PR5-f) may be reacted with carbonylhydridotris(triphenylphosphine)rhodium(I) and diphenylsilane in an appropriate solvent such as tetrahydrofuran to yield compound (PR5-g).

Step 7 represents a step of reacting compound (PR5-g) in 5% hydrochloric acid-tetrahydrofuran to yield the ketal-deprotected compound (PR5-h).

Compounds (PR5-d), (PR5-e) and (PR5-h) obtained in this Scheme PR-5 may be converted to the final target compounds by Production Process A.

<Production Process PS>

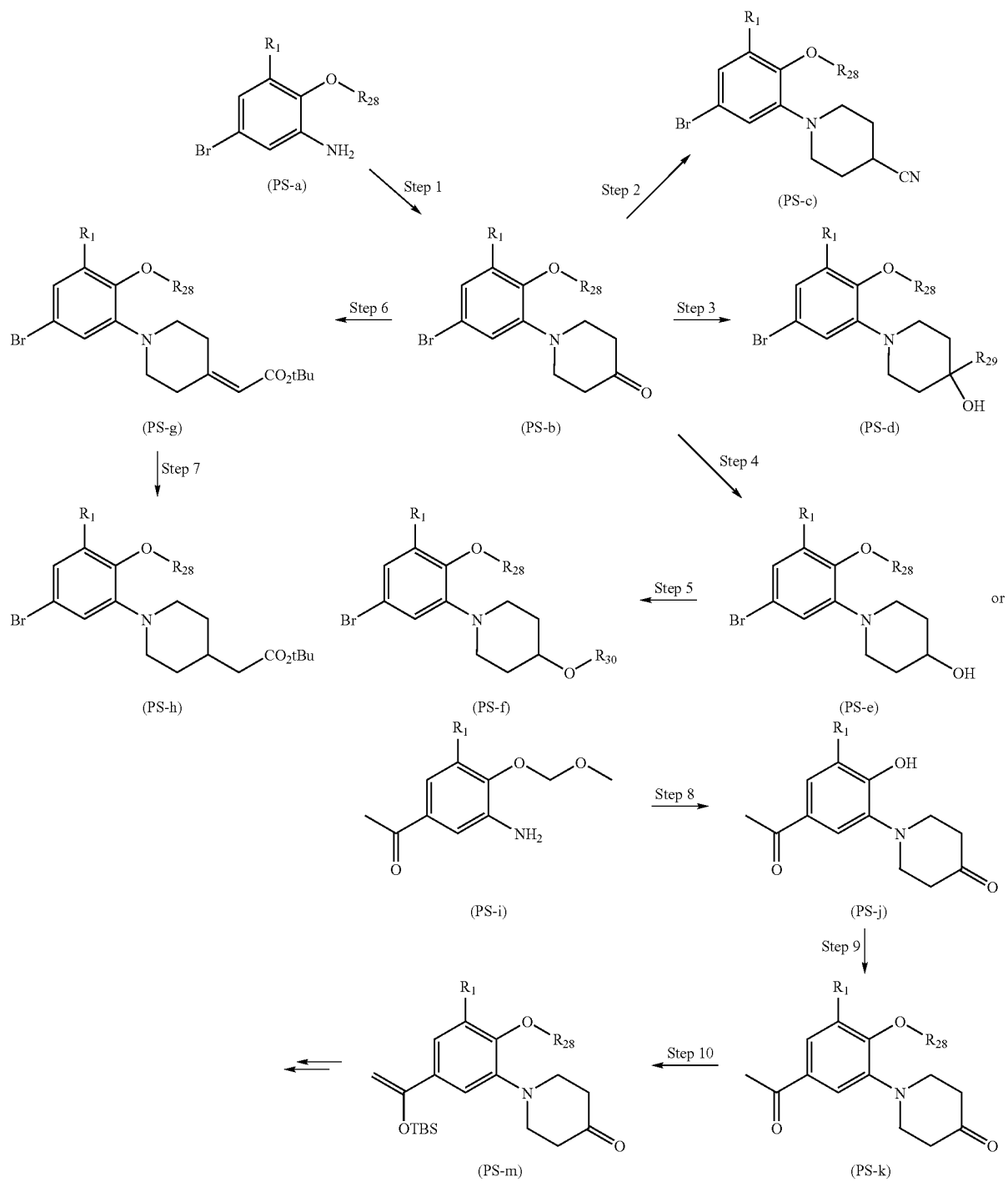

This Production Process PS is an exemplary synthetic method for a piperidine derivative. In the formulas, R1 has the same definition as R1 in Step 1 of Production Process PP. R28 and R30 have the same definitions as R6 and R7 in Production Process MO.

Step 1 represents a step of reacting compound (PS-a) with formaldehyde to produce an imine, and then subjecting it to hetero Diels-Alder reaction with a diene having an enol ether structure to form an oxopiperidine ring. Preferably, Compound (PS-a) is reacted with 37% formalin in dichloromethane in the presence of magnesium sulfate to produce an imine, and the reaction mixture is filtered through celite. After adding 2-trimethylsilyloxy-1,3-butadiene and toluene to the filtrate and cooling to −70° C., a 1 M hexane solution of diethylaluminum chloride is added dropwise and the temperature is raised. After completion of the reaction, the mixture is replaced with a tetrahydrofuran solution and is treated with 1 N hydrochloric acid to yield compound (PS-b) having the silylenol ether converted to a ketone.

Step 2 represents a step of treating compound (PS-b) with p-toluenesulfonylmethyl isocyanide (TosMIC) in dimethoxyethane-tert-butanol in the presence of potassium tert-butoxide, to yield compound (PS-c) having oxo converted to cyano.

Step 3 represents a step of reacting the carbonyl group of compound (PS-b) with any of various organometallic reagents to yield a tert-alcohol (PS-d) having an added substituent R29. For example, compound (PS-b) may be reacted with methylmagnesium bromide in diethyl ether to yield compound (PS-d) having an added methyl group. R29 represents alkyl, alkenyl or alkynyl.

Step 4 represents a step of treating compound (PS-b) with a reducing agent for conversion to an alcohol compound (PS-e). Various reducing agents may be used, and treatment with sodium borohydride in a methanol-dichloromethane mixed solvent is preferred to yield compound (PS-e).

Step 5 represents a step of treating compound (PS-e) in the same manner as Step 1 of Scheme PR-1 of Production Process PR to yield compound (PS-f) having a newly introduced substituent R30 at the hydroxyl group. Substituent R30 has the same definition as R6 and R7 in Production Process MO.

Step 6 represents a step of Horner-Emmons reaction at the carbonyl group of compound (PS-b) to yield the carbon-carbon bond formed unsaturated ester (PS-g). After treating a tert-butyl diethylphosphonoacetate with sodium hydride in 1,2-dimethoxyethane, compound (PS-b) dissolved in 1,2-dimethoxyethane is added to yield Compound (PS-g).

Step 7 represents a step of 1,4-reduction of the unsaturated ester. Compound (PS-g) may be treated with sodium borohydride in a dichloromethane-methanol mixed solvent in the presence of a catalytic amount of nickel (II) chloride-6 hydrate, or reacted with magnesium in methanol for selective 1,4-reduction of the unsaturated ester to yield compound (PS-h).

A piperidine derivative may also be synthesized by the following Steps 8 to 10.

Step 8 represents a step of treating compound (PS-i) in the same manner as Step 1 to yield compound (PS-j), with simultaneous formation of an oxopiperidine ring and deprotection of the methoxymethyl group serving as the phenolic hydroxyl group-protecting group.

Step 9 represents a step of treating compound (PS-j) in the same manner as for introduction of R7 in Step 3 of Production Process MO, to yield compound (PS-k) substituted with substituent R28.

Step 10 represents a step of selectively protecting the carbonyl group of the acetophenone of compound (PS-k). After adding compound (PS-k) to tetrahydrofuran, adding triethylamine and cooling to −70° C., the mixture is treated with tert-butyldimethylsilyl trifluoromethanesulfonate. The state of the reaction is periodically examined by thin-layer column chromatography, and the temperature is gradually raised if necessary. Water may be added at low temperature to stop the reaction to yield compound (PS-m).

Finally, compound (PS-m) may be treated in the same manner as in Steps 2, 3 and 4. Alternatively, it may be converted directly to an acyl bromide according to Production Process A for conversion to the final target compound.

Compounds (PS-b), (PS-c), (PS-d), (PS-e), (PS-f), (PS-g), (PS-h), (PS-j) and (PS-k) obtained in this Production Process may be converted to the final target compounds by Production Process A.

<Production Process AN>

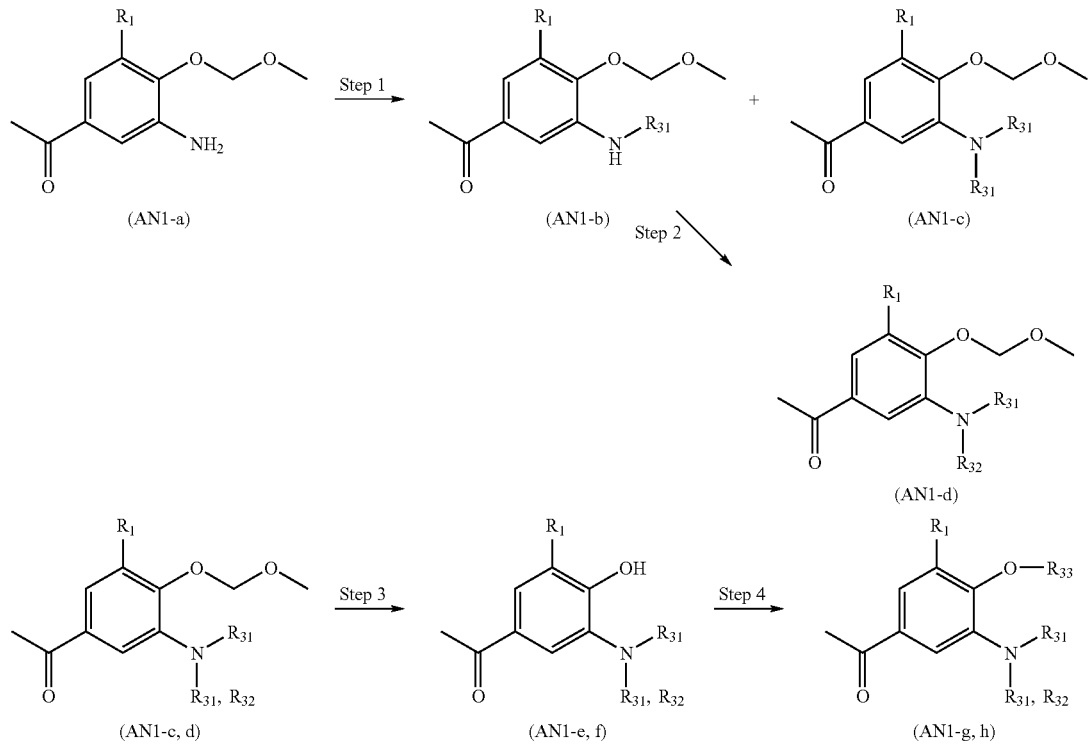

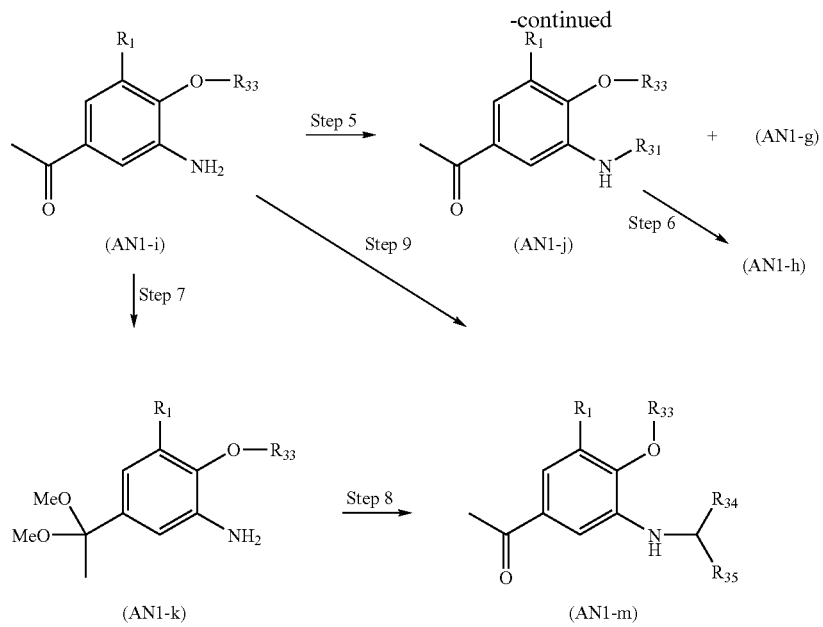

This scheme is an exemplary synthesis for an aniline derivative. In the formulas, R1 has the same definition as in Step 1 of Production Process PP. R31, R32 and R33 have the same definitions as R6 and R7 in Production Process MO.

Step 1 represents a step of introducing one or two substituents R31 at the amino group of compound (AN1-a). Compound (AN1-a) may be treated in approximately the same manner as for introduction of R7 at the hydroxyl group in Step 3 of Production Process MO to yield compounds (AN1-b) and (AN1-c). When R31 is bonded to the aniline amino group as simple alkyl and not via acyl or sulfonyl (when R31-I or R31-Br is used as the reagent, etc.), a prolonged reaction with heating may be necessary to introduce the substituent R31. Incidentally, compounds (AN1-b) and (AN1-c) may be easily separated and purified by silica gel column chromatography.

Step 2 represents a step of treating compound (AN1-b) in the same manner as Step 1 to yield compound (AN1-d) having a newly introduced substituent R32.

Step 3 represents a step of treating compounds (AN1-c) and (AN1-d) in the same manner as Step 2 of Production Process MO to yield the respective compounds (AN1-e) and (AN1-f).

Step 4 represents a step of treating compounds (AN1-e) and (AN1-f) in the same manner as for introduction of R7 in Step 3 of Production Process MO to yield the respective compounds (AN1-g) and (AN1-h).

Step 5 represents a step of using compound (AN1-i) as the starting material for treatment in the same manner as Step 1 to yield compound (AN1-j) having substituents R31 and R33. Compound (AN1-g) can also be obtained by this method.

Step 6 represents a step of treating compound (AN1-j) in the same manner as Step 2 to yield compound (AN1-h).

Step 7 represents a step of treating compound (AN1-i) in the same manner as the ketalizing reaction of Step 6 in Scheme PR-2, to yield compound (AN1-k).

Step 8 represents a step of reductive amination of compound (AN1-k) using an aldehyde or ketone (represented by R34-(C=O)—R35) and a reducing agent to obtain compound (AN1-m).

Compound (AN1-k) may be reacted with sodium cyanoborohydride in a methanol-acetic acid mixed solvent or reacted with sodium triacetoxyborohydride in a 1,2-dichloroethane-acetic acid mixed solvent, to directly yield compound (AN1-m) having the ketal protecting group also deprotected. Either R34 and R35 may be hydrogen, or R34 and R35 may together form a ring.

Step 9 represents a step of reductive amination of compound (AN1-i) without ketal protection, using an aldehyde or ketone (represented by R34-(C=O)—R35) and a reducing agent to yield compound (AN1-m). Reaction will usually be conducted with sodium triacetoxyborohydride in a 1,2-dichloroethane-acetic acid mixed solvent.

Compounds (AN1-b), (AN1-c), (AN1-d), (AN1-e), (AN1-f), (AN1-g), (AN1-h), (AN1-j) and (AN1-m) obtained in this Scheme AN-1 may be converted to the final target compounds by Production Process A.

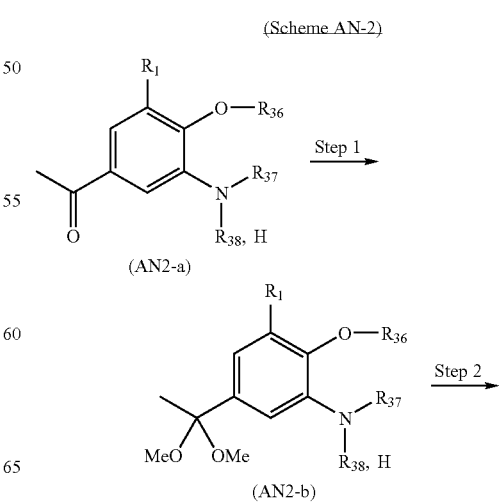

(Scheme AN-2)

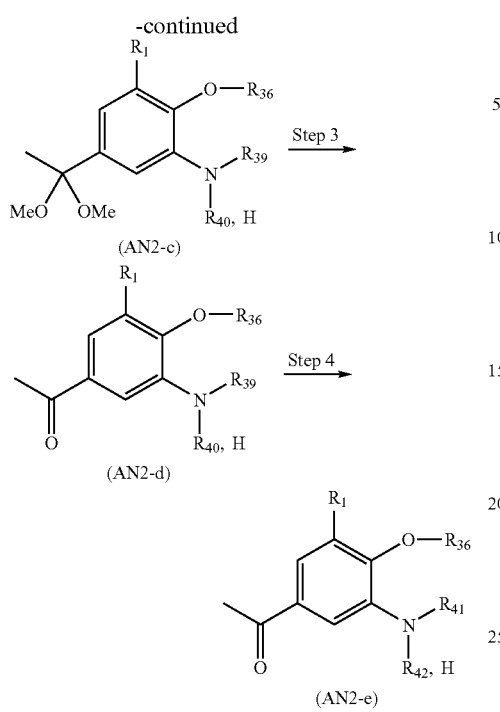

(AN2-c)

(AN2-d)

(AN2-e)

Scheme AN-2 is an exemplary synthetic method for further structural conversion of the substituents on the aniline nitrogen of the intermediate synthesized in Scheme AN-1. In the formulas, R1 has the same definition as R1 in Step 1 of Production Process PP. R36 has the same definition as R6 and R7 in Production Process MO. Either or both R37 and R38 may form an amide bond with the aniline nitrogen, or the substituents may have ester structures. One of the substituents on the aniline nitrogen of the starting material (AN2-a) may be hydrogen.

Step 1 represents a step of treating compound (AN2-a) in the same manner as the ketalizing reaction of Step 6 in Scheme of Production Process PR, to yield compound (AN2-b) having the carbonyl group protected.

Step 2 represents a step of treating compound (AN2-b) with a reducing agent for conversion of amide to methyleneamino (from —N—CO— to —N—CH2-), or of an ester to an alcohol (from —CO—O— to —CH2-OH, from —O—CO— to —OH). Preferably, compound (AN2-b) is treated with lithium aluminum hydride in diethyl ether to yield compound (AN2-c). Substituents R39 and R40 are defined as the structures resulting after this conversion of R37 and R38.

Step 3 represents a step of treating compound (AN2-c) in the same manner as the ketal deprotection reaction of Step 7 in Scheme PR-2, to yield compound (AN2-d).

Step 4 represents a step carried out only when compound (AN2-d) has a hydroxyl group on substituent R39 or R40, and here a new substituent is introduced at the hydroxyl group to yield compound (AN2-e) by conversion to substituents R41 and R42.

The reaction of this step is conducted in the same manner as Step 1 in Scheme PR-1 of Production Process PR. Compounds (AN2-d) and (AN2-e) obtained in this Scheme (AN-2) may be converted to the final target compounds by Production Process A.

<Production Process BO>

The following Schemes BO-1, 2, 3 and 4 of Production Process BO are exemplary synthetic methods for benzoxazine derivatives.

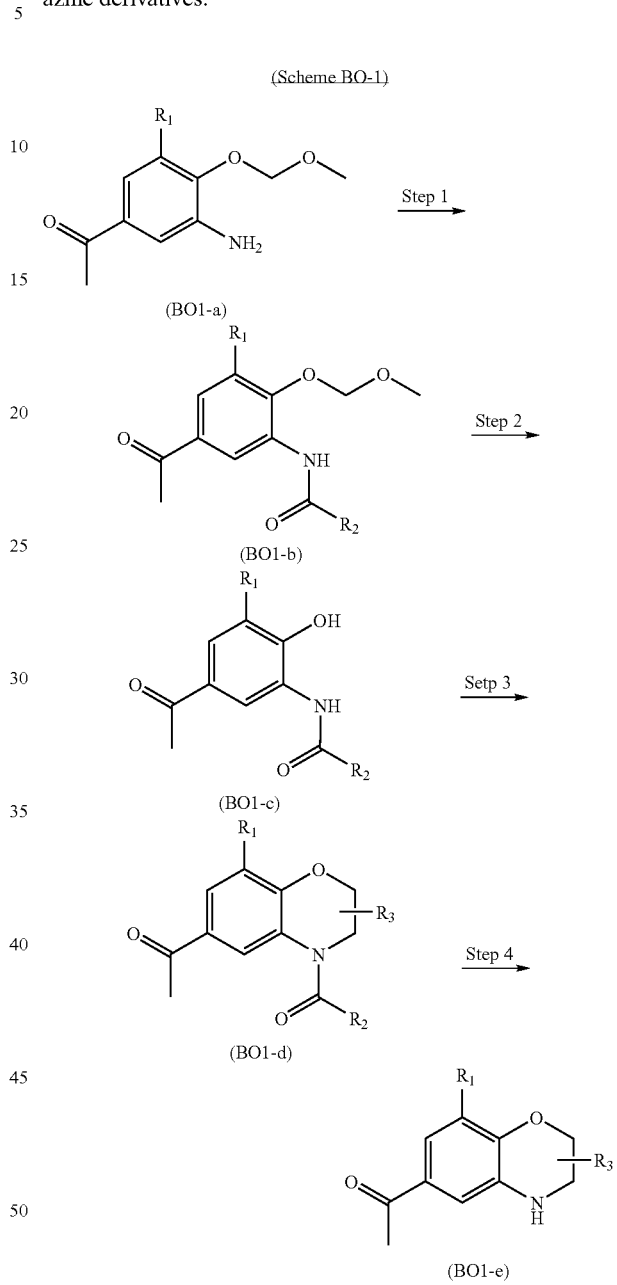

In the formulas, R1 has the same definition as R1 in Step 1 of Production Process PP. R2 represents hydrogen, optionally substituted alkyl or the like. R3 represents hydrogen, halogeno, oxo, optionally substituted alkyl, optionally substituted alkoxy, optionally substituted acyl, optionally substituted carboxyl or optionally substituted carbamoyl.

Step 1 represents a step of acylation of the amino group. Compound (BO1-b) may be obtained either by reaction with an acyl chloride at room temperature in a solvent such as tetrahydrofuran, methylene chloride or acetonitrile in the presence of a base such as pyridine or triethylamine, or by reaction with an acid anhydride in a pyridine solution.

Step 2 represents a step of deprotection of the methoxymethyl group protecting the alcohol. Compound (BO1-c) may be obtained by reaction with dilute aqueous hydrochloric acid and 10% aqueous perchloric acid in a solvent such as tetrahydrofuran or acetone at room temperature.

Step 3 represents a step of alkylation of the hydroxyl group and the amino group. Compound (BO1-d) may be obtained by reaction with a dihalide, dimesylate or ditosylate in a dimethylformamide solution in the presence of a base such as potassium carbonate, cesium carbonate or sodium hydride, while heating from room temperature to 150° C.

Step 4 represents a step of deacylation. Compound (BO1-e) may be obtained either by reaction with an aqueous sodium hydroxide solution in a solvent such as methanol, ethanol or tetrahydrofuran, at room temperature to the reflux temperature of the solvent, or by reaction in an aqueous hydrochloric acid solution at room temperature to the reflux temperature of the solvent.

Compounds (BO1-d) and (BO1-e) obtained in this Scheme BO-1 may be converted to the final target compounds by Production Process A.

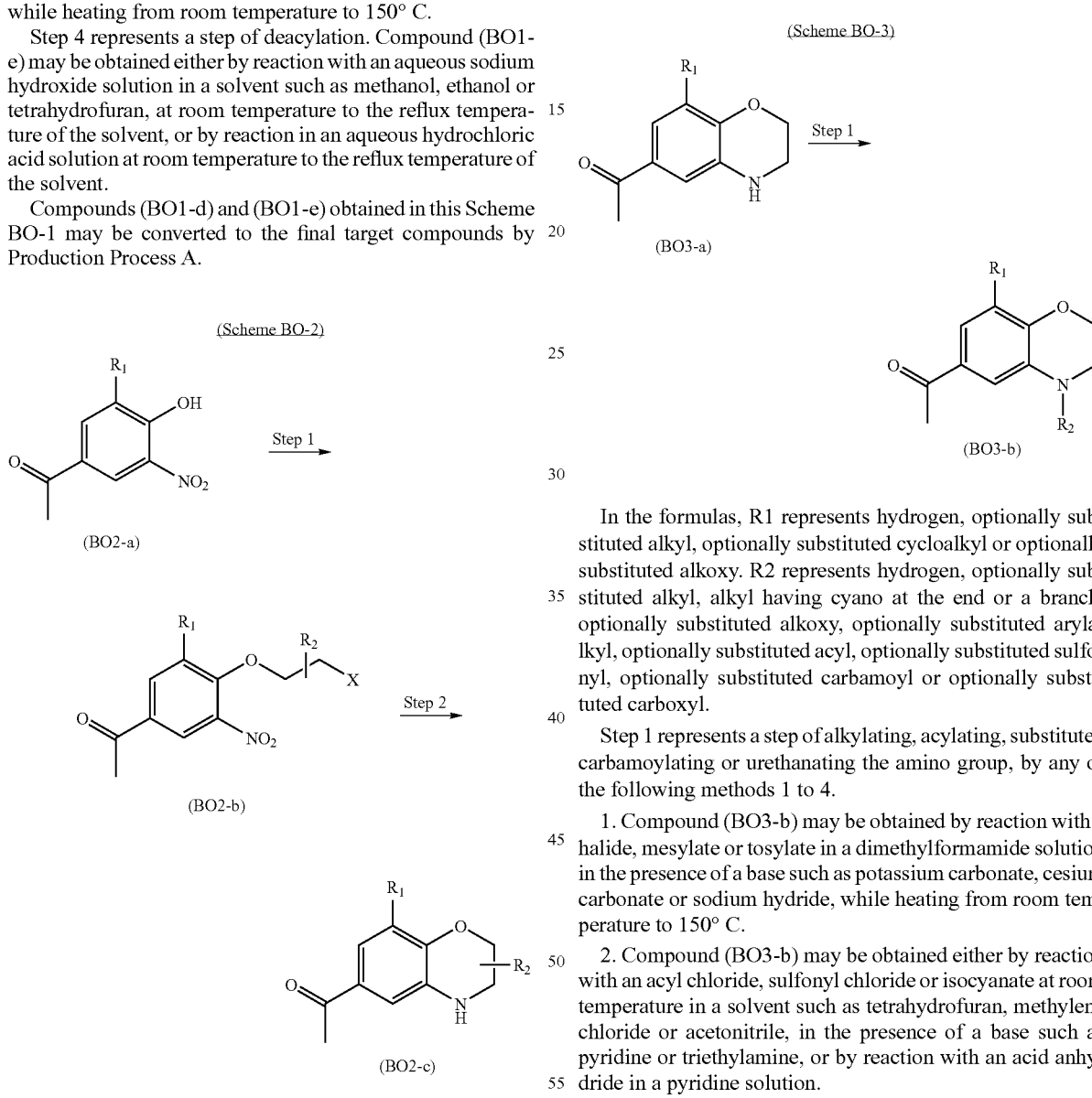

In the formulas, R1 has the same definition as R1 in Step 1 of Production Process PP. R2 has the same definition as R3 in Scheme BO-1.

Step 1 represents a step of alkylation of the hydroxyl group. Compound (BO2-b) may be obtained by reaction with a dihalide, dimesylate or ditosylate in a dimethylformamide solution while heating from room temperature to 150° C.

Step 2 represents a step of forming an oxazine ring. Reaction is conducted with a dihalide, dimesylate or ditosylate in a dimethylformamide solution in the presence of a base such as potassium carbonate, cesium carbonate or sodium hydride, while heating from room temperature to 150° C. Reaction is then conducted at room temperature in an ethanol or methanol solution in the presence of a catalytic amount of palladium-carbon in a hydrogen atmosphere to yield compound (BO2-c).

Compound (BO2-c) obtained in this Scheme BO-2 may be converted to the final target compound by Production Process A.

In the formulas, R1 represents hydrogen, optionally substituted alkyl, optionally substituted cycloalkyl or optionally substituted alkoxy. R2 represents hydrogen, optionally substituted alkyl, alkyl having cyano at the end or a branch, optionally substituted alkoxy, optionally substituted arylalkyl, optionally substituted acyl, optionally substituted sulfonyl, optionally substituted carbamoyl or optionally substituted carboxyl.

Step 1 represents a step of alkylating, acylating, substituted carbamoylating or urethanating the amino group, by any of the following methods 1 to 4.

1. Compound (BO3-b) may be obtained by reaction with a halide, mesylate or tosylate in a dimethylformamide solution in the presence of a base such as potassium carbonate, cesium carbonate or sodium hydride, while heating from room temperature to 150° C.

2. Compound (BO3-b) may be obtained either by reaction with an acyl chloride, sulfonyl chloride or isocyanate at room temperature in a solvent such as tetrahydrofuran, methylene chloride or acetonitrile, in the presence of a base such as pyridine or triethylamine, or by reaction with an acid anhydride in a pyridine solution.

3. Compound (BO3-b) may be obtained by reaction with ethyl N-(1-cyano)iminoformate in methanol or ethanol in the presence of a catalytic amount of 4-dimethylaminopyridine, at room temperature to the reflux temperature of the solvent.

4. Compound (BO3-b) may be obtained by reaction with trimethyl orthoformate or triethyl orthoformate in methanol or ethanol in the presence of a catalytic amount of p-toluenesulfonic acid or camphorsulfonic acid, ketal protection of the acetyl group and introduction of different substituents by methods 1 to 3 above, followed by deprotection under acidic conditions.

Compound (BO3-b) obtained in this Scheme BO-3 may be converted to the final target compound by Production Process A.

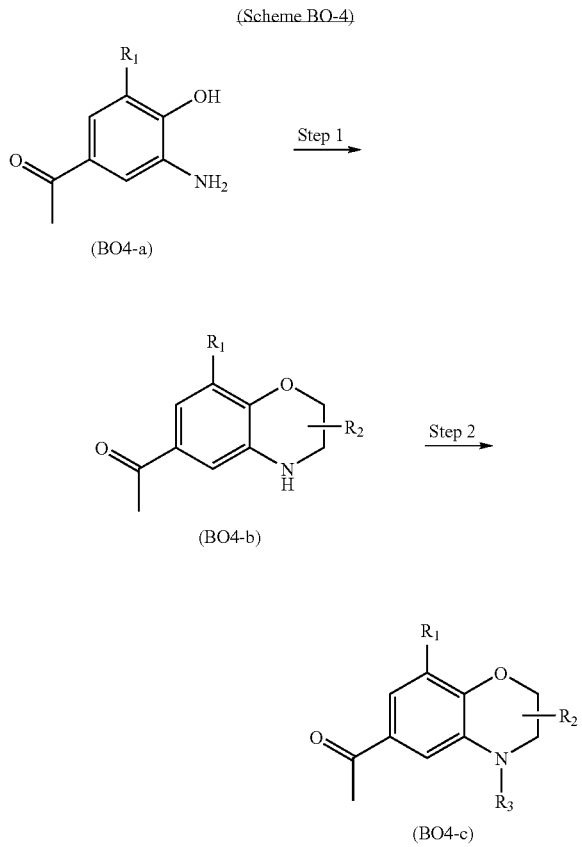

In the formulas, R1 has the same definition as R1 in Step 1 of Production Process PP. R2 has the same definition as R3 in Scheme BO-1. R3 has the same definition as R2 in Scheme BO-3.

Step 1 represents a step of alkylation. Compound (BO4-b) may be obtained by the method described in Tawada, H., Sugiyama, Y., Ikeda, H., Yamamoto, Y., Meguro, K; Chem. Pharm. Bull., 38(5), 1238-1245 (1990), or by reaction with allyl bromide, maleic anhydride or the like in a solvent such as methanol, ethanol or toluene in the presence of a base such as potassium carbonate, cesium carbonate or sodium hydrogencarbonate at room temperature to the reflux temperature of the solvent, followed by reaction in methanol or ethanol in the presence of a base such as potassium carbonate or triethylamine, at room temperature to the reflux temperature of the solvent.

Step 2 represents a step of alkylating, acylating, substituted carbamoylating or urethanating the amino group. Compound (BO4-c) may be obtained by treatment in the same manner as Step 1 of Scheme BO-3. Compounds (BO4-b) and (BO4-c) obtained in Scheme BO-4 may be converted to the final target compound by Production Process A.

<Production Process BOL>

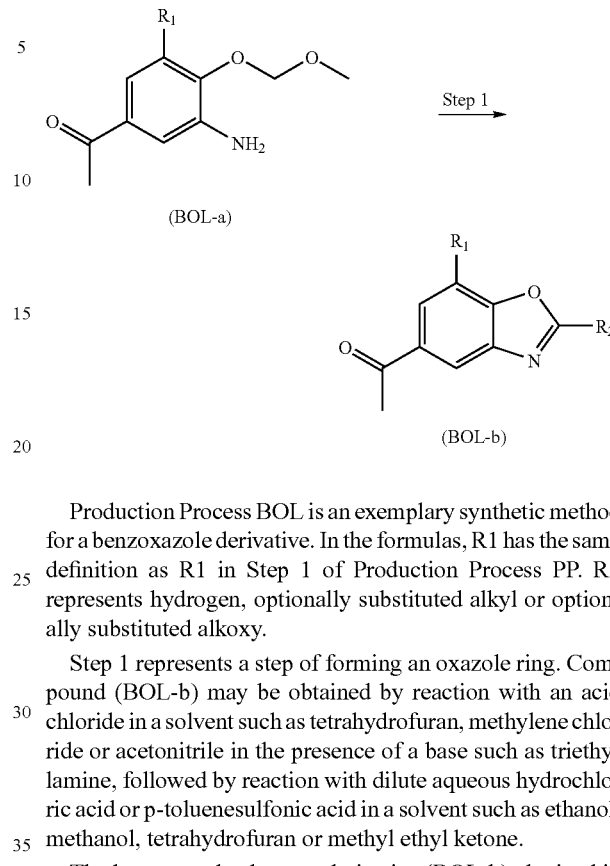

Production Process BOL is an exemplary synthetic method for a benzoxazole derivative. In the formulas, R1 has the same definition as R1 in Step 1 of Production Process PP. R2 represents hydrogen, optionally substituted alkyl or optionally substituted alkoxy.

Step 1 represents a step of forming an oxazole ring. Compound (BOL-b) may be obtained by reaction with an acid chloride in a solvent such as tetrahydrofuran, methylene chloride or acetonitrile in the presence of a base such as triethylamine, followed by reaction with dilute aqueous hydrochloric acid or p-toluenesulfonic acid in a solvent such as ethanol, methanol, tetrahydrofuran or methyl ethyl ketone.

The benzoxazoleethanone derivative (BOL-b) obtained in Production Process BOL may be converted to the final compound by Production Process A.

<Production Process CA>

Schemes CA-1, 2 and 3 below in Production Process CA are exemplary synthetic methods for catechol derivatives.

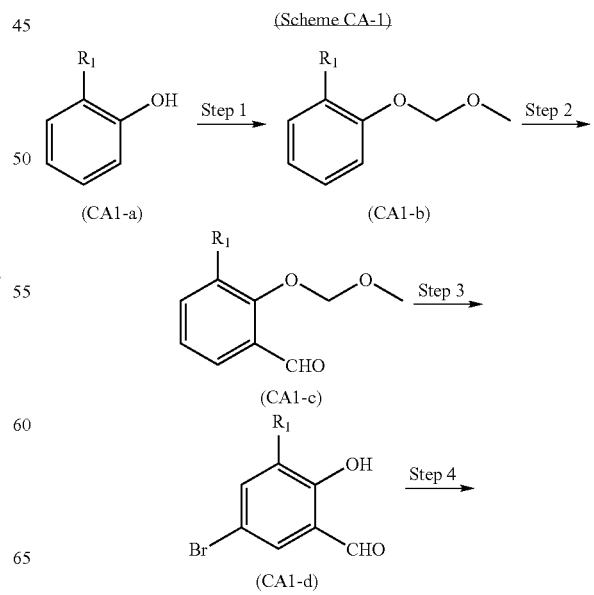

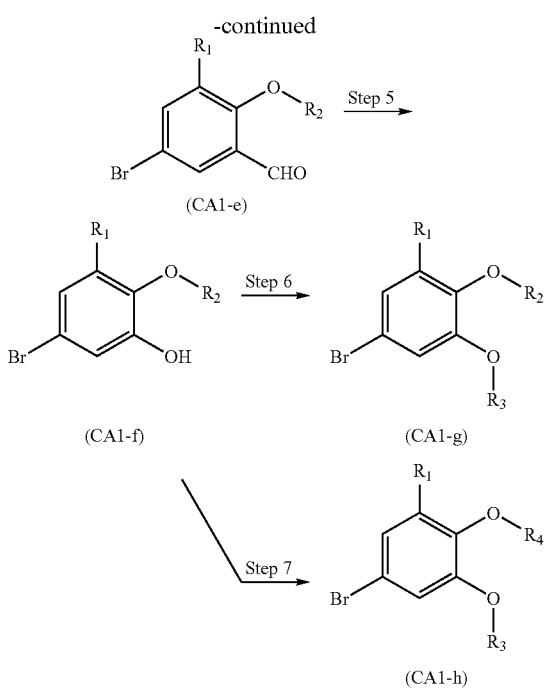

(CA1-e)

(CA1-f) (CA1-g)

(CA1-h)

In the formulas, R1 has the same definition as R1 in Step 1 of Production Process PP. R2, R3 and R4 have the same definitions as R6 and R7 in Production Process MO.

Step 1 represents a step of methoxymethylating the hydroxyl group of compound (CA1-a). Compound (CA1-b) is obtained by reaction of compound (CA1-a) and sodium hydride in dimethylformamide at room temperature, followed by reaction with methoxymethyl chloride (MOM-Cl).

Step 2 represents a step of introducing a formyl group by ortholithiation utilizing the substituent effect of the methoxymethyl group of compound (CA1-b). The orthoformylated compound (CA1-c) is obtained by treatment of compound (CA1-b) with n-butyllithium in diethyl ether while cooling on ice in the presence of tetramethylethylenediamine, followed by treatment with a formylating agent such as dimethylformamide or N-formylmorpholine.

Step 3 represents a step of brominating the para-position relative to the methoxymethyl group of compound (CA1-c). Compound (CA1-d) is obtained by reaction of compound (CA1-c) with bromine in methanol at room temperature, and removal of the methoxymethyl group by the hydrogen bromide generated in the system.

Step 4 represents a step of introducing any of various substituents at the hydroxyl group of compound (CA1-d). Compound (CA1-e) is obtained by the same method as for introduction of R7 in Step 3 of Production Process MO.

Step 5 represents a step of oxidative conversion of the formyl group to a hydroxyl group. Compound (CA1-f) is obtained by reacting compound (CA1-e) with m-chloroperbenzoic acid in dichloromethane at room temperature or with heating, and then hydrolyzing the purified ester using potassium carbonate in methanol.

Step 6 represents a step of obtaining R3 introduced compound (CA1-g) by the same method as in Step 4 of Scheme CA-1.

Step 7 represents a step of conversion to substituent R4 when R2 is a hydroxyl-protecting group. Compound (CA1-h) is obtained in the same manner as the continuous treatment in Steps 2 and 3 of Production Process MO.

Compounds (CA1-g) and (CA1-h) obtained in this Scheme CA-1 may be converted to the final target compound by Production Process A.

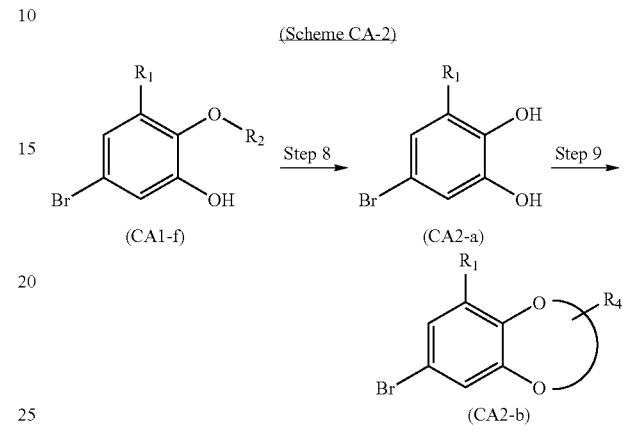

(CA1-f) (CA2-a)

(CA2-b)

Scheme CA-2 is an exemplary synthetic method for a cyclic catechol derivative. In the formulas, R1 has the same definition as R1 in Step 1 of Production Process PP. R2 and R4 have the same definitions as R6 and R7 in Production Process MO.

Step 8 represents a step of conversion to a catechol when R2 is an eliminable hydroxyl-protecting group. When R2 is methoxymethyl, a diol (catechol) (CA2-a) is obtained by treating compound (CA1-f) with 6 N hydrochloric acid.

Step 9 represents a step of cyclizing the catechol by alkylation. Compound (CA2-a) is reacted with a 1,2-dibromoethyl derivative in a solvent such as dimethylformamide, acetonitrile or acetone in the presence of a base such as potassium carbonate, cesium carbonate or sodium hydride, to yield a fused dioxane ring (CA2-b). Compound (CA2-a) may also be treated with acetone in the presence of phosphorus pentaoxide to yield a 5-membered cyclic product (CA2-b) as an acetonide.

Compound (CA2-b) obtained in this Scheme CA-2 may be converted to the final target compound by Production Process A.

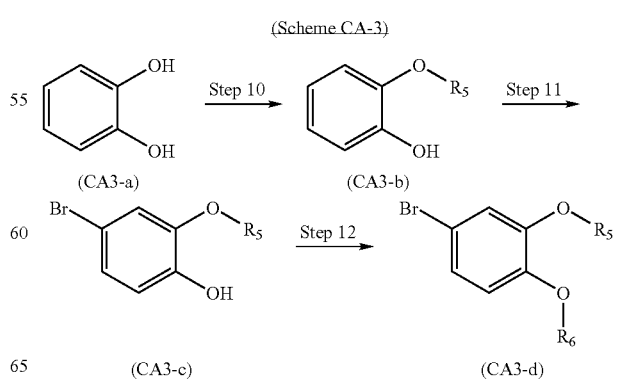

(CA3-a) (CA3-b)

(CA3-c) (CA3-d)

Scheme CA-3 is an exemplary synthetic method for a disubstituted catechol derivative. In the formulas, R5 and R6 have the same definitions as R6 and R7 in Production Process MO.

Step 10 represents a step of obtaining compound (CA3-b) by the same method as in Step 4 of Scheme CA-1 using the catechol (CA3-a) as the starting material.

Step 11 represents a step of treating compound (CA3-b) by the same method as in Step 3 of Scheme CA-1 to yield compound (CA3-c) which is selectively brominated at the para-position relative to the non-substituted hydroxyl group.

Step 12 represents a step of obtaining R6 introduced compound (CA3-d) by the same method as in Step 4 of Scheme CA-1.

Compound (CA3-d) obtained by Scheme CA-3 may be converted to the final target compound by Production Process A.

<Production Process CO>

Schemes CO-1, CO-2, CO-3, CO-4, CO-5, CO-6, CO-7, CO-8 and CO-9 in Production Process CO are exemplary synthetic methods for phenol and phenoxy derivatives.

in the presence of a base such as potassium carbonate, cesium carbonate or sodium hydride, while heating from room temperature to 150° C.

2. Compound (CO1-c) may be obtained either by reaction with an acyl chloride, sulfonyl chloride or isocyanate in a solvent such as tetrahydrofuran, methylene chloride or acetonitrile in the presence of a base such as pyridine or triethylamine, at −15° C. to room temperature, or by reaction with an acid anhydride in a pyridine solution.

3. Compound (CO1-c) may also be obtained by reaction with phenyl chloroformate in a solvent such as tetrahydrofuran, methylene chloride or acetonitrile in the presence of a base such as pyridine or triethylamine, followed by reaction with an amine.

Compounds (CO1-b) and (CO1-c) obtained in this Scheme CO-1 may be converted to the final target compounds by Production Process A. Compound (CO1-a) may also be used in the conversion of compound (A4-c) in Scheme A-4 of Production Process A.

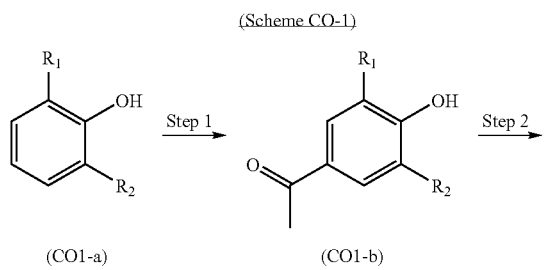

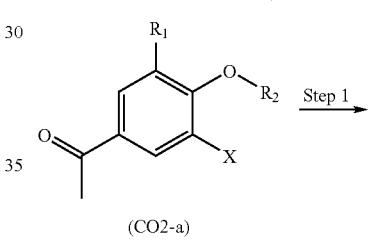

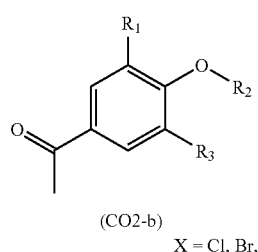

In the formulas of Scheme CO-1, R1 and R2 have the same definition as R1 in Step 1 of Production Process PP. R3 has the same definition as R6 and R7 in Production Process MO.

Step 1 represents a step of Friedel-Crafts acylation. Compound (CO1-b) is obtained by reaction with acetyl chloride in methylene chloride or toluene in the presence of a Lewis acid such as aluminum chloride, zinc chloride or tin (II) chloride, at −70° C. to room temperature.

Step 2 represents a step of alkylation, carbonation, sulfonation or the like.

1. Compound (CO1-c) may be obtained by reaction with a halide, mesylate or tosylate in a dimethylformamide solution Scheme CO-2 is an exemplary synthetic method for an aromatic-substituted benzene derivative. In the formulas, R1 has the same definition as R1 in Step 1 of Production Process PP. R2 has the same definition as R6 and R7 in Production Process MO. R3 represents an aromatic ring.

Step 1 represents a step of introducing an aromatic substituent using the Stille coupling method. Compound (CO2-b) is obtained by reaction with aromatic-substituted tributyltin in a solvent such as toluene or xylene under a nitrogen atmosphere in the presence of a catalytic amount of tetrakis (triphenylphosphine)palladium, at the reflux temperature of the solvent.

Compound (CO2-b) obtained in this Scheme CO-2 may be converted to the final target compound by Production Process A.

(Scheme CO-3)

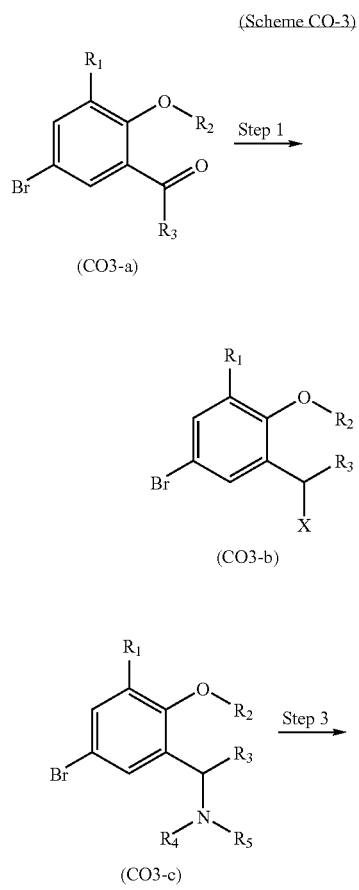

(CO3-a)

(CO3-b)

(CO3-c) (CO3-d)

Scheme CO-3 is an exemplary synthetic method for a benzylamine derivative. In the formulas, R1 and R3 have the same definition as R1 in Step 1 of Production Process PP. R2 and R2' have the same definitions as R6 and R7 in Production Process MO. R4 and R5 have the same definition as R2 in Scheme BO-3. R4 and R5 may also form a ring together. X represents hydroxyl or sulfonate.

Step 1 represents a step of introducing an alkyl halide. Compound (CO3-b) is obtained by reaction with sodium borohydride in methanol or ethanol, followed by reaction with methanesulfonyl chloride or the like in dimethylformamide, in the presence of a base such as pyridine or triethylamine.

Step 2 represents a step of amination.

1. Compound (CO3-c) may be obtained by reaction with an amine in methanol, ethanol, acetonitrile or tetrahydrofuran.

2. Compound (CO3-c) may be obtained by reaction with an amine in dimethylformamide in the presence of a base such as potassium carbonate or sodium hydride.

3. When X is hydroxyl, compound (CO3-c) may be obtained by reaction with diphenylphosphoryl azide in toluene in the presence of a base such as 1,8-diazabicyclo[5.4.0]undec-7-ene to yield an azide, followed by reaction with a trialkylphosphine or triphenylphosphine in tetrahydrofuran-water.

Step 3 represents a step of converting R2 to substituent R2' when R2 is a hydroxyl-protecting group. Compound (CO3-d) is obtained in the same manner as the continuous treatment in Steps 2 and 3 of Production Process MO.

Compounds (CO3-c) and (CO3-d) obtained in this Scheme CO-3 may be converted to the final target compounds by Production Process A.

(Scheme CO-4)

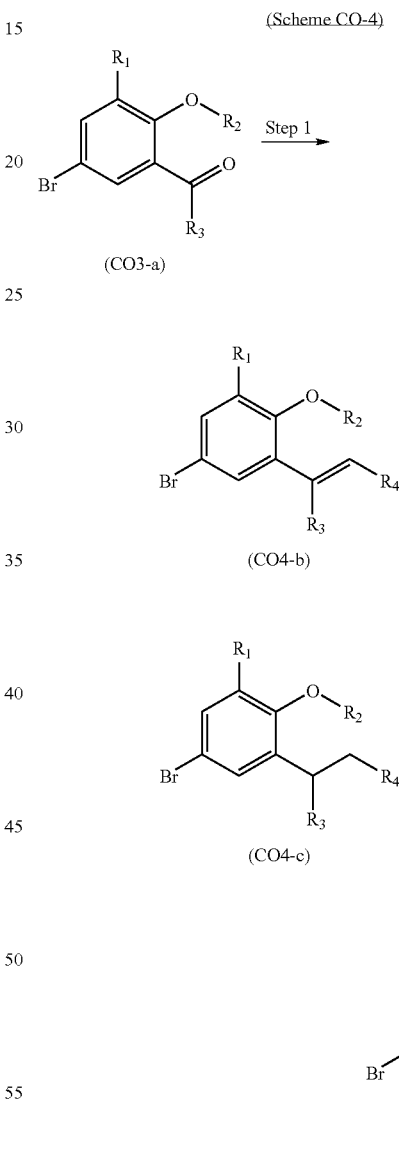

(CO3-a)

(CO4-b)

(CO4-c)

(CO4-d)

Scheme CO-4 is an exemplary synthetic method for phenol and phenoxy derivatives by Wittig reaction. In the formulas, R1 has the same definition as R1 in Production Process PP. R2 and R2' have the same definitions as R6 and R7 in Production Process MO. R3 represents hydrogen or lower alkyl. R4 represents optionally substituted alkyl, optionally substituted carboxyl, cyano or the like.

Step 1 represents a step of alkylation utilizing Wittig reaction. Reaction is conducted with a phosphorane derivative in methylene chloride or tetrahydrofuran. Alternatively, compound (CO4-b) may be obtained by reaction with a phosphonium salt or phosphonate in tetrahydrofuran or dimethylformamide in the presence of a base such as potassium tert-butoxide or sodium hydride.

Step 2 represents a step of reducing the olefin. Compound (CO4-c) may be obtained by accomplishing reduction by reaction in ethyl acetate, tetrahydrofuran or methanol under a hydrogen atmosphere in the presence of palladium-carbon, or by reaction with magnesium in methanol.

Step 3 represents a step of conversion to substituent R2' when R2 is a hydroxyl-protecting group. Compound (CO4-d) is obtained in the same manner as the continuous treatment in Steps 2 and 3 of Production Process MO.

Compounds (CO4-b), (CO4-c) and (CO4-d) obtained in this Scheme CO-4 may be converted to the final target compounds by Production Process A.

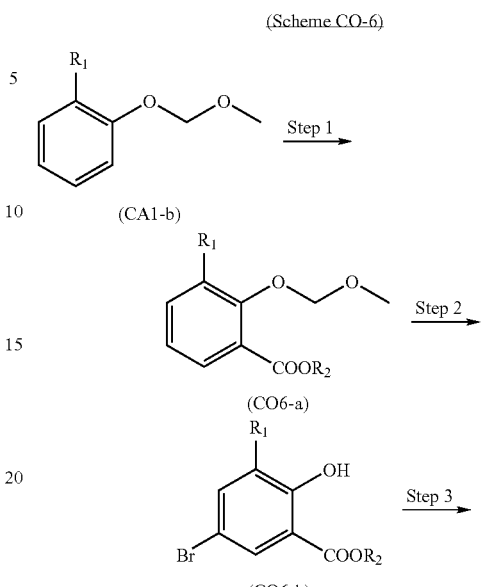

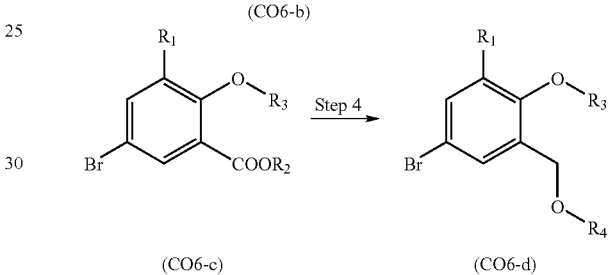

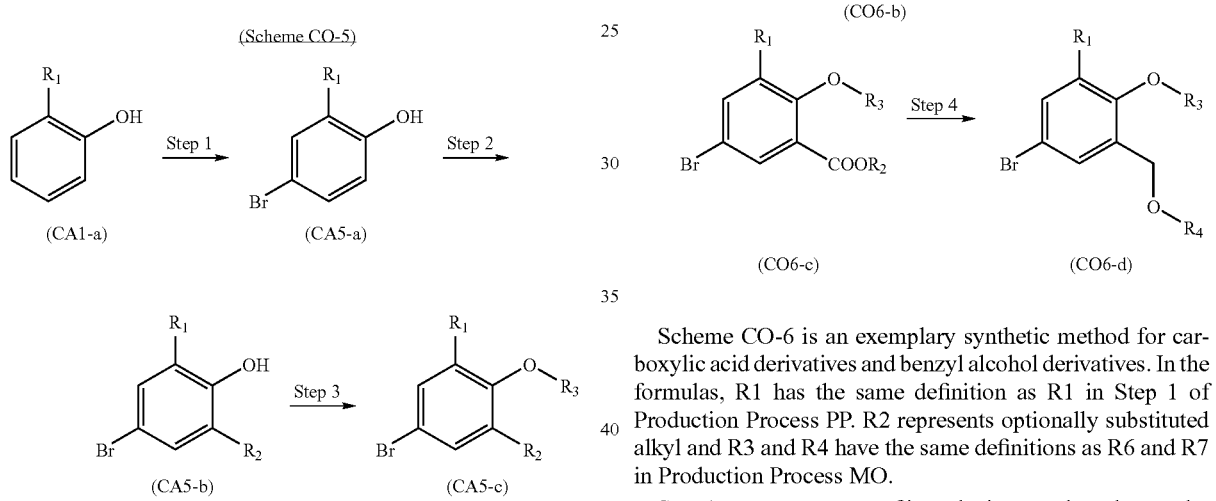

Scheme CO-5 is an exemplary synthetic method for phenol and phenoxy derivatives utilizing Friedel-Crafts reaction. In the formulas, R1 has the same definition as R1 in Step 1 of Production Process PP. R2 represents hydrogen, optionally substituted alkyl or optionally substituted cycloalkyl. R3 has the same definition as R6 and R7 in Production Process MO.

Step 1 represents a step of bromination at the para-position of phenyl. Reaction may be conducted either with bromine in methanol or ethanol or with N-bromosuccinimide in acetonitrile to yield Compound (CO5-a).

Step 2 represents a step of alkylation by Friedel-Crafts reaction. Compound (CO5-b) is obtained by reaction with alkyl mesylate in benzene or dichloroethane in the presence of scandium triflate, by the method described in H. Katsuki et al., Synthesis 603 (1999).

Step 3 represents a step of introducing a substituent R3 at the hydroxyl group. Compound (CO5-c) is obtained by treatment in the same manner as for introduction of R7 in Step 3 of Production Process MO.

Compounds (CO5-b) and (CO5-c) obtained in Scheme CO-5 may be converted to the final target compounds by Production Process A.

Scheme CO-6 is an exemplary synthetic method for carboxylic acid derivatives and benzyl alcohol derivatives. In the formulas, R1 has the same definition as R1 in Step 1 of Production Process PP. R2 represents optionally substituted alkyl and R3 and R4 have the same definitions as R6 and R7 in Production Process MO.

Step 1 represents a step of introducing a carboxyl group by ortholithiation utilizing the substituent effect of the methoxymethyl group of compound (CA1-b). Compound (CO6-a) is obtained by treating compound (CA1-b) with n-butyl-lithium in diethyl ether in the presence of tetramethylethylenediamine while cooling on ice, and then reacting it with an alkyl dicarbonate.

Step 2 represents a step of deprotection of the methoxymethyl group serving as the alcohol-protecting group. Compound (CO6-b) is obtained by reaction with dilute aqueous hydrochloric acid and 10% aqueous perchloric acid in tetrahydrofuran or acetone at room temperature.

Step 3 represents a step of introducing a substituent R3 at the hydroxyl group. Compound (CO6-c) is obtained by treatment in the same manner as for introduction of R7 in Step 3 of Production Process MO.

Step 4 represents a step of reduction and alkylation of the carboxyl group. Compound (CO6-d) is obtained by reaction with lithium aluminum hydride in diethyl ether or tetrahydrofuran while cooling on ice, followed by the same method as in Step 3.

Compounds (CO6-b), (CO6-c) and (CO6-d) obtained in this Scheme CO-6 may be converted to the final target compounds by Production Process A.

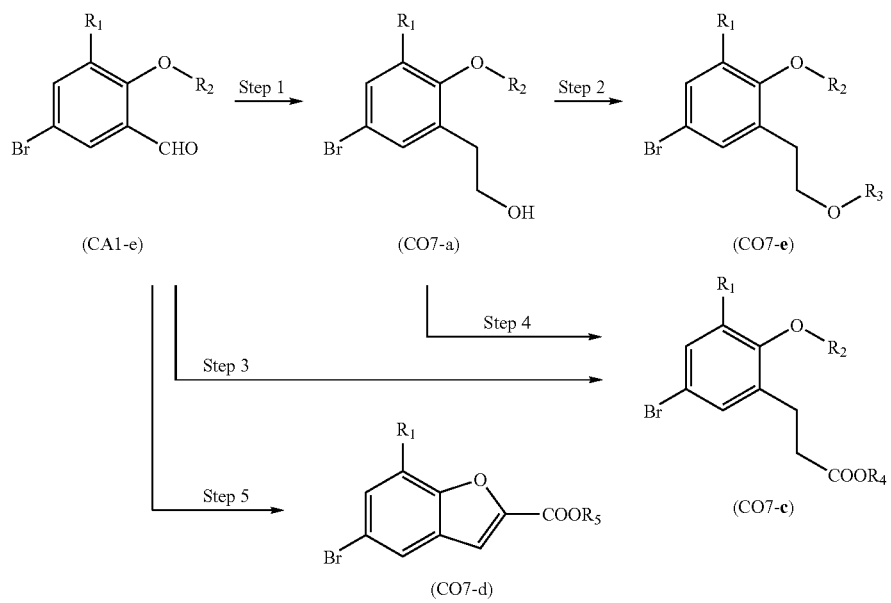

Scheme CO-7 is an exemplary synthetic method for phenethyl alcohol derivatives, phenylacetic acid derivatives and benzofuran derivatives. In the formulas, R1 has the same definition as R1 in Step 1 of Production Process PP. R2 and R3 have the same definitions as R6 and R7 in Production Process MO. R4 and R5 represent optionally substituted alkyl.

Step 1 represents a step of introducing a hydroxyl group by Wittig reaction followed by hydroboration reaction. The reaction is conducted with methyltriphenylphosphonium bromide in tetrahydrofuran in the presence of potassium tert-butoxide. Reaction is then conducted with borane-tetrahydrofuran in tetrahydrofuran and with 30% aqueous hydrogen peroxide to yield compound (CO7-a).

Step 2 represents a step of introducing a substituent R3 at the hydroxyl group. Compound (CO7-b) is obtained by treatment in the same manner as for introduction of R7 in Step 3 of Production Process MO.

Step 3 represents a step of carbon-carbon bond formation. Compound (CO7-c) is obtained by reaction with methyl methylthiomethyl sulfoxide in tetrahydrofuran in the presence of Triton B, at the reflux temperature of the solvent, followed by reaction with dilute aqueous hydrochloric acid in methanol or ethanol.

Step 4 represents a step of oxidation. Compound (CO7-c) is obtained by the method described in Mangzho Zhao et al., Tetrahedron Lett. 39, 5323 (1998) or the method described in Ryoji Noyori et al., J. Am. Chem. Soc., 119, 12386 (1997).

Step 5 represents a step of forming a furan ring when R2 is hydrogen. Compound (CO7-d) is obtained by reaction with a bromoacetic acid ester in dimethylformamide in the presence of potassium carbonate, at the reflux temperature of the solvent.

Compounds (CO7-a), (CO7-b), (CO7-c) and (CO7-d) obtained in this Scheme CO-7 may be converted to the final target compounds by Production Process A.

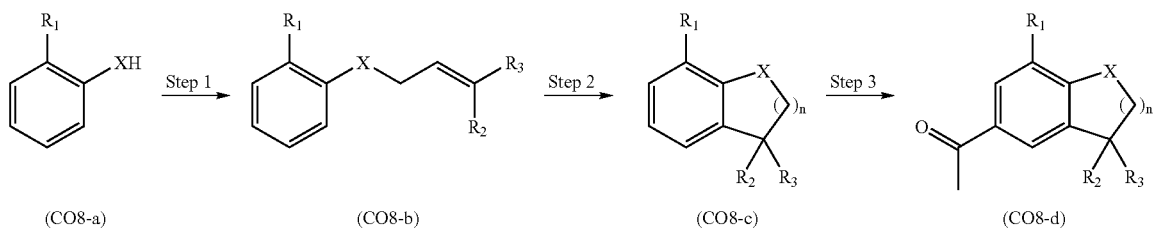

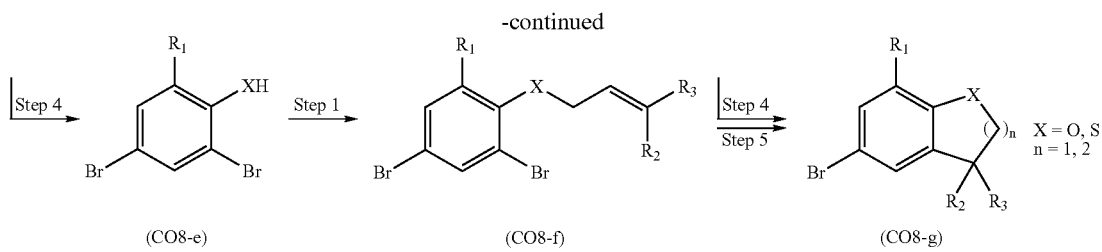

Scheme CO-8 is an exemplary synthetic method for 2,3-dihydrobenzofuran derivatives or 2,3-dihydrobenzothiophene derivatives. In the formulas, R1 has the same definition as R1 in Step 1 of Production Process PP. R2 and R3 represent hydrogen, optionally substituted alkyl or optionally substituted alkoxy.

Step 1 represents a step of alkylation of the hydroxyl group. Compound (CO8-b) is obtained by reaction with an allyl halide, allyl mesylate or allyl tosylate in a solvent such as dimethylformamide, acetonitrile or acetone, in the presence of sodium iodide and in the presence of a base such as potassium carbonate, cesium carbonate or sodium hydride, according to the method described in J. M. Janusz et al., J. Med. Chem. 41, 1112 (1998).

Step 2 represents a step of forming a furan or thiophene ring. Compound (CO8-c) is obtained by the method described in J. M. Janusz et al., J. Med. Chem. 41, 1112 (1998), or by reaction at 210° C. in magnesium chloride.

Step 3 represents a step of Friedel-Craft acylation. Compound (CO8-d) is obtained by reaction with acetyl chloride in methylene chloride or toluene in the presence of a Lewis acid such as aluminum chloride, zinc chloride or tin (II) chloride, at −70° C. to room temperature.

Step 4 represents a step of bromination by reaction with bromine in methanol or ethanol. Alternatively, compounds (CO8-e) and (CO8-g) are obtained by reaction with N-bromosuccinimide in acetonitrile or dimethylformamide.

Step 5 represents a step of forming a furan or thiophene ring. Compound (CO8-g) is obtained by reaction with sodium borohydride at 75° C. in dimethylacetamide in the presence of cyclopentadienyldichlorotitanium, by the method described in J. Schwaltz et al., J. Org. Chem. 59, 940 (1994).

Compounds (CO8-d) and (CO8-g) obtained in this Scheme CO-8 may be converted to the final target compounds by Production Process A.

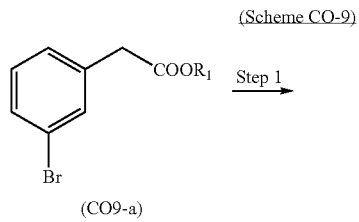

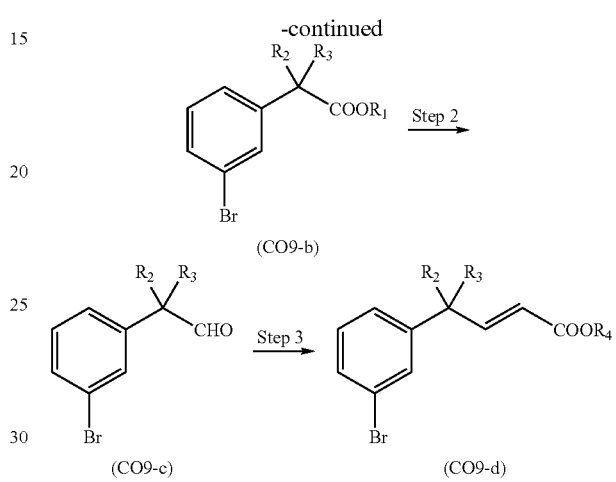

Scheme CO-9 is an exemplary synthetic method for carboxylic acid derivatives. In the formulas, R1, R2, R3 and R4 represent hydrogen or optionally substituted alkyl.

Step 1 represents a step of alkylation. Compound (CO9-b) is obtained by reaction with an alkyl halide, mesylate or tosylate in tetrahydrofuran or dimethylformamide, in the presence of potassium tert-butoxide or sodium hydride.

Step 2 represents a step of reduction. Compound (CO9-c) is obtained by reaction with diisobutylaluminum hydride in tetrahydrofuran.

Step 3 represents a step of carbon-carbon bond formation utilizing Wittig reaction. The reaction is conducted with a phosphorane derivative in methylene chloride or tetrahydrofuran. Alternatively, compound (CO9-d) is obtained by reaction with either a phosphonium salt or phosphonate in tetrahydrofuran or dimethylformamide in the presence of a base such as potassium tert-butoxide or sodium hydride.

Compounds (CO9-b) and (CO9-d) obtained in this Scheme CO-9 may be converted to the final target compounds by Production Process A.

Representative production processes for compounds according to the invention and salts thereof have been described above, but the starting compounds and reagents used for production of the compounds of the invention may also form salts or hydrates, and these are not particularly restricted so long as the reaction is not inhibited. When compound (1) of the invention is obtained as a free compound, a common method may be used to convert it to a salt which compound (1) may form. The different isomers (for example, geometric isomers, optical isomers based on asymmetric carbon, stereoisomers, tautomers or the like) obtained for compound (1) according to the invention may be purified and isolated using common separation means such as recrystallization, diastereomer salt methods, enzymatic resolution methods and chromatography methods (for example, thin-layer chromatography, column chromatography, gas chromatography, etc.).

In certain embodiments, compounds of the invention represented by formula (I) and salts thereof exhibit excellent thrombin receptor antagonism and especially selective antagonism against PAR1 thrombin receptors. In certain other embodiments, compounds of the invention and their salts also exhibit excellent inhibition against platelet aggregation and smooth muscle cell proliferation, with high oral efficacy. In yet other embodiments, compounds of the invention and salts thereof can therefore inhibit the cellular response to thrombin which includes platelet aggregation, without inhibiting the catalytic activity of thrombin which converts fibrinogen to fibrin, and can also inhibit vascular smooth muscle proliferation occurring as a result of damage to vascular walls by coronary angioplasty and the like, through selective inhibition of PAR1.

Thus, the compounds of the invention and salts thereof may be used to obtain pharmaceutical compositions (formulations) as (i) thrombin receptor antagonists (especially PAR1 thrombin receptor antagonists), (ii) platelet aggregation inhibitors, (iii) smooth muscle cell proliferation inhibitors, (iv) endothelial cell, fibroblast, nephrocyte, osteosarcoma cell, muscle cell, cancer cell and/or glia cell proliferation inhibitors and (v) therapeutic or prophylactic agents for thrombosis, vascular restenosis, deep venous thrombosis, pulmonary embolism, cerebral infarction, heart diseases, disseminated intravascular coagulation, hypertension, inflammatory diseases, rheumatism, asthma, glomerulonephritis, osteoporosis, neurological diseases and/or malignant tumors.

In certain embodiments, compounds of the invention and their salts may be administered for treatment of patients suffering from diseases associated with thrombin receptors, and for treatment of patients suffering from proliferative diseases of, for example, endothelial cell, fibroblast, nephrocyte, osteosarcoma cell, muscle cell, cancer cell and/or glia cell.

A compound of the invention represented by formula (I) above, a salt thereof or a hydrate of the foregoing may be formulated by a conventional method. Exemplary dosage forms include tablets, powders, fine particles, granules, coated tablets, capsules, syrups, lozenges, inhalants, suppositories, injections, ointments, eye salves, eye drops, nasal drops, ear drops, paps, lotions and the like. Formulations may be prepared with any commonly used excipients, binders, disintegrators, lubricants, coloring agents, corrective coatings, and if necessary, stabilizers, emulsifiers, absorbefacients, surfactants, pH adjustors, preservatives, antioxidants, or the like, in combination with various components that are ordinarily used as materials for pharmaceutical formulations.

For example, such components include (1) animal and vegetable oils such as soybean oil, beef tallow and synthetic glycerides; (2) hydrocarbons such as liquid paraffin, squalane and solid paraffin; (3) ester oils such as octyldodecyl myristate and isopropyl myristate; (4) higher alcohols such as cetostearyl alcohol and behenyl alcohol; (5) silicone resins; (6) silicone oils; (7) surfactants such as polyoxyethylene fatty acid esters, sorbitan fatty acid esters, glycerin fatty acid esters, polyoxyethylene sorbitan fatty acid esters, polyoxyethylene hydrogenated castor oil and polyoxyethylene/polyoxypropylene block copolymer; (8) water-soluble polymers such as hydroxyethylcellulose, polyacrylic acid, carboxyvinyl polymer, polyethylene glycol, polyvinylpyrrolidone and methylcellulose; (9) lower alcohols such as ethanol and isopropanol; (10) polyhydric alcohols such as glycerin, propylene glycol, dipropylene glycol and sorbitol; (11) sugars such as glucose and sucrose; (12) inorganic powders such as silicic anhydride, magnesium aluminum silicate and aluminum silicate; (13) purified water, and the like.

Examples of (1) excipients which may be used include lactose, corn starch, white soft sugar, glucose, mannitol, sorbit, crystalline cellulose and silicon dioxide; examples of (2) binders which may be used include polyvinyl alcohol, polyvinyl ether, methylcellulose, ethylcellulose, gum arabic, tragacanth, gelatin, shellac, hydroxypropylcellulose, hydroxypropylmethylcellulose, polyvinylpyrrolidone, polypropylene glycol/polyoxyethylene block polymer, meglumine, calcium citrate, dextrin and pectin; examples of (3) disintegrators which may be used include starch, agar, gelatin powder, crystalline cellulose, calcium carbonate, sodium hydrogencarbonate, calcium citrate, dextrin, pectin and calcium carboxymethylcellulose; examples of (4) lubricants which may be used include magnesium stearate, talc, polyethylene glycol, silica and hydrogenated vegetable oils; examples of (5) coloring agents which may be used include any of those approved for addition to drugs; examples of (6) corrective coatings which may be used include cocoa powder, menthol, aromatic powders, mentha oil, borneol and powdered cinnamon; and examples of (7) antioxidants which may be used include those approved for addition to drugs, such as ascorbic acid, α-tocopherol and the like.

(i) An oral formulation may be prepared by combining a compound of the invention or its salt with an excipient, if necessary adding a binder, disintegrator, lubricant, coloring agent, corrective coating or the like, and forming a powder, fine particles, granules, tablets, coated tablets, capsules, etc. by a common method. (ii) Tablets or granules may, of course, also be coated with a sugar coating, gelatin coating or other type of suitable coating if necessary. (iii) In the case of a liquid formulation such as syrup, injection, eye drops or the like, a common method may be used for formulation with a pH adjustor, solubilizer, isotonizing agent or the like, as well as a solubilizing aid, stabilizer, buffering agent, suspending agent, antioxidant, etc. if necessary. In the case of a liquid formulation, it may also be lyophilized, and an injection may be administered intravenously, subcutaneously or intramuscularly. As preferred examples of suspending agents there may be mentioned methylcellulose, polysorbate 80, hydroxyethylcellulose, gum arabic, tragacanth powder, sodium carboxymethylcellulose, polyoxyethylene sorbitan monolaurate and the like; as preferred examples of solubilizing aids there may be mentioned polyoxyethylene hydrogenated castor oil, polysorbate 80, nicotinamide, polyoxyethylene sorbitan monolaurate and the like; as preferred examples of stabilizing agents there may be mentioned sodium sulfite, sodium metasulfite, ether and the like; and as preferred examples of preservatives there may be mentioned methyl p-oxybenzoate, ethyl p-oxybenzoate, sorbic acid, phenol, cresol, chlorocresol, and the like. (iv) There are no particular restrictions on the method of preparing an external application, and any common method may be employed. The base materials used may be any raw materials commonly employed in drugs, quasi drugs, cosmetics and the like, and as examples there may be mentioned raw materials such as animal and vegetable oils, mineral oils, ester oils, waxes, higher alcohols, fatty acids, silicone oils, surfactants, phospholipids, alcohols, polyhydric alcohols, water-soluble polymers, clay minerals, purified water and the like, with addition of pH adjustors, antioxidants, chelating agents, antiseptics and fungicides, coloring agents, aromas and the like if necessary. Also, there may be included differentiation-inducing components, or other components such as circulation promoters, microbicides, antiphlogistic agents, cell activators, vitamins, amino acids, humectants, keratolytic agents and the like, as necessary.

The dosage of a drug according to the invention will differ depending on the patient's severity of symptoms, age, gender and body weight, the dosage form and type of salt, drug sensitivity, the specific type of disease, etc. In certain embodiment, the dosage ranges from about 30 μg to 1000 mg, preferably from 100 μg to 500 mg and more preferably from 100 μg to 100 mg per day for adults in the case of oral administration or about 1-3000 μg/kg and preferably 3-1000 μg/kg per day for adults in the case of injection, administered once or divided over several times a day.

EXAMPLES

Preferred embodiments of the compounds of the invention represented by formula (I) above and salts thereof will now be explained, with the understanding that the following examples and test examples are only representative and are not intended to be restrictive on the compounds of the invention or their salts in any way. It will be apparent to those skilled in the art that the present invention can be carried out with various modifications added beyond these examples, and such modifications are also encompassed within the claims of the present specification.

Example 1

1-(3,5-Di-tert-butyl-4-hydroxy-phenyl)-2-(2-imino-4-propyl-pyrrolidin-1-yl)-ethanone hydrobromide

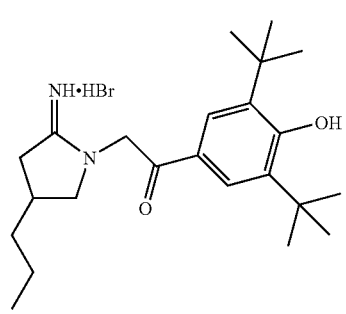

(Step 1) Methyl (E)-2-hexenoate

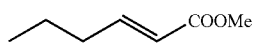

Methyl 2-[(Z)-1-triphenylphosphinylidene]acetate (21 g, 63 mmol) was added to a solution of n-butyraldehyde (4.5 g, 62 mmol) in acetonitrile (90 ml) and the reaction mixture was stirred at room temperature for 12 hours. After distilling off the solvent under reduced pressure, the residue was purified by silica gel column chromatography (solvent: n-hexane-ethyl acetate) to yield the title compound (4.62 g) as a light yellow oil. 1H-NMR (CDCl3) δ(ppm) 0.93 (3H, t, J=7.2 Hz), 1.44-1.54 (2H, m), 2.17 (2H, q, J=7.2 Hz), 3.72 (3H, s), 5.82 (1H, d, J=15.6 Hz), 6.97 (1H, dt, J=15.6 Hz, 7.2 Hz).

(Step 2) Methyl 3-(nitromethyl)hexanoate

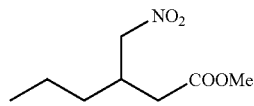

Nitromethane (2.54 ml, 46 mmol) and 1,8-diazabicyclo[5.4.0]undec-7-ene (5.4 ml, 36 mmol) were added to a solution of methyl (E)-2-hexenoate (4.62 g, 36 mmol) in acetonitrile (20 ml) and the reaction mixture was stirred at room temperature for 14 hours. The reaction mixture was acidified by addition of a 1N HCl aqueous solution and then extracted with ethyl acetate. After washing the organic layer with brine and drying over anhydrous magnesium sulfate, the solvent was distilled off under reduced pressure. The residue was purified by silica gel column chromatography (solvent: n-hexane-ethyl acetate) to yield the title compound (3.64 g) as a light yellow oil. 1H-NMR (CDCl3) δ(ppm) 0.92 (3H, t, J=0.8 Hz), 1.29-1.48 (4H, m), 2.45 (2H, d, J=6.4 Hz), 2.57-2.68 (1H, m), 3.69 (3H, s), 4.43 (1H, dd, J=14.0 Hz, 6.0 Hz), 4.50 (1H, dd, J=14.0, 6.8 Hz)

(Step 3) 4-Propyl-2-pyrrolidinone

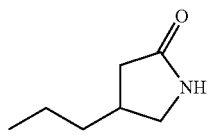

Platinum oxide (0.4 g) was added to a solution of methyl 3-(nitromethyl)hexanoate (3.64 g, 19.2 mmol) in ethanol (20 ml) was added and the mixture was stirred at room temperature for 18 hours under a hydrogen stream. The reaction mixture was filtered through celite, and then the solvent of the filtrate was distilled off under reduced pressure. The residue was purified by silica gel column chromatography (solvent: n-hexane-ethyl acetate, ethyl acetate: methanol) to yield the title compound (1.63 g) as a light yellow oil. $^1$H-NMR (CDCl$_3$) δ(ppm) 0.92 (3H, t, J=7.2 Hz), 1.27-1.53 (4H, m), 1.93-2.05 (1H, m), 2.37-2.53 (2H, m), 3.01 (1H, dd, J=9.2 Hz, 6.4 Hz), 3.48 (1H, dd, J=9.2 Hz, 9.2 Hz), 5.67-5.97 (1H, m)

(Step 4) 5-Methoxy-3-propyl-3,4-dihydro-2H-pyrrole

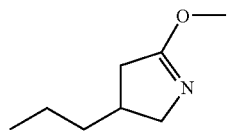

Trimethyloxonium tetrafluoroborate (715 mg, 4.83 mmol) was added to a solution of 4-propyl-2-pyrrolidinone (410 mg, 3.22 mmol) in methylene chloride (8 ml) and the mixture was stirred at room temperature for 14 hours. Saturated aqueous sodium hydrogencarbonate solution was added to the reaction mixture to render it weekly basic and then it was extracted with ethyl acetate. After washing the organic layer with brine and drying over anhydrous magnesium sulfate, the organic layer was subjected to distillation under reduced pressure. The residue was purified by silica gel column chromatography (solvent: n-hexane-ethyl acetate) to yield the title compound (306 mg) as a light yellow oil. 1H-NMR (CDCl3) δ(ppm) 0.90 (3H, t, J=7.2 Hz), 1.21-1.50 (4H, m), 2.13 (1H, dd, J=16.4 Hz, 16.8 Hz), 2.34-2.48 (1H, m), 2.57 (1H, dd, J=16.4 Hz, 9.2 Hz), 3.24 (1H, dd, J=13.6 Hz, 6.0 Hz), 3.71-3.90 (4H, m)

(Step 5)
(4-Propyltetrahydro-1H-2-pyrrolylidene)ammonium chloride

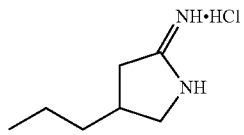

Ammonium chloride (110 mg, 2.06 mmol) was added to a solution of 5-methoxy-3-propyl-3,4-dihydro-2H-pyrrole (306 mg, 2.17 mmol) in ethanol (12 ml) and the mixture was heated to reflux for 4 hours. The reaction mixture was filtered and the filtrate was distilled off under reduced pressure to yield a crude product of the title compound (257 mg) as a white solid. 1H-NMR (DMSO-d6) δ(ppm) 0.86 (3H, t, J=7.2 Hz), 1.12-1.52 (4H, m), 2.34-2.60 (1H and DMSO, m), 2.78-2.93 (1H, m), 3.05-3.22 (2H, m), 3.54-3.70 (1H, m)

Example 1

Final Step

2-Bromo-1-[3,5-di-tert-butyl-4-hydroxyphenyl]-1-ethanone (569 mg, 1.74 mmol) was added to a solution of (4-propyltetrahydro-1H-2-pyrrolylidene)ammonium chloride (257 mg, 1.58 mmol) and 1,8-diazabicyclo[5.4.0]undec-7-ene (236 µl, 1.58 mmol) in acetonitrile (15 ml) while cooling on ice and the mixture was stirred at room temperature for 15 hours. The crystals precipitated during the reaction were filtered to yield the title compound (100 mg) as light yellow crystals. The solvent was distilled off from the mother liquor. The residue was purified by silica gel column chromatography (solvent: ethyl acetate: methanol) to yield the additional title compound (64 mg) as light yellow crystals. 1H-NMR (DMSO-d6) δ(ppm) 0.88 (3H, t, J=7.2 Hz), 1.10-1.63 (23H, m), 2.50-2.68 (1H, m), 3.08 (1H, dd, J=17.6 Hz, 8.4 Hz), 3.63-3.80 (1H, m), 5.13 (2H, s), 7.71 (2H, s), 8.03 (1H, brs), 8.71 (1H, s), 9.20 (1H, s). MS: m/e(ESI) 373.2 (MH+)

Example 2

2-((3R,4R)-3-Benzyl-2-imino-4-propyl-pyrrolidin-1-yl)-1-(3,5-di-tert-butyl-4-hydroxy-phenyl)-ethanone hydrobromide

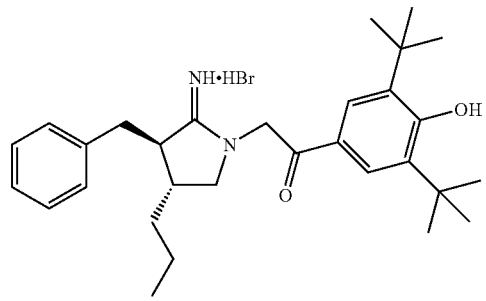

(Step 1) tert-Butyl 2-oxo-4-propyl-1-pyrrolidinecarboxylate

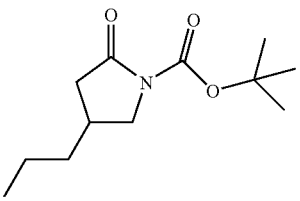

Triethylamine (81.4 ml, 10 mmol), tert-butyl dicarbonate (4.2 g, 19.2 mmol) and dimethylaminopyridine (1.18 g, 9.58 mmol) were added to a solution of 4-propyl-2-pyrrolidinone (1.22 g, 9.59 mmol) in methylene chloride (20 ml) and the mixture was stirred at room temperature for 12 hours. After distilling off the solvent under reduced pressure, the residue was purified by silica gel column chromatography (solvent: n-hexane-ethyl acetate) to yield the title compound (1.35 g) as a colorless oil. 1H-NMR (CDCl3) δ(ppm) 0.93 (3H, t, J=7.2 Hz), 1.28-1.50 (4H, m), 1.52 (9H, s), 2.14-2.32 (2H, m), 2.61 (1H, dd, J=15.0 Hz, 7.0 Hz), 3.30 (1H, dd, J=10.8 Hz, 7.2 Hz), 3.87 (1H, dd, J=10.8 Hz, 8.0 Hz)

(Step 2) tert-Butyl 3-benzyl-2-oxo-4-propyl-1-pyrrolidinecarboxylate

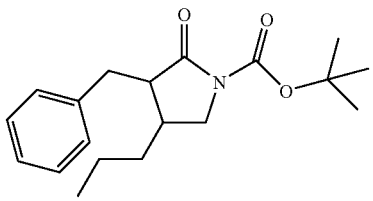

A 1.0 M tetrahydrofuran solution of lithium hexamethyldisilazane (6.2 ml, 6.2 mmol) was gradually added to a solution of tert-butyl. 2-oxo-4-propyl-1-pyrrolidinecarboxylate (1.35 g, 5.94 mmol) in tetrahydrofuran (20 ml) at −70° C. and the mixture was stirred for 15 minutes. Benzyl bromide was added to the reaction mixture and the temperature of the mixture was gradually raised to 0° C. and it was stirred for 3 hours. Saturated aqueous ammonium chloride solution was added to the reaction mixture and extraction was performed with ethyl acetate. After washing the organic layer with brine and drying over anhydrous magnesium sulfate, the solvent was distilled off under reduced pressure. The residue was purified by silica gel column chromatography (solvent: n-hexane-ethyl acetate) to yield the title compound (1.22 g) as a light yellow oil. $^1$H-NMR (CDCl$_3$) δ(ppm) 0.80 (3H, t, J=7.2 Hz), 1.10-1.40 (4H, m), 1.52 (9H, s), 1.87-1.95 (1H, m), 2.44-2.52 (1H, m), 2.90 (1H, dd, J=14.4 Hz, 7.2 Hz), 3.10 (1H, dd, J=14.4 Hz, 5.2 Hz), 3.15 (1H, dd, J=10.8 Hz, 8.0 Hz), 3.71 (1H, dd, J=10.8 Hz, 8.0 Hz), 7.15-7.33 (5H, m)

(Step 3) 3-Benzyl-4-propyl-2-pyrrolidinone

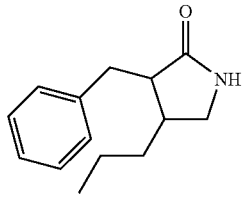

Trifluoroacetic acid (10 ml) was added to a solution of tert-butyl 3-benzyl-2-oxo-4-propyl-1-pyrrolidinecarboxylate (1.22 g, 3.84 mmol) in methylene chloride (10 ml) while cooling on ice and the mixture was stirred for 14 hours. Saturated aqueous sodium hydrogencarbonate solution was added to the reaction mixture and extraction was performed with ethyl acetate. After washing the organic layer with brine and drying over anhydrous magnesium sulfate, the solvent was distilled off under reduced pressure to yield a crude product of the title compound (0.83 g) as white crystals. 1H-NMR (CDCl3) δ(ppm) 0.79 (3H, t, J=7.2 Hz), 1.08-1.36 (4H, m), 2.04-2.21 (1H, m), 2.28-2.40 (1H, m), 2.81-2.96 (2H, m), 3.09 (1H, dd, J=14.0 Hz, 4.8 Hz), 3.29 (1H, dd, J=8.4 Hz, 8.4 Hz), 5.73 (1H, brs), 7.15-7.36 (5H, m)

(Step 4)
4-Benzyl-3-propyl-3,4-dihydro-2H-5-pyrrolyl methyl ether

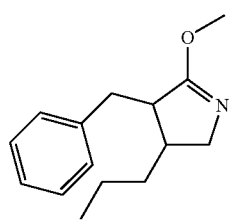

Trimethyloxonium tetrafluoroborate (0.85 g, 5.7 mmol) was added to a solution of 3-benzyl-4-propyl-2-pyrrolidinone (0.83 g, 3.8 mmol) in methylene chloride (15 ml) and the mixture was stirred at room temperature for 14 hours. Saturated aqueous sodium hydrogencarbonate solution was added to the reaction mixture to render it weekly basic and then extraction was performed with ethyl acetate. After washing the organic layer with brine and drying over anhydrous magnesium sulfate, the solvent was distilled off under reduced pressure. The residue was purified by silica gel column chromatography (solvent: n-hexane-ethyl acetate) to yield the title compound (0.67 g) as a light yellow oil. 1H-NMR (CDCl3) δ(ppm) 0.75 (3H, t, J=7.2 Hz), 1.02-1.28 (4H, m), 2.02-2.16 (1H, m), 2.55-2.66 (1H, m), 2.69 (1H, dd, J=13.2 Hz, 8.4 Hz), 2.99 (1H, dd, J=13.2 Hz, 4.8 Hz), 3.10 (1H, dd, J=13.2 Hz, 5.2 Hz), 3.58 (1H, dd, J=13.2 Hz, 8.8 Hz), 3.83 (3H, s), 7.05-7.40 (5H, m)

(Step 5) (3-Benzyl-4-propyltetrahydro-1H-2-pyrrolylidene)ammonium chloride

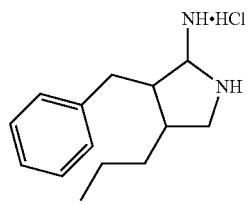

Ammonium chloride (155 mg, 2.9 mmol) was added to a solution of 4-benzyl-3-propyl-3,4-dihydro-2H-5-pyrrolyl methyl ether (0.67 g, 2.9 mmol) in ethanol (15 ml) and the mixture was heated to reflux for 4 hours. The reaction mixture was filtered and the filtrate was distilled off under reduced pressure. The residue was crystallized from ethyl acetate to yield the title compound (440 mg) as a white crude product. 1H-NMR (DMSO-d6) δ(ppm) 0.62 (3H, t, J=7.2 Hz), 0.87-1.20 (4H, m), 2.01-2.15 (1H, m), 2.72-2.85 (1H, m), 2.88-2.98 (1H, m), 3.05-3.25 (1H, m), 3.50-3.62 (1H, m), 7.19-7.40 (5H, m)

Example 2

Final Step

Method A

A basic resin-DIAION SA10A (14.5 g) that had been treated with aqueous sodium hydroxide solution was thoroughly washed with water and ethanol. The resin was then added to a solution of dl-[(3S,4R)-4-benzyl-3-propyl-3,4-dihydro-2H-5-pyrroleamine hydrochloride (1.63 g, 7.5 mmol) in methanol (30 ml) and the mixture was stirred for 30 minutes. After filtering the resin, the solvent was distilled off under reduced pressure to yield dl-[(3S,4R)-4-benzyl-3-propyl-3,4-dihydro-2H-5-pyrroleamine (1.45 g).

Subsequently, a solution of the dl-[(3S,4R)-4-benzyl-3-propyl-3,4-dihydro-2H-5-pyrroleamine and phenacyl bromide (2.7 g, 8.3 mmol) in ethanol was heated to reflux for 6 hours. After distilling off the solvent under reduced pressure, crystallization from ether yielded the title compound (2.54 g) as a white amorphous solid.

Method B

2-Bromo-1-[3,5-di-tert-butyl-4-hydroxyphenyl]-1-ethanone (405 mg, 1.03 mmol) was added to a solution of (3-benzyl-4-propyltetrahydro-1H-2-pyrrolylidene)ammonium chloride (223 mg, 1.03 mmol) and 1,8-diazabicyclo[5.4.0]undec-7-ene (154 μl, 1.03 mmol) in acetonitrile (10 ml) while cooling on ice and the mixture was stirred at room temperature for 7 hours and further at 60° C. for 3 hours. The solvent was distilled off and the residue was purified by silica gel column chromatography (solvent: ethyl acetate: methanol) to yield title compound (107 mg) as a white amorphous solid. 1H-NMR (DMSO-d6) δ(ppm) 0.61 (3H, t, J=7.2 Hz), 0.85-

1.30 (5H, m), 1.41 (18H, s), 2.05-2.16 (1H, m), 2.75-2.88 (1H, m), 3.02-3.28 (2H, m), 3.75-3.86 (1H, m), 5.17 (2H, s), 7.20-7.42 (5H, m), 7.73 (2H, s), 8.05 (1H, s), 8.94 (1H, s), 9.41 (1H, s). MS: m/e(ESI) 463.2 (MH+)

Example 3

N-{3-tert-Butyl-2-hydroxy-5-[2-((3S,4S)-2-imino-3-phenyl-4-propyl-pyrrolidin-1-yl)-acetyl]-phenyl}-N-methyl-methanesulfonamide hydrobromide

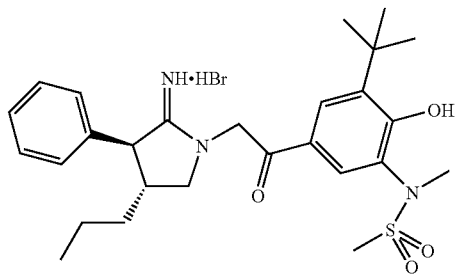

(Step 1) [(3S,4R)-3-Phenyl-4-propyltetrahydro-1H-2-pyrrolylidene]ammonium chloride

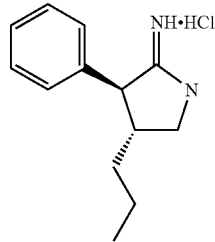

Potassium t-butoxide (8.48 g, 76 mmol) was added to a suspension of n-butyltriphenylphosphonium bromide (30.17 g, 76 mmol) in tetrahydrofuran (140 ml) and the mixture was stirred at room temperature for 1 hour. The reaction mixture was water-cooled and a solution of ethyl benzoylformate (10.0 ml, 63 mmol) in tetrahydrofuran (50 ml) was added dropwise so that the internal temperature did not exceed 20° C. After stirring the reaction mixture for 1.5 hours, water was poured into the mixture and extraction was performed with ethyl acetate. After washing the organic layer with brine and drying over anhydrous magnesium sulfate, the solvent was distilled off under reduced pressure. n-Hexane was added to the residue and the insoluble portion was filtered off. Purification on silica gel chromatography (solvent: n-hexane-ethyl acetate) yielded a colorless oil (13.27 g).

To a solution of this oil (13.27 g, 61 mmol) in dimethyl sulfoxide (80 ml) was added anhydrous potassium carbonate (4.21 g, 30 mmol). The mixture was heated at 90° C. A solution of nitromethane (4.95 ml, 91 mmol) in dimethyl sulfoxide (40 ml) was added to the reaction mixture while stirring over 40 minutes. After stirring the reaction mixture for 3 hours, it was poured into an aqueous acetic acid solution and extraction was performed with ethyl acetate. The organic layer was washed with 1N hydrochloric acid, a saturated aqueous sodium carbonate solution and brine; then it was dried over anhydrous magnesium sulfate and the solvent was distilled off under reduced pressure. The residue was purified by silica gel column chromatography (solvent: n-hexane-ethyl acetate) to yield a yellow oil (6.40 g).

To a solution of this oil (12.3 g, 44 mmol) in ethanol (200 ml) was added platinum oxide (1.2 g). The mixture was stirred at room temperature under a hydrogen stream for 15 hours. After filtering off the reaction mixture, the solvent was distilled under reduced pressure and the residue was heated at 110° C. for 1 hour. Water was added to the residue and extraction was performed with ethyl acetate. The organic layer was washed with 1N hydrochloric acid, a saturated aqueous sodium carbonate solution and brine; then it was dried over anhydrous magnesium sulfate and the solvent was distilled off under reduced pressure. The residue was purified by silica gel column chromatography (solvent: n-hexane-ethyl acetate) to yield a white solid (5.95 g).

To a solution of this solid (5.95 g, 29 mmol) in methylene chloride (100 ml) was added trimethyloxonium tetrafluoroborate (5.2 g, 35 mmol). The mixture was stirred at room temperature for 15 hours. Saturated aqueous sodium hydrogencarbonate solution was added to the reaction mixture and extraction was performed with chloroform. After drying the organic layer over anhydrous magnesium sulfate, the organic layer was subjected to distillation under reduced pressure. The residue was dissolved in ethyl acetate and filtered through alumina-silica gel. Distillation under reduced pressure then yielded a light yellow oil (6.91 g).

To a solution of this oil (6.31 g, 29 mmol) in methanol (60 ml) was added ammonium chloride (1.56 g, 29 mmol). The mixture was heated to reflux for 21 hours. The reaction mixture was distilled off under reduced pressure and ethyl acetate was added to the residue. The precipitates were filtered off to yield a crude product of the titled compound (5.40 g) as a white solid. 1H-NMR (DMSO-d6) δ(ppm) 0.77 (3H, t, J=7.2 Hz), 1.09-1.25 (2H, m), 1.35-1.47 (2H, m), 2.39 (1H, m), 3.26 (1H, m), 3.77 (1H, dd, J=10.8 Hz, 8.8 Hz), 3.96 (1H, d, J=8.8 Hz), 7.22-7.44 (5H, m), 8.52 (1H, brs), 9.05 (1H, brs)

Example 3

Final Step

Phenacyl bromide (1.32 g, 3.5 mmol) was added to a solution of [(3S,4R)-3-phenyl-4-propyltetrahydro-1H-2-pyrolidene]ammonium chloride (800 mg, 3.5 mmol) and 1,8-diazabicyclo[5.4.0]undec-7-ene (0.52 ml, 3.5 mmol) in acetonitrile (10 ml). The mixture was stirred at 60° C. for 9 hours. The reaction mixture was distilled off under reduced pressure, the residue was purified by silica gel column chromatography (solvent: ethyl acetate: methanol) and crystallized from ethyl acetate-diisopropyl ether to yield the titled compound (710 mg) as a slightly palomino powder. 1H-NMR (DMSO-d6) δ: 0.83 (3H, t, J=7.6 Hz), 1.20-1.33 (2H, m), 1.40 (9H, s), 1.47-1.58 (2H, m), 2.42 (1H, m), 3.16 (3H, s), 3.46 (1H, m), 3.93 (1H, m), 4.16 (1H, d, J=7.2 Hz), 5.27 (2H, s), 7.35-7.50 (5H, m), 7.82 (1H, s), 7.94 (1H, s), 8.89 (1H, s), 9.01 (1H, s), 10.03 (1H, brs).

Example 4

1-(3,5-Di-tert-butyl-4-hydroxy-phenyl)-2-[(3S,4S)-2-imino-4-(2-methoxy-ethyl)-3-phenyl-pyrrolidin-1-yl]-ethanone hydrobromide

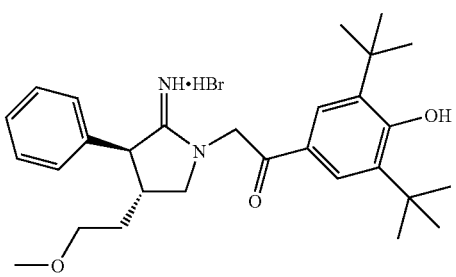

(Step 1) [(3S,4R)-4-(2-Methoxyethyl)-3-phenyltetrahydro-1H-2-pyrrolylidene]ammonium chloride

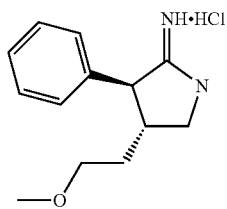

A suspension of 3-benzyloxypropyltriphenylphosphonium bromide (21.8 g, 44 mmol) in tetrahydrofuran (100 ml) was cooled to −30° C. To this was added dropwise n-butyllithium (2.6 M, 17.8 ml, 44 mmol) and the mixture was stirred for 1 hour. The mixture was cooled to −50° C. and a solution of ethyl benzoylformate (7.2 g, 40 mmol) in tetrahydrofuran (10 ml) was added dropwise so that the internal temperature did not exceed −40° C. After stirring the reaction mixture for 7 hours, water was added to the mixture and extraction was performed with ethyl acetate. After washing the organic layer with water and then brine and drying over anhydrous magnesium sulfate, the solvent was distilled off under reduced pressure. Toluene was added to the residue and the insoluble portion was filtered off. Then purification on silica gel chromatography (solvent: n-hexane-ethyl acetate) yielded a colorless oil (3.66 g).

To a solution of this oil (4.17 g, 14 mmol) in dimethyl sulfoxide (15 ml) was added anhydrous potassium carbonate (0.93 g, 6.7 mmol). The mixture was heated at 90° C. A solution of nitromethane (1.1 ml, 20 mmol) in dimethyl sulfoxide (10 ml) was added to the reaction mixture while stirring over 40 minutes. After stirring the reaction mixture for 3 hours, it was poured into 1N hydrochloric acid and extraction was performed with ethyl acetate. The organic layer was washed with water, a saturated aqueous sodium carbonate solution and brine; then it was dried over anhydrous magnesium sulfate and the solvent was distilled off under reduced pressure. The residue was purified by silica gel column chromatography (solvent: n-hexane-ethyl acetate) to yield a yellow oil (3.07 g).

To a solution of this oil (3.07 g, 8.3 mmol) in ethanol (50 ml) were added concentrated hydrochloric acid (6.9 ml, 83 mmol) and zinc (2.7 g, 42 mmol), and the mixture was stirred at room temperature for 1 hour. The reaction mixture was cooled on ice, to which 5N aqueous sodium hydroxide solution (17 ml, 85 mmol) was added. The mixture was stirred at room temperature for 11 hours. After filtering the reaction mixture through celite, the solvent was distilled off under reduced pressure and the residue was heated at 120° C. for 1 hour. The residue was purified by silica gel column chromatography (solvent: n-hexane-ethyl acetate) to yield a slightly yellow oil (1.03 g).

To a solution of this slightly yellow oil (1.03 g, 3.5 mmol) in ethanol (20 ml) were added 10% palladium-carbon (1.0 g) and ammonium formate (1.1 g, 18 mmol). The mixture was heated to reflux for 6 hours. The reaction mixture was filtered off and was subjected to distillation under reduced pressure. The residue was purified by silica gel column chromatography (solvent: ethyl acetate-methanol) to yield a white solid (669 mg).

To a solution of this solid (600 mg, 2.9 mmol) in methylene chloride (10 ml) was added trimethyloxonium tetrafluoroborate (1.1 g, 7.0 mmol). The mixture was stirred at room temperature for 15 hours. The reaction was poured into a saturated aqueous sodium hydrogencarbonate solution and extraction was performed with chloroform. After drying the organic layer over anhydrous magnesium sulfate, the organic layer was subjected to distillation under reduced pressure. The residue was purified by silica gel column chromatography (solvent: n-hexane-ethyl acetate) to yield a colorless oil (515 mg).

To a solution of this oil (515 mg, 2.2 mmol) in methanol (5 ml) was added ammonium chloride (118 mg, 2.2 mmol). The mixture was heated to reflux for 21 hours. The reaction mixture was subjected to distillation under reduced pressure. Ethyl acetate was added to the residue. The precipitates were filtered out to yield a crude product of the title compound (471 mg) as a white powder. 1H-NMR (DMSO-d6) δ(ppm) 1.62-1.78 (2H, m), 2.42-2.56 (1H and DMSO, m), 3.11 (3H, s), 3.18-3.42 (3H and H$_2$O, m), 3.78 (1H, dd, J=10.8 Hz, 8.8 Hz), 4.04 (1H, d, J=8.8 Hz), 7.26-7.32 (2H, m), 7.34-7.45 (3H, m)

Example 4

Final Step

Phenacyl bromide (408 mg, 1.3 mmol) was added to a solution of [(3S,4R)-4-(2-methoxyethyl)-3-phenyltetrahydro-1H-2-pyrrolylidene]ammonium chloride (300 mg, 1.3 mmol) and 1,8-diazabicyclo[5.4.0]undec-7-ene (0.19 ml, 1.3 mmol) in acetonitrile (5 ml). The mixture was stirred at 60° C. for 5 hours. The reaction mixture was subjected to distillation under reduced pressure. The residue was purified by silica gel chromatography (solvent: ethyl acetate: methanol) and crystallization from ethyl acetate-diisopropyl ether to yield the title compound (273 mg) as a slightly palomino powder. 1H-NMR (DMSO-d6) δ: 1.43 (18H, s), 1.44-1.60 (2H, m), 2.55 (1H, m), 3.15 (3H, s), 3.24-3.42 (3H, m), 3.51 (1H, dd, J=6.8, 10.4 Hz), 3.90 (1H, dd, J=7.6, 10.4 Hz), 4.24 (2H, d, J=7.2 Hz), 5.30 (2H, s), 7.36-7.50 (5H, m), 7.78 (2H, s), 8.07 (1H, brs), 8.86 (1H, brs), 8.96 (1H, brs).

Example 5

1-(3,5-Di-tert-butyl-4-hydroxy-phenyl)-2-[(3S,4S)-2-imino-4-(3-methoxy-propyl)-3-phenyl-pyrrolidin-1-yl]-ethanone hydrobromide

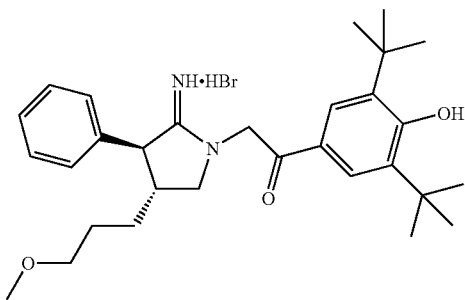

(Step 1) [(3S,4R)-4-(3-methoxypropyl)-3-phenyltetrahydro-1H-2-pyrrolylidene]ammonium chloride

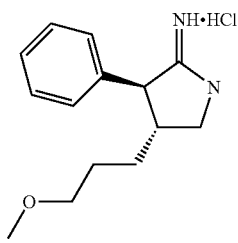

A suspension of sodium hydride (70%, 1.06 g, 31 mmol) in tetrahydrofuran (80 ml) was cooled on ice, to which a solution of methyl 2-phenyl-2-diethylphosphonoacetate (8.00 g, 28 mmol) in tetrahydrofuran (10 ml) was added dropwise. The mixture was stirred for 1 hour. A solution of 4-benzyloxybutanal (5.48 g, 31 mmol) in tetrahydrofuran (10 ml) was added dropwise to the reaction mixture and stirred at room temperature for 17 hours. Water was then added to the reaction mixture and extraction was performed with ethyl acetate. After washing the organic layer with water and brine and drying over anhydrous magnesium sulfate, the solvent was distilled off under reduced pressure. The residue was purified by silica gel column chromatography (solvent: n-hexane-ethyl acetate) to yield a colorless oil (4.05 g).

To a solution of this oil (4.05 g, 12.5 mmol) in dimethyl sulfoxide (15 ml) was added anhydrous potassium carbonate (0.86 g, 6.3 mmol). The mixture was heated at 80° C. A solution of nitromethane (1.0 ml, 19 mmol) in dimethyl sulfoxide (15 ml) was added to the reaction mixture while stirring over 55 minutes. After stirring the reaction mixture for 2.5 hours, it was poured into 1N hydrochloric acid and extraction was performed with ethyl acetate. The organic layer was washed with water, a saturated aqueous sodium carbonate solution and brine; then it was dried over anhydrous magnesium sulfate and the solvent was distilled off under reduced pressure. The residue was purified by silica gel column chromatography (solvent: n-hexane-ethyl acetate) to yield a yellow oil (2.04 g).

To a solution of this oil (2.04 g, 5.5 mmol) in ethanol (35 ml) were added concentrated hydrochloric acid (4.6 ml, 55 mmol) and zinc (1.8 g, 28 mmol), and after stirring the mixture at room temperature for 20 minutes, it was further stirred at 60° C. for 1 hour. The reaction mixture was cooled on ice, to which 5N aqueous sodium hydroxide solution (12 ml, 60 mmol) was added. The mixture was stirred at room temperature for 15 minutes. After filtering the reaction mixture through celite, the solvent was distilled off under reduced pressure and the residue was heated at 110° C. for 1 hour. The residue was purified by silica gel column chromatography (solvent: n-hexane-ethyl acetate) to yield a slightly yellow oil (1.03 g).

To a solution of this slightly yellow oil (1.03 g, 3.3 mmol) in ethanol (20 ml) were added 10% palladium-carbon (1.0 g) and ammonium formate (1.05 g, 17 mmol). The mixture was heated to reflux for 6 hours. The reaction mixture was filtered and was subjected to distillation under reduced pressure. The residue was purified by silica gel column chromatography (solvent: ethyl acetate-methanol) to yield a white solid (649 mg).

To a solution of this solid (600 mg, 2.7 mmol) in methylene chloride (10 ml) was added trimethyloxonium tetrafluoroborate (973 mg, 6.6 mmol). The mixture was stirred at room temperature for 15 hours. The reaction was poured into a saturated aqueous sodium hydrogencarbonate solution and extraction was performed with chloroform. After drying the organic layer over magnesium sulfate, the organic layer was subjected to distillation under reduced pressure. The residue was purified by silica gel column chromatography (solvent: n-hexane-ethyl acetate) to yield a colorless oil (503 mg).

To a solution of this oil (503 mg, 2.0 mmol) in methanol (5 ml) was added ammonium chloride (109 mg, 2.0 mmol). The mixture was heated to reflux for 19 hours. The reaction mixture was subjected to distillation under reduced pressure. Ethyl acetate was added to the residue. The precipitates were filtered out to yield a crude product of the title compound (410 mg) as a white powder. 1H-NMR (DMSO-d6) δ(ppm) 1.32-1.54 (4H, m), 2.41 (1H, m), 3.15 (3H, s), 3.22 (2H, t, J=6.0 Hz), 3.27 (1H, dd, J=10.8 Hz, 8.0 Hz), 3.80 (1H, dd, J=10.8 Hz, 8.8 Hz), 3.99 (1H, d, J=8.8 Hz), 7.27-7.31 (2H, m), 7.34-7.45 (3H, m)

Example 5

Final Step

Phenacyl bromide (386 mg, 1.2 mmol) was added to a solution of [(3S,4R)-4-(3-methoxypropyl)-3-phenyltetrahydro-1H-2-pyrrolylidene]ammonium chloride (300 mg, 1.2 mmol) and 1,8-diazabicyclo[5.4.0]undec-7-ene (0.18 ml, 1.2 mmol) in acetonitrile (5 ml). The mixture was stirred at 60° C. for 5 hours. The reaction mixture was distilled off under reduced pressure and the residue was purified by silica gel column chromatography (solvent: ethyl acetate: methanol) and crystallized from ethyl acetate-diisopropyl ether to yield the titled compound (273 mg) as white cotton-like crystals. 1H-NMR (DMSO-d6) δ: 1.43 (18H, s), 1.44-1.62 (4H, m), 2.42 (1H, m), 3.18 (3H, s), 3.26 (2H, t, J=6.0 Hz), 3.36 (1H, m), 3.46 (1H, dd, J=6.0, 10.8 Hz), 3.92 (1H, dd, J=7.6, 10.8 Hz), 4.16 (2H, d, J=7.2 Hz), 5.29 (2H, s), 7.36-7.50 (5H, m), 7.78 (2H, s), 8.07 (1H, brs), 8.86 (1H, brs), 8.96 (1H, brs).

Example 6

1-(3,5-Di-tert-butyl-4-hydroxy-phenyl)-2-((3S,4S)-2-imino-4-methoxymethyl-3-phenyl-pyrrolidin-1-yl)-ethanone hydrobromide

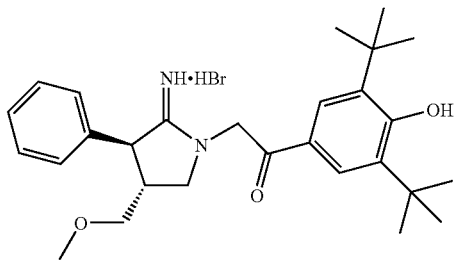

(Step 1) (3S,4R)-4-[(Benzyloxy)methyl]-3-phenyltetrahydro-1H-2-pyrrolone

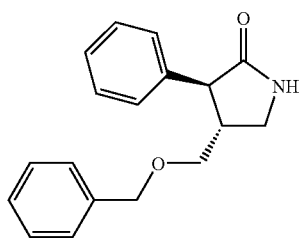

A suspension of sodium hydride (70%, 0.87 g, 25 mmol) in tetrahydrofuran (40 ml) was cooled on ice, to which a solution of methyl 2-phenyl-2-diethylphosphonoacetate (6.03 g, 21 mmol) in tetrahydrofuran (10 ml) was added dropwise. The mixture was stirred for 1 hour. The reaction mixture was cooled on ice, to which a solution of 2-benzyloxyethanal (4.74 g, 32 mmol) in tetrahydrofuran (10 ml) was added dropwise. The mixture was stirred at room temperature for 1.5 hours. 2-Benzyloxyethanal (2.14 g, 14 mmol) was further added to the reaction mixture and stirred at room temperature for 17 hours. The reaction mixture was poured into brine and extraction was performed with ethyl acetate. After washing the organic layer with water and brine and drying over anhydrous magnesium sulfate, the solvent was distilled off under reduced pressure. The residue was purified by silica gel column chromatography (solvent: n-hexane-ethyl acetate) to yield a slightly yellow oil (3.89 g).

To a solution of this oil (3.89 g, 13.8 mmol) in dimethyl sulfoxide (15 ml) was added anhydrous potassium carbonate (0.95 g, 6.9 mmol). The mixture was heated at 90° C. A solution of nitromethane (1.1 ml, 21 mmol) in dimethyl sulfoxide (20 ml) was added to the reaction mixture while stirring over 40 minutes. After stirring the reaction mixture for 3.5 hours, acetic acid (2 ml) and water were added to the reaction mixture and extraction was performed with ethyl acetate. The organic layer was washed with water, a saturated aqueous sodium carbonate solution and brine; then it was dried over anhydrous magnesium sulfate and the solvent was distilled off under reduced pressure. The residue was purified by silica gel column chromatography (solvent: n-hexane-ethyl acetate) to yield a slightly yellow oil (3.28 g).

To a solution of this oil (3.28 g, 9.6 mmol) in ethanol (65 ml) were added concentrated hydrochloric acid (8.0 ml, 96 mmol), and zinc (5.0 g, 77 mmol), and the mixture was stirred at room temperature for 1 hour. The reaction mixture was cooled on ice, to which 5N aqueous sodium hydroxide solution (19 ml, 95 mmol) was added. After filtering the reaction mixture through celite, the solvent was distilled off under reduced pressure. Water was added to the residue and extraction was performed with ethyl acetate. The organic layer was washed with 1N hydrochloric acid, a saturated aqueous sodium carbonate solution and brine; then it was dried over anhydrous magnesium sulfate and the solvent was distilled off under reduced pressure. The residue was purified by silica gel column chromatography (solvent: n-hexane-ethyl acetate) to yield a colorless oil (1.73 g). 1H-NMR (CDCl3) δ(ppm) 2.78 (1H, m), 3.36 (1H, dd, J=9.6 Hz, 8.0 Hz), 3.47-3.60 (4H, m), 4.47 (1H, d, J=12.0 Hz), 4.54 (1H, d, J=12.0 Hz), 6.06 (1H, brs), 7.17-7.21 (2H, m), 7.24-7.38 (8H, m)

(Step 2) (3S,4R)-4-(Hydroxymethyl)-3-phenyltetrahydro-1H-2-pyrrolone

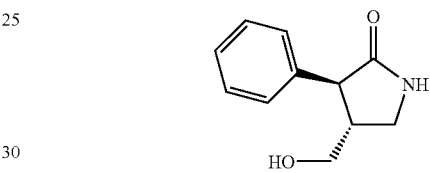

10% Palladium-carbon (1.7 g) was added to a solution of (3S,4R)-4-[(benzyloxy)methyl]-3-phenyltetrahydro-1H-2-pyrrolone (1.73 g, 6.2 mmol) in methanol (40 ml). The mixture was stirred at room temperature under a hydrogen stream for 15 hours and further stirred at 60° C. for 3 hours. The reaction mixture was filtered and was subjected to distillation under reduced pressure. Ether was added to the residue and the precipitates were filtered out to yield the title compound as a white solid (1.05 g). 1H-NMR (CDCl3) δ(ppm) 1.90 (1H, brs), 2.69 (1H, m), 3.32 (1H, dd, J=10.0 Hz, 8.0 Hz), 3.46 (1H, d, J=9.2 Hz), 3.56 (1H, t, J=8.8 Hz), 3.67 (1H, m), 3.75 (1H, m), 6.50 (1H, brs), 7.19-7.30 (3H, m), 7.32-7.38 (2H, m)

(Step 3) [(3S,4R)-4-(Methoxymethyl)-3-phenyltetrahydro-1H-2-pyrrolylidene]ammonium chloride

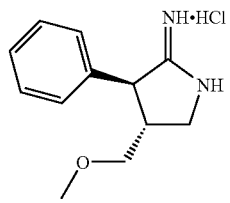

Trimethyloxonium tetrafluoroborate (1.12 g, 7.5 mmol) was added to a solution of (3S,4R)-4-(hydroxymethyl)-3-phenyltetrahydro-1H-2-pyrrolone (600 mg, 3.1 mmol) in methylene chloride. The mixture was stirred at room temperature for 14 hours. The reaction was poured into a saturated aqueous sodium hydrogencarbonate solution and extraction was performed with methylene chloride. After drying the organic layer over anhydrous magnesium sulfate, the organic layer was subjected to distillation under reduced pressure. The residue was purified by silica gel column chromatography (solvent: n-hexane-ethyl acetate) to yield a colorless oil (431 mg).

To a solution of this oil (431 mg, 2.0 mmol) in methanol (5 ml) was added ammonium chloride (105 mg, 2.0 mmol). The mixture was heated to reflux for 5 hours. The residue was purified by silica gel column chromatography (solvent: ethyl acetate: methanol) to yield the title compound as a colorless glassy solid (335 mg). 1H-NMR (DMSO-d6) δ(ppm) 2.64 (1H, m), 3.26 (3H, s), 3.37-3.46 (3H, m), 3.83 (1H, dd, J=10.2 Hz, 8.8 Hz), 4.07 (1H, d, J=8.8 Hz), 7.26-7.30 (2H, m), 7.33-7.44 (3H, m)

Example 6

Final Step

Phenacyl bromide (481 mg, 1.5 mmol) was added to a solution of [(3S,4R)-4-(methoxymethyl)-3-phenyltetrahydro-1H-2-pyrrolylidene]ammonium chloride (333 mg, 1.5 mmol) and 1,8-diazabicyclo[5.4.0]undec-7-ene (0.22 ml, 1.5 mmol) in acetonitrile (5 ml). The mixture was stirred at 60° C. for 5 hours. The reaction mixture was distilled off under reduced pressure. The residue was purified by silica gel column chromatography (solvent: ethyl acetate: methanol) and crystallized from ethyl acetate-diisopropyl ether to yield the titled compound (217 mg) as a dark palomino powder. 1H-NMR (DMSO-d6) δ: 1.44 (18H, s), 2.63 (1H, m), 3.31 (3H, s), 3.44-3.64 (3H, m), 3.96 (1H, dd, J=8.0, 10.8 Hz), 4.24 (1H, d, J=7.2 Hz), 5.27 (1H, d, J=18.0 Hz), 5.34 (1H, d, J=18.0 Hz), 7.39 (1H, m), 7.42-7.52 (4H, m), 7.78 (2H, s), 8.07 (1H, brs), 8.97 (1H, m), 9.06 (1H, brs).

The compounds of the following examples were synthesized by the same method as the final step of Example 1 above, from various 2-iminopyrrolidine derivatives and various 2-bromo-1-ethanone derivatives.

Example 7

2-(3-Benzyl-2-imino-pyrrolidin-1-yl)-1-(3,5-di-tert-butyl-4-hydroxy-phenyl)-ethanone hydrobromide

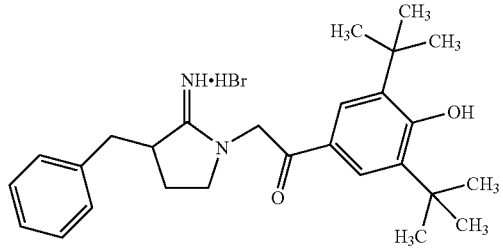

1H-NMR (DMSO-d6) δ: 1.40 (18H, s), 1.70-2.12 (2H, m), 2.68-2.81 (1H, m), 3.17-3.64 (4H, m), 5.18 (2H, s), 7.15-7.40 (5H, m), 7.73 (2H, s), 7.96-8.08 (1H, m), 8.90-9.00 (1H, m), 9.35-9.47 (1H, m). MS: m/e(ESI) 421.2 (MH+)

Example 8

2-(3-Benzyl-2-imino-4-isobutyl-pyrrolidin-1-yl)-1-(3,5-di-tert-butyl-4-hydroxy-phenyl)-ethanone hydrobromide

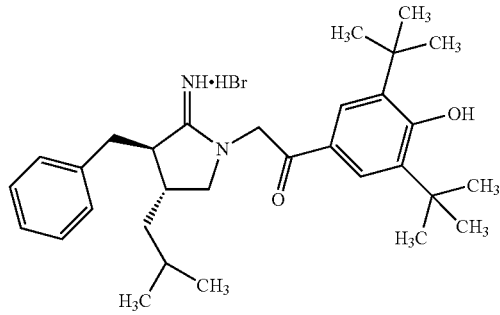

1H-NMR (DMSO-d6) δ: 0.43 (3H, d, J=6.2 Hz), 0.65 (3H, d, J=6.2 Hz), 1.00-1.30 (3H, m), 1.41 (18H, s), 2.12-2.22 (1H, m), 2.81 (1H, dd, J=10.7, J=13.2 Hz), 3.01-3.09 (1H, m), 3.14-3.24 (2H, m), 3.87 (1H, dd, J=8.8, J=10.7 Hz), 5.16 (2H, s), 7.21-7.40 (5H, m), 7.73 (2H, s), 8.06 (1H, s), 8.92 (1H, s), 9.37 (1H, s). MS: m/e(ESI) 477.2 (MH+)

Example 9

2-(3-Benzyl-4-butyl-2-imino-pyrrolidin-1-yl)-1-(3,5-di-tert-butyl-4-hydroxy-phenyl)-ethanone hydrobromide

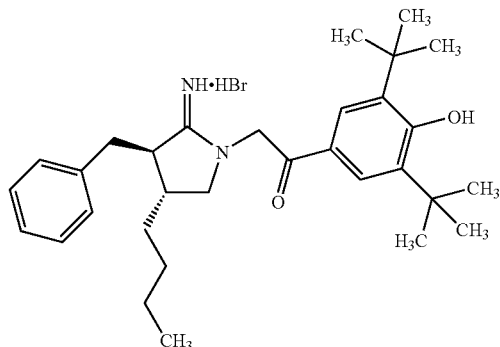

1H-NMR (DMSO-d6) δ: 0.68 (3H, t, J=7.2 Hz), 0.80-1.30 (6H, m), 1.41 (18H, s), 2.02-2.15 (1H, m), 2.78-2.84 (1H, dd, J=10.6, J=13.2 Hz), 3.02-3.09 (1H, m), 3.16-3.27 (2H, m), 3.81 (1H, dd, J=7.2, J=10.6 Hz), 5.15 (2H, s), 7.24-7.38 (5H, m), 7.73 (2H, s), 8.90 (1H, s), 9.35 (1H, s). MS: m/e(ESI) 477.2 (MH+)

Example 10

2-(3-Benzyl-2-methylimino-4-propyl-pyrrolidin-1-yl)-1-(3,5-di-tert-butyl-4-hydroxy-phenyl)-ethanone hydrobromide

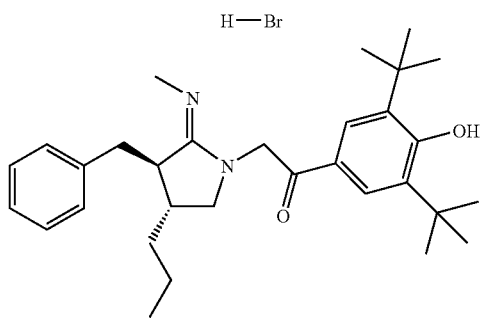

1H-NMR (DMSO-d6) δ: 0.64 (3H, t, J=7.6 Hz), 0.92-1.36 (4H, m), 1.40 (18H, s), 2.09 (1H, dd, J=5.6, J=10.6 Hz), 2.78 (1H, dd, J=10.6 Hz, J=12.6 Hz), 3.03 (3H, s), 3.13 (1H, dd, J=3.6 Hz, J=12.6 Hz), 3.23 (1H, d, J=12.6 Hz), 3.42 (1H, dd, J=5.0 Hz, J=10.6 Hz), 3.92 (1H, dd, J=5.0 Hz, J=10.6 Hz), 5.15 (2H, s), 7.24-7.42 (5H, m), 7.73 (2H, s). MS: m/e(ESI) 477.3 (MH+)

Example 11

N-{5-[2-(3-Benzyl-2-imino-4-propyl-pyrrolidin-1-yl)-acetyl]-3-tert-butyl-2-hydroxy-phenyl}-N-methyl-methanesulfonamide hydrobromide

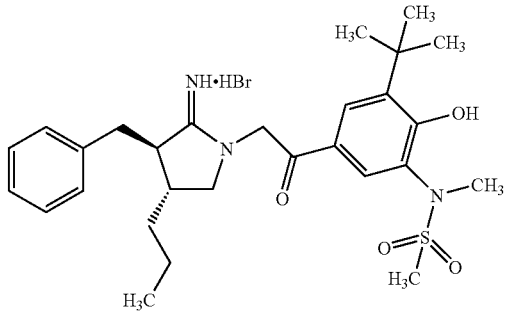

1H-NMR (DMSO-d6) δ: 0.62 (3H, t, J=7.8 Hz), 0.80-2.20 (14H, m), 2.82 (1H, t, J=10.9 Hz), 3.00-3.40 (9H, m), 3.74-3.86 (1H, m), 5.11 (2H, brs), 7.20-7.40 (5H, m), 7.77 (1H, brs), 7.88 (1H, brs), 8.97 (1H, brs), 9.38 (1H, brs), 10.01 (1H, brs). MS: m/e(ESI) 514.3 (MH+)

Example 12

1-(3,5-Di-tert-butyl-4-hydroxy-phenyl)-2-[3-(3-ethyl-pentyl)-2-imino-pyrrolidin-1-yl]-ethanone hydrobromide

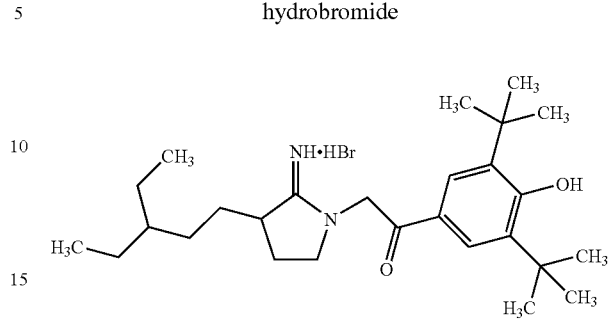

1H-NMR (DMSO-d6) δ: 0.84 (6H, t, J=7.2 Hz), 1.17-1.55 (8H, m), 1.40 (18H, s), 1.74-1.90 (2H, m), 2.23-2.34 (1H, m), 3.08-3.19 (1H, m), 3.53-3.70 (2H, m), 5.16 (2H, s), 7.72 (2H, s), 8.04 (1H, s), 8.76 (1H, s), 9.10 (1H, s). MS: m/e(ESI) 429.3 (MH+)

Example 13

2-(3-Benzyl-2-imino-4-propyl-pyrrolidin-1-yl)-1-(3,5-di-tert-butyl-4-hydroxy-phenyl)-ethanone hydrobromide

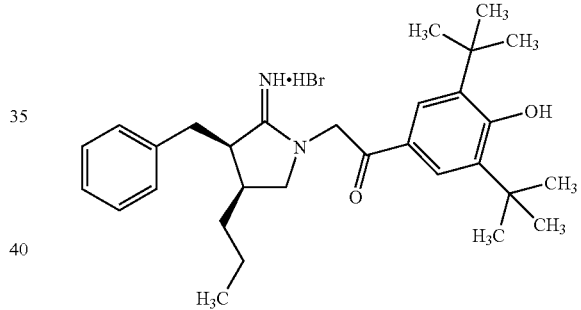

1H-NMR (DMSO-d6) δ: 0.69 (3H, t, J=7.6 Hz), 0.82-1.50 (5H, m), 1.41 (18H, s), 2.86-3.00 (1H, m), 3.05-3.20 (1H, m), 3.41-3.45 (1H, m), 3.57-3.64 (2H, m), 5.24 (2H, s), 7.20-7.42 (5H, m), 7.74 (2H, s).

Example 14

1-(3,5-Di-tert-butyl-4-hydroxy-phenyl)-2-(3-imino-8-oxa-2-aza-spiro[4.5]dec-2-yl)-ethanone hydrobromide

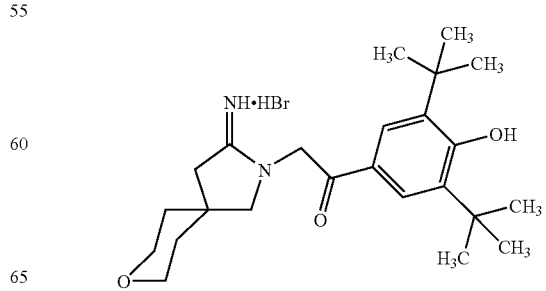

1H-NMR (DMSO-d6) δ: 1.39 (18H, s), 1.55-1.77 (4H, m), 2.88 (2H, s), 3.37-3.70 (6H, m), 5.17 (2H, s), 7.71 (2H, s), 7.93-8.11 (1H, m), 8.83 (1H, brs), 9.30 (1H, brs). MS: m/e (ESI) 401.2 (MH+)

Example 15

Ethyl 4-benzyl-1-[2-(3,5-di-tert-butyl-4-hydroxy-phenyl)-2-oxo-ethyl]-5-imino-pyrrolidine-2-carboxylate trifluoroacetate

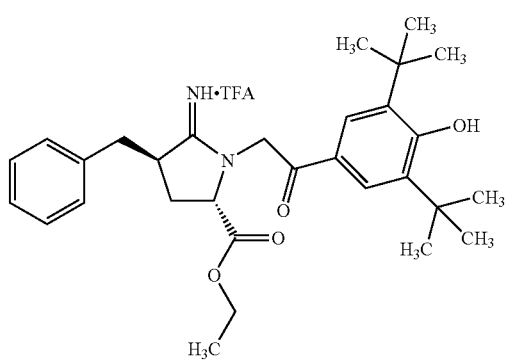

1H-NMR (DMSO-d6) δ: 1.14 (3H, t, J=7.0 Hz), 1.43 (18H, s), 2.05-2.13 (1H, m), 2.21-2.26 (1H, m), 2.78 (1H, dd, J=11.2 Hz, 13.2 Hz), 3.36 (1H, dd, J=3.2 Hz, 10.0 Hz), 4.02-4.20 (2H, m), 4.63 (1H, dd, J=4.8 Hz, 8.8 Hz), 5.17 (1H, d, J=18.4 Hz), 5.32 (1H, d, J=18.4 Hz), 7.23-7.42 (5H, m), 7.74 (2H, s), 8.07 (1H, s), 9.33 (1H, s), 9.77 (1H, s).

Example 16

1-(3,5-Di-tert-butyl-4-hydroxy-phenyl)-2-(3-imino-2-aza-spiro[4.5]dec-2-yl)-ethanone hydrobromide

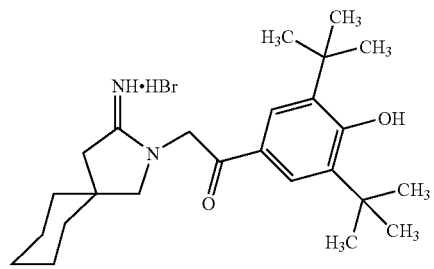

1H-NMR (DMSO-d6) δ: 1.20-1.65 (28H, s), 2.77 (2H, s), 3.44 (2H, s), 5.15 (2H, s), 7.72 (2H, s), 7.92-8.11 (1H, m), 8.76 (1H, brs), 9.21 (1H, brs). MS: m/e(ESI) 399.2 (MH+)

Example 17

N-{1-[2-(3,5-Di-tert-butyl-4-hydroxy-phenyl)-2-oxo-ethyl]-2-imino-pyrrolidin-3-yl}-2-ethyl-butylamide hydrobromide

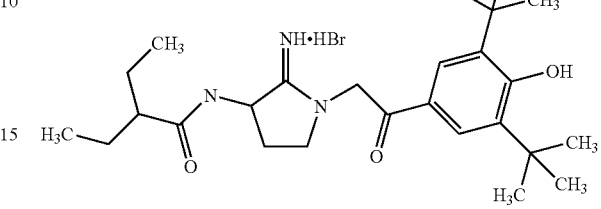

1H-NMR (DMSO-d6) δ: 0.80 (3H, t, J=7.2 Hz), 0.83 (3H, t, J=7.6 Hz), 1.40 (18H, s), 1.41-1.56 (m, 4H), 1.99-2.10 (2H, m), 2.40-2.46 (1H, m), 3.55-3.70 (2H, m), 5.07 (1H, q, J=8.0 Hz), 5.21 (2H, s), 7.73 (2H, s), 8.05 (1H, br), 8.67 (1H, d, J=7.6 Hz), 8.78 (1H, br), 8.95 (1H, br).

Example 18

2-(3-Benzyl-2-imino-4,4-dimethyl-pyrrolidin-1-yl)-1-(3,5-di-tert-butyl-4-hydroxy-phenyl)-ethanone hydrobromide

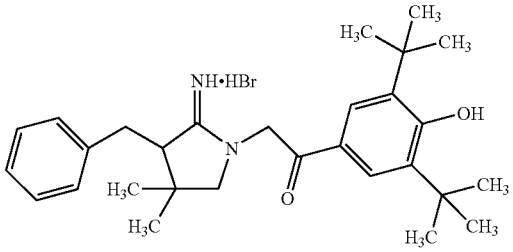

1H-NMR (DMSO-d6) δ: 0.82 (3H.s), 1.05 (3H.s), 1.40 (18.s), 2.47 (2H.s), 2.85 (1H.m), 5.15 (2H.s), 7.20-7.38 (5H.m), 7.72 (2H.s).

Example 19

1-(3,5-Di-tert-butyl-4-hydroxy-phenyl)-2-[3-(4-ethyl-4-hydroxy-hexyl)-2-imino-pyrrolidin-1-yl]-ethanone hydrobromide

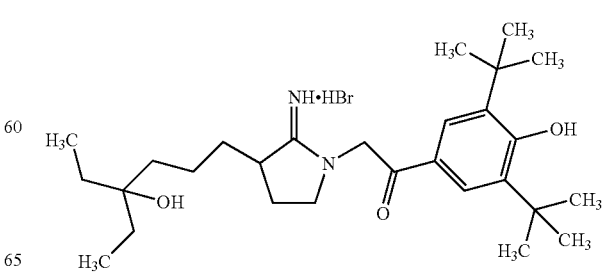

1H-NMR (DMSO-d6) δ: 0.77 (6H, t, J=7.2 Hz), 1.22-1.42 (8H, m), 1.40 (18H, s), 1.49-1.56 (1H, m), 1.71-1.89 (2H, m), 2.21-2.33 (1H, m), 3.09-3.19 (1H, m), 3.53-3.66 (1H, m), 5.14 (s, 2H), 7.71 (2H, s), 8.05 (1H, br), 8.74 (1H, br), 9.06 (1H, br).

Example 20

2-(5-Benzhydroxymethyl-3-benzyl-2-imino-pyrrolidin-1-yl)-1-(3,5-di-tert-butyl-4-hydroxy-phenyl)-ethanone hydrobromide

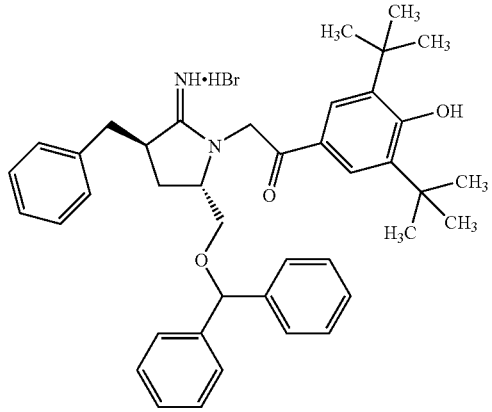

1H-NMR (DMSO-d6) δ: 1.40 (18H, s), 1.77-2.00 (2H, m), 2.70 (1H, t, J=12.4 Hz), 3.40-3.60 (2H, m), 4.10-4.16 (1H, m), 5.06 (1H, d, J=18.0 Hz), 5.17 (1H, d, J=18.0 Hz), 5.39 (1H, s), 7.10-7.40 (15H, m), 7.69 (2H, s), 8.04 (1H, s), 8.97 (1H, s), 9.40 (1H, s).

Example 21

2-(3-Benzyl-5-hydroxymethyl-2-imino-pyrrolidin-1-yl)-1-(3,5-di-tert-butyl-4-hydroxy-phenyl)-ethanone trifluoroacetate

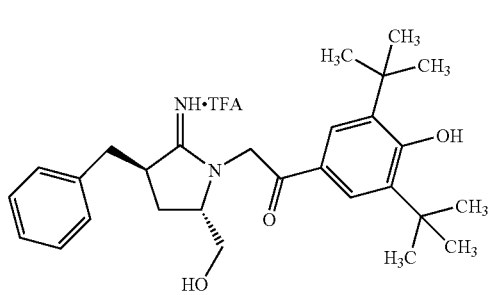

1H-NMR (DMSO-d6) δ: 1.43 (18H, s), 1.91 (2H, m), 2.69 (1H, t, J=12.4 Hz), 3.50 (1H, m), 3.68 (1H, m), 3.89 (1H, m), 4.99 (1H, t, J=5.2 Hz), 5.15 (1H, d, J=18.4 Hz), 5.20 (1H, d, J=18.4 Hz), 7.24-7.40 (5H, m), 7.77 (2H, s), 8.07 (1H, s), 8.94 (1H, s), 9.35 (1H, s).

Example 22

2-[2-(3-Benzyl-2-imino-4-propyl-pyrrolidin-1-yl)-acetylamino]-N-tert-butyl-benzamide hydrobromide

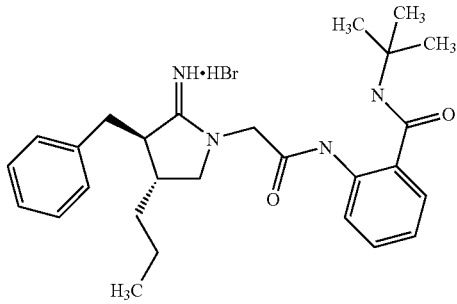

1H-NMR (DMSO-d6) δ: 0.53-1.30 (7H, m), 1.399 (9H, s), 2.15-2.26 (1H, m), 2.84 (1H, dd, J=13.5, 10.5 Hz), 3.04-3.18 (1H, m), 3.23-3.39 (2H, m), 3.86 (1H, dd, J=10.5, 8.4 Hz), 4.41 (2H, s), 7.17 (1H, t, J=7.7 Hz), 7.21-7.39 (6H, m), 7.49 (1H, brt, J=7.7 Hz), 7.72 (1H, d, J=7.7 Hz), 8.15 (1H, s), 8.29 (1H, brd, J=8.1 Hz), 11.43 (1H, brs). MS: m/e(ESI) 449.2 (MH+)

Example 23

1-(3,5-Di-tert-butyl-4-hydroxy-phenyl)-2-[3-(2-fluoro-benzyl)-2-imino-4-propyl-pyrrolidin-1-yl]-ethanone hydrobromide

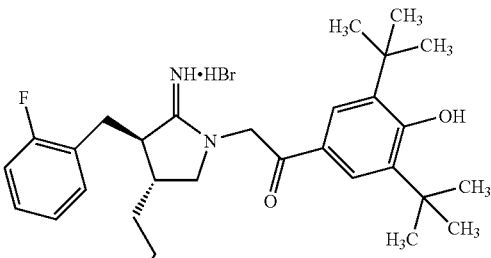

1H-NMR (DMSO-d6) δ: 0.63 (3H, t, J=7.2 Hz), 0.93-1.32 (4H, m), 1.40 (18H, s), 2.01-2.12 (1H, m), 2.93 (1H, dd, J=13.2, 10.8 Hz), 3.08-3.15 (1H, m), 3.19-3.28 (2H, m), 3.81 (1H, dd, J=11.2, 7.2 Hz), 5.14 (2H, s), 7.20 (1H, d, J=7.2 Hz), 7.24 (1H, d, J=8.8 Hz), 7.35 (1H, dd, J=8.2, 7.2 Hz), 7.43 (1H, dd, J=8.8, 8.2 Hz), 7.71 (2H, s), 8.80-9.01 (1H, brs), 9.30-9.42 (1H, brs).

Example 24

2-[3-(2-Benzyloxy-ethyl)-2-imino-pyrrolidin-1-yl]-1-(3,5-di-tert-butyl-4-hydroxy-phenyl)-ethanone hydrobromide

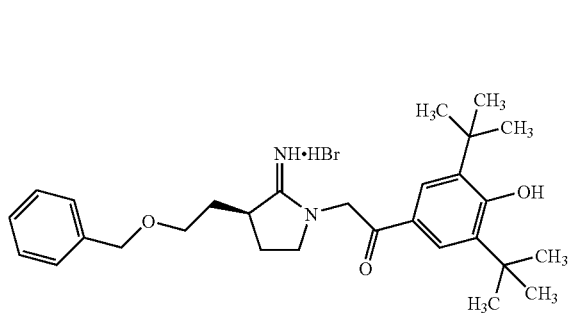

1H-NMR (DMSO-d6) δ: 1.39 (18H, s), 1.75-1.86 (1H, m), 1.87-1.98 (1H, m), 2.11-2.32 (2H, m), 3.24-3.33 (1H, m), 3.53-3.66 (4H, m), 4.48 (2H, ABq, J=10.0 Hz), 5.16 (2H, s), 7.26-7.37 (5H, m), 7.73 (2H, s), 8.79 (1H, br), 9.14 (1H, br).

Example 25

1-(3,5-Di-tert-butyl-4-hydroxy-phenyl)-2-[2-imino-3-(2-methoxy-benzyl)-4-propyl-pyrrolidin-1-yl]-ethanone hydrobromide

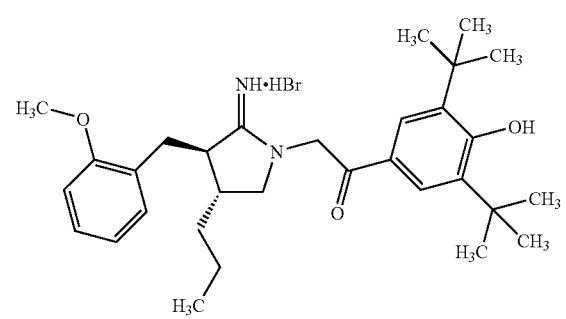

1H-NMR (DMSO-d6) δ: 0.61 (3H, t, J=7.2 Hz), 0.90-1.20 (4H, m), 1.41 (18H, s), 2.00-2.12 (1H, m), 2.80-2.90 (1H, m), 3.10-3.46 (4H, m), 3.81 (3H, s), 5.18 (2H, s), 6.90-6.96 (1H, m), 7.22-7.30 (2H, m), 7.73 (2H, s), 8.80-8.90 (1H, brs), 9.24-9.30 (1H, brs).

Example 26

2-(4-Benzyl-2-imino-3-propyl-pyrrolidin-1-yl)-1-(3,5-di-tert-butyl-4-hydroxy-phenyl)-ethanone hydrobromide

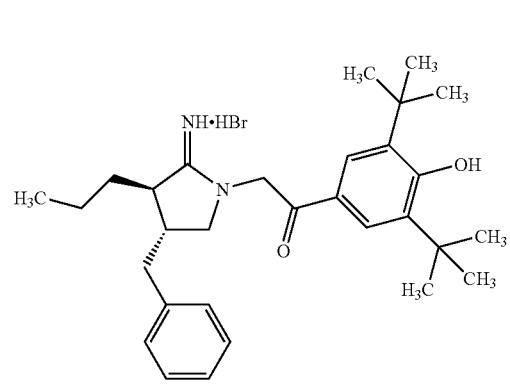

1H-NMR (DMSO-d6) δ: 0.79 (3H, t, J=7.2 Hz), 1.12-1.48 (2H, m), 1.42 (18H, s), 1.48-1.70 (2H, m), 2.73-2.86 (3H, m), 3.25-3.38 (3H, m), 3.78 (1H, dd, J=11.2, 7.2 Hz), 5.15 (1H, d, J=14.4 Hz), 5.20 (1H, d, J=14.4 Hz), 7.20-7.36 (3H, m), 7.74 (2H, s), 8.06 (1H, s), 8.82 (1H, brd, J=4.8 Hz), 9.19 (1H, brd, J=4.4 Hz).

Example 27

Methyl 4-benzyl-1-[2-(3,5-di-tert-butyl-4-hydroxy-phenyl)-2-oxo-ethyl]-5-imino-pyrrolidine-3-carboxylate hydrobromide

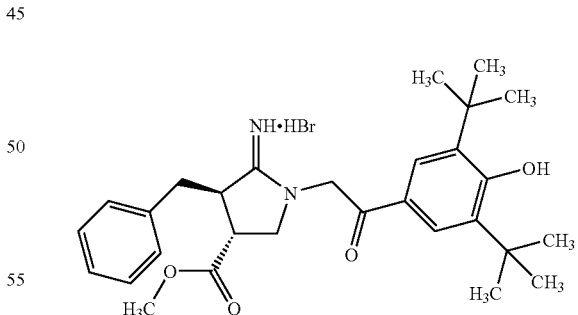

1H-NMR (DMSO-d6) δ: 1.43 (18H, s), 2.94 (1H, dd, J=13.6, 10.8 Hz), 3.14 (1H, quintet, J=4.0 Hz), 3.27-3.36 (1H, m), 3.53 (3H, s), 3.74-3.82 (2H, m), 3.96 (1H, dd, J=11.2, 8.4 Hz), 5.22 (1H, d, J=18.0 Hz), 5.28 (1H, d, J=18.0 Hz), 7.25-7.40 (5H, m), 7.75 (2H, s), 8.08 (1H, brs), 9.26 (1H, brs), 9.75 (1H, brs).

Example 28

1-(3,5-Di-tert-butyl-4-hydroxy-phenyl)-2-{3-[(2-ethyl-butyl)-methyl-amino]-2-imino-pyrrolidin-1-yl}-ethanone hydrobromide

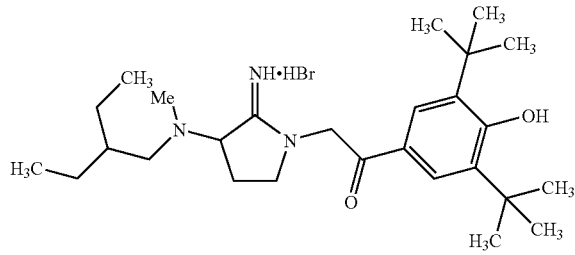

1H-NMR (DMSO-d6) δ: 0.85 (3H, t, J=7.2 Hz), 0.87 (3H, t, J=7.2 Hz), 1.20-1.48 (7H, m), 1.43 (18H, s), 2.29-2.43 (2H, m), 3.54-3.60 (1H, m), 3.68-3.75 (1H, m), 4.18-4.24 (1H, m), 5.69 (1H, d, J=15.9 Hz), 6.03 (1H, d, J=15.9 Hz), 7.93 (2H, s).

Example 29

1-(3,5-Di-tert-butyl-4-hydroxy-phenyl)-2-[3-(2-ethyl-butylamino)-2-imino-pyrrolidin-1-yl]-ethanone dihydrochloride

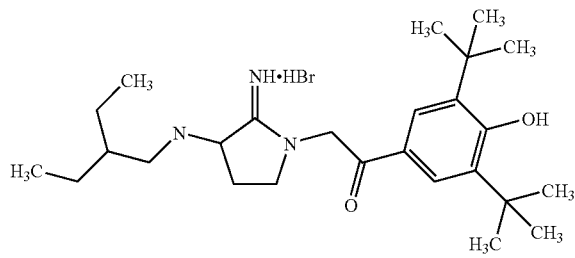

1H-NMR (DMSO-d6) δ: 0.82 (3H, t, J=7.2 Hz), 0.83 (3H, t, J=7.2 Hz), 1.13-1.42 (6H, m), 1.40 (18H, s), 1.58-1.64 (1H, m), 2.03-2.12 (1H, m), 2.37-2.44 (1H, m), 2.70-2.78 (1H, m), 3.07-3.15 (1H, m), 3.94-3.99 (1H, m), 5.33 (2H, s), 7.73 (2H, s), 8.37 (2H, br).

Example 30

N-{1-[2-(3,5-Di-tert-butyl-4-hydroxy-phenyl)-2-oxo-ethyl]-2-imino-pyrrolidin-3-yl}-N-(2-ethyl-butyl)-acetamide hydrobromide

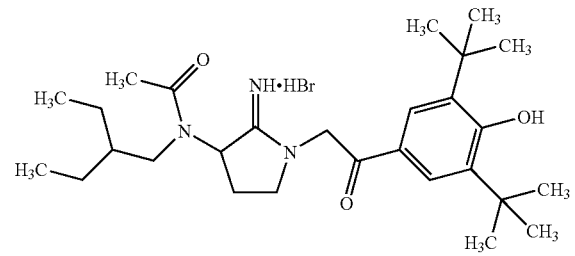

1H-NMR (DMSO-d6) δ: 0.84 (3H, t, J=7.4 Hz), 0.89 (3H, t, J=7.4 Hz), 1.19-1.48 (6H, m), 1.39 (18H, s), 1.49-1.56 (1H, m), 2.01 (3H, s), 2.26-2.34 (2H, m), 3.52-3.69 (2H, m), 4.67-4.74 (1H, m), 5.23 (2H, s), 7.74 (2H, s), 8.03 (1H, br), 8.81 (1H, br), 9.03 (1H, br).

Example 31

2-(3-Benzyl-4,4-diethyl-2-imino-pyrrolidin-1-yl)-1-(3,5-di-tert-butyl-4-hydroxy-phenyl)-ethanone hydrobromide

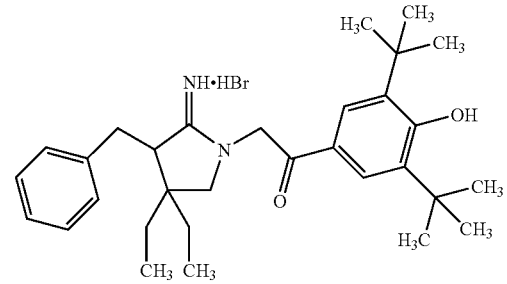

1H-NMR (DMSO-d6) δ: 1.09 (3H, t, J=6.0 Hz), 1.20 (3H, t, J=6.0 Hz), 1.40 (18H, s), 1.45-1.60 (4H, m), 2.91 (1H, d, J=10.0 Hz), 3.12 (1H, d, J=10.0 Hz), 3.32 (1H, d, J=10.0 Hz), 3.58 (1H, d, J=10.0 Hz), 5.23 (2H, s), 7.25 (2H, m), 7.30 (3H, m), 7.83 (2H, s). MS: m/e(ESI) 477.2 (MH+)

Example 32

2-(3-Benzyl-2-imino-5-propyl-pyrrolidin-1-yl)-1-(3,5-di-tert-butyl-4-hydroxy-phenyl)-ethanone hydrobromide

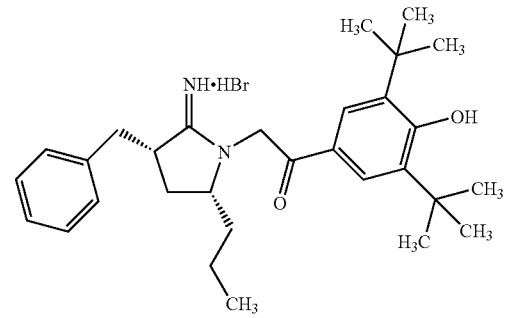

1H-NMR (DMSO-d6) δ: 0.82 (3H, t, J=7.2 Hz), 1.00-1.30 (3H, m), 1.43 (18H, s), 1.50 (1H, td, J=6.8 Hz, 13.2 Hz), 1.72 (1H, m), 2.26 (1H, td, J=8.8 Hz, 13.2 Hz), 2.78 (1H, dd, J=10.4 Hz, 13.6 Hz), 3.53 (1H, m), 3.75 (1H, m), 5.03 (1H, d, J=18.0 Hz), 5.27 (1H, d, J=18.0 Hz), 7.25-7.40 (5H, m), 7.78 (2H, s), 8.06 (1H, s), 8.91 (1H, s), 9.30 (1H, s).

Example 33

2-(3-Benzyl-2-imino-5-propyl-pyrrolidin-1-yl)-1-(3,5-di-tert-butyl-4-hydroxy-phenyl)-ethanone hydrobromide

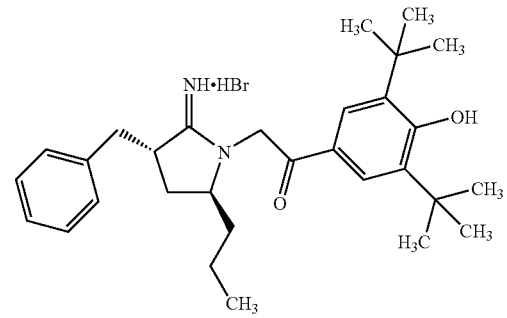

1H-NMR (DMSO-d6) δ: 0.84 (3H, t, J=7.2 Hz), 1.05-1.35 (3H, m), 1.43 (18H, s), 1.65-1.85 (2H, m), 1.98 (1H, m), 2.75 (1H, dd, J=11.2 Hz, 13.2 Hz), 3.28 (1H, dd, J=4.0 Hz, 13.2 Hz), 3.52 (1H, m), 3.83 (1H, m), 5.06 (1H, d, J=18.4 Hz), 5.25 (1H, d, J=18.4 Hz), 7.20-7.40 (5H, m), 7.79 (2H, s), 8.06 (1H, s), 8.90 (1H, s), 9.35 (1H, s).

Example 34

2-(4-Benzyl-5-imino-2,2-dimethyl-pyrrolidin-1-yl)-1-(3,5-di-tert-butyl-4-hydroxy-phenyl)-ethanone hydrobromide

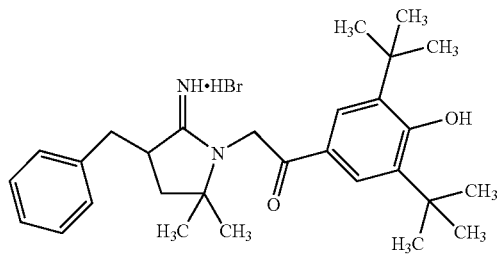

1H-NMR (DMSO-d6) δ: 1.21 (3H, s), 1.22 (3H, s), 1.44 (18H, s), 1.74 (dd, J=8.0 Hz, 12.8 Hz), 1.98 (1H, dd, J=8.8 Hz, 12.8 Hz), 2.70 (1H, dd, J=11.2 Hz, 13.2 Hz), 3.45 (1H, dd, J=3.6 Hz, 13.2 Hz), 3.64 (1H, m), 5.03 (1H, d, J=18.8 Hz), 5.13 (1H, d, J=18.8 Hz), 7.25-7.40 (5H, m), 7.81 (2H, s), 8.04 (1H, s), 8.78 (1H, s), 9.16 (1H, s).

Example 35

2-(3-Benzyl-2-imino-4-methoxymethyl-pyrrolidin-1-yl)-1-(3,5-di-tert-butyl-4-hydroxy-phenyl)-ethanone hydrobromide

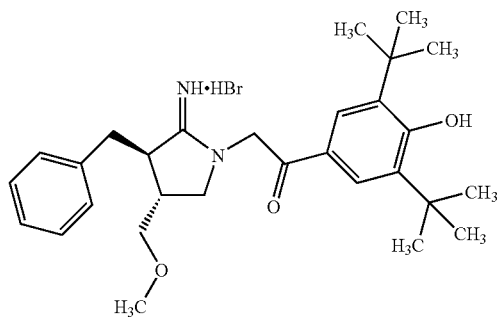

1H-NMR (DMSO-d6) δ: 1.43 (18H, s), 2.42 (1H, m), 2.87 (1H, m), 3.06 (3H, s), 3.08-3.16 (2H, m), 3.21-3.37 (3H, m), 3.76 (1H, dd, J=10.8, 7.6 Hz), 5.19 (1H, d, J=18.4 Hz), 7.29 (1H, m), 7.32-7.40 (4H, m), 7.76 (2H, s), 8.07 (1H, s), 9.12 (1H, brd, J=8.0 Hz), 9.65 (1H, brd, J=6.8 Hz).

Example 36

2-(4-Benzyl-2-imino-pyrrolidin-1-yl)-1-(3,5-di-tert-butyl-4-hydroxy-phenyl)-ethanone hydrobromide

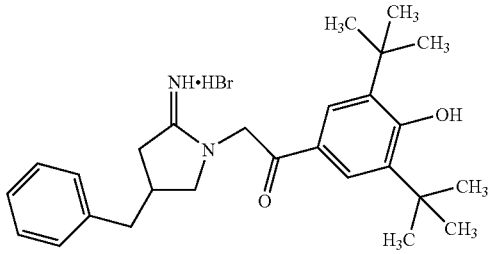

1H-NMR (DMSO-d6) δ: 1.42 (18H, s), 2.72 (1H, dd, J=17.6, 4.8 Hz), 2.85 (1H, m), 3.06 (1H, dd, J=17.6, 7.6 Hz), 3.40 (1H, dd, J=10.4, 5.2 Hz), 3.68 (1H, dd, J=10.4, 6.8 Hz), 5.17 (2H, s), 7.20-7.36 (5H, m), 7.74 (2H, s), 8.07 (1H, s), 8.80 (1H, m), 9.25 (1H, m).

Example 37

Methyl 4-benzyl-1-[2-(3,5-di-tert-butyl-4-hydroxy-phenyl)-2-oxo-ethyl]-5-imino-pyrrolidine-2-carboxylate trifluoroacetate

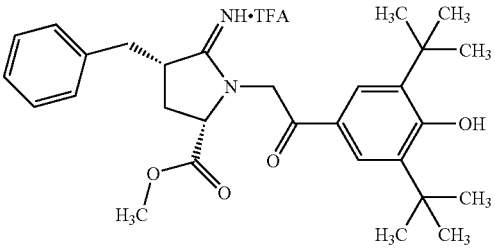

1H-NMR (DMSO-d6) δ: 1.43 (18H, s), 1.89 (1H, td, J=4.0 Hz, 13.6 Hz), 2.56 (1H, td, J=10.0 Hz, 13.6 Hz), 2.66 (1H, dd, J=10.8 Hz, 13.6 Hz), 3.28 (1H, dd, J=4.0 Hz, 13.6 Hz), 3.61 (1H, m), 3.68 (3H, s), 4.58 (1H, dd, J=4.0 Hz, 13.6 Hz), 5.13 (2H, d, J=18.8 Hz), 5.38 (1H, d, J=18.8 Hz), 7.20-7.40 (5H, m), 7.73 (2H, s), 8.08 (1H, s), 9.41 (1H, s), 9.93 (1H, s).

Example 38

Methyl 4-benzyl-1-[2-(3,5-di-tert-butyl-4-hydroxy-phenyl)-2-oxo-ethyl]-5-imino-pyrrolidine-2-carboxylate trifluoroacetate

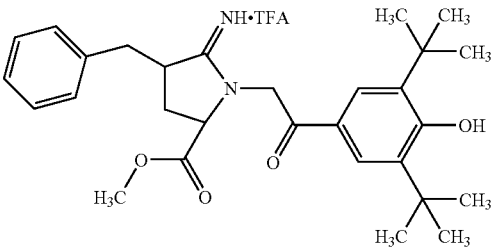

1H-NMR (DMSO-d6) δ: 1.43 (18H, s), 2.11 (1H, m), 2.24 (1H, m), 2.78 (1H, t, J=12.4 Hz), 3.60 (1H, m), 3.64 (3H, s), 4.64 (1H, m), 5.17 (1H, d, J=18.0 Hz), 5.33 (1H, d, J=18.0 Hz), 7.20-7.40 (5H, m), 7.74 (2H, s), 8.08 (1H, s), 9.38 (1H, s), 9.81 (1H, s).

Example 39

Ethyl 4-benzyl-1-[2-(3,5-di-tert-butyl-4-hydroxy-phenyl)-2-oxo-ethyl]-5-imino-pyrrolidine-2-carboxylate trifluoroacetate

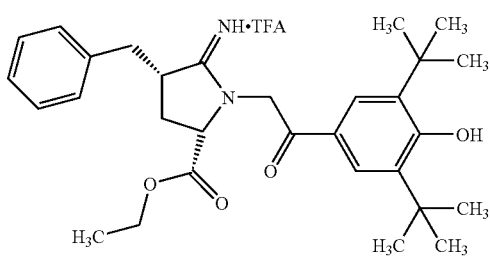

1H-NMR (DMSO-d6) δ: 1.16 (3H, t, J=7.2 Hz), 2.56 (1H, m), 2.67 (1H, dd, J=12.4 Hz, 12.8 Hz), 3.27 (1H, m), 3.59 (1H, m), 4.04-4.20 (2H, m), 4.57 (1H, dd, J=4.0 Hz, 10.0 Hz), 5.13 (1H, d, J=18.4 Hz), 5.35 (1H, d, J=18.4 Hz), 7.20-7.40 (5H, m), 7.73 (2H, s), 8.08 (1H, s), 9.33 (1H, s), 9.85 (1H, s).

Example 40

1-(3,5-Di-tert-butyl-4-hydroxy-phenyl)-2-(2-imino-3-phenyl-pyrrolidin-1-yl)-ethanone hydrobromide

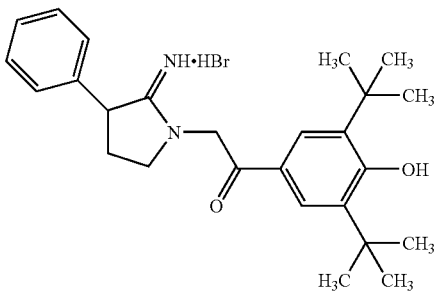

1H-NMR (DMSO-d6) δ: 1.42 (18H, s), 2.03 (1H, m), 2.67 (1H, m), 3.72 (1H, m), 3.81 (1H, m), 4.51 (1H, dd, J=9.6, 5.6 Hz), 5.33 (2H, s), 7.36 (1H, m), 7.40-7.51 (4H, m), 7.77 (2H, s), 8.07 (1H, brs), 9.03 (1H, brs).

Example 41

1-(3,5-Di-tert-butyl-4-hydroxy-phenyl)-2-(2-imino-4-phenyl-pyrrolidin-1-yl)-ethanone hydrobromide

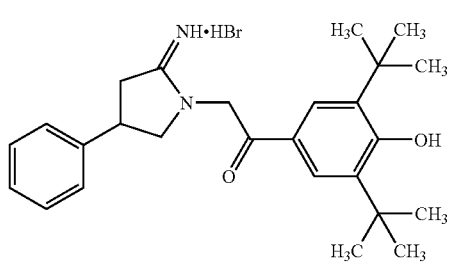

1H-NMR (DMSO-d6) δ: 1.41 (18H, s), 3.05 (1H, dd, J=17.6, 7.6 Hz), 3.46 (1H, dd, J=17.6, 9.2 Hz), 3.67 (1H, dd, J=10.4, 6.4 Hz), 3.85 (1H, m), 4.03 (1H, dd, J=10.4, 8.4 Hz), 5.26 (2H, s), 7.29 (1H, m), 7.33-7.41 (4H, m), 7.75 (2H, s), 8.06 (1H, brs), 9.00 (1H, brs), 9.45 (1H, brs).

Example 42

N-{1-[2-(3,5-Di-tert-butyl-4-hydroxy-phenyl)-2-oxo-ethyl]-2-imino-pyrrolidin-3-ylmethyl}-isobutylamide hydrobromide

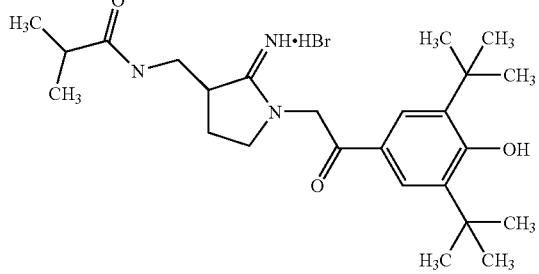

1H-NMR (DMSO-d6) δ: 1.02 (6H, t, J=6.8 Hz), 1.40 (18H, s), 1.89-1.98 (1H, m), 2.16-2.26 (1H, m), 2.41 (1H, sept, J=6.8 Hz), 3.30-3.38 (2H, m), 3.48-3.62 (3H, m), 5.17 (2H, s), 7.72 (2H, s), 7.99-8.09 (2H, m), 8.83 (1H, br), 9.26 (1H, br).

Example 43

2-{3-[2-(1-Acetyl-piperidin-4-yl)-ethyl]-2-imino-pyrrolidin-1-yl}-1-(3,5-di-tert-butyl-4-hydroxy-phenyl)-ethanone hydrobromide

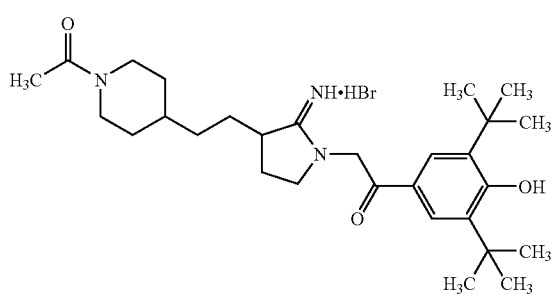

1H-NMR (DMSO-d6) δ: 0.88-0.97 (1H, m), 0.90-0.99 (1H, m), 1.27-1.33 (1H, m), 1.34-1.55 (5H, m), 1.39 (18H, s), 1.61-1.74 (1H, m), 1.80-1.90 (1H, m), 1.96 (3H, s), 2.93-3.03 (1H, m), 3.10-3.19 (1H, m), 3.52-3.64 (2H, m), 3.72-3.82 (1H, m), 4.31-4.38 (1H, m), 5.24 (2H, s), 7.72 (2H, s), 8.75 (1H, br), 9.09 (1H, br).

Example 44

2-(4-Benzyl-5-imino-2,2-dimethyl-2,5-dihydro-pyrrol-1-yl)-1-(3,5-di-tert-butyl-4-hydroxy-phenyl)-ethanone hydrobromide

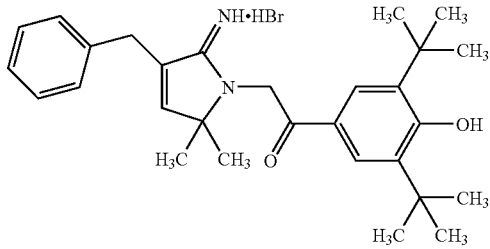

1H-NMR (DMSO-d6) δ: 1.03 (3H, t, J=7 Hz), 1.37 (6H, s), 1.48 (18H, s), 1.55-1.62 (2H, m), 2.40 (2H, m), 3.80 (2H, s), 5.77 (2H, s), 5.80 (brs, 1H), 7.15 (2H, d, J=7 Hz), 7.28-7.39 (3H, m), 7.93 (2H, s). MS: m/e(ESI) 489.3 (MH+)

Example 45

2-(3-Benzyl-4-tert-butoxymethyl-2-imino-pyrrolidin-1-yl)-1-(3,5-di-tert-butyl-4-hydroxy-phenyl)-ethanone hydrobromide

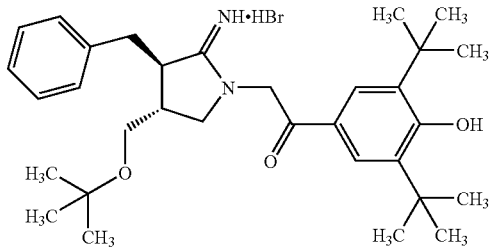

1H-NMR (DMSO-d6) δ: 1.00 (9H, s), 1.43 (18H, s), 2.30 (1H, m), 2.86 (1H, dd, J=14.4, 11.2 Hz), 3.01-3.16 (2H, m), 3.19-3.40 (3H, m), 3.74 (1H, dd, J=10.4, 8.0 Hz), 5.17 (2H, s), 7.24-7.42 (5H, m), 7.75 (2H, s), 8.07 (1H, s), 8.94 (1H, brs), 9.40 (1H, brm).

Example 46

2-(3-Benzyl-4-hydroxymethyl-2-imino-pyrrolidin-1-yl)-1-(3,5-di-tert-butyl-4-hydroxy-phenyl)-ethanone hydrobromide

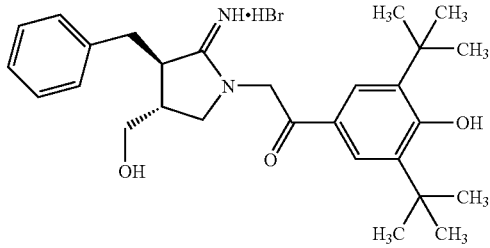

1H-NMR (DMSO-d6) δ: 1.43 (18H, s), 2.25 (1H, m), 2.88 (1H, dd, J=14.8, 11.2 Hz), 3.13-3.27 (4H, m), 3.41 (1H, dd, J=10.8, 8.0 Hz), 3.72 (1H, dd, J=11.2, 8.0 Hz), 5.17 (2H, s), 7.26-7.40 (5H, m), 7.75 (2H, s), 8.08 (1H, s), 8.91 (1H, brm), 9.40 (1H, brm).

Example 47

1-(3,5-Di-tert-butyl-4-hydroxy-phenyl)-2-[2-imino-3-(2-piperidin-4-yl-ethyl)-pyrrolidin-1-yl]-ethanone dihydrobromide

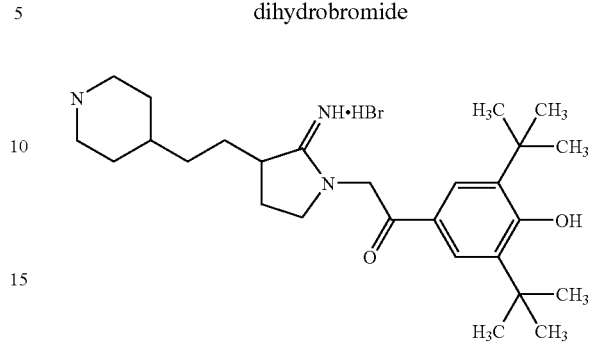

1H-NMR (DMSO-d6) δ: 1.18-1.38 (6H, m), 1.45-1.58 (2H, m), 1.76-1.91 (4H, m), 2.22-2.32 (1H, m), 2.85 (2H, brt, J=11.2 Hz), 3.12-3.21 (1H, m), 3.54-3.65 (2H, m), 5.18 (2H, s), 7.72 (2H, s), 8.06 (1H, br), 8.79 (1H, br), 9.14 (1H, br).

Example 48

2-(3-Benzyl-5-hydroxymethyl-2-imino-pyrrolidin-1-yl)-1-(3,5-di-tert-butyl-4-hydroxyphenyl)-ethanone hydrobromide

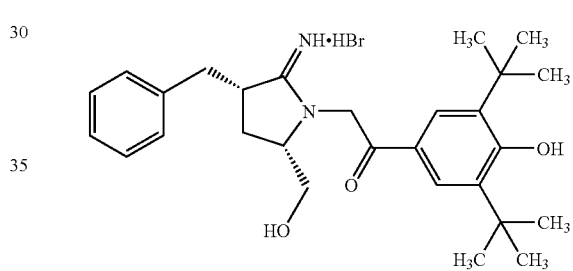

1H-NMR (DMSO-d6) δ: 1.40 (18H, s), 1.88 (1H, m), 2.03 (1H, dd, J=6.0 Hz, 13.2 Hz), 2.90 (1H, dd, J=10.8 Hz, 13.2 Hz), 3.12 (1H, dd, J=4.0 Hz, 13.2 Hz), 3.40 (1H, m), 3.81 (2H, t, J=10.4 Hz), 3.98 (1H, m), 4.68 (1H, d, J=10.4 Hz), 5.15 (1H, d, J=18.4 Hz), 5.31 (1H, d, J=18.4 Hz), 7.25-7.40 (5H, m) 7.78 (2H, s).

Example 49

2-(3-Benzylidene-2-imino-pyrrolidin-1-yl)-1-(3,5-di-tert-butyl-4-hydroxy-phenyl)-ethanone hydrochloride

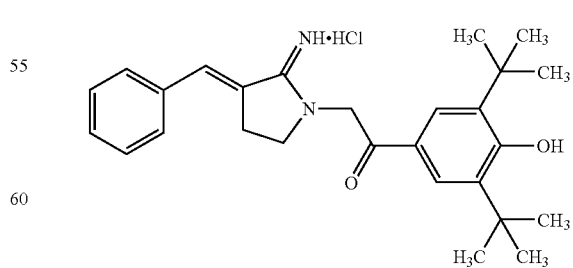

1H-NMR (DMSO-d6) δ: 1.41 (18H, s), 3.20-3.26 (2H, m), 3.77 (2H, t, J=6.8 Hz), 5.32 (2H, s), 7.46-7.60 (5H, m), 7.65-7.68 (1H, brs), 7.75 (2H, s), 8.74-8.88 (1H, brs), 9.20-9.32 (1H, brs).

Example 50

1-(3,5-Di-tert-butyl-4-hydroxy-phenyl)-2-(2-imino-3-phenyl-4-propyl-pyrrolidin-1-yl)-ethanone hydrochloride

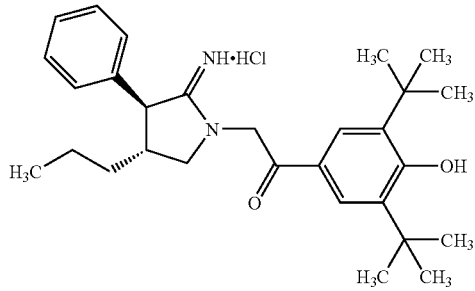

1H-NMR (DMSO-d6) δ: 0.84 (3H, t, J=7.6 Hz), 1.20-1.32 (2H, m), 1.44 (18H, s), 1.46-1.58 (2H, m), 2.42 (1H, m), 3.45 (1H, dd, J=6.8, 10.8 Hz), 3.92 (1H, dd, J=8.4, 10.8 Hz), 4.15 (1H, d, J=6.8 Hz), 5.30 (2H, s), 7.36-7.50 (5H, m), 7.78 (2H, s), 8.08 (1H, brs), 8.86 (1H, brs), 8.95 (1H, brs).

Example 51

N-(2-{1-[2-(3,5-Di-tert-butyl-hydroxy-phenyl)-2-oxo-ethyl]-2-imino-pyrrolidin-3-yl}-ethyl)-acetamide hydrobromide

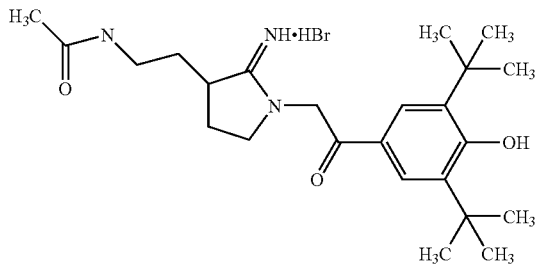

1H-NMR (DMSO-d6) δ: 1.40 (18H, s), 1.80-2.00 (2H, br), 1.89 (3H, s), 2.16-2.40 (2H, m), 3.10-3.18 (1H, m), 3.32-3.41 (1H, m), 3.45-3.58 (2H, m), 3.68-3.80 (1H, m), 5.05 (1H, d, J=18.2 Hz), 5.75 (1H, d, J=18.2 Hz), 5.79 (1H, s), 7.79 (2H, s). MS: m/e(ESI) 416.2 (MH+)

Example 52

1-(3,5-Di-tert-butyl-4-hydroxy-phenyl)-2-[1-(3-ethyl-pentyl)-2-imino-pyrrolidin-3-yl]-ethanone hydrochloride

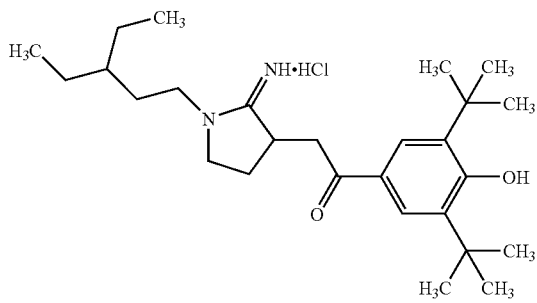

1H-NMR (DMSO-d6) δ: 0.86 (6H, t, J=7 Hz), 1.23-1.60 (7H, m), 1.93 (1H, m), 2.46 (1H, m), 3.47-3.56 (3H, m), 3.64-3.77 (3H, m), 3.83 (1H, td, J=10.6 Hz), 1.45 (18H, s), 5.80 (1Hs), 7.80 (2H, s), 9.03 (1H, s), 9.66 (1H, s). MS: m/e(ESI) 429.3 (MH+)

Example 53

2-(5-Benzyl-2-imino-3-propyl-pyrrolidin-1-yl)-1-(3,5-di-tert-butyl-4-hydroxy-phenyl)-ethanone hydrobromide

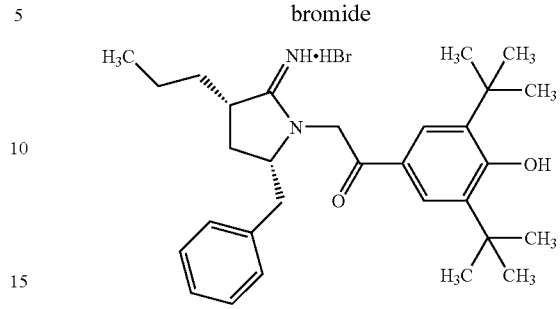

1H-NMR (DMSO-d6) δ: 0.90 (3H, t, J=7.2 Hz), 1.10-1.40 (3H, m), 1.44 (18H, s), 1.58 (1H, m), 1.80 (1H, m), 2.22 (1H, m), 2.61 (1H, dd, J=6.4 Hz, 13.2 Hz), 3.10 (1H, m), 3.18 (1H, dd, J=4.0 Hz, 13.2 Hz), 4.11 (1H, m), 5.18 (1H, d, J=18.8 Hz), 5.34 (1H, d, J=18.8 Hz), 7.20-7.35 (5H, m), 7.78 (2H, s), 8.06 (1H, s), 8.83 (1H, s), 9.08 (1H, s).

Example 54

2-(5-Benzyl-2-imino-3-propyl-pyrrolidin-1-yl)-1-(3,5-di-tert-butyl-4-hydroxy-phenyl)-ethanone hydrobromide

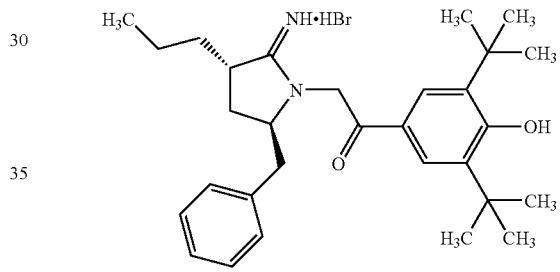

1H-NMR (DMSO-d6) δ: 0.88 (3H, t, J=7.2 Hz), 1.10-1.40 (3H, m), 1.44 (18H, s), 1.80 (2H, m), 2.03 (1H, m), 2.71 (1H, dd, J=9.6 Hz, 13.2 Hz), 3.02 (1H, m), 3.10 (1H, dd, J=4.0 Hz, 13.2 Hz), 4.10 (1H, m), 5.18 (1H, d, J=18.8 Hz), 5.28 (1H, d, J=18.8 Hz), 7.20-7.35 (5H, m), 7.77 (2H, s), 8.06 (1H, s), 8.82 (1H, s), 9.05 (1H, s).

Example 55

2-[3-(2-Chloro-benzyl)-2-imino-4-propyl-pyrrolidin-1-yl]-1-(3,5-di-tert-4-hydroxy-phenyl)-ethanone hydrobromide

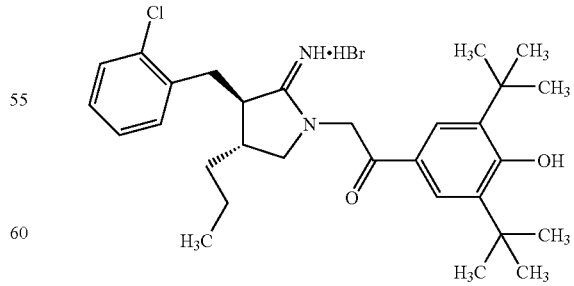

1H-NMR (DMSO-d6) δ: 0.60 (3H, t, J=7.2 Hz), 0.80-1.26 (4H, m), 1.41 (18H, s), 2.06-2.16 (1H, m), 2.99-3.07 (1H, m), 3.16-3.38 (3H, m), 3.84-3.92 (1H, m), 5.18 (2H, s), 7.30-7.40 (2H, m), 7.46-7.52 (2H, m), 7.73 (2H, s), 9.25-9.30 (1H, brs).

Example 56

2-(4-Benzyl-3-imino-5-propyl-3H-isoxazol-2-yl)-1-(3,5-di-tert-butyl-4-hydroxy-phenyl)-ethanone hydrobromide

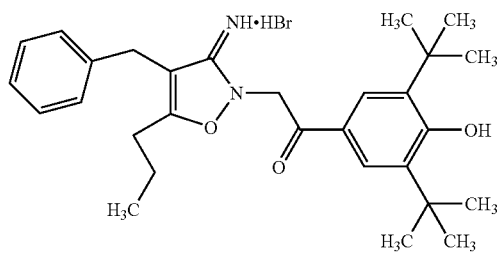

1H-NMR (DMSO-d6) δ: 0.86 (3H, t, J=7 Hz), 1.47 (18H, s), 1.48-1.60 (2H, m), 2.43 (2H, t, J=7 Hz), 3.74 (2H, s), 6.40 (2H, s), 7.18 (2H, d, J=7 Hz), 7.27 (1H, t, J=7 Hz), 7.35 (2H, t, J=7 Hz), 7.89 (2H, s). MS: m/e(ESI) 463.3 (MH+)

Example 57

1-(3,5-Di-tert-butyl-4-hydroxy-phenyl)-2-(2-imino-4-propyl-3-thiophen-3-ylmethyl-pyrrolidin-1-yl)-ethanone hydrobromide

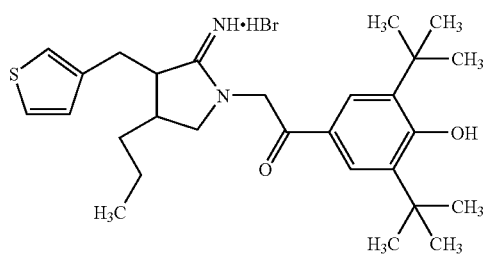

1H-NMR (DMSO-d6) δ: 0.71 (3H, t, J=6.0 Hz), 1.10 (2H, m), 1.33 (1H, m), 1.40 (18H, s), 1.60 (2H, m), 3.20 (2H, m), 3.65 (1H, m), 5.36 (1H, d, J=14.0 Hz), 5.47 (1H, d, J=14.0 Hz), 7.05 (1H, d, J=4.5 Hz), 7.09 (1H, brs), 7.20 (1H, d, J=4.5 Hz), 7.80 (2H, s). MS: m/e(ESI) 469.2 (MH+)

Example 58

1-(3,5-Di-tert-butyl-4-hydroxy-phenyl)-2-[2-imino-3-(2-isopropoxy-ethyl)-pyrrolidin-1-yl]-ethanone hydrobromide

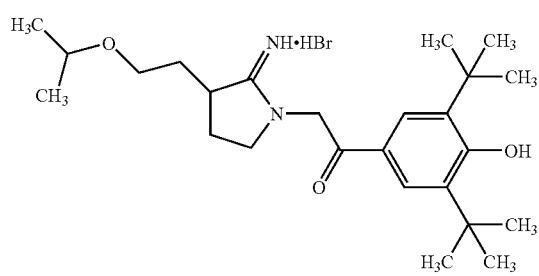

1H-NMR (DMSO-d6) δ: 1.09 (3H, d, J=6.0 Hz), 1.10 (3H, d, J=6.0 Hz), 1.40 (18H, s), 1.68-1.75 (1H, m), 1.89-1.98 (1H, m), 2.04-2.10 (1H, m), 2.22-2.31 (1H, m), 3.20-3.29 (1H, m), 3.42-3.48 (1H, m), 3.50-3.66 (4H, m), 5.15 (2H, s), 7.71 (2H, s), 8.05 (1H, br), 8.77 (1H, br), 9.09 (1H, br).

Example 59

1-(3,5-Di-tert-butyl-4-hydroxy-phenyl)-2-[2-imino-3-(2-nitro-benzyl)-4-propyl-pyrrolidin-1-yl]-ethanone hydrobromide

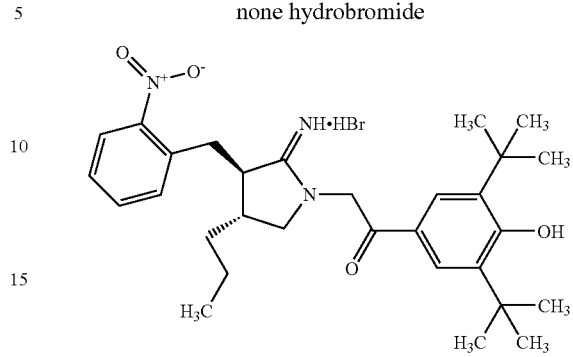

1H-NMR (DMSO-d6) δ: 0.67 (3H, t, J=6.8 Hz), 0.90-1.35 (4H, m), 1.48 (18H, s), 2.20-2.30 (1H, m), 3.20-3.27 (1H, m), 3.40-3.55 (2H, m), 3.60-3.73 (1H, m), 4.04-4.11 (1H, m), 5.38 (1H, d, J=18 Hz), 5.73 (1H, d, J=18 Hz), 5.84 (1H, s), 7.41 (1H, t, J=7.4 Hz), 7.61 (1H, t, J=7.4 Hz), 7.89 (2H, s), 7.92 (1H, d, J=8.0 Hz), 8.03 (1H, d, J=8.0 Hz). MS: m/e(ESI) 508.3 (MH+)

Example 60

2-[3-(2-Amino-benzyl)-2-imino-4-propyl-pyrrolidin-1-yl]-1-(3,5-di-tert-butyl-4-hydroxy-phenyl)-ethanone hydrobromide

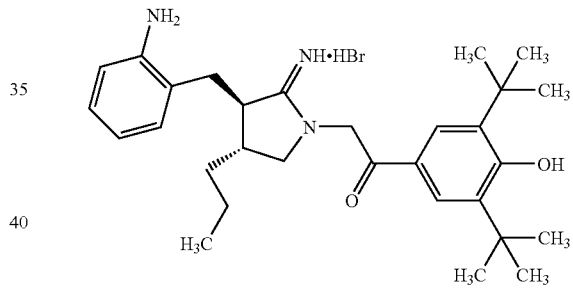

1H-NMR (DMSO-d6) δ: 0.61 (3H, t, J=7.2 Hz), 0.80-1.32 (4H, m), 1.47 (18H, s), 2.17-2.26 (1H, m), 2.58-2.67 (1H, m), 3.18 (1H, dd, J=3.6 Hz, J=10.4 Hz), 3.58-3.78 (2H, m), 3.92 (1H, dd, J=8.0 Hz, J=13.6 Hz), 5.21 (1H, d, J=18 Hz), 5.81 (1H, d, J=18 Hz), 5.84 (1H, s), 6.59-6.64 (2H, m), 6.96-7.05 (2H, m), 7.89 (2H, s).

Example 61

1-(3,5-Di-tert-butyl-4-hydroxy-phenyl)-2-[5-(2-ethyl-butyl)-1-imino-3a,6a-dimethyl-hexahydro-cyclopenta[c]pyrrol-2-yl]-ethanone hydrobromide

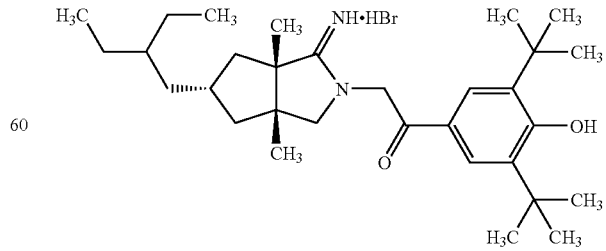

1H-NMR (DMSO-d6) δ: 0.81 (6H, t, J=7.2 Hz), 1.04 (1H, q, 12.0 Hz), 1.17-1.32 (8H, m), 1.40 (18H, s), 1.92-2.03 (1H, m), 2.09-2.16 (1H, m), 2.29-2.36 (1H, m), 2.81 (1H, brt, J=8.4 Hz), 3.76 (1H, dd, J=2.0, 11.2 Hz), 3.59 (1H, q, J=9.2 Hz), 3.79 (1H, dd, J=8.4, 11.2 Hz), 5.10 (2H, s), 7.71 (2H, s), 8.65 (1H, br), 9.14 (1H, br).

Example 62

1-(3,5-Di-tert-butyl-4-hydroxy-phenyl)-2-(2-imino-4-propyl-3-thiazol-2-ylmethyl-pyrrolidin-1-yl)-ethanone hydrobromide

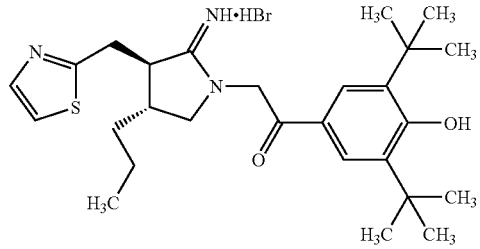

1H-NMR (DMSO-d6) δ: 0.75 (3H, t, J=6.0 Hz), 1.14 (2H, m), 1.23 (1H, m), 1.35 (2H, m), 1.40 (18H, s), 3.26 (2H, m), 3.47 (2H, d, J=6.0 Hz), 3.76 (1H, m), 5.13 (2H, s), 7.68 (1H, d, J=4.5 Hz), 7.70 (2H, s), 7.78 (1H, d, J=4.5 Hz). MS: m/e(ESI) 470.2 (MH+)

Example 63

1-(3,5-Di-tert-butyl-4-hydroxy-phenyl)-2-(2-imino-4-propyl-3-thiophen-2-ylmethyl-pyrrolidin-1-yl)-ethanone hydrobromide

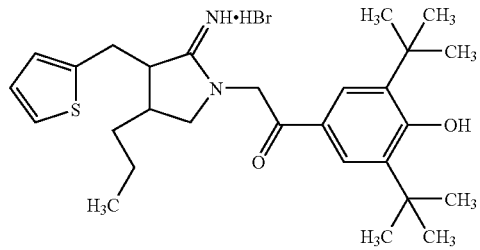

1H-NMR (DMSO-d6) δ: 0.73 (3H, t, J=6.0 Hz), 1.12 (2H, m), 1.30 (3H, m), 1.40 (18H, s), 3.07 (2H, m), 3.25 (2H, d, J=6.0 Hz), 3.75 (1H, m), 5.12 (2H, s), 7.01 (2H, m), 7.42 (1H, d, J=4.5 Hz), 7.70 (2H, s). MS: m/e(ESI) 469.2 (MH+)

Example 64

1-(3,5-Di-tert-butyl-4-hydroxy-phenyl)-2-[3-(4-fluoro-benzyl)-2-imino-4-propyl-pyrrolidin-1-yl]-ethanone hydrobromide

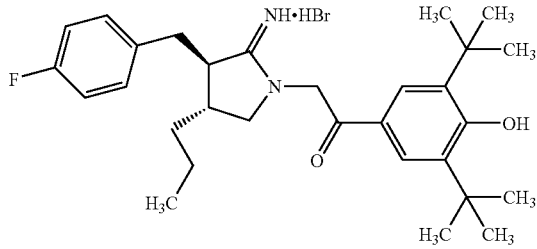

1H-NMR (DMSO-d6) δ: 0.64 (3H, t, J=7.2 Hz), 0.88-1.35 (4H, m), 1.40 (18H, s), 2.05-2.15 (1H, m), 2.85 (1H, dd, J=12.8, 10.8 Hz), 3.00-3.08 (1H, m), 3.15 (1H, dd, J=12.8, 5.1 Hz), 3.22 (1H, dd, J=12.8, 4.6 Hz), 3.81 (1H, dd, J=12.8, 9.2 Hz), 5.15 (2H, s).

Example 65

1-(3,5-Di-tert-butyl-4-hydroxy-phenyl)-2-[5-(2-ethyl-2-hydroxy-butyl)-1-imino-hexahydro-cyclopenta[c]pyrrol-2-yl]-ethanone hydrobromide

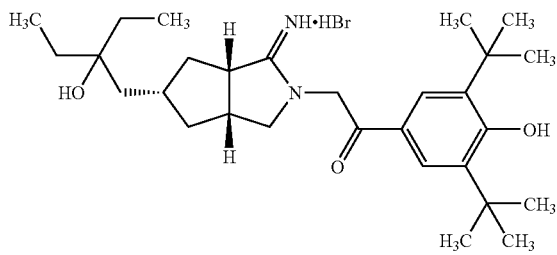

1H-NMR (DMSO-d6) δ 0.76 (3H, t, J=6.9 HZ), 0.77 (3H, t, J=6.9 Hz), 1.09-1.14 (1H, m), 1.20-1.27 (1H, m), 1.48-1.61 (6H, m), 1.92-2.02 (1H, m), 2.14-2.22 (1H, m), 2.39-2.48 (1H, m), 2.73-2.82 (1H, m), 3.33-3.35 (1H, m), 3.54 (1H, dd, J=8.7, 17.4 Hz), 3.77-3.82 (1H, m), 5.13 (2H, s), 7.73 (2H, s), 8.02 (1H, br), 8.64 (1H, br), 9.14 (1H, br).

Example 66

1-(3,5-Di-tert-butyl-4-hydroxy-phenyl)-2-(1-imino-5-methoxy-hexahydro-cyclopenta[c]pyrrol-2-yl)-ethanone hydrobromide

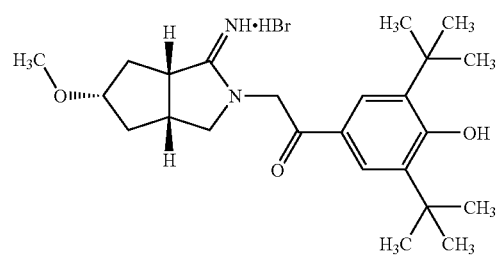

1H-NMR (DMSO-d6) δ: 1.39 (18H, s), 1.76 (1H, brd, J=17.0 Hz), 1.95-2.03 (2H, m), 2.13 (1H, brd, J=14.2 Hz), 2.87-2.97 (1H, br), 3.15 (3H, s), 3.40-3.46 (1H, m), 3.58-3.66 (1H, m), 3.83-3.87 (2H, m), 5.16-5.20 (2H, m), 7.73 (2H, s), 8.02 (1H, br), 8.61 (1H, br), 9.14 (1H, br).

Example 67

1-(3,5-Di-tert-butyl-4-hydroxy-phenyl)-2-(1-imino-5-methoxy-hexahydro-cyclopenta[c]pyrrol-2-yl)-ethanone hydrobromide

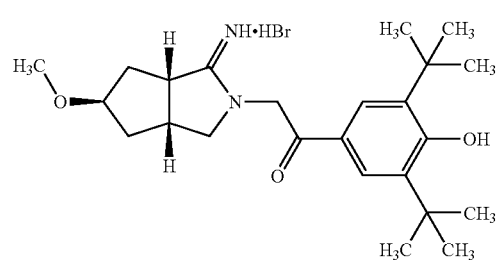

1H-NMR (DMSO-d6) δ: 1.39 (18H, s), 1.61-1.69 (1H, m), 1.90-2.07 (2H, m), 2.09-2.19 (1H, m), 2.90-2.99 (1H, br), 3.21 (3H, s), 3.30-3.38 (1H, m), 3.61-3.70 (1H, m), 3.85 (1H, t, J=8.7 Hz), 3.93 (1H, m), 5.22 (2H, s), 7.71 (2H, s), 8.04 (1H, br), 8.72 (1H, br), 9.23 (1H, br).

Example 68

2-[2-(3,5-Di-tert-butyl-4-hydroxy-phenyl)-2-oxo-ethyl]-1-imino-6-phenyl-hexahydro-cyclopenta[c]pyrrol-5-one hydrobromide

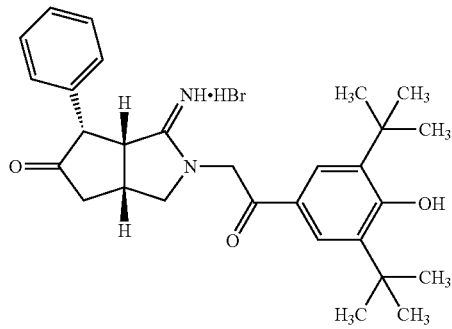

1H-NMR (DMSO-d6) δ: 1.38 (18H, s), 1.84-1.93 (1H, m), 2.55 (1H, dd, J=4.6, 18.4 Hz), 2.82 (1H, dd, J=9.2, 20.0 Hz), 3.63 (1H, dd, J=4.5, 10.8 Hz), 3.88 (1H, d, =6.0 Hz), 3.95-4.40 (2H, m), 5.21 (2H, s), 7.25-7.43 (5H, m), 7.74 (2H, s), 9.25 (1H, br), 9.50 (1H, br).

Example 69

1-(3,5-Di-tert-butyl-4-hydroxy-phenyl)-2-[2-imino-3-(3-isopropoxy-benzyl)-5-propyl-pyrrolidin-1-yl]-ethanone hydrobromide

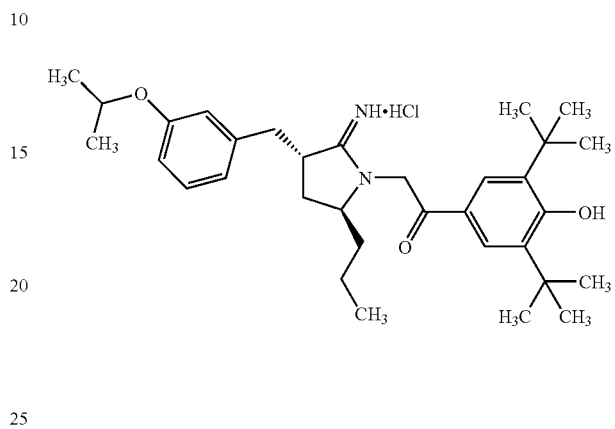

1H-NMR (DMSO-d6) δ: 0.82 (3H, t, J=7.2 Hz), 1.00-1.40 (3H, m), 1.27 (6H, d, J=6 Hz), 1.43 (18H, s), 1.52 (1H, m), 1.71 (1H, m), 2.27 (1H, m), 2.75 (1H, dd, J=10.4, 13.2 Hz), 3.30 (1H, m), 3.53 (1H, m), 3.74 (1H, m), 4.69 (1H, m), 5.02 (1H, d, J=19.2H), 5.26 (1H, d, J=19.2 Hz), 6.82 (2H, m), 6.86 (1H, s), 7.25 (1H, t, J=7.6 Hz), 7.78 (2H, s), 8.06 (1H, s), 8.89 (1H, s), 9.26 (1H, s).

Example 70

1-(3,5-Di-tert-butyl-4-hydroxy-phenyl)-2-[2-imino-3-(3-isopropoxy-benzyl)-5-propyl-pyrrolidin-1-yl]-ethanone hydrochloride

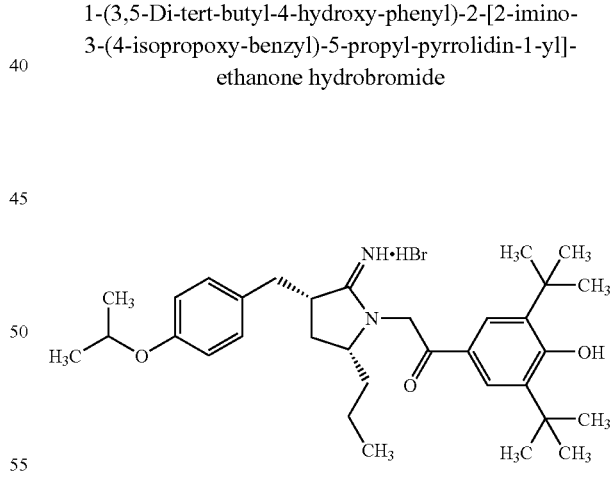

1H-NMR (DMSO-d6) δ: 0.84 (3H, t, J=7.2 Hz), 1.00-1.40 (3H, m), 1.27 (6H, d, J=6.0 Hz), 1.43 (18H, s), 1.72 (1H, m), 1.79 (1H, m), 2.00 (1H, m), 2.73 (1H, t, J=12.0 Hz), 3.21 (1H, m), 3.52 (1H, m), 3.81 (1H, m), 4.63 (1H, m), 5.05 (1H, d, J=18.8 Hz), 5.25 (1H, d, J=18.8 Hz), 6.82 (1H, d, J=7.6 Hz), 6.87 (1H, d, J=7.6 Hz), 6.89 (1H, s), 7.25 (1H, t, J=7.6 Hz), 7.78 (2H, s), 8.06 (1H, s), 8.88 (1H, s), 9.30 (1H, s).

Example 71

1-(3,5-Di-tert-butyl-4-hydroxy-phenyl)-2-[2-imino-3-(4-isopropoxy-benzyl)-5-propyl-pyrrolidin-1-yl]-ethanone hydrobromide 1H-NMR (DMSO-d6) δ: 0.81 (3H, t, J=7.2 Hz), 1.00-1.40 (3H, m), 1.26 (6H, d, J=6 Hz), 1.43 (18H, s), 1.51 (1H, m), 1.70 (1H, m), 2.26 (1H, m), 2.73 (1H, dd, J=10.0 Hz, 13.6 Hz), 3.24 (1H, m), 3.47 (1H, m), 3.74 (1H, m), 4.59 (1H, m), 5.01 (1H, d, J=18.4 Hz), 5.26 (1H, d, J=18.4 Hz), 6.89 (2H, d, J=7.2 Hz), 7.18 (2H, d, J=7.2 Hz), 7.78 (2H, s), 8.06 (1H, s), 8.87 (1H, s), 9.26 (1H, s).

Example 72

1-(3,5-Di-tert-butyl-4-hydroxy-phenyl)-2-[2-imino-3-(4-isopropoxy-benzyl)-5-propyl-pyrrolidin-1-yl]-ethanone hydrobromide

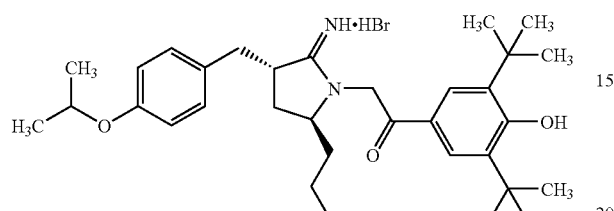

1H-NMR (DMSO-d6) δ: 0.84 (3H, t, J=7.2 Hz), 1.00-1.40 (3H, m), 1.26 (6H, d, J=6.0 Hz), 1.43 (18H, s), 1.71 (1H, m), 1.77 (1H, m), 1.98 (1H, m), 2.68 (1H, dd, J=10.8 Hz, 13.2 Hz), 3.18 (1H, dd, J=3.6 Hz, 13.2 Hz), 3.45 (1H, m), 3.81 (1H, m), 4.59 (1H, m), 5.04 (1H, d, J=18.8 Hz), 5.23 (1H, d, J=18.8 Hz), 6.89 (2H, d, J=8.4 Hz), 7.22 (2H, d, J=8.4 Hz), 7.78 (2H, s), 8.05 (1H, s), 8.87 (1H, s), 9.30 (1H, s).

Example 73

2-[3-Benzyl-2-imino-4-(2-methoxy-ethyl)-pyrrolidin-1-yl]-1-(3,5-di-tert-butyl-4-hydroxy-phenyl)-ethanone hydrobromide

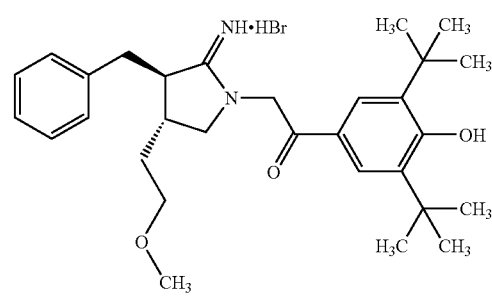

1H-NMR (DMSO-d6) δ: 1.43 (18H, s), 1.44-1.60 (2H, m), 2.25 (1H, m), 2.87 (1H, dd, J=11.2, 14.4 Hz), 3.01 (3H, s), 3.02-3.25 (5H, m), 3.82 (1H, dd, J=7.6, 11.6 Hz), 5.19 (2H, s), 7.25-7.40 (5H, m), 7.75 (2H, s), 8.06 (1H, brs), 8.96 (1H, brs), 9.43 (1H, brs).

Example 74

2-(3-Benzyl-4-ethoxymethyl-2-imino-pyrrolidin-1-yl)-1-(3,5-di-tert-butyl-4-hydroxy-phenyl)-ethanone hydrobromide

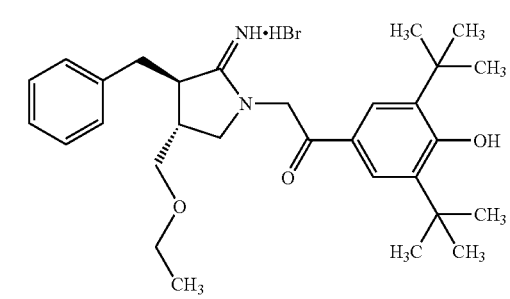

1H-NMR (DMSO-d6) δ: 0.98 (3H, t, J=6.8 Hz), 1.43 (18H, s), 1.44-1.60 (2H, m), 2.44 (1H, m), 2.88 (1H, dd, J=10.4, 14.4 Hz), 3.10-3.40 (7H, m), 3.76 (1H, dd, J=7.6, 10.8 Hz), 5.15 (1H, d, J=18.0 Hz), 5.20 (1H, d, J=18.0 Hz), 7.25-7.40 (5H, m), 7.75 (2H, s), 8.06 (1H, brs), 8.96 (1H, brs), 9.42 (1H, brs).

Example 75

2-(4-Benzyl-3-imino-2-aza-spiro[4.4]nona-2-yl)-1-(3,5-di-tert-butyl-4-hydroxy-phenyl)-ethanone hydrobromide

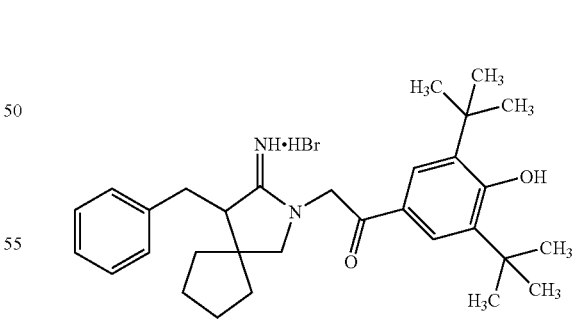

1H-NMR (DMSO-d6) δ 1.40 (18H, s), 1.35-1.55 (8H, m), 3.03 (2H, brs), 3.25 (2H, m), 3.57 (1H, d, J=8.0 Hz), 5.13 (2H, s), 7.23 (1H, m), 7.32 (2H, t, J=8.0 Hz), 7.38 (2H, d, J=8.0 Hz), 7.72 (2H, s).

Example 76

1-(3,5-Di-tert-butyl-4-hydroxy-phenyl)-2-[1-imino-5-(4-nitro-phenoxy)-hexahydro-cyclopenta[c]pyrrol-2-yl]-ethanone hydrobromide

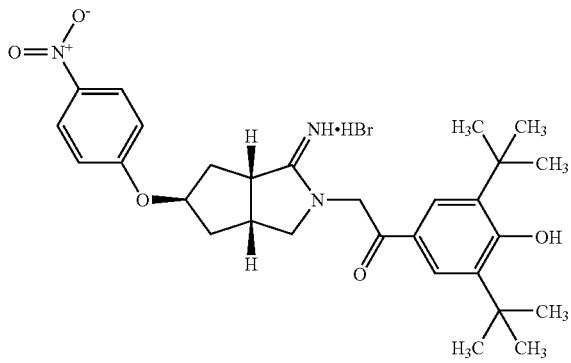

1H-NMR (DMSO-d6) δ: 1.39 (18H, s), 1.91-2.01 (1H, m), 2.19-2.27 (2H, m), 2.32-2.36 (1H, m), 3.08-3.14 (1H, m), 3.43 (1H, dd, J=2.0, 8.4 Hz), 3.42-3.53 (2H, m), 5.17 (2H, s), 5.22 (1H, brs), 7.16 (2H, d, J=12.4 Hz), 7.73 (2H, s), 8.05 (1H, br), 8.22 (2H, d, J=12.0 Hz), 8.78 (1H, brs), 9.27 (1H, brs).

Example 77

2-[5-(4-Amino-phenoxy)-1-imino-hexahydro-cyclopenta[c]pyrrol-2-yl]-1-(3,5-di-tert-butyl-4-hydroxy-phenyl)-ethanone hydrobromide

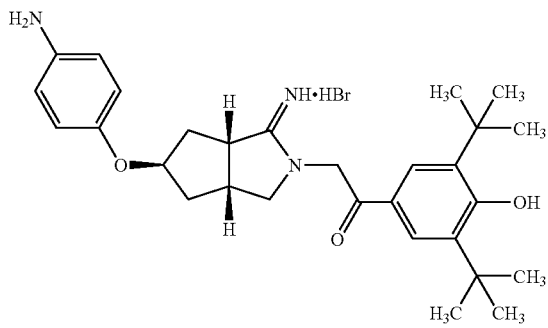

1H-NMR (DMSO-d6) δ: 1.31 (18H, s), 1.76-1.84 (1H, m), 2.01-2.14 (2H, m), 2.16-2.28 (1H, m), 2.89-3.06 (2H, m), 3.51-3.58 (1H, m), 3.65-3.74 (1H, m), 3.82-3.90 (1H, m), 4.83 (2H, s), 6.49 (2H, d, J=8.8 Hz), 6.66 (2H, d, J=8.8 Hz), 7.14 (2H, s), 7.40 (2H, br).

Example 78

N-(4-{2-[2-(3,5-di-tert-butyl-4-hydroxy-phenyl)-2-oxo-ethyl]-1-imino-octahydro-cyclopenta[c]pyrrol-5-yloxy}-phenyl)-acetamide hydrobromide

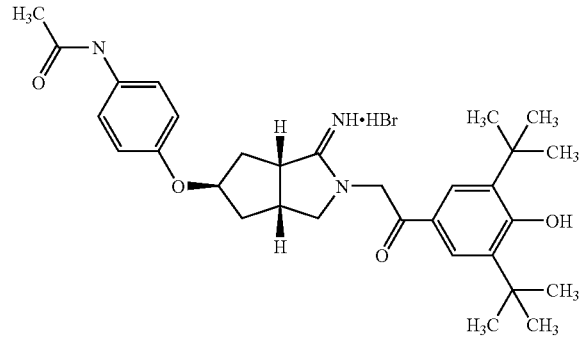

1H-NMR (DMSO-d6) δ: 1.39 (18H, s), 1.82-1.91 (1H, m), 2.09-2.18 (2H, m), 2.46-2.34 (1H, m), 3.05-3.12 (1H, m), 3.40 (1H, dd, J=2.4, 12.0 Hz), 3.77 (1H, dd, J=10.0, 12.4 Hz), 3.88 (1H, dd, J=6.8, 12.0 Hz), 4.94 (1H, br), 5.14 (2H, s), 6.87 (2H, d, J=12.4 Hz), 7.46 (2H, d, J=11.6 Hz), 7.72 (2H, s), 8.75 (1H, br), 9.23 (1H, br), 9.80 (1H, br).

Example 79

1-(3,5-Di-tert-butyl-4-hydroxy-phenyl)-2-(2-imino-3-isopropyl-4-propyl-pyrrolidin-1-yl)-ethanone hydrobromide

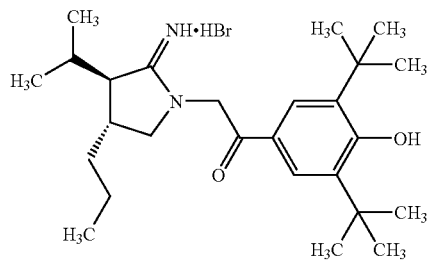

1H-NMR (DMSO-d6) δ: 0.92 (3H, t, J=6.8 Hz), 0.98 (3H, d, J=6.4 Hz), 1.04 (3H, d, J=6.4 Hz), 1.23-1.42 (3H, m), 1.42 (18H, s), 2.20-2.36 (2H, m), 2.73 (1H, brs), 3.30 (1H, d, J=11.2 Hz), 3.60 (1H, m), 3.79 (1H, dd, J=8.0, 10.4 Hz), 5.16 (1H, d, J=18.4 Hz), 5.22 (1H, d, J=18.4 Hz), 7.74 (2H, s), 8.05 (1H, brs), 8.80 (1H, brs), 9.10 (1H, brs).

Example 80

1-(3,5-Di-tert-butyl-4-hydroxy-phenyl)-2-(2-imino-3-isopropyl-4-propyl-pyrrolidin-1-yl)-ethanone hydrobromide

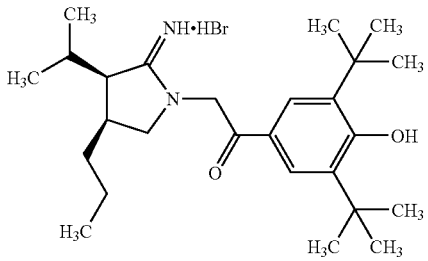

1H-NMR (DMSO-d6) δ: 0.92 (3H, t, J=7.2 Hz), 1.05 (3H, d, J=6.8 Hz), 1.11 (3H, d, J=6.8 Hz), 1.23-1.34 (2H, m), 1.42 (18H, s), 1.55 (1H, m), 2.20-2.36 (2H, m), 2.17 (1H, m), 2.68 (1H, m), 2.96 (1H, dd, J=3.2, 8.8 Hz), 3.44 (1H, t, J=10.0 Hz), 3.55-3.64 (2H, m), 5.18 (1H, d, J=18.0 Hz), 5.24 (1H, d, J=18.0 Hz), 7.75 (2H, s), 8.04 (1H, brs), 8.86 (1H, brs), 8.96 (1H, brs).

Example 81

2-(3-Benzylidene-2-imino-4-propyl-pyrrolidin-1-yl)-1-(3,5-di-tert-butyl-4-hydroxy-phenyl)-ethanone hydrobromide

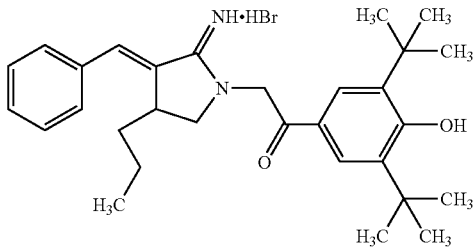

1H-NMR (DMSO-d6) δ: 0.85 (3H, t, J=7.2 Hz), 1.20-1.55 (4H, m), 1.41 (18H, s), 3.49 (1H, d, J=10.6 Hz), 3.70-3.80 (1H, m), 3.90 (1H, dd, J=10.6, 6.8 Hz), 5.27 (1H, d, J=18.0 Hz), 5.34 (1H, d, J=18.0 Hz), 7.46 (1H, dd, J=7.2, 7.2 Hz), 7.52 (2H, t, J=7.2 Hz), 7.59 (2H, t, J=7.2 Hz), 7.64 (1H, brs), 7.75 (2H, s).

Example 82

2-(3-Benzyl-2-imino-5-methoxymethyl-pyrrolidin-1-yl)-1-(3,5-di-tert-butyl-4-hydroxy-phenyl)-ethanone hydrobromide

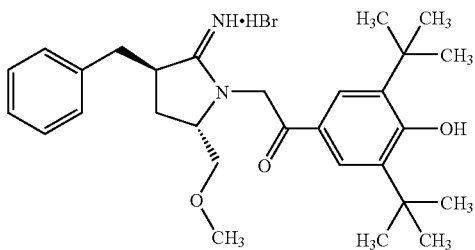

1H-NMR (DMSO-d6) δ: 1.43 (18H, s), 1.83 (1H, m), 1.97 (1H, m), 2.71 (1H, t, J=12.0 Hz), 3.15 (3H, s), 3.36 (2H, m), 3.52 (2H, m), 4.04 (1H, m), 5.08 (1H, d, J=17.6 Hz), 5.20 (1H, d, J=17.6 Hz), 7.25-7.40 (5H, m), 7.76 (2H, s), 8.05 (1H, s), 8.99 (1H, s), 9.40 (1H, s).

Example 83

4-Benzyl-1-[2-(3,5-di-tert-butyl-4-hydroxy-phenyl)-2-oxo-ethyl]-5-imino-pyrrolidine-2-carboxamide hydrobromide

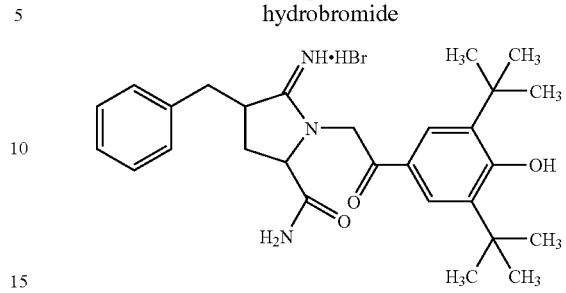

1H-NMR (DMSO-d6) δ: 1.42 (18H, s), 1.77 (1H×0.5, td, J=4.4, 13.6 Hz), 1.96 (1H×0.5, m), 2.17 (1H×0.5, m), 2.45 (1H×0.5, m), 2.75 (1H, m), 3.27 (1H, m), 3.55 (1H, m), 4.38 (1H×0.5, dd, J=4.4, 9.2 Hz), 4.44 (1H×0.5, dd, J=4.8, 8.4 Hz), 4.95 (1H, d, J=18.8 Hz), 5.30 (1H×1.5, d, J=18.8 Hz), 5.32 (1H×0.5, d, J=18.8 Hz), 7.20-7.40 (5H, m), 7.46 (1H×0.5, s), 7.66 (1H×0.5, s), 7.73 (2H×0.5, s), 7.74 (2H×0.5, s), 8.06 (1H, s), 9.17 (1H×0.5, s), 9.19 (1H×0.5, s), 9.60 (1H×0.5, s), 9.62 (1H×0.5, s).

Example 84 tert-Butyl (4-{1-[2-(3,5-di-tert-butyl-4-hydroxy-phenyl)-2-oxo-ethyl]-2-imino-4-propyl-pyrrolidin-3-ylmethyl}-phenyl)-carbamate hydrobromide

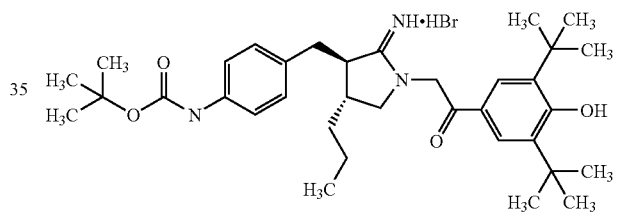

1H-NMR (DMSO-d6) δ: 0.67 (3H, t, J=6.8 Hz), 1.12-1.50 (4H, m), 1.40 (18H, s), 1.46 (9H, s), 2.06-2.14 (1H, m), 2.72-2.82 (1H, m), 2.97-3.11 (2H, m), 3.18-3.26 (1H, m), 3.71-3.84 (1H, m), 5.14 (2H, s), 7.18 (2H, d, J=8.2 Hz), 7.41 (2H, d, J=8.2 Hz), 7.71 (2H, s), 9.35 (2H, s). MS: m/e(ESI) 578.3 (MH+)

Example 85

2-[3-(4-Amino-benzyl)-2-imino-4-propyl-pyrrolidin-1-yl]-1-(3,5-di-tert-butyl-4-hydroxy-phenyl)-ethanone dihydrochloride

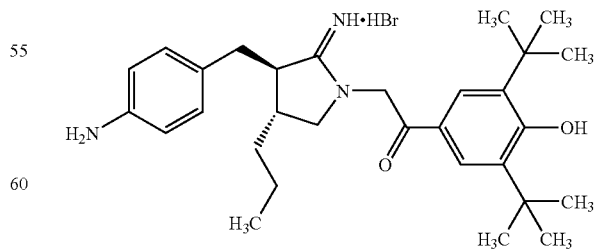

1H-NMR (DMSO-d6) δ: 0.64 (3H, t, J=7.2 Hz), 0.85-1.30 (4H, m), 1.40 (18H, s), 2.04-2.13 (1H, m), 2.85 (1H, dd, J=10.6 Hz. J=12.8 Hz), 3.06-3.12 (1H, m), 3.18-3.28 (2H, m), 3.83 (1H, dd, J=7.6 Hz. J=10.6 Hz), 5.22 (2H, s), 7.29 (2H, d,

J=8.4 Hz), 7.41 (2H, d, J=8.4 Hz), 7.73 (2H, s), 8.05 (1H, s), 9.73 (1H, s). MS: m/e(ESI) 478.2 (MH+)

Example 86

N-(4-{1-[2-(3,5-di-tert-butyl-4-hydroxy-phenyl)-2-oxo-ethyl]-2-imino-4-propyl-pyrrolidin-3-ylmethyl}-phenyl)-acetamide hydrobromide

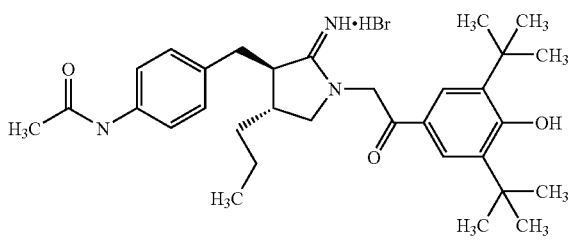

1H-NMR (DMSO-d6) δ: 0.65 (3H, t, J=7.2 Hz), 0.90-1.30 (4H, m), 1.40 (18H, s), 2.02 (3H, s), 2.06-2.16 (1H, m), 2.74-2.82 (1H, m), 3.00-3.18 (2H, m), 3.20-3.26 (1H, m), 3.73-3.82 (1H, m), 5.13 (2H, s), 7.23 (2H, d, J=8.6 Hz), 7.54 (2H, d, J=8.6 Hz), 7.72 (2H, s). MS: m/e(ESI) 520.3 (MH+)

Example 87

1-(3,5-di-tert-butyl-4-hydroxy-phenyl)-2-(2-imino-4-propyl-3-pyridin-2-ylmethylene-pyrrolidin-1-yl)-ethanone hydrobromide

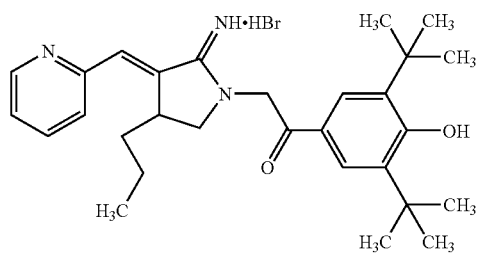

1H-NMR (DMSO-d6) δ: 0.89 (3H, t, J=6.0 Hz), 1.34-1.40 (5H, m), 1.40 (18H, s), 3.50 (2H, d, J=10.0 Hz), 5.30 (1H, s), 7.42 (1H, d, J=8.0 Hz), 7.60 (1H, s), 7.71 (2H, s), 7.92 (1H, t, J=8.0 Hz), 8.73 (1H, d, J=8.0 Hz). MS: m/e(ESI) 462.2 (MH+)

Example 88

Methyl 5-{1-[2-(3,5-di-tert-butyl-4-hydroxy-phenyl)-2-oxo-ethyl]-2-imino-4-propyl-pyrrolidin-3-ylidenemethyl}-thiophene-2-carboxylate hydrobromide

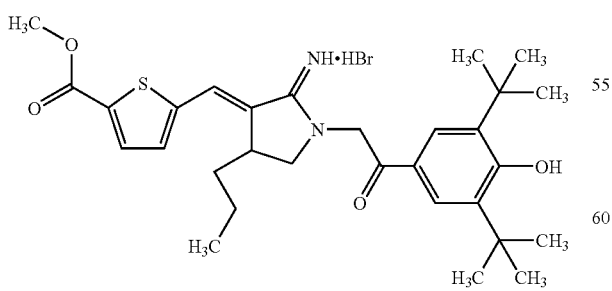

1H-NMR (DMSO-d6) δ: 0.93 (3H, t, J=6.0 Hz), 1.35-1.60 (5H, m), 1.40 (18H, s), 3.54 (2H, d, J=10.0 Hz), 3.85 (3H,s), 5.28 (1H, s), 7.47 (1H, d, J=4.5 Hz), 7.73 (2H, s), 7.86 (1H, s), 7.88 (1H, d, J=4.5 Hz).

Example 89

1-(3,5-Di-tert-butyl-4-hydroxy-phenyl)-2-[(3S,4S)-2-imino-3-(2-methoxy-phenyl)-4-propyl-pyrrolidin-1-yl]-ethanone hydrobromide

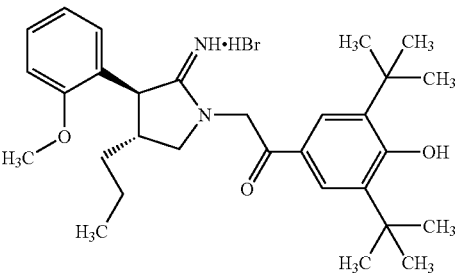

1H-NMR (DMSO-d6) δ: 0.84 (3H, t, J=7.2 Hz), 1.20-1.32 (2H, m), 1.44 (18H, s), 1.40-1.56 (2H, m), 2.42 (1H, m), 3.41 (1H, dd, J=6.4, 10.8 Hz), 3.86 (3H, s), 3.86 (1H, m), 4.24 (1H, d, J=7.2 Hz), 5.28 (2H, s), 7.03 (1H, t, J=7.6 Hz), 7.10 (1H, d, J=7.6 Hz), 7.37 (1H, d, J=7.6 Hz), 7.78 (2H, s), 8.06 (1H, brs), 8.83 (1H, brs), 8.87 (1H, brs).

Example 90

1-(3,5-Di-tert-butyl-4-hydroxy-phenyl)-2-[2-imino-3-(4-methoxy-benzylidene-4-propyl-pyrrolidin-1-yl)-ethanone hydrobromide

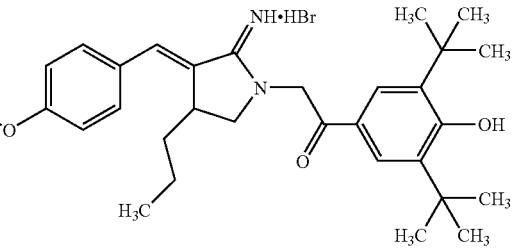

1H-NMR (DMSO-d6) δ: 0.86 (3H, t, J=7.2 Hz), 1.10-1.50 (4H, m), 1.29 (18H, s), 3.30-3.38 (1H, m), 3.39-3.46 (1H, m), 3.56-3.65 (1H, m), 3.81 (3H, s), 4.88 (1H, d, J=17.2 Hz), 4.95 (1H, d, J=17.2 Hz), 7.07 (2H, d, J=8.8 Hz), 7.34 (2H, br), 7.51 (1H, s), 7.52 (2H, d, J=8.8 Hz). MS: m/e(ESI) 491.2 (MH+)

Example 91

1-(3,5-Di-tert-butyl-4-hydroxy-phenyl)-2-[2-imino-3-(2-isopropoxy-benzylidene)-4-propyl-pyrrolidin-1-yl]-ethanone hydrobromide

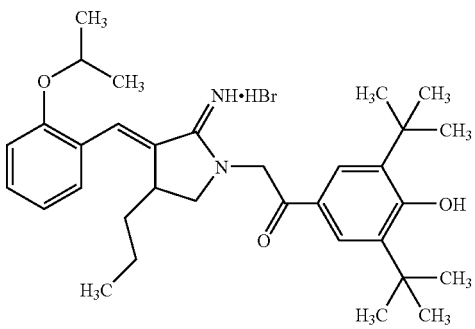

1H-NMR (DMSO-d6) δ: 0.74 (3H, t, J=7.2 Hz), 1.10-1.50 (4H, m), 1.30 (6H, t, J=6.0 Hz), 1.41 (18H, s), 3.42 (1H, dd, J=2.0 Hz, J=11.2 Hz), 3.58-3.69 (1H, m), 3.87 (1H, dd, J=7.6

Hz, J=11.2 Hz), 4.66-4.76 (1H, m), 5.28 (1H, d, J=18.4 Hz), 5.34 (1H, d, J=18.4 Hz), 7.01 (1H, t, J=7.2 Hz), 7.14 (1H, d, J=8.0 Hz), 7.36-7.44 (1H, m), 7.54 (1H, d, J=6.8 Hz), 7.76 (3H, s), 8.71 (1H, br), 9.34 (1H, br). MS: m/e(ESI) 519.2 (MH+)

Example 92

1-(3,5-Di-tert-butyl-4-hydroxy-phenyl)-2-[3-(2,4-dimethoxy-benzylidene)-2-imino-4-propyl-pyrrolidin-1-yl]-ethanone hydrobromide

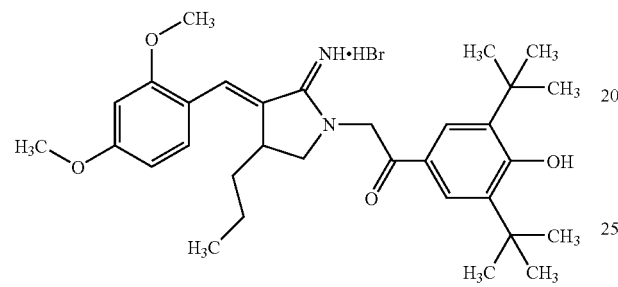

1H-NMR (DMSO-d6) δ: 0.82 (3H, t, J=7.2 Hz), 1.20-1.40 (4H, m), 1.41 (18H, s), 3.42 (1H, d, J=10.4 Hz), 3.80-3.85 (1H, m), 3.55-3.65 (1H, m), 3.83 (3H, s), 3.87 (3H, s), 5.23 (1H, d, J=18.0 Hz), 5.29 (1H, d, J=18.0 Hz), 6.66 (1H, d, J=8.8 Hz), 6.67 (1H, s), 7.53 (1H, d, J=8.8 Hz), 7.70 (1H, s), 7.74 (2H, s), 8.54-8.65 (1H, brs), 9.15-9.22 (1H, brs).

Example 93

1-(3,5-Di-tert-butyl-4-hydroxy-phenyl)-2-[3-(2-hydroxymethyl-benzyl)-2-imino-4-propyl-pyrrolidin-1-yl]-ethanone hydrobromide

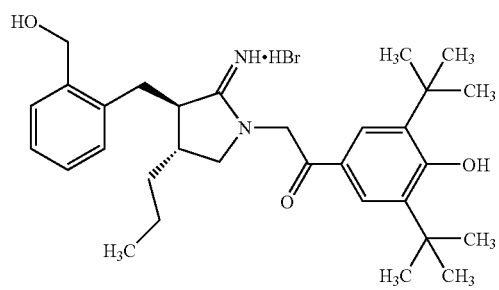

1H-NMR (DMSO-d6) δ: 0.58 (3H, t, J=7.6 Hz), 0.80-1.35 (4H, m), 1.41 (18H, s), 2.10-2.20 (1H, m), 2.80 (1H, dd, J=12.8, 12.8 Hz), 3.10-3.40 (3H, m), 3.90 (1H, dd, J=10.0, 7.2 Hz), 4.58 (2H, s), 5.18 (2H, s), 5.10-5.22 (1H, m), 7.20-7.32 (3H, m), 7.40 (1H, dd, J=4.8, 4.0 Hz), 7.73 (2H, s), 8.90-9.00 (1H, brs), 9.25-9.35 (1H, brs).

Example 94

1-(3,5-Di-tert-butyl-4-hydroxy-phenyl)-2-[(3S,4S)-2-imino-3-(4-methoxy-phenyl)-4-propyl-pyrrolidin-1-yl]-ethanone hydrobromide

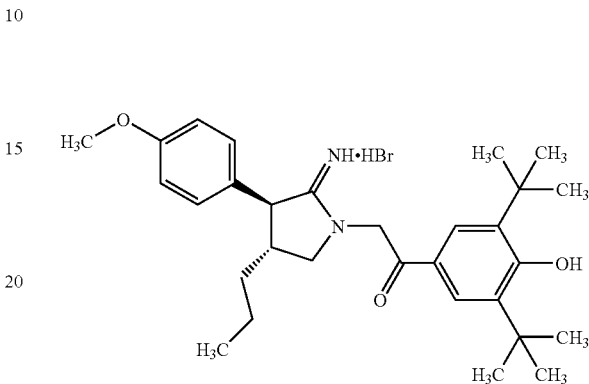

1H-NMR (DMSO-d6) δ: 0.83 (3H, t, J=7.6 Hz), 1.15-1.30 (2H, m), 1.43 (18H, s), 1.40-1.55 (2H, m), 2.40 (1H, m), 3.43 (1H, dd, J=8.8, 10.4 Hz), 3.78 (3H, s), 3.88 (1H, dd, J=8.4, 10.4 Hz), 4.08 (1H, d, J=7.2 Hz), 5.27 (2H, s), 7.02 (2H, d, J=8.4 Hz), 7.34 (2H, d, J=8.4 Hz), 7.77 (2H, s), 8.07 (1H, brs), 8.73 (1H, brs), 8.92 (1H, brs).

Example 95

4-(3-Benzyl-2-imino-4-propyl-pyrrolidin-1-ylmethyl)-2,6-di-tert-butyl-phenol hydrobromide

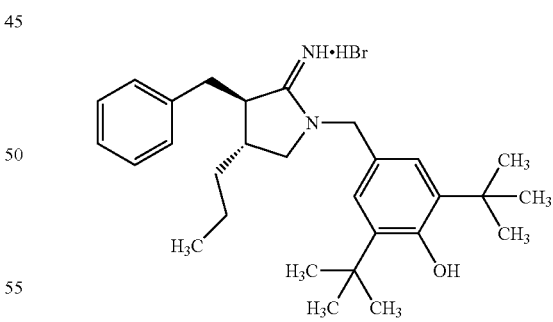

1H-NMR (DMSO-d6) δ: 0.62 (3H, t, J=7.2 Hz), 0.95 (2H, m), 1.11 (2H, m), 1.37 (18H, s), 2.06 (1H, m), 2.84 (1H, dd, J=8.8 Hz, 13.2 Hz), 3.05-3.16 (3H, m), 3.55 (1H, dd, J=7.6 Hz, 11.2 Hz), 4.52 (1H, d, J=19.2 Hz), 4.55 (1H, d, J=19.2 Hz), 6.98 (2H, s), 7.22 (1H, s), 7.20-7.35 (5H, m), 9.28 (1H, s), 9.46 (1H, s).

Example 96

2-(3-Benzyl-2-imino-4-propyl-pyrrolidin-1-yl)-1-(3,5-di-tert-butyl-4-hydroxy-phenyl)-ethanone O-methyl-oxime hydrobromide

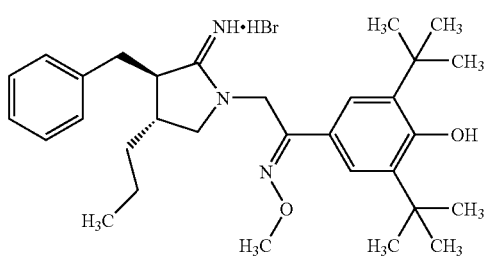

1H-NMR (DMSO-d6) δ: 0.43 (3H, t, J=6.8 Hz), 0.55-0.80 (4H, m), 1.38 (18H, s), 1.81 (1H, m), 2.41 (1H, m), 2.77 (1H, m), 2.84 (1H, m), 2.99 (1H, dd, J=3.6, 12.8 Hz), 3.28 (1H, m), 3.55 (1H, dd, J=7.2, 10.8 Hz), 3.94 (3H, s), 4.71 (1H, d, J=16.4 Hz), 4.83 (1H, d, J=16.4 Hz), 7.15-7.35 (7H, m), 7.41 (1H, s), 9.34 (1H, s), 9.69 (1H, s).

Example 97

1-(3,5-Di-tert-butyl-4-hydroxy-phenyl)-2-[2-imino-3-(4-methyl-benzylidene)-4-propyl-pyrrolidin-1-yl]-ethanone hydrobromide 1H-NMR (DMSO-d6) δ: 0.86 (3H, t, J=7.2 Hz), 1.20-1.60 (4H, m), 1.41 (18H, s), 2.36 (3H, s), 3.49 (1H, d, J=10.6 Hz), 3.68-3.76 (1H, m), 3.89 (1H, dd, J=6.8 Hz, J=10.6 Hz), 5.28 (1H, d, J=18.4 Hz), 5.34 (1H, d, J=18.4 Hz), 7.34 (2H, d, J=8.2 Hz), 7.49 (2H, d, J=8.2 Hz), 7.61 (1H, s), 7.75 (2H, s), 8.07 (1H, s), 8.76 (1H, s), 9.21 (1H, s). MS: m/e(ESI) 475.3 (MH+)

Example 98

1-(3,5-Di-tert-butyl-4-hydroxy-phenyl)-2-[2-imino-3-(4-isopropoxy-benzylidene)-4-propyl-pyrrolidin-1-yl]-ethanone hydrobromide

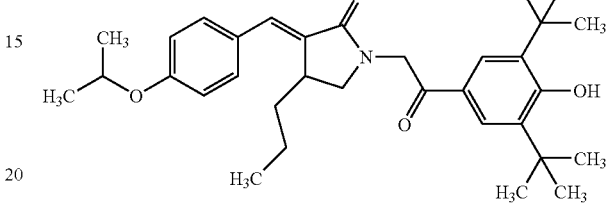

1H-NMR (DMSO-d6) δ: 0.88 (3H, t, J=7.2 Hz), 1.20-1.60 (4H, m), 1.27 (3H, d, J=2.2 Hz), 1.29 (3H, d, J=2.2 Hz), 1.41 (18H, s), 3.48 (1H, d, J=10.8 Hz), 3.63-3.70 (1H, m), 3.87 (1H, dd, J=6.8 Hz, J=10.8 Hz), 4.67-4.76 (1H, m), 5.26 (1H, d, J=18.6 Hz), 5.33 (1H, d, J=18.6 Hz), 7.06 (2H, d, J=8.8 Hz), 7.52 (2H, d, J=8.8 Hz), 7.57 (1H, s), 7.75 (2H, s), 8.06 (1H, s), 8.69 (1H, s), 9.15 (1H, s). MS: m/e(ESI) 519.4 (MH+)

Example 99

1-(3,5-Di-tert-butyl-4-hydroxy-phenyl)-2-[2-imino-3-(4-nitro-benzylidene)-4-propyl-pyrrolidin-1-yl]-ethanone hydrobromide

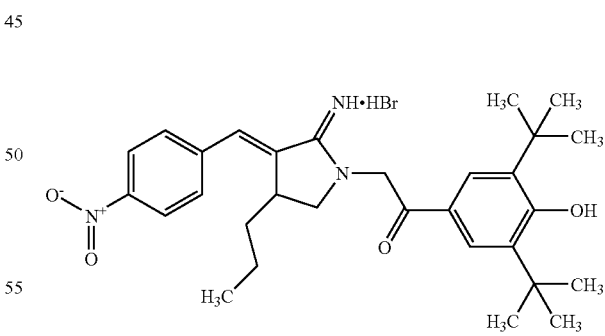

1H-NMR (DMSO-d6) δ: 0.83 (3H, t, J=7.2 Hz), 1.00-1.50 (4H, m), 1.40 (18H, s), 3.52 (1H, d, J=11.2 Hz), 3.75-3.83 (1H, m), 3.93 (1H, dd, J=11.2, 6.8 Hz), 5.20-5.35 (2H, m), 7.71 (2H, s), 7.74 (1H, s), 7.83 (2H, d, J=8.8 Hz), 8.34 (2H, d, J=8.8 Hz).

Example 100

1-(3,5-Di-tert-butyl-4-hydroxy-phenyl)-2-[2-imino-3-(4-methyl-benzylidene)-pyrrolidin-1-yl]-ethanone hydrobromide

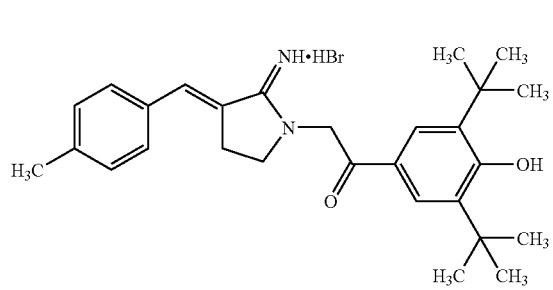

1H-NMR (DMSO-d6) δ: 1.41 (18H, s), 2.36 (3H, s), 3.18-3.28 (2H, m), 3.73-3.80 (2H, m), 5.29 (2H, s), 7.33 (2H, d, J=8.0 Hz), 7.43 (2H, d, J=8.0 Hz), 7.62 (1H, s), 7.73 (2H, s).

Example 101

2-(3-Benzyl-2-ethylimino-4-propyl-pyrrolidin-1-yl)-1-(3,5-di-tert-butyl-4-hydroxy-phenyl)-ethanone hydrobromide

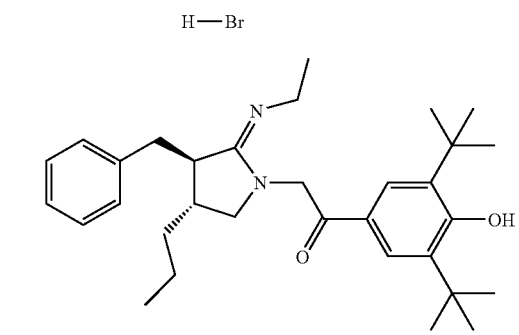

1H-NMR (DMSO-d6) δ: 0.67 (3H, t, J=7.2 Hz), 0.96-1.25 (2H, m), 1.16 (3H, t, J=7.2 Hz), 1.30 (2H, q, J=7.2 Hz), 1.43 (18H, s), 2.09 (1H, dd, J=7.2 Hz, 13.2 Hz), 2.82 (1H, dd, J=10.8 Hz, 13.6 Hz), 3.09 (1H, dd, J=3.6 Hz, 13.6 Hz), 3.25 (1H, d, J=11.2 Hz), 3.43 (1H, m), 3.52 (1H, m), 3.93 (1H, dd, J=6.8 Hz, 11.2 Hz), 5.16 (1 h, d, J=18.4 Hz), 5.21 (1H, d, J=18.4 Hz), 7.25-7.45 (5H, m), 7.76 (2H, s), 8.08 (1H, s), 8.94 (1H, s).

Example 102

2-[3-Benzyl-2-(2-hydroxy-ethylimino)-4-propyl-pyrrolidin-1-yl]-1-(3,5-di-tert-butyl-4-hydroxy-phenyl)-ethanone hydrobromide

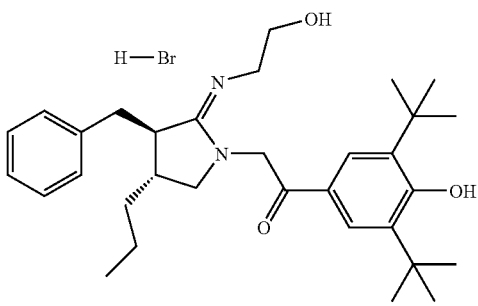

1H-NMR (DMSO-d6) δ: 0.64 (3H, t, J=7.2 Hz), 0.96-1.22 (2H, m), 1.31 (2H, q, J=7.2 Hz), 1.43 (18H, s), 2.09 (1H, dd, J=7.2 Hz, 13.2 Hz), 2.81 (1H, dd, J=12.0 Hz, 13.6 Hz), 3.14 (1H, dd, J=3.6 Hz, 13.6 Hz), 3.27 (1H, d, J=11.2 Hz), 3.35-3.60 (5H, m), 3.97 (1H, dd, J=6.8 Hz, 10.8 Hz), 5.02 (1H, t, J=4.8 Hz), 5.20 (1 h, d, J=18.4 Hz), 5.27 (1H, d, J=18.4 Hz), 7.25-7.45 (5H, m), 7.77 (2H, s), 8.08 (1H, s), 9.04 (1H, s).

Example 103

2-[3-Benzyl-2-(2-methoxy-ethylimino)-4-propyl-pyrrolidin-1-yl]-1-(3,5-di-tert-butyl-4-hydroxy-phenyl)-ethanone hydrobromide

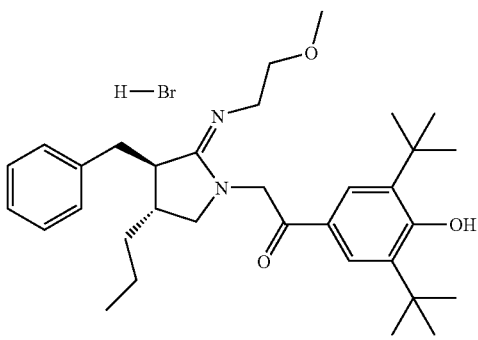

1H-NMR (DMSO-d6) δ: 0.66 (3H, t, J=7.2 Hz), 0.96-1.06 (1H, m), 1.10-1.23 (1H, m), 1.31 (2H, q, J=7.2 Hz), 1.43 (18H, s), 2.09 (1H, m), 2.82 (1H, dd, J=10.4 Hz, 13.6 Hz), 3.14 (1H, dd, J=4.0 Hz, 13.6 Hz), 3.27 (1H, d, J=10.8 Hz), 3.28 (3H, s), 3.35-3.65 (5H, m), 3.96 (1H, dd, J=6.8 Hz, 10.8 Hz), 5.20 (1 h, d, J=18.4 Hz), 5.26 (1H, d, J=18.4 Hz), 7.25-7.45 (5H, m), 7.77 (2H, s), 8.08 (1H, s), 9.14 (1H, s).

Example 104

Methyl [1-[2-(3,5-di-tert-butyl-4-hydroxy-phenyl)-2-oxo-ethyl]-4-(hydroxy-phenyl-methyl)-5-imino-pyrrolidin-3-yl]-acetate hydrobromide

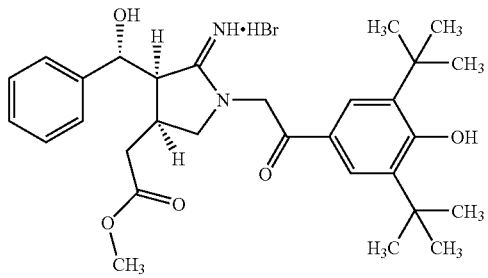

1H-NMR (DMSO-d6) δ: 1.46 (18H, s), 2.32 (1H, dd, J=18, 9 Hz), 2.36 (1H, dd, J=18, 10 Hz), 2.90 (1H, t, J=8 Hz), 3.04 (1H, m), 3.18 (1H, dd, J=10, 8 Hz), 3.45 (3H, s), 3.77 (1H, dd, J=10, 9 Hz), 5.01 (1H, d, J=9 Hz), 5.34 (1H, d, J=18 Hz), 5.76 (1H, d, J=18 Hz), 5.85 (1H, s), 7.27-7.43 (5H, m), 7.87 (2H, s), 8.75 (1H, s), 9.80 (1H, s). MS: m/e(ESI) 509.4 (MH+)

Example 105

4-{1-[2-(3,5-Di-tert-butyl-4-hydroxy-phenyl)-2-oxo-ethyl]-2-imino-4-propyl-pyrrolidin-3-ylmethyl}-benzonitrile hydrobromide

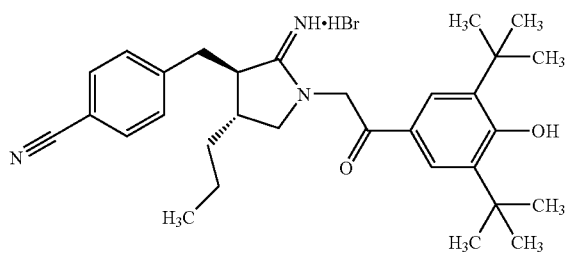

1H-NMR (DMSO-d6) δ: 0.63 (3H, t, J=7.2 Hz), 0.80-1.30 (4H, m), 1.38 (18H, s), 2.05-2.16 (1H, m), 2.96 (1H, dd, J=12.8, 10.0 Hz), 3.07-3.12 (1H, m), 3.20-3.35 (2H, m), 3.83 (1H, dd, J=10.0, 7.2 Hz), 5.09 (2H, s), 7.56 (2H, d, J=8.4 Hz), 7.66 (2H, s), 7.84 (2H, d, J=8.4 Hz).

Example 106

1-(3,5-Di-tert-butyl-4-hydroxy-phenyl)-2-[2-imino-3-(3-methoxy-benzylidene)-4-propyl-pyrrolidin-1-yl]-ethanone hydrobromide

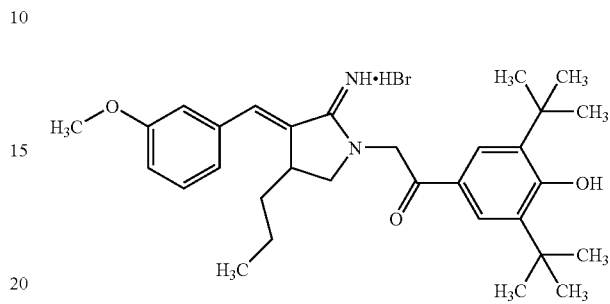

1H-NMR (DMSO-d6) δ: 0.85 (3H, t, J=7.2 Hz), 1.20-1.58 (4H, m), 1.41 (18H, s), 3.49 (1H, d, J=11.2 Hz), 3.70-3.80 (1H, m), 3.81 (3H, s), 3.89 (1H, dd, J=11.2, 7.2 Hz), 5.25 (1H, d, J=18.4 Hz), 5.32 (1H, d, J=18.4 Hz), 7.05 (1H, dd, J=8.6, 2.0 Hz), 7.09 (1H, brs), 7.16 (1H, dd, J=8.6, 1.2 Hz), 7.44 (1H, dd, J=8.6, 8.6 Hz), 7.59 (1H, s), 7.72 (2H, s).

Example 107

Methyl 4-{3-[2-(3,5-di-tert-butyl-4-hydroxy-phenyl)-2-oxo-ethyl]-2-imino-5-propyl-cyclopentylidenemethyl}-benzoate hydrobromide

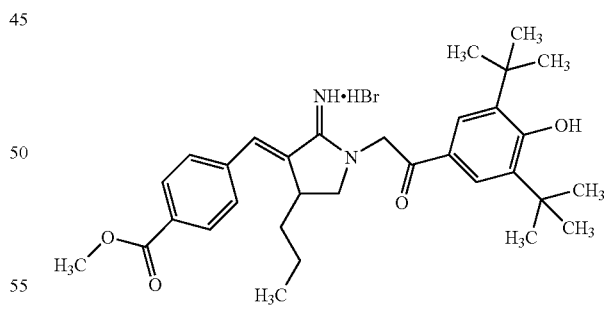

1H-NMR (DMSO-d6) δ: 0.83 (3H, t, J=7.2 Hz), 1.20-1.50 (4H, m), 1.41 (18H, s), 3.51 (1H, d, J=10.6 Hz), 3.75-3.84 (1H, m), 3.87 (3H, s), 3.92 (1H, dd, J=6.8 Hz, J=10.6 Hz), 5.31 (1H, d, J=18.4 Hz), 5.37 (1H, d, J=18.4 Hz), 7.73 (2H, d, J=8.8 Hz), 7.76 (2H, s), 8.07 (2H, d, J=8.8 Hz), 8.07 (1H, s), 8.91 (1H, s), 9.35 (1H, s). MS: m/e(ESI) 519.4 (MH+)

Example 108

4-{1-[2-(3,5-Di-tert-butyl-4-hydroxy-phenyl)-2-oxo-ethyl]-2-imino-4-propyl-pyrrolidin-3-ylidenemethyl}-benzoic acid hydrochloride

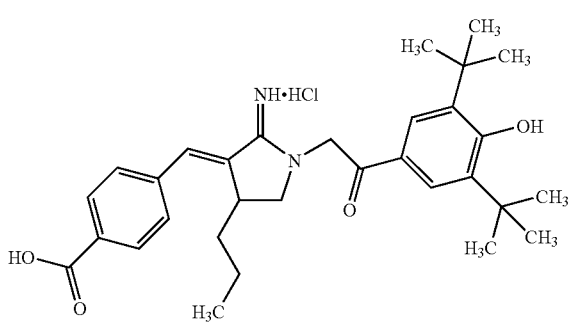

1H-NMR (DMSO-d6) δ: 0.83 (3H, t, J=7.2 Hz), 1.22-1.53 (4H, m), 1.41 (18H, s), 3.50 (1H, d, J=10.6 Hz), 3.74-3.83 (1H, m), 3.91 (1H, dd, J=6.4 Hz, J=10.6 Hz), 5.31 (1H, d, J=18.6 Hz), 5.38 (1H, d, J=18.6 Hz), 7.70 (2H, d, J=8.4 Hz), 7.75 (2H, s), 7.79 (1H, s), 8.04 (2H, d, J=8.4 Hz). MS: m/e (ESI) 505.4 (MH+)

Example 109

1-(3,5-Di-tert-butyl-4-hydroxy-phenyl)-2-[2-imino-3-(6-methyl-pyridin-2-ylmethylene)-4-propyl-pyrrolidin-1-yl]-ethanone hydrobromide

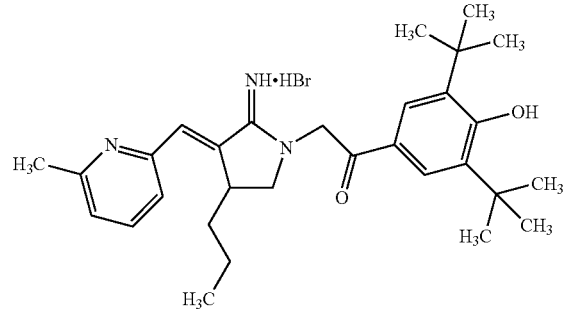

1H-NMR (DMSO-d6) δ: 0.90 (3H, t, J=7.2 Hz), 1.20-1.80 (4H, m), 1.41 (18H, s), 2.53 (3H, s), 3.51 (1H, d, J=10.8 Hz), 3.88 (1H, dd, J=6.4 Hz, J=10.8 Hz), 4.04-4.12 (1H, m), 5.29 (1H, d, J=18.4 Hz), 5.36 (1H, d, J=18.4 Hz), 7.30 (1H, d, J=7.8 Hz), 7.33 (1H, d, J=7.8 Hz), 7.60 (1H, d, J=1.6 Hz), 7.75 (2H, s), 7.81 (1H, t, J=7.8 Hz), 8.85 (1H, s), 9.30 (1H, s). MS: m/e(ESI) 476.3 (MH+)

Example 110

1-(3,5-Di-tert-butyl-4-hydroxy-phenyl)-2-[2-imino-3-(2-methoxy-benzylidene)-4-propyl-pyrrolidin-1-yl]-ethanone hydrobromide

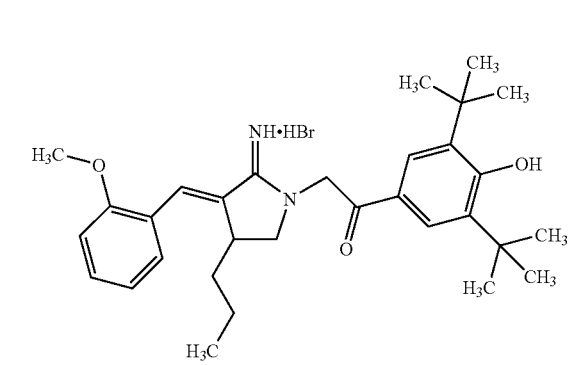

1H-NMR (DMSO-d6) δ: 0.76 (3H, t, J=7.2 Hz), 1.15-1.48 (4H, m), 1.41 (18H, s), 3.40-3.45 (2H, m), 3.80-3.90 (1H, m), 3.87 (3H, s), 5.23 (1H, d, J=18.4 Hz), 5.29 (1H, d, J=18.4 Hz), 7.05 (1H, dd, J=8.0, 8.0 Hz), 7.14 (1H, d, J=8.4 Hz), 7.45 (1H, dd, J=8.4, 8.0 Hz), 7.56 (1H, d, J=8.0 Hz), 7.72 (2H, s), 7.77 (1H, s).

Example 111

4-(3-Benzyl-2-imino-4-propyl-pyrrolidin-1-yl)-3-(3,5-di-tert-butyl-4-hydroxy-phenyl)-but-2-enenitrile hydrochloride

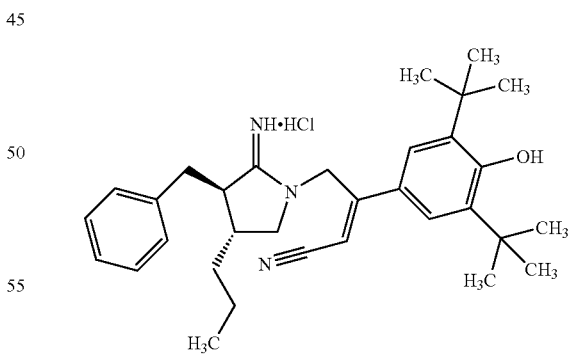

1H-NMR (DMSO-d6) δ: 0.39 (3H, t, J=6.8 Hz), 0.45-0.70 (2H, m), 1.30-1.50 (20H, m), 1.81 (1H, m), 2.45 (1H, m), 2.80 (2H, m), 3.00 (1H, m), 3.57 (1H, m), 4.71 (1H, d, J=16.4 Hz), 5.27 (1H, d, J=16.4 Hz), 6.22 (1H, s), 7.15-7.35 (7H, m), 7.59 (1H, s), 9.77 (1H, s), 9.93 (1H, s).

Example 112

4-(3-Benzyl-2-imino-4-propyl-pyrrolidin-1-yl)-3-(3,5-di-tert-butyl-4-hydroxy-phenyl)-but-2-enenitrile hydrochloride

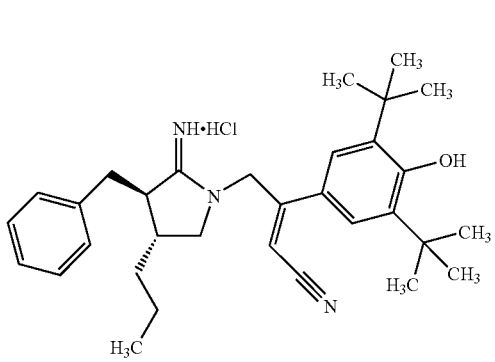

1H-NMR (DMSO-d6) δ: 0.49 (3H, t, J=6.8 Hz), 0.50-0.85 (4H, m), 1.40 (18H, s), 1.93 (1H, m), 2.88 (1H, m), 3.02 (2H, m), 3.60 (1H, m), 4.62 (1H, d, J=17.6 Hz), 4.91 (1H, d, J=17.6 Hz), 5.73 (1H, s), 7.20-7.40 (7H, m), 7.59 (1H, s), 9.55 (1H, s), 9.81 (1H, s).

Example 113

N-{3-Benzyl-1-[2-(3,5-di-tert-butyl-4-hydroxy-phenyl)-2-oxo-ethyl]-4-propyl-pyrrolidin-2-ylidene}-methanesulfonamide

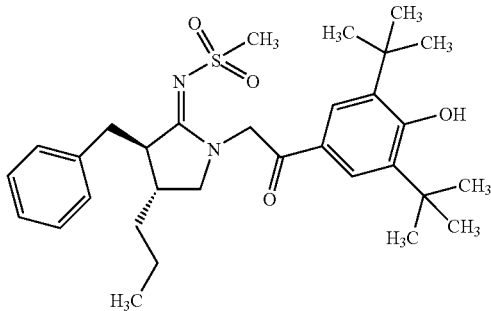

1H-NMR (DMSO-d6) δ: 0.61 (3H, t, J=7.2 Hz), 0.88-1.30 (4H, m), 1.42 (18H, s), 2.03 (1H, q, J=7.2 Hz), 2.64 (1H, dd, J=11.2 Hz, 12.8 Hz), 3.08 (1H, d, J=11.2 Hz), 3.35 (1H, m), 3.48 (d, J=11.2 Hz), 3.75 (1H, dd, J=7.2 Hz, 11.2 Hz), 4.91 (1H, d, J=17.6 Hz), 4.96 (1H, d, J=17.6 Hz), 7.20-7.35 (5H, m), 7.77 (2H, s), 7.98 (1H, s).

Example 114

1-(3,5-di-tert-butyl-4-hydroxy-phenyl)-2-(2-imino-4-propyl-3-pyridin-3-yl-pyrrolidin-1-yl)-ethanone hydrobromide

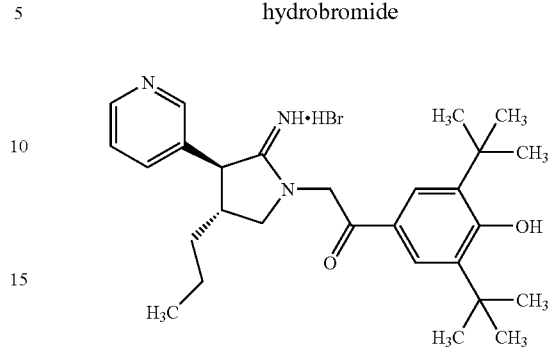

1H-NMR (DMSO-d6) δ: 0.90 (3H, s), 1.29-1.38 (2H, m), 11.47 (18H, s), 1.59-1.66 (2H, m), 2.63 (1H, hex, J=8 Hz), 3.62 (1H, dd, J=11, 8 Hz), 4.01 (1H, dd, J=11, 8 Hz), 4.30 (1H, d, J=8 Hz), 5.25 (2H, s), 7.57 (1H, ddd, J=8.5, 1 Hz), 7.91 (2H, s), 8.00 (1H, dt, J=8, 1 Hz), 8.59 (1H, dd, J=5, 1 Hz), 8.66 (1H, br.d, J=1 Hz). MS: m/e(ESI) 450.3 (MH+)

Example 115

1-(3,5-Di-tert-butyl-4-hydroxy-phenyl)-2-(2-imino-4-propyl-3-thiophen-2-yl-pyrrolidin-1-yl)-ethanone hydrobromide

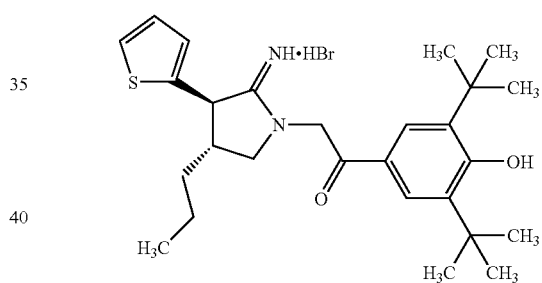

1H-NMR (DMSO-d6) δ: 0.89 (3H, t, J=7 Hz), 1.23-1.35 (3H, m), 1.47 (18H, s), 1.62-1.73 (1H, m), 2.75-2.84 (1H, m), 3.64 (1H, t, J=10 Hz), 3.81 (1H, dd, J=10, 8 Hz), 4.37 (1H, d, J=10 Hz), 5.56 (1H, d, J=19 Hz), 5.86 (1H, s), 6.06 (1H, d, J=19 Hz), 6.35 (1H, s), 7.08 (1H, dd, J=10, 8 Hz), 7.18 (1H, dd, J=8, 2 Hz), 7.39 (1H, dd, J=5, 2 Hz), 7.92 (2H, s), 10.83 (1H, s). MS: m/e(ESI) 455.3 (MH+)

Example 116

4-{1-[2-(3,5-Di-tert-butyl-4-hydroxy-phenyl)-2-oxo-ethyl]-2-imino-4-propyl-pyrrolidin-3-ylidenemethyl}-N,N-dimethyl-benzamide hydrobromide

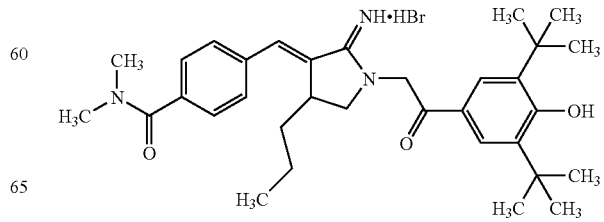

1H-NMR (DMSO-d6) δ: 0.85 (3H, t, J=7.2 Hz), 1.20-1.53 (4H, m), 1.41 (18H, s), 2.91 (3H, s), 2.99 (3H, s), 3.50 (1H, d, J=10.4 Hz), 3.72-3.79 (1H, m), 3.91 (1H, dd, J=7.2 Hz, J=10.4 Hz), 5.28 (1H, d, J=18.2 Hz), 5.35 (1H, d, J=18.2 Hz), 7.54 (2H, d, J=8.4 Hz), 7.63 (2H, d, J=8.4 Hz), 7.65 (1H, s), 7.76 (2H, s), 8.08 (1H, s), 8.82 (1H, s), 9.28 (1H, s). MS: m/e(ESI) 532.4 (MH+)

Example 117

1-(3,5-Di-tert-butyl-4-hydroxy-phenyl)-2-[2-imino-3-(3-isopropoxy-benzylidene)-4-propyl-pyrrolidin-1-yl]-ethanone hydrobromide

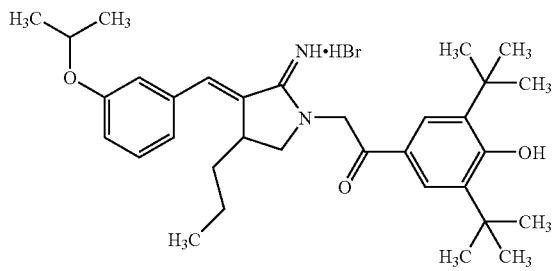

1H-NMR (DMSO-d6) δ: 0.85 (3H, t, J=6.8 Hz), 1.20-1.30 (6H, m), 1.20-1.50 (4H, m), 1.41 (18H, s), 3.49 (1H, d, J=11.0 Hz), 3.70-3.78 (1H, m), 3.88 (1H, dd, J=11.0, 6.8 Hz), 4.60-4.70 (1H, m), 5.25 (1H, d, J=18.0 Hz), 5.32 (1H, d, J=18.0 Hz), 7.03 (1H, d, J=8.8 Hz), 7.06 (1H, brs), 7.12 (1H, d, J=7.2 Hz), 7.42 (1H, dd, J=8.8, 7.2 Hz), 7.58 (1H, s), 7.73 (2H, s).

Example 118 tert-Butyl {3-benzyl-1-[2-(3,5-di-tert-butyl-4-hydroxy-phenyl)-2-oxo-ethyl]-4-propyl-pyrrolidin-2-ylideneamino}-acetate hydrobromide

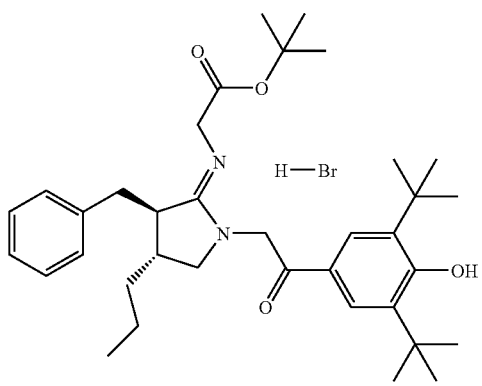

1H-NMR (DMSO-d6) δ: 0.65 (3H, t, J=7.2 Hz), 0.92-1.40 (4H, m), 1.43 (18H, s), 1.45 (9H, s), 2.10 (1H, q, J=7.2 Hz), 2.79 (1H, dd, J=11, 2 Hz, 13.6 Hz), 3.05 (1H, dd, J=4.4 Hz, 13.6 Hz), 3.29 (1H, m), 3.36 (1H, m), 3.94 (1H, dd, J=6.0 Hz, 11.2 Hz), 4.28 (2H, s), 5.22 (1H, d, J=18.4 Hz), 5.27 (1H, d, J=18.4 Hz), 7.25-7.50 (5H, m), 7.76 (2H, s).

Example 119

2-[3-Benzyl-4-propyl-2-(2,2,2-trifluoro-ethylimino)-pyrrolidin-1-yl]-1-(3,5-di-tert-butyl-4-hydroxy-phenyl)-ethanone hydrobromide

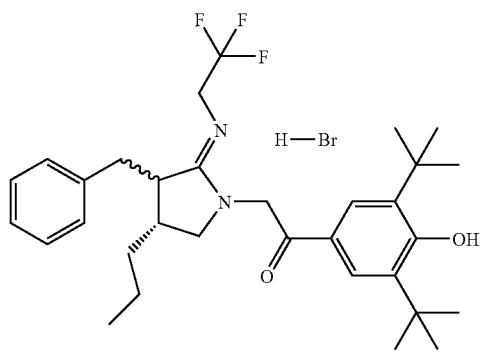

1H-NMR (DMSO-d6) δ: 0.85 (3HX0.5, t, J=7 Hz), 0.89 (3HX0.5, t, J=7 Hz), 1.0-1.5 (4H, m), 1.43 (18H, s), 2.07-2.20 (1H, s), 2.80-2.90 (1H, m), 2.95-2.20 (1H, m), 3.20-3.40 (2H, m), 3.80 (1H, m), 4.40-4.80 (2H, m), 4.85 (1HX0.5, d, J=18 Hz), 5.18 (1HX0.5, d, J=18 Hz), 5.22 (1HX0.5, d, J=18 Hz), 5.41 (1HX0.5, d, J=18 Hz), 7.25-7.50 (5H, m), 7.70 (2HX0.5, s), 7.75 (2HX0.5, s), 8.10 (1HX0.5, s), 8.12 (1HX0.5, s), 10.22 (1HX0.5, s), 10.65 (1HX0.5, s).

Example 120

{3-Benzyl-1-[2-(3,5-di-tert-butyl-4-hydroxy-phenyl)-2-oxo-ethyl]-4-propyl-pyrrolidin-2-ylidene-amino}-acetic acid hydrochloride

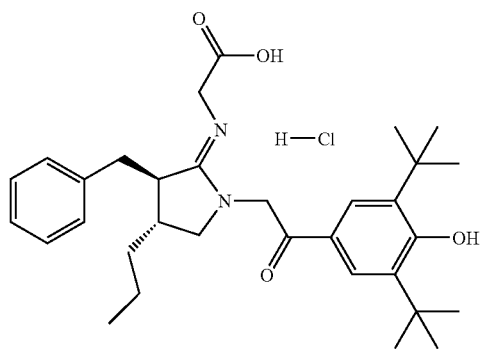

1H-NMR (DMSO-d6) δ: 0.66 (3H, t, J=7.2 Hz), 0.92-1.40 (4H, m), 1.43 (18H, s), 2.09 (1H, q, J=7.2 Hz), 2.80 (1H, dd, J=11, 2 Hz, 13.6 Hz), 3.07 (1H, dd, J=4.0 Hz, 13.6 Hz), 3.31 (1H, m), 3.39 (1H, m), 3.95 (1H, dd, J=6.4 Hz, 11.2 Hz), 4.22 (2H, m), 5.32 (2H, s), 7.25-7.45 (5H, m), 7.70 (2H, s), 8.08 (1H, s), 9.62 (1H, s), 13.37 (1H, s).

Example 121

1-(3,5-Di-tert-butyl-4-hydroxy-phenyl)-2-[3-(hydroxy-phenyl-methyl)-2-imino-4-propyl-pyrrolidin-1-yl]-ethanone hydrobromide

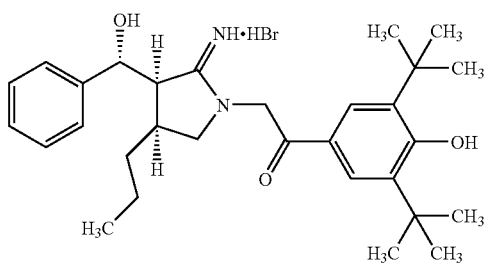

1H-NMR (DMSO-d6) δ: 0.59 (3H, t, J=7 Hz), 0.64-0.73 (1H, m), 0.88-1.04 (3H, m), 1.47 (18H, s), 2.17 (1H, brs), 3.27-3.33 (3H, m), 3.72-3.81 (1H, s), 4.93 (1H, d, J=8 Hz), 5.57 (1H, d, J=18 Hz), 5.73 (1H, d, J=18 Hz), 5.87 (1H, s), 7.29-7.44 (5H, m), 7.90 (2H, s), 8.43 (1H, s), 9.87 (1H, s). MS: m/e(ESI) 479.3 (MH+)

Example 122

1-(3,5-Di-tert-butyl-4-hydroxy-phenyl)-2-(2-imino-4-propyl-3-pyridin-2-yl-pyrrolidin-1-yl)-ethanone hydrobromide

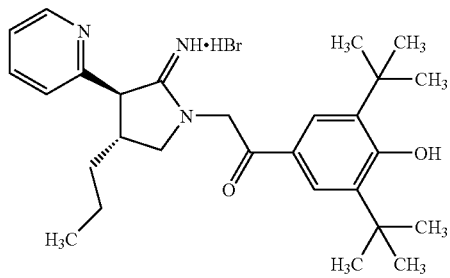

1H-NMR (DMSO-d6) δ: 0.94 (3H, t, J=7 Hz), 1.28-1.40 (4H, m), 1.47 (18H, s), 3.04 (1H, m), 3.66 (1H, t, J=9 Hz), 3.89 (1H, t, J=9 Hz), 4.22 (1H, d, J=9 Hz), 5.41 (1H, d, J=18 Hz), 5.86 (1H, s), 6.17 (1H, d, J=18 Hz), 7.36 (1H, dd, J=8, 6 Hz), 7.45 (1H, d, J=8 Hz), 7.83 (1H, t, J=8 Hz), 7.93 (2H, s), 8.06 (1H, brs), 8.63 (1H, d, J=6 Hz), 10.54 (1H, brs). MS: m/e(ESI) 450.3 (MH+)

Example 123

2-[(3S,4S)-3-(3-Chloro-4-methoxy-phenyl)-2-imino-4-propyl-pyrrolidin-1-yl]-1-(3,5-di-tert-butyl-4-hydroxy-phenyl)-ethanone hydrobromide

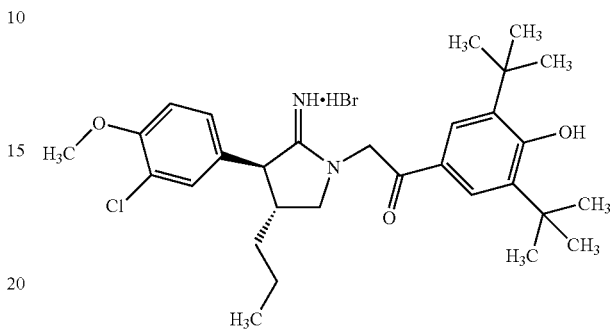

1H-NMR (DMSO-d6) δ: 0.83 (3H, t, J=7.2 Hz), 1.16-1.30 (2H, m), 1.43 (18H, s), 1.40-1.55 (2H, m), 2.44 (1H, m), 3.44 (1H, dd, J=6.8, 10.8 Hz), 3.89 (3H, s), 3.89 (1H, m), 4.15 (1H, d, J=8.0 Hz), 5.27 (2H, s), 7.24 (1H, d, J=8.8 Hz), 7.38 (1H, dd, J=2.0, 8.8 Hz), 7.52 (1H, d, J=2.0 Hz), 7.77 (2H, s), 8.07 (1H, s), 8.78 (1H, brs), 8.93 (1H, brs).

Example 124

2-{3-Benzyl-1-[2-(3,5-di-tert-butyl-4-hydroxy-phenyl)-2-oxo-ethyl]-4-propyl-pyrrolidin-2-ylidene-amino}-acetamide hydrobromide

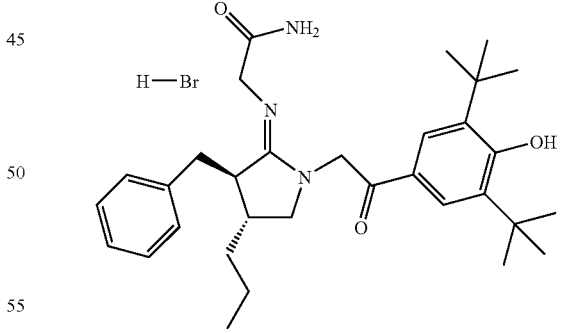

1H-NMR (DMSO-d6) δ: 0.64 (3H, t, J=7.2 Hz), 0.95-1.40 (4H, m), 1.43 (18H, s), 1.45 (9H, s), 2.09 (1H, q, J=7.2 Hz), 2.78 (1H, dd, J=11, 2 Hz, 13.6 Hz), 3.08 (1H, dd, J=3.6 Hz, 13.6 Hz), 3.29 (2H, m), 3.98 (1H, dd, J=6.0 Hz, 10.6 Hz), 4.04 (2H, s), 5.22 (1H, d, J=18.4 Hz), 5.28 (1H, d, J=18.4 Hz), 7.25-7.45 (5H, m), 7.67 (1H, s), 7.76 (2H, s), 8.07 (1H, s), 9.29 (1H, s).

Example 125

2-[3-(3-Benzyl-3H-imidazol-4-yl)-2-imino-4-propyl-pyrrolidin-1-yl]-1-(3,5-di-tert-butyl-4-hydroxy-phenyl)-ethanone hydrobromide

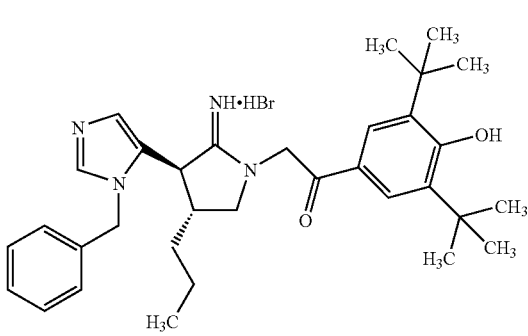

1H-NMR (DMSO-d6) δ: 0.67 (3H, t, J=7 Hz), 0.84-1.33 (4H, m), 1.47 (18H, s), 2.20 (1H, m), 3.33 (1H, dd, J=10, 6 Hz), 3.79 (1H, dd, J=10, 7 Hz), 4.13 (1H, d, J=7 Hz), 5.31 (1H, d, 16 Hz), 5.48 (1H, d, J=16 Hz), 5.54 (1H, d, J=18 Hz), 5.85 (2H, s), 5.89 (1H, d, J=18 Hz), 6.99 (1H, s), 7.13-7.40 (5H, m), 7.42 (1H, s), 7.88 (2H, s). MS: m/e(ESI) 529.3 (MH+)

Example 126

1-(3,5-Di-tert-butyl-4-hydroxy-phenyl)-2-[3-(3H-imidazol-4-yl)-2-imino-4-propyl-pyrrolidin-1-yl]-ethanone hydrobromide

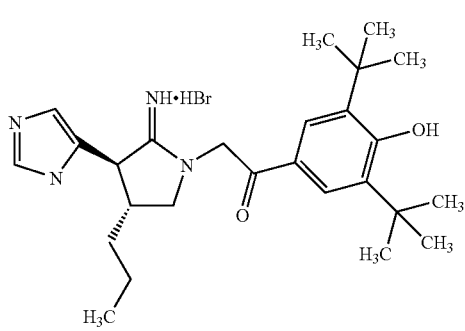

1H-NMR (DMSO-d6) δ: 0.88 (3H, t, J=7 Hz), 1.23-1.33 (2H, m), 1.45 (18H, s), 1.48-1.56 (1H, m), 1.60-1.71 (1H, m), 2.80 (1H, m), 3.56 (1H, t, J=9 Hz), 3.79 (1H, t, J=9 Hz), 4.09 (1H, d, J=9 Hz), 5.28 (1H, d, J=18 Hz), 5.86 (1H, brs), 6.02 (1H, d, J=18 Hz), 7.02 (1H, s), 7.44 (1H, s), 7.88 (1H, s), 9.67 (1H, brs). MS: m/e(ESI) 439.2 (MH+)

Example 127

N-(3-tert-Butyl-2-hydroxy-5-{2-[(3S,4R)-2-imino-4-(2-methoxy-ethyl)-3-phenyl-pyrrolidin-1-yl]-acetyl}-phenyl)-N-methyl-methanesulfonamide hydrobromide

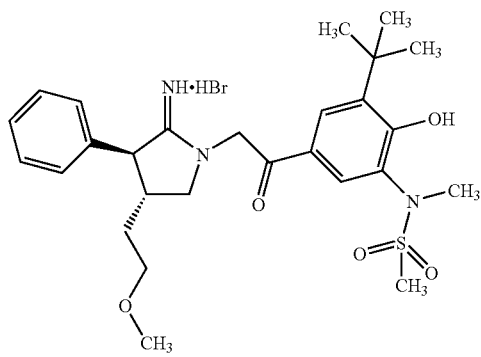

1H-NMR (DMSO-d6) δ: 1.38 (9H, s), 1.72-1.82 (2H, m), 2.75-2.87 (1H, m), 3.12 (3H, s), 3.15 (3H, s), 3.10-3.20 (2H, m), 3.30-3.42 (1H, m), 3.34 (3H, s), 3.50 (1H, dd, J=10.8, 6.8 Hz), 3.89 (1H, dd, J=10.4, 8.0 Hz), 4.23 (1H, d, J=6.8 Hz), 5.24 (2H, s), 7.33-7.54 (5H, m), 7.80 (1H, s), 7.91 (1H, s), 8.87 (1H, brs), 8.98 (1H, brs), 10.02 (1H, brs). MS: m/e(ESI) 516.3 (MH+)

Example 128

N-(3-Ethyl-2-hydroxy-5-{2-[(3S,4R)-2-imino-4-(2-methoxy-ethyl)-3-phenyl-pyrrolidin-1-yl]-acetyl}-phenyl)-N-methyl-methanesulfonamide hydrobromide

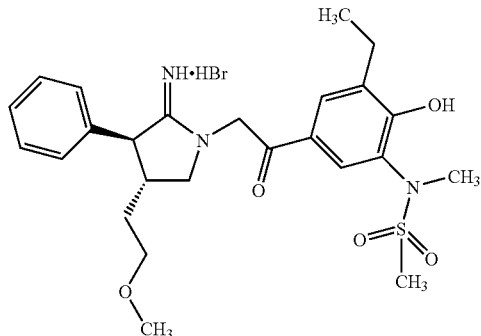

1H-NMR (DMSO-d6) δ: 1.19 (3H, t, J=6.8 Hz), 1.54 (9H, s), 1.74-1.82 (2H, m), 2.78 (q, 2H, J=6.8 Hz), 3.09 (3H, s), 3.14 (3H, s). MS: m/e(ESI) 488.2 (MH+)

Example 129

Ethyl 4-{1-[2-(3,5-di-tert-butyl-4-hydroxy-phenyl)-2-oxo-ethyl]-(3S,4R)-2-imino-4-propyl-pyrrolidin-3-yl}-benzoate hydrobromide

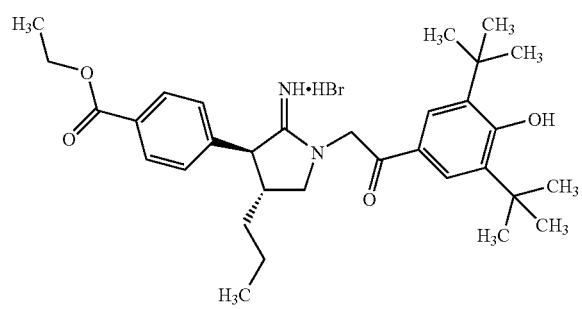

1H-NMR (DMSO-d6) δ: 0.82 (3H, t, J=7.2 Hz), 1.24 (2H, m), 1.33 (3H, t, J=7.2 Hz), 1.43 (18H, s), 1.53 (2H, m), 2.46 (1H, q, J=7.2 Hz), 3.48 (1H, dd, J=7.2 Hz, 10.4 Hz), 3.92 (1H, dd, J=8.0 Hz, 10.8 Hz), 4.31 (1H, m), 4.35 (2H, q, J=7.2 Hz), 5.30 (2H, s), 7.58 (2H, d, J=8.0 Hz), 7.78 (2H, s), 8.03 (2H, d, J=8.0 Hz), 8.09 (1H, s), 8.90 (1H, s), 8.99 (1H, s).

Example 130

2-((3S,4R)-4-Benzyloxymethyl-2-imino-3-phenyl-pyrrolidin-1-yl)-1-(3,5-di-tert-butyl-4-hydroxy-phenyl)-ethanone hydrobromide

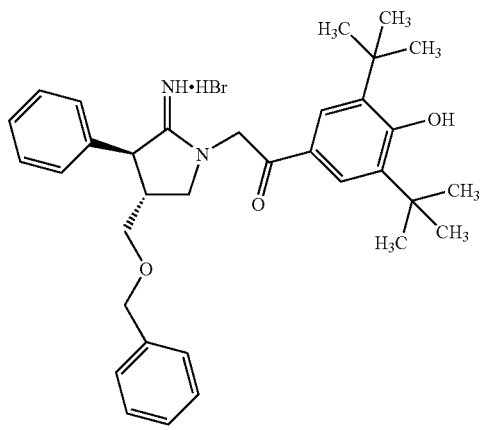

1H-NMR (DMSO-d6) δ: 1.43 (18H, s), 2.69 (1H, m), 3.58 (3H, m), 3.97 (1H, dd, J=8.0 Hz, 11.2 Hz), 4.29 (1H, d, J=5.2 Hz), 4.53 (1H, d, J=17.2 Hz), 4.55 (1H, d, J=17.2 Hz), 5.27 (1H, d, J=18.4 Hz), 5.34 (1H, d, J=18.4 Hz), 7.30-7.50 (10H, m), 7.78 (2H, s), 8.09 (1H, s), 8.97 (1H, s), 9.04 (1H, s).

Example 131

1-(3,5-Di-tert-butyl-4-hydroxy-phenyl)-2-((3S,4R)-4-hydroxymethyl-2-imino-3-phenyl-pyrrolidin-1-yl)-ethanone hydrobromide

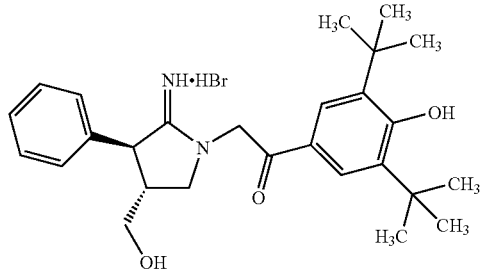

1H-NMR (DMSO-d6) δ: 1.44 (18H, s), 2.46 (1H, m), 3.53 (3H, m), 3.92 (1H, dd, J=8.0 Hz, 11.2 Hz), 4.27 (1H, d, J=5.2 Hz), 5.12 (1H, t, J=5.2 Hz), 5.32 (2H, s), 7.35-7.50 (5H, m), 7.79 (2H, s), 8.08 (1H, s), 8.95 (1H, s), 9.06 (1H, s).

Example 132

4-{1-[2-(3,5-Di-tert-butyl-4-hydroxy-phenyl)-2-oxo-ethyl]-(3S,4R)-2-imino-4-propyl-pyrrolidin-3-yl}-N,N-dimethyl-benzamide hydrobromide

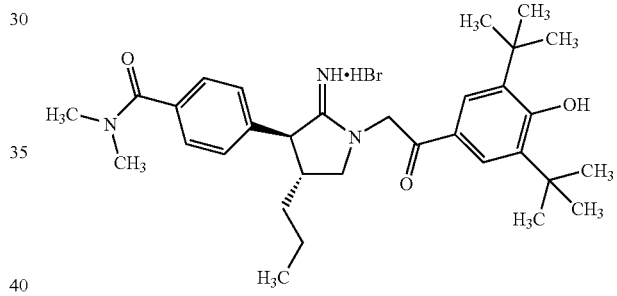

1H-NMR (DMSO-d6) δ: 0.83 (3H, t, J=7.2 Hz), 1.25 (2H, m), 1.43 (18H, s), 1.53 (2H, m), 2.45 (1H, m), 2.94 (3H, s), 3.00 (3H, s), 3.47 (1H, dd, J=6.8 Hz, 10.4 Hz), 3.92 (1H, dd, J=8.4 Hz, 10.4 Hz), 4.22 (1H, d, J=6.8 Hz), 5.30 (2H, s), 7.49 (4H, s), 7.78 (2H, s), 8.09 (1H, s), 8.90 (1H, s), 8.96 (1H, s).

Example 133 tert-Butyl 4-{1-[2-(3,5-di-tert-butyl-4-hydroxy-phenyl)-2-oxo-ethyl]-(3S,4R)-2-imino-4-propyl-pyrrolidin-3-yl}-benzoate hydrobromide

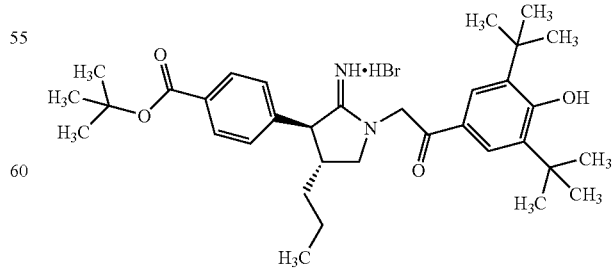

1H-NMR (DMSO-d6) δ: 0.82 (3H, t, J=7.2 Hz), 1.23 (2H, m), 1.43 (18H, s), 1.52 (2H, m), 1.56 (9H, s), 2.45 (1H, m), 3.47 (1H, dd, J=7.6 Hz, 10.8 Hz), 3.91 (1H, dd, J=8.0 Hz, 10.8 Hz), 4.29 (1H, d, J=7.6 Hz), 5.30 (2H, s), 7.55 (2H, d, J=8.4 Hz), 7.78 (2H, s), 7.97 (2H, d, J=8.4 Hz), 8.09 (1H, s), 8.84 (1H, s), 8.98 (1H, s).

Example 134

4-{1-[2-(3,5-Di-tert-butyl-4-hydroxy-phenyl)-2-oxo-ethyl]-2-imino-4-propyl-pyrrolidin-3-yl}-benzoic acid hydrochloride

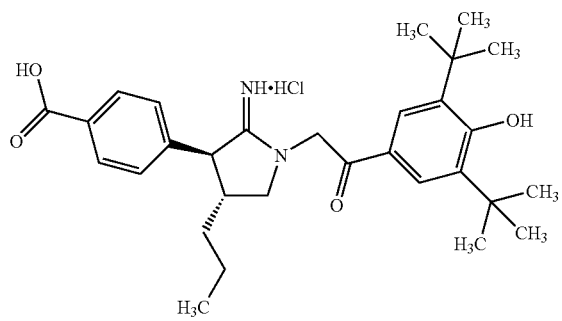

1H-NMR (DMSO-d6) δ: 0.83 (3H, t, J=7.2 Hz), 1.25 (2H, m), 1.43 (18H, s), 1.53 (2H, m), 1.56 (9H, s), 2.46 (1H, m), 3.47 (1H, dd, J=7.2 Hz, 10.8 Hz), 3.92 (1H, dd, J=8.0 Hz, 10.8 Hz), 4.29 (1H, d, J=7.2 Hz), 5.32 (2H, s), 7.55 (2H, d, J=8.4 Hz), 7.78 (2H, s), 8.01 (2H, d, J=8.4 Hz), 8.05 (1H, s), 8.92 (1H, s), 9.06 (1H, s), 13.05 (1H, s).

Example 135

N-{3-tert-Butyl-2-hydroxy-5-[2-(2-imino-3-phenyl-4-propyl-pyrrolidin-1-yl)-acetyl]-benzyl}-N-methyl-acetamide hydrobromide

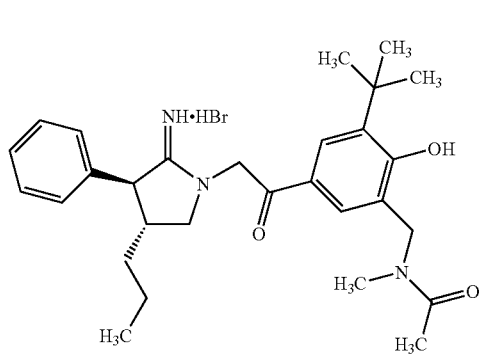

1H-NMR (DMSO-d6) δ: 0.80 (3H, t, J=7.2 Hz), 1.06-1.54 (4H, m), 1.36 (9H, s), 2.10 (3H, s), 2.10-2.45 (1H, m), 3.09 (3H, s), 3.88-3.91 (1H, m), 4.14 (1H, d, J=7.2 Hz), 4.46 (2H, s), 5.25 (2H, s), 7.32-7.48 (5H, m), 7.80 (1H, d, J=2.0 Hz), 7.88 (1H, d, J=2.0 Hz), 8.85 (1H, s).

Example 136

1-(3,5-Di-tert-butyl-4-hydroxy-phenyl)-2-(3-hydroxy-2-imino-3-phenyl-4-propyl-pyrrolidin-1-yl)-ethanone hydrobromide

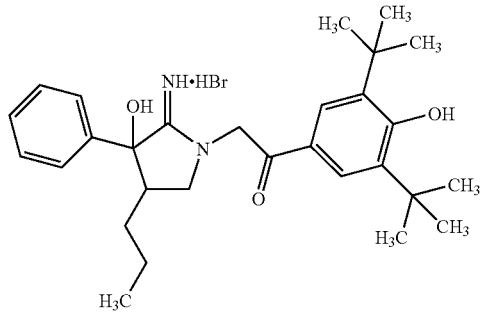

1H-NMR (DMSO-d6) δ: 0.79 (3H, t, J=7 Hz), 1.08-1.17 (2H, m), 1.46 (18H, s), 1.47-1.56 (2H,), 2.61 (1H, td, J=9, 7 Hz), 3.74 (1H, t, J=9 Hz), 3.78 (1H, t, J=9 Hz), 5.00 (1H, d, J=18 Hz), 5.85 (1H, s), 5.91 (1H, s), 6.22 (1H, d, J=18 Hz), 7.01 (1H, s), 7.33 (1H, t, J=8 Hz), 7.40 (2H, t, J=8 Hz), 7.55 (2H, d, J=8 Hz), 7.88 (2H, s), 9.22 (1H, s). MS: m/e(ESI) 465.2 (MH+)

Example 137

1-(3,5-Di-tert-butyl-4-hydroxy-phenyl)-2-(2-imino-4-phenyl-3-propyl-pyrrolidin-1-yl)-ethanone hydrobromide

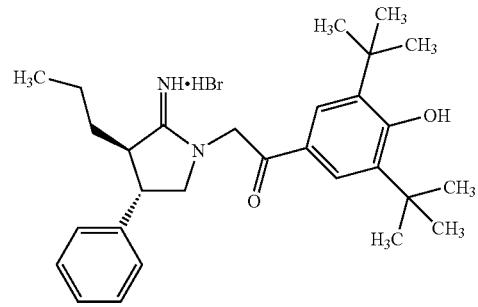

1H-NMR (DMSO-d6) δ: 0.89 (3H, t, J=7.6 Hz), 1.32-1.52 (2H, m), 1.43 (18H, s), 1.75-1.83 (2H, m), 3.21 (1H, m), 3.57 (1H, m), 3.64 (1H, m), 4.08 (1H, dd, J=8.8, 10.8 Hz), 5.24 (2H, s), 7.31 (1H, m), 7.34-7.44 (4H, m), 7.77 (2H, s), 8.07 (1H, s), 8.99 (1H, s), 9.23 (1H, s).

Example 138

1-(3,5-Di-tert-butyl-4-hydroxy-phenyl)-2-[(3S,4R)-3-(3-ethoxy-phenyl)-2-imino-4-propyl-pyrrolidin-1-yl]-ethanone hydrobromide

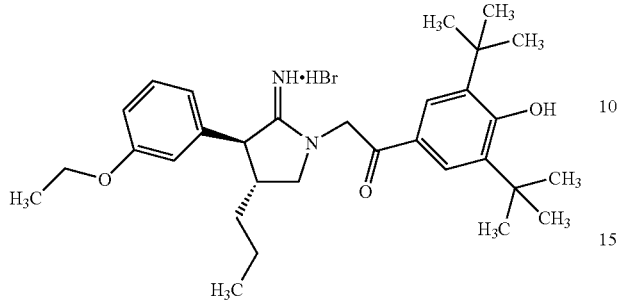

1H-NMR (DMSO-d6) δ: 0.84 (3H, t, J=7.2 Hz), 1.20-1.32 (2H, m), 1.36 (3H, t, J=6.8 Hz), 1.44 (18H, s), 1.48-1.58 (2H, m), 2.44 (1H, m), 3.45 (1H, dd, J=6.4, 10.0 Hz), 3.92 (1H, t, J=10.0 Hz), 4.02-4.14 (3H, m), 5.29 (2H, s), 6.91-7.02 (3H, m), 7.36 (1H, t, J=8.0 Hz), 7.77 (2H, s), 8.07 (1H, s), 8.83 (1H, s), 8.95 (1H, s).

Example 139

N-(4-{1-[2-(3,5-Di-tert-butyl-4-hydroxy-phenyl)-2-oxo-ethyl]-(3S,4R)-2-imino-4-propyl-pyrrolidin-3-yl}-phenyl)-acetamide hydrobromide

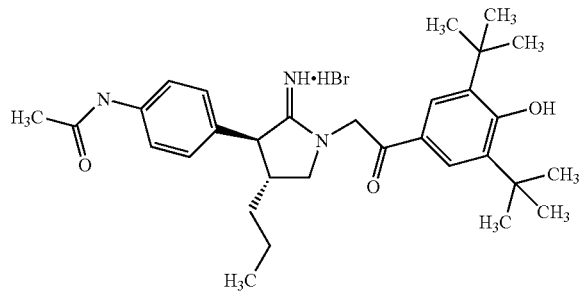

1H-NMR (DMSO-d6) δ: 0.83 (3H, t, J=6.8 Hz), 1.15-1.30 (2H, m), 1.43 (18H, s), 1.36-1.60 (2H, m), 2.06 (3H, s), 2.42 (1H, m), 3.43 (1H, dd, J=6.8, 10.4 Hz), 3.89 (1H, dd, J=7.6, 10.4 Hz), 4.08 (1H, d, J=7.6 Hz), 5.29 (2H, s), 7.32 (2H, d, J=8.8 Hz), 7.64 (2H, d, J=8.8 Hz), 7.77 (2H, s), 8.07 (1H, brs), 8.78 (1H, s), 8.95 (1H, brs), 10.06 (1H, s).

Example 140

N-(4-{1-[2-(3,5-Di-tert-butyl-4-hydroxy-phenyl)-2-oxo-ethyl]-(3S,4R)-2-imino-4-propyl-pyrrolidin-3-yl}-phenyl)-methanesulfonamide hydrobromide

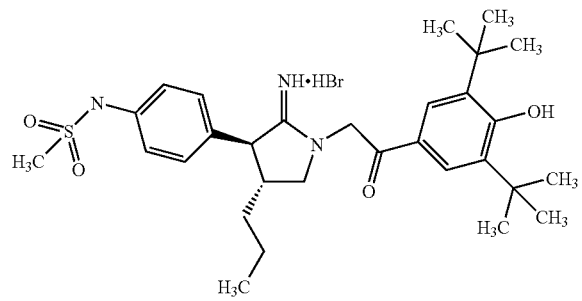

1H-NMR (DMSO-d6) δ: 0.83 (3H, t, J=7.2 Hz), 1.12-1.30 (2H, m), 1.43 (18H, s), 1.32-1.60 (2H, m), 2.41 (1H, m), 3.03 (3H, s), 3.45 (1H, dd, J=7.2, 10.0 Hz), 3.90 (1H, m), 4.11 (1H, d, J=7.6 Hz), 5.30 (2H, s), 7.26 (2H, d, J=8.0 Hz), 7.38 (2H, d, J=8.0 Hz), 7.78 (2H, s), 8.07 (1H, s), 8.81 (1H, s), 8.97 (1H, brs), 9.89 (1H, s).

Example 141

4-{1-[2-(3,5-Di-tert-butyl-4-hydroxy-phenyl)-2-oxo-ethyl]-2-imino-4-propyl-pyrrolidin-3-yl}-N-methyl-benzamide hydrobromide

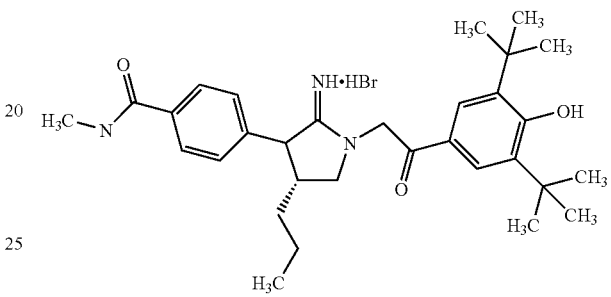

1H-NMR (DMSO-d6) δ: 0.83 (3H, t, J=7.2 Hz), 1.24 (2H, m), 1.43 (18H, s), 1.53 (2H, m), 2.44 (1H, q, J=7.2 Hz), 2.80 (3H, d, J=4.4 Hz), 3.47 (1H, dd, J=6.4, 10.8 Hz), 3.92 (1H, dd, J=7.6 Hz, 10.8 Hz), 4.23 (1H, d, J=7.2 Hz), 5.30 (2H, s), 7.51 (2H, d, J=8.4 Hz), 7.78 (2H, s), 7.91 (2H, D, J=8.4 Hz), 8.09 (1H, s), 8.48 (1H, q, J=4.4 Hz), 8.90 (1H, s), 8.97 (1H, s).

Example 142

1-(3,5-Di-tert-butyl-4-hydroxy-phenyl)-2-[2-imino-3-(2-methoxy-phenyl)-4-propyl-pyrrolidin-1-yl]-ethanone hydrobromide

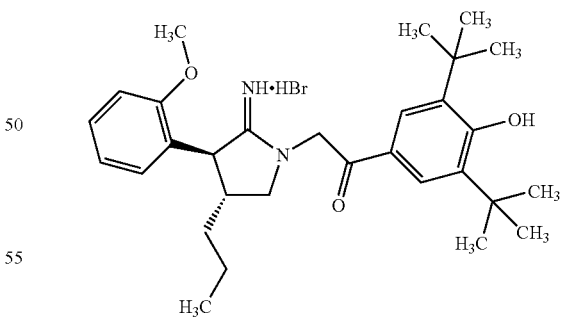

1H-NMR (DMSO-d6) δ: 0.85 (3H, t, J=7 Hz), 1.20-1.27 (2H, m), 1.49 (18H, s), 1.58-1.78 (2H, m), 2.81 (1H, m), 3.57 (1H, t, J=9 Hz), 3.85 (1H, dd, J=9, 8 Hz), 3.89 (3H, s), 4.14 (1H, d, J=9 Hz), 5.57 (1H, d, J=18 Hz), 5.87 (1H, s), 5.90 (1H, s), 6.12 (1H, d, J=18 Hz), 6.97 (1H, d, J=8 Hz), 7.03 (1H, t, J=8 Hz), 7.20 (1H, dd, J=8, 2 Hz), 7.40 (1H, td, J=8, 2 Hz), 7.95 (2H, s). MS: m/e(ESI) 479.3 (MH+)

Example 143

N-[3-(4-{1-[2-(3,5-Di-tert-butyl-4-hydroxy-phenyl)-2-oxo-ethyl]-(3S,4S)-2-imino-4-propyl-pyrrolidin-3-yl}-phenoxy)-propyl]-acetamide hydrobromide

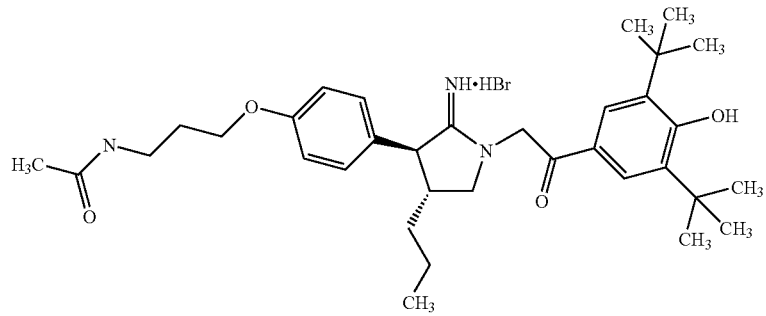

1H-NMR (DMSO-d6) δ: 0.81 (3H, t, J=7.2 Hz), 1.10-1.28 (2H, m), 1.30-1.50 (2H, m), 1.40 (18H, s), 1.78 (3H, s), 1.78-1.86 (2H, m), 2.34-2.40 (1H, m), 3.17 (2H, dd, J=12.8, 6.4 Hz), 3.41 (1H, dd, J=11.1, 7.6 Hz), 3.87 (1H, dd, J=10.4, 7.6 Hz), 3.96 (2H, t, J=6.0 Hz), 4.06 (1H, d, J=7.2 Hz), 5.23 (2H, s), 6.98 (2H, d, J=8.8 Hz), 7.30 (2H, d, J=8.8 Hz), 7.72 (2H, s), 7.85-7.95 (1H, brs), 8.68-8.71 (1H, brs).

Example 144

4-{1-[2-(3,5-Di-tert-butyl-4-hydroxy-phenyl)-2-oxo-ethyl]-(3S,4R)-2-imino-4-propyl-pyrrolidin-3-yl}-N-methyl-benzenesulfonamide hydrobromide

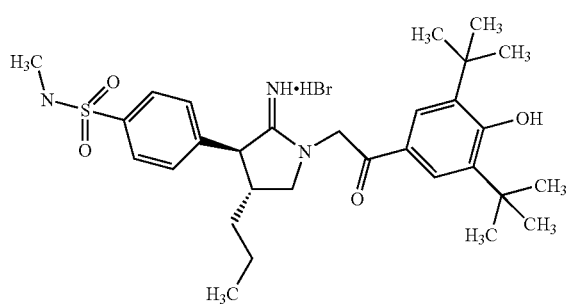

1H-NMR (DMSO-d6) δ: 0.83 (3H, t, J=7.2 Hz), 1.20-1.30 (2H, m), 1.44 (18H, s), 1.38-1.60 (2H, m), 2.45 (1H, m), 2.45 (3H, d, J=6.0 Hz), 3.48 (1H, dd, J=6.0, 10.4 Hz), 3.93 (1H, dd, J=7.2, 10.4 Hz), 4.13 (1H, d, J=7.2 Hz), 5.31 (2H, s), 7.54 (1H, q, J=6.0 Hz), 7.66 (2H, d, J=8.4 Hz), 7.78 (2H, s), 7.86 (2H, d, J=8.4 Hz), 8.96 (1H, brs), 9.00 (1H, brm).

Example 145

Methyl (4-{1-[2-(3,5-di-tert-butyl-4-hydroxy-phenyl)-2-oxo-ethyl]-(3S,4R)-2-imino-4-propyl-pyrrolidin-3-yl}-phenyl)-carbamate hydrobromide

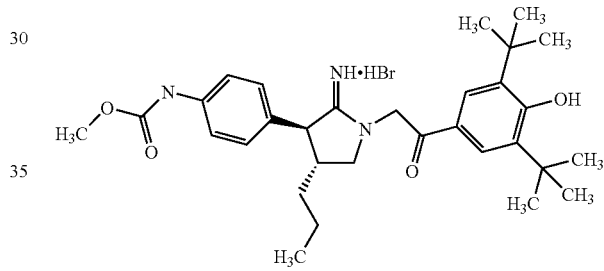

1H-NMR (DMSO-d6) δ: 0.83 (3H, t, J=7.2 Hz), 1.20-1.30 (2H, m), 1.43 (18H, s), 1.40-1.55 (2H, m), 2.41 (1H, m), 3.33 (3H, s), 3.43 (1H, dd, J=7.2, 10.4 Hz), 3.89 (1H, dd, J=8.0, 10.4 Hz), 4.07 (1H, d, J=8.0 Hz), 5.27 (2H, s), 7.32 (2H, d, J=8.4 Hz), 7.52 (2H, d, J=8.4 Hz), 7.77 (2H, s), 8.07 (1H, brs), 8.77 (1H, brs), 8.93 (1H, brs), 9.76 (1H, s).

Example 146

1-(3,5-Di-tert-butyl-4-hydroxy-phenyl)-2-[(3S,4R)-3-(4-ethoxy-phenyl)-2-imino-4-propyl-pyrrolidin-1-yl]-ethanone hydrobromide

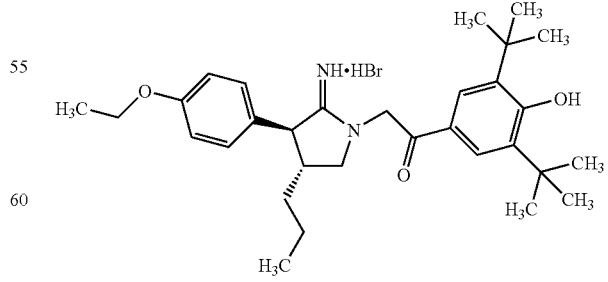

1H-NMR (DMSO-d6) δ: 0.83 (3H, t, J=7.2 Hz), 1.17-1.30 (2H, m), 1.34 (3H, t, J=6.8 Hz), 1.43 (18H, s), 1.38-1.56 (2H, m), 2.40 (1H, m), 3.43 (1H, dd, J=7.2, 11.2 Hz), 3.88 (1H, dd,

J=7.6, 11.2 Hz), 4.00-4.12 (3H, m), 5.28 (2H, s), 7.00 (2H, d, J=8.8 Hz), 7.32 (2H, d, J=8.8 Hz), 7.77 (2H, s), 8.07 (1H, s), 8.74 (1H, s), 8.93 (1H, brs).

Example 147

2-((3R,4S)-4-Azidomethyl-2-imino-3-phenyl-pyrrolidin-1-yl)-1-(3,5-di-tert-butyl-4-hydroxy-phenyl)-ethanone hydrobromide

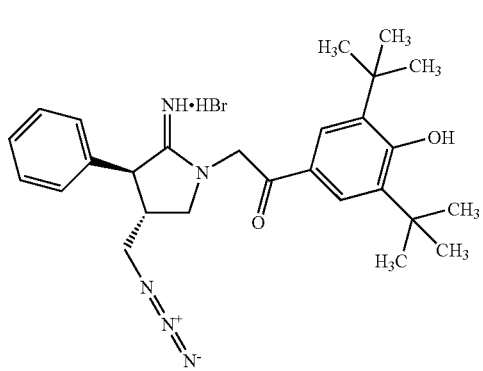

1H-NMR (DMSO-d6) δ: 1.44 (18H, s), 2.65 (1H, m), 3.53 (1H, dd, J=4.4 Hz, 11.2 Hz), 3.67 (2H, d, J=6.4 Hz), 3.98 (1H, dd, J=8.0 Hz, 11.2 Hz), 4.27 (1H, d, J=4.4 Hz), 5.27 (1H, d, J=18.0 Hz), 5.34 (1H, d, J=18.0 Hz), 7.35-7.55 (5H, m), 7.78 (2H, s), 8.09 (1H, s), 9.00 (1H, s), 9.09 (1H, s).

Example 148

2-((3S,4S)-4-Aminomethyl-2-imino-3-phenyl-pyrrolidin-1-yl)-1-(3,5-di-tert-butyl-4-hydroxy-phenyl)-ethanone hydrobromide

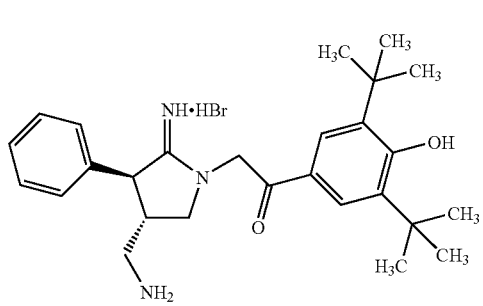

1H-NMR (DMSO-d6) δ: 1.39 (18H, s), 2.45 (1H, m), 2.85 (2H, d, J=6.0 Hz), 3.57 (1H, dd, J=4.4 Hz, 11.2 Hz), 3.92 (1H, dd, J=8.0 Hz, 11.2 Hz), 4.27 (1H, d, J=4.4 Hz), 5.18 (2H, s), 7.36-7.50 (5H, m), 7.64 (2H, s).

Example 149

Methyl 1-[(3R,4S)-2-(3,5-di-tert-butyl-4-hydroxy-phenyl)-2-oxo-ethyl]-5-imino-4-phenyl-pyrrolidine-3-carboxylate hydrobromide

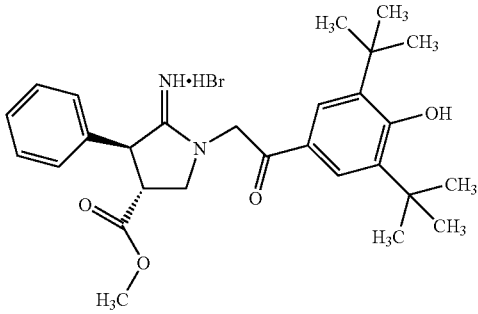

1H-NMR (DMSO-d6) δ: 1.43 (18H, s), 3.46 (1H, td, J=5.6 Hz, 8.8 Hz), 3.71 (3H, s), 3.98 (1H, dd, J=5.6 Hz, 11.2 Hz), 4.10 (1H, dd, J=8.8 Hz, 11.2 Hz), 4.77 (1H, d, J=5.6 Hz), 5.28 (1H, d, J=18.4 Hz), 5.37 (1H, d, J=18.4 Hz), 7.38-7.55 (5H, m), 7.78 (2H, s), 8.09 (1H, s), 9.08 (1H, s), 9.15 (1H, s).

Example 150

1-[(3R,4S)-2-(3,5-Di-tert-butyl-4-hydroxy-phenyl)-2-oxo-ethyl]-5-imino-4-phenyl-pyrrolidine-3-carboxamide hydrobromide

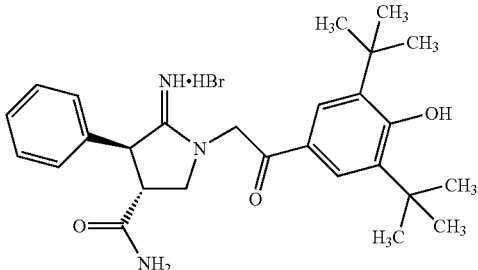

1H-NMR (DMSO-d6) δ: 1.43 (18H, s), 3.20 (1H, td, J=5.2 Hz, 8.8 Hz), 3.76 (1H, dd, J=5.2 Hz, 11.2 Hz), 4.05 (1H, dd, J=8.8 Hz, 11.2 Hz), 4.64 (1H, d, J=5.2 Hz), 5.29 (1H, d, J=18.4 Hz), 5.36 (1H, d, J=18.4 Hz), 7.30 (1H, s), 7.38-7.55 (5H, m), 7.64 (1H, s), 7.78 (2H, s), 8.09 (1H, s), 9.05 (1H, s), 9.11 (1H, s).

Example 151

1-[(3R,4S)-2-(3,5-Di-tert-butyl-4-hydroxy-phenyl)-2-oxo-ethyl]-5-imino-4-phenyl-pyrrolidine-3-carboxylic acid methylamide hydrobromide

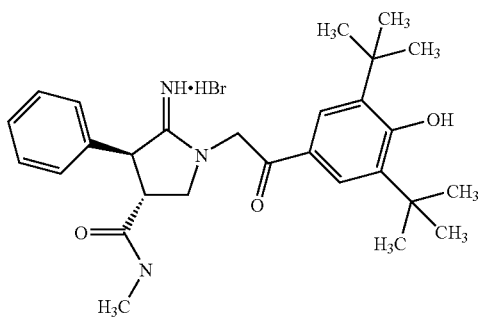

1H-NMR (DMSO-d6) δ: 1.43 (18H, s), 2.61 (3H, d, J=4.8 Hz), 3.19 (1H, td, J=5.6 Hz, 8.4 Hz), 3.74 (1H, dd, J=5.6 Hz, 10.8 Hz), 4.03 (1H, dd, J=8.4 Hz, 10.8 Hz), 4.64 (1H, d, J=5.6 Hz), 5.29 (1H, d, J=18.4 Hz), 5.35 (1H, d, J=18.4 Hz), 7.37-7.55 (5H, m), 7.78 (2H, s), 8.09 (1H, s), 8.13 (1H, q, J=4.8 Hz), 9.06 (1H, s), 9.09 (1H, s).

Example 152

N-[2-(4-{1-[2-(3,5-Di-tert-butyl-4-hydroxy-phenyl)-2-oxo-ethyl]-(3S,4S)-2-imino-4-propyl-pyrrolidin-3-yl}-phenoxy)-ethyl]-methanesulfonamide hydrobromide

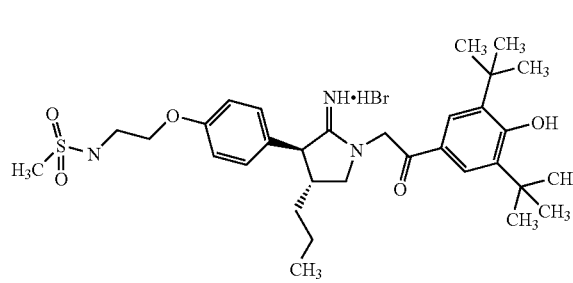

1H-NMR (DMSO-d6) δ: 0.81 (3H, t, J=7.2 Hz), 1.15-1.28 (2H, m), 1.41 (18H, s), 1.40-1.51 (2H, m), 1.85-1.93 (2H, m), 2.35-2.42 (1H, m), 2.89 (3H, s), 3.09 (2H, t, J=5.6 Hz), 3.38-3.45 (1H, m), 3.80-3.90 (1H, m), 4.03 (2H, t, J=6.0 Hz), 4.06 (1H, d, J=8.4 Hz), 5.25 (2H, s), 7.00 (2H, d, J=8.4 Hz), 7.04-7.10 (1H, m), 7.31 (2H, d, J=8.4 Hz), 7.75 (2H, s), 8.00-8.10 (0.5H, brs), 8.67-8.75 (1H, brs), 8.85-8.95 (0.5H, brs).

Example 153

1-(3,5-Di-tert-butyl-4-hydroxy-phenyl)-2-{(3S,4S)-2-imino-3-[4-(2-methoxy-ethoxy)-phenyl]-4-propyl-pyrrolidin-1-yl}-ethanone hydrobromide

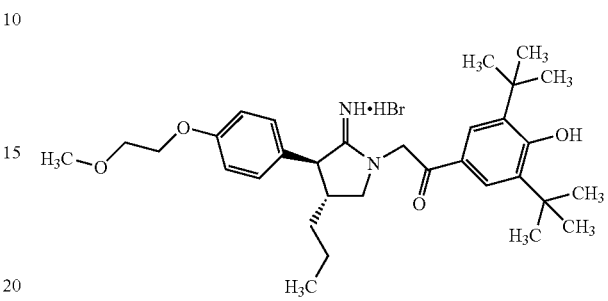

1H-NMR (DMSO-d6) δ: 0.81 (3H, t, J=7.6 Hz), 1.18-1.27 (2H, m), 1.41 (18H, s), 1.38-1.52 (2H, m), 2.35-2.42 (1H, m), 3.28 (3H, s), 3.38-3.52 (1H, m), 3.64 (2H, dd, J=4.4, 3.2 Hz), 3.86 (1H, dd, J=10.8, 7.8 Hz), 4.05 (1H, d, J=7.8 Hz), 4.08 (2H, dd, J=4.4, 3.2 Hz), 5.22 (2H, s), 7.00 (2H, d, J=8.8 Hz), 7.31 (2H, d, J=8.8 Hz), 7.75 (2H, s).

Example 154

N-(2-{1-[2-(3,5-Di-tert-butyl-4-hydroxy-phenyl)-2-oxo-ethyl]-2-imino-4-propyl-pyrrolidin-3-yl}-phenyl)-methanesulfonamide hydrobromide

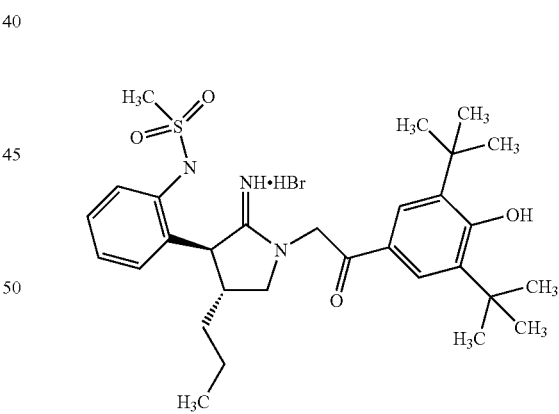

1H-NMR (DMSO-d6) δ: 0.92 (3H, t, J=7 Hz), 1.21-1.32 (2H, m), 1.45 (18H, s), 1.48-1.60 (2H, m), 2.57 (1H, dt, J=8, 7 Hz), 3.35 (3H, s), 3.52 (1H, dd, J=10, 7 Hz), 4.04 (1H, dd, J=10, 8 Hz), 4.50 (1H, d, J=7 Hz), 4.63 (1H, d, J=19 Hz), 5.60 (1H, d, J=19 Hz), 5.87 (1H, s), 7.03 (1H, s), 7.31 (1H, d, J=7 Hz), 7.42 (1H, t, J=7 Hz), 7.49 (1H, td, J=7, 2 Hz), 7.76 (2H, s), 7.87 (1H, dd, J=7, 2 Hz), 9.13 (1H, s), 10.61 (1H, s). MS: m/e(ESI) 542.2 (MH+)

Example 155

N-(2-{1-[2-(3,5-Di-tert-butyl-4-hydroxy-phenyl)-2-oxo-ethyl]-2-imino-4-propyl-pyrrolidin-3-yl}-phenyl)-acetamide hydrobromide

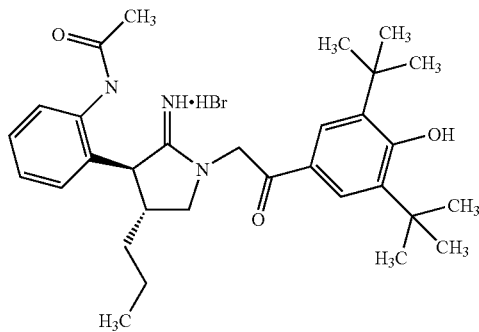

1H-NMR (DMSO-d6) δ: 0.83 (3H, t, J=7 Hz), 1.18-1.27 (2H, m), 1.48 (18H, s), 1.47-1.56 (2H, m), 2.20 (3H, s), 2.60 (1H, m), 3.54 (1H, dd, J=10, 7 Hz), 4.05 (1H, dd, J=10, 8 Hz), 4.55 (1H, d, J=6 Hz), 5.08 (1H, d, J=18 Hz), 5.88 (1H, s), 5.89 (1H, d, J=18 Hz), 7.27-7.38 (3H, m), 7.51 (1H, d, J=8 Hz), 7.89 (2H, s), 8.20 (1H, s), 8.86 (1H, s), 8.99 (1H, s). MS: m/e(ESI) 506.3 (MH+)

Example 156

2-{1-[2-(3,5-Di-tert-butyl-4-hydroxy-phenyl)-2-oxo-ethyl]-2-imino-4-propyl-pyrrolidin-3-yl}-benzyl acetate hydrobromide

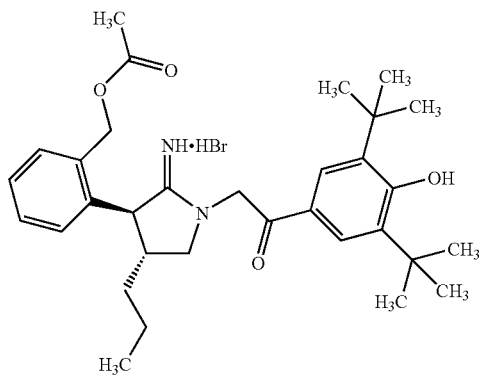

1H-NMR (DMSO-d6) δ: 0.86 (3H, t, J=7 Hz), 1.19-1.27 (2H, m), 1.48 (18H, s), 1.53-1.64 (2H, m), 2.07 (3H, s), 2.83 (1H, m), 3.64 (1H, t, J=9 Hz), 3.91 (1H, dd, J=10, 9 Hz), 4.38 (1H, d, J=9 Hz), 5.08 (1H, d, J=13 Hz), 5.28 (1H, d, J=13 Hz), 5.77 (1H, d, J=19 Hz), 5.83 (1H, d, J=19 Hz), 5.87 (1H, s), 6.40 (1H, s), 7.37-7.51 (4H, m), 7.93 (2H, s), 10.78 (1H, s). MS: m/e(ESI) 521.2 (MH+)

Example 157

1-(3,5-Di-tert-butyl-4-hydroxy-phenyl)-2-[2-imino-4-propyl-3-(2-pyrrolidin-1-yl-phenyl)-pyrrolidin-1-yl]-ethanone hydrobromide

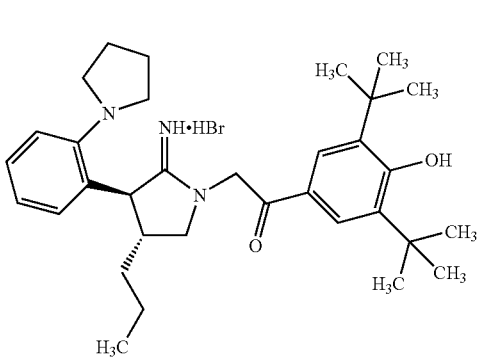

1H-NMR (DMSO-d6) δ: 0.87 (3H, t, J=7 Hz), 1.23-1.36 (2H, m), 1.48 (18H, s), 1.50-1.63 (2H, m), 1.93-2.05 (4H, m), 2.60 (1H, m), 2.96-3.02 (2H, m), 1.37-3.23 (2H, m), 3.54 (1H, t, J=9 Hz), 3.91 (1H, dd, J=10, 9 Hz), 4.64 (2H, br.d), 5.19 (1H, d, J=7 Hz), 7.11 (1H, ddd, J=7.6, 2 Hz), 7.34-7.41 (3H, m), 7.90 (2H, s). MS: m/e(ESI) 518.2 (MH+)

Example 158

1-(3,5-Di-tert-butyl-4-hydroxy-phenyl)-2-{3-[4-(3-hydroxy-propoxy)-phenyl]-2-imino-4-propyl-pyrrolidin-1-yl}-ethanone hydrochloride

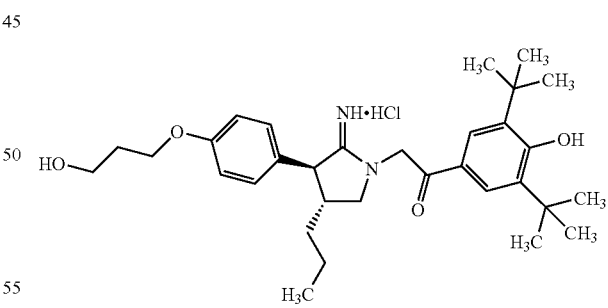

1H-NMR (DMSO-d6) δ: 0.80 (3H, t, J=7.2 Hz), 1.18-1.40 (2H, m), 1.41 (18H, s), 1.43-1.53 (2H, m), 2.35-2.42 (1H, m), 3.41 (1H, dd, J=10.8, 7.6 Hz), 3.70 (2H, t, J=5.2 Hz), 3.85 (1H, dd, J=10.8, 8.4 Hz), 3.99 (2H, t, J=5.2 Hz), 4.06 (1H, d, J=8.0 Hz), 4.80-4.88 (1H, m), 5.24 (2H, s), 7.00 (2H, d, J=8.8 Hz), 7.30 (2H, d, J=8.8 Hz), 7.74 (2H, s), 8.68-8.72 (1H, brs), 8.80-8.95 (1H, brs).

Example 159

1-[2-(3,5-Di-tert-butyl-4-hydroxy-phenyl)-2-oxo-ethyl]-(3R,4S)-5-imino-4-phenyl-pyrrolidine-3-carboxylic acid dimethylamide hydrobromide

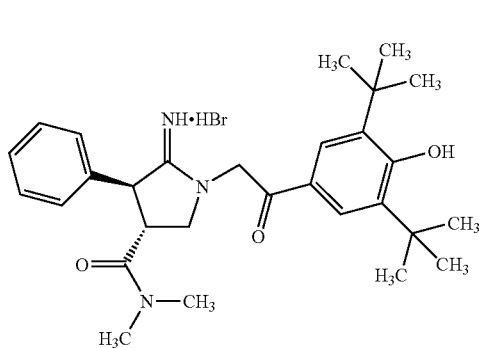

1H-NMR (DMSO-d6) δ: 1.43 (18H, s), 2.85 (3H, s), 2.87 (3H, s), 3.21 (1H, td, J=4.4 Hz, 8.4 Hz), 3.77 (1H, m), 4.18 (1H, dd, J=8.4 Hz, 10.8 Hz), 4.76 (1H, d, J=4.4 Hz), 5.28 (1H, d, J=18.4 Hz), 5.35 (1H, d, J=18.4 Hz), 7.37-7.55 (5H, m), 7.78 (2H, s), 8.09 (1H, s), 9.15 (1H, s).

Example 160

N-{1-[2-(3,5-Di-tert-butyl-4-hydroxy-phenyl)-2-oxo-ethyl]-(3R,4S)-5-imino-4-phenyl-pyrrolidin-3-ylmethyl}-N-methyl-methanesulfonamide hydrobromide

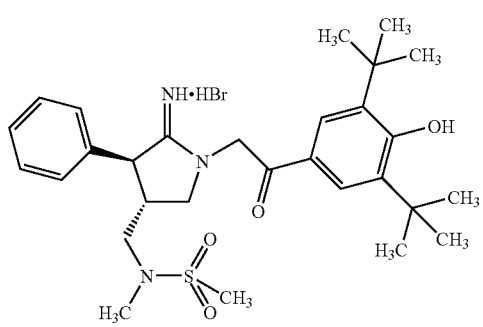

1H-NMR (DMSO-d6) δ: 1.44 (18H, s), 2.72 (3H, s), 2.75 (1H, m), 2.93 (3H, s), 3.21 (1H, dd, J=7.2 Hz, 13.6 Hz), 3.35 (1H, m), 3.48 (1H, dd, J=4.0 Hz, 11.2 Hz), 3.99 (1H, dd, J=7.2 Hz, 11.2 Hz), 4.32 (1H, d, J=4.0 Hz), 5.33 (2H, s), 7.36-7.52 (5H, m), 7.79 (2H, s), 8.09 (1H, s), 9.03 (1H, s), 9.21 (1H, s).

Example 161

Benzyl {1-[2-(3,5-di-tert-butyl-4-hydroxy-phenyl)-2-oxo-ethyl]-(3R,4S)-5-imino-4-phenyl-pyrrolidin-3-ylmethyl}-methylcarbamate hydrobromide

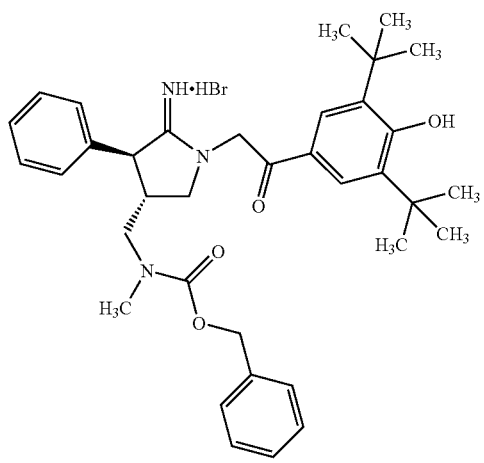

1H-NMR (DMSO-d6) δ: 1.44 (18H, s), 2.76 (3H, s), 2.80 (1H, m), 3.50 (1H, dd, J=5.2 Hz, 11.2 Hz), 3.92 (1H, dd, J=7.6 Hz, 11.2 Hz), 4.22 (1H, m), 5.08 (2H, s), 5.30 (2H, s), 7.25-7.55 (10H, m), 7.78 (2H, s), 8.09 (1H, s), 9.00 (2H, s).

Example 162

1-(3,5-Di-tert-butyl-4-hydroxy-phenyl)-2-((3S,4S)-2-imino-4-methylaminomethyl-3-phenyl-pyrrolidin-1-yl)-ethanone hydrobromide

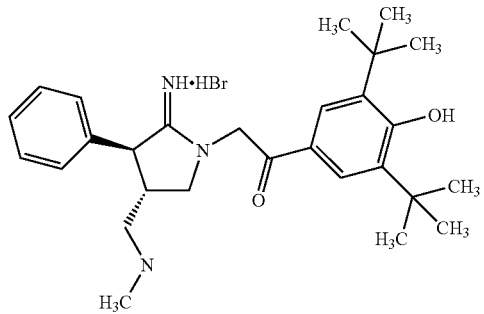

1H-NMR (DMSO-d6) δ: 1.42 (18H, s), 2.31 (3H, s), 2.71 (2H, m), 3.53 (1H, dd, J=4.4 Hz, 11.2 Hz), 3.93 (1H, dd, J=7.6 Hz, 11.2 Hz), 4.31 (1H, d, J=4.4 Hz), 5.24 (2H, s), 7.35-7.55 (6H, m), 7.72 (2H, s), 9.09 (1H, s).

Example 163

1-(3,5-Di-tert-butyl-4-hydroxy-phenyl)-2-[3-(2-hydroxymethyl-phenyl)-2-imino-4-propyl-pyrrolidin-1-yl]-ethanone hydrobromide

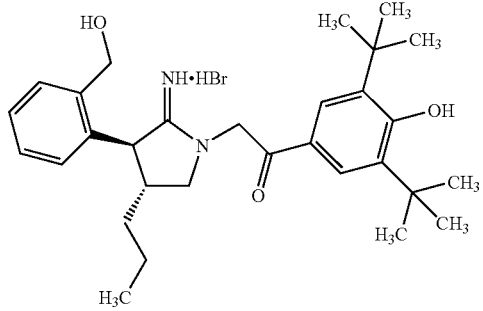

1H-NMR (DMSO-d6) δ: 0.84 (3H, t, J=7 Hz), 1.19-1.28 (2H, m), 1.46 (18H, s), 1.57-1.64 (2H, m), 2.83 (1H, m), 3.50 (1H, dd, J=10, 7 Hz), 4.02 (1H, dd, J=10, 9 Hz), 4.53 (1H, d, J=13 Hz), 4.72 (1H, d, J=7 Hz), 4.93 (1H, d, J=13 Hz), 5.23 (1H, d, J=18 Hz), 5.83 (1H, s), 6.02 (1H, d, J=18 Hz), 7.27-7.41 (4H, m), 7.89 (2H, s). MS: m/e(ESI) 479.2 (MH+)

Example 164

1-(3,5-Di-tert-butyl-4-hydroxy-phenyl)-2-[2-imino-3-(2-methoxymethyl-phenyl)-4-propyl-pyrrolidin-1-yl]-ethanone hydrobromide

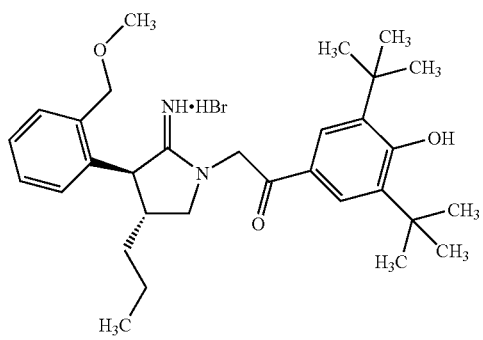

1H-NMR (DMSO-d6) δ: 0.88 (3H, t, J=7 Hz), 1.22-1.30 (2H, m), 1.48 (18H, s), 1.57-1.64 (2H, m), 2.87 (1H, m), 3.47 (3H, s), 3.56 (1H, dd, J=10, 7 Hz), 4.05 (1H, t, J=10 Hz), 4.19 (1H, d, J=7 Hz), 4.33 (1H, d, J=11 Hz), 4.64 (1H, d, J=11 Hz), 5.87 (2H, brs), 5.89 (1H, s), 7.31-7.50 (4H, m), 7.96 (2H, s). MS: m/e(ESI) 493.3 (MH+)

Example 165

4-{5-[2-(4-Benzyl-3-imino-5-propyl-3H-isoxazol-2-yl)-acetyl]-3-tert-butyl-2-methoxyphenoxy}-butylamide hydrobromide

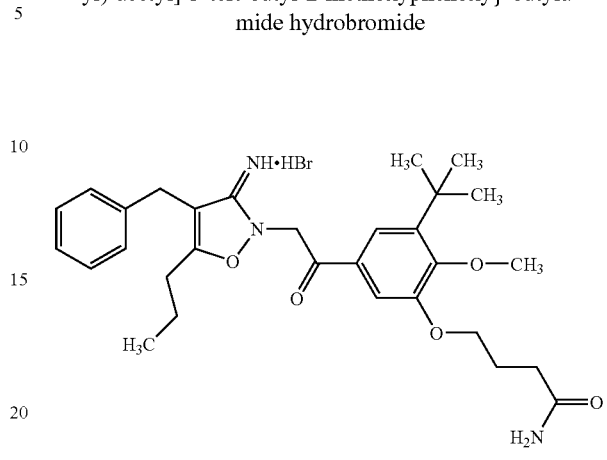

1H-NMR (DMSO-d6) δ: 0.91 (3H, t, J=7 Hz), 1.38 (9H, s), 1.60 (2H, m), 2.18 (2H, m), 2.42-2.51 (4H, m), 3.69 (1H, d, J=18 Hz), 3.78 (1H, d, J=18 Hz), 3.96 (3H, s), 4.15 (1H, m), 4.27 (1H, m), 5.93 (1H, brs), 6.32 (1H, brs), 6.70 (1H, s), 7.17 (2H, d, J=8 Hz), 7.22-7.33 (3H, m), 7.61 (1H, s), 7.63 (1H, s). MS: m/e(ESI) 522.3 (MH+)

Example 166

4-(3-tert-Butyl-2-hydroxy-5-{2-[2-imino-4-(2-methoxy-ethyl)-3-phenyl-pyrrolidin-1-yl]-acetyl}-phenoxy)-butylamide hydrobromide

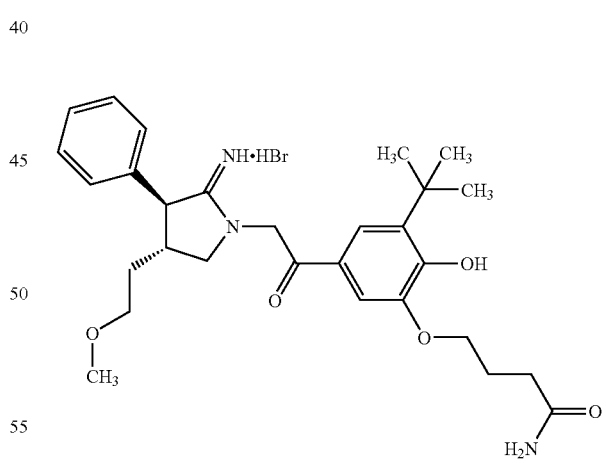

1H-NMR (DMSO-d6) δ: 1.38 (9H, s), 1.82 (2H, m), 2.11 (2H, quint, J=6 Hz), 2.43 (2H, t, J=6 Hz), 2.75 (1H, m), 3.18 (3H, s), 3.31-3.37 (2H, m), 3.74 (1H, dd, J=9, 8 Hz), 3.95 (1H, d, J=10, 9 Hz), 4.06 (1H, d, J=9 Hz), 4.20 (2H, t, J=6 Hz), 5.48 (1H, d, J=19 Hz), 5.70 (1H, d, J=19 Hz), 5.71 (1H, s), 7.22 (1H, s), 7.28 (1H, s), 7.30-7.41 (5H, m), 7.61 (1H, s), 7.62 (1H, s), 11.36 (2H, s). MS: m/e(ESI) 510.2 (MH+)

Example 167

1-(3,5-Di-tert-butyl-4-hydroxy-phenyl)-2-[3-(3-ethyl-pentyl)-2-methylimino-2H-pyridin-1-yl]-ethanone hydrobromide

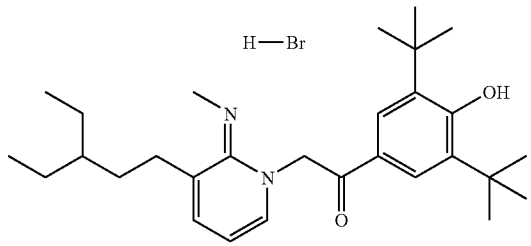

1H-NMR (DMSO-d6) δ: 0.79 (6H, t, J=7 Hz), 1.15-1.23 (1H, m), 1.23-1.32 (6H, m), 1.43 (18H, s), 2.58 (2H, m), 2.99 (3H, s), 4.66 (2H, s), 6.83 (1H, dd, J=8, 5 Hz), 7.42 (1H, dd, J=8, 2 Hz), 7.83 (2H, s), 8.06 (1H, dd, J=5, 2 Hz). MS: m/e(ESI) 453.3 (MH+)

Example 168

Ethyl (4-{3-tert-butyl-5-[2-(2-imino-3-phenyl-4-propyl-pyrrolidin-1-yl)-acetyl]-benzyl}-piperazin-1-yl)-acetate hydrobromide

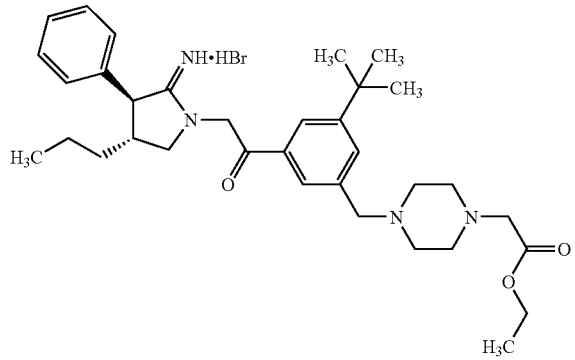

MS: m/e(ESI) 561.3 (MH+)

Example 169

{2-tert-butyl-6-dimethylamino-4-[2-(2-imino-3-phenyl-4-propyl-pyrrolidin-1-yl)-acetyl]-phenoxy}-acetic acid hydrobromide

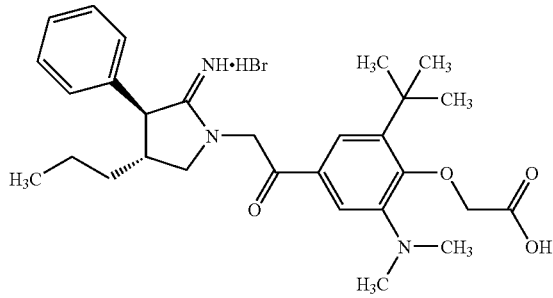

MS: m/e(ESI) 494.4 (MH+)

Example 170

{2-tert-Butyl-4-[2-(2-imino-3-phenyl-4-propyl-pyrrolidin-1-yl)-acetyl]-6-pyrrolidin-1-yl-phenoxy}-acetic acid hydrobromide

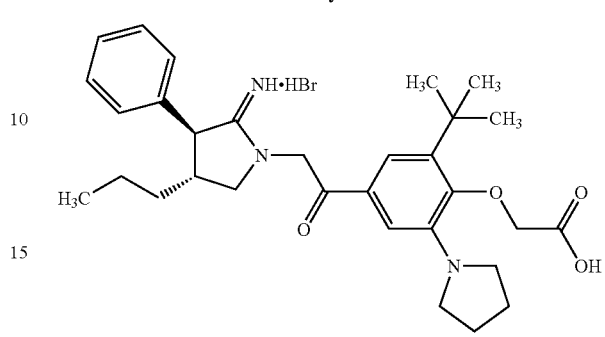

MS: m/e(ESI) 520.5 (MH+)<

Example 171

4-{3-tert-Butyl-5-[2-(2-imino-3-phenyl-4-propyl-pyrrolidin-1-yl)-acetyl]-2-methoxy-phenoxy}-butylamide hydrobromide

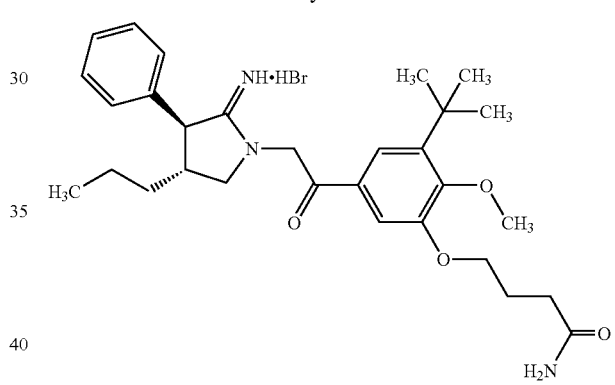

MS: m/e(ESI) 508.5 (MH+)

Example 172

4-{3-tert-Butyl-2-hydroxy-5-[2-(2-imino-3-phenyl-4-propyl-pyrrolidin-1-yl)-acetyl]-phenoxy}-butylamide hydrobromide

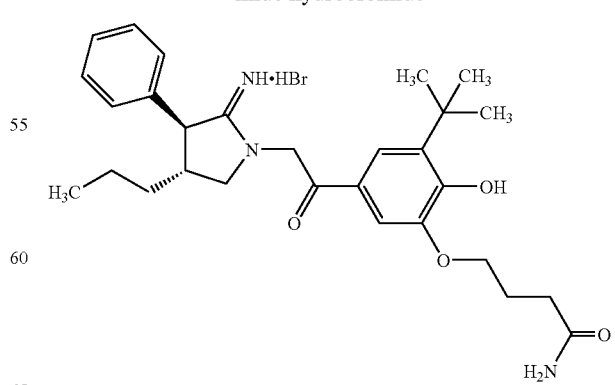

MS: m/e(ESI) 494.5 (MH+)

Example 173

(1-{3-tert-Butyl-2-hydroxy-5-[2-(2-imino-3-phenyl-4-propyl-pyrrolidin-1-yl)-acetyl]-phenyl}-pyrrolidin-3-yloxy)-acetic acid hydrobromide

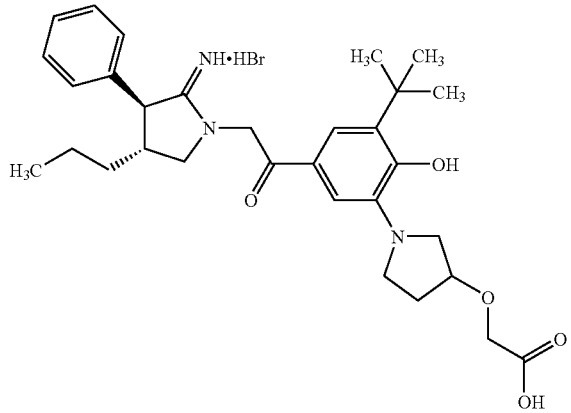

MS: m/e(ESI) 536.4 (MH+)

Example 174

Ethyl [4-(3-tert-butyl-5-{2-[2-imino-4-(2-methoxy-ethyl)-3-phenyl-pyrrolidin-1-yl]-acetyl}-benzyl)-piperazin-1-yl]-acetate hydrobromide

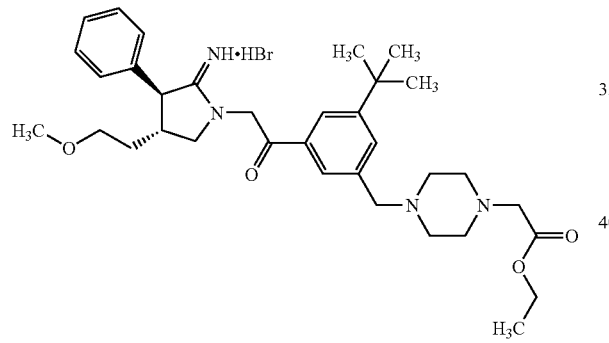

MS: m/e(ESI) 577.4 (MH+)

Example 175

(2-tert-Butyl-6-dimethylamino-4-{2-[2-imino-4-(2-methoxy-ethyl)-3-phenyl-pyrrolidin-1-yl]-acetyl}-phenoxy)-acetic acid hydrobromide

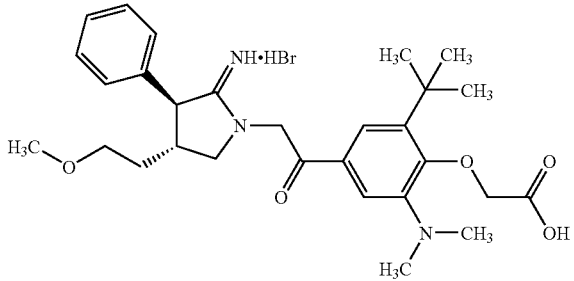

MS: m/e(ESI) 510.4 (MH+)

Example 176

(2-tert-Butyl-4-{2-[2-imino-4-(2-methoxy-ethyl)-3-phenyl-pyrrolidin-1-yl]-acetyl}-6-pyrrolidin-1-ylphenoxy)-acetic acid hydrobromide

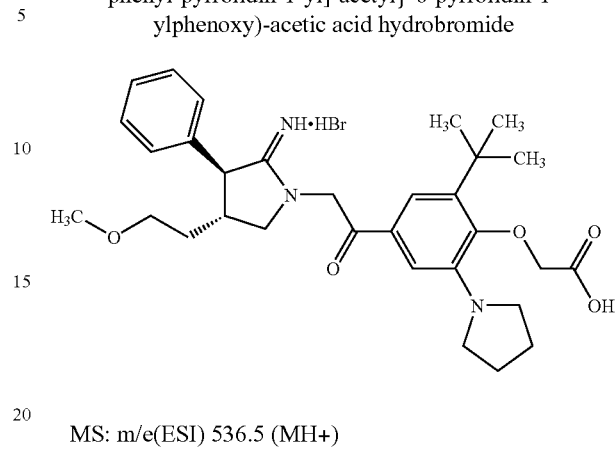

MS: m/e(ESI) 536.5 (MH+)

Example 177

4-(3-tert-Butyl-5-{2-[2-imino-4-(2-methoxy-ethyl)-3-phenyl-pyrrolidin-1-yl]-acetyl}-2-methoxyphenoxy)-butylamide hydrobromide

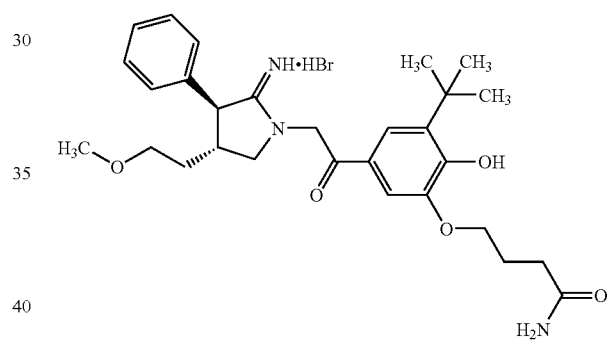

MS: m/e(ESI) 524.5 (MH+)

Example 178

4-(3-tert-Butyl-2-hydroxy-5-{2-[2-imino-4-(2-methoxy-ethyl)-3-phenyl-pyrrolidin-1-yl]-acetyl}-phenoxy)-butylamide hydrobromide

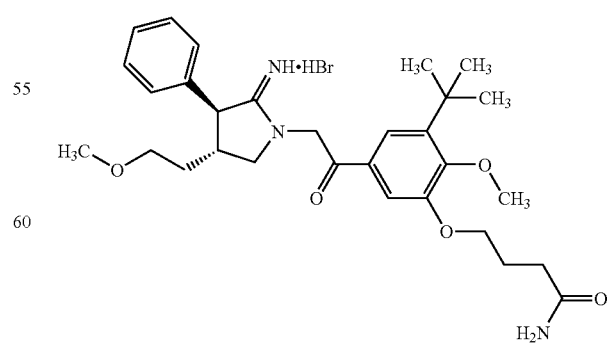

MS: m/e(ESI) 510.3 (MH+)

Example 179

[1-(3-tert-Butyl-2-hydroxy-5-{2-[2-imino-4-(2-methoxy-ethyl)-3-phenyl-pyrrolidin-1-yl]-acetyl}-phenyl)-pyrrolidin-3-yloxy]-acetic acid hydrobromide

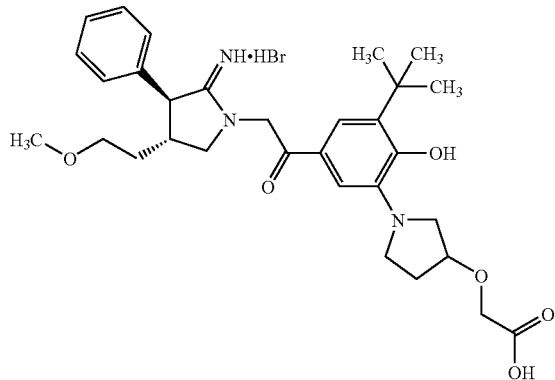

MS: m/e(ESI) 552.4 (MH+)

TEST EXAMPLES

The biochemical activities of compounds of the invention and salts thereof and their actions and effects as medicines (thrombin receptor binding capacity, platelet aggregation inhibitory action and smooth muscle cell proliferation inhibitory action) were evaluated by the following methods.

Test Example 1

Receptor Binding Assay

Blood was sampled from a healthy adult who had taken no drugs for one week, and 3.8% citric acid (a ratio of 1:9 with respect to the blood) was added as an anticoagulant. The mixture was then centrifuged at 100 g for 10 minutes at room temperature to yield platelet rich plasma (PRP). The platelet precipitate obtained, by centrifuging the PRP was homogenized with a Dounce homogenizer, and then centrifuged at 40,000 g for 60 minutes to yield platelet membrane. The platelet membrane was suspended in a solution prepared by adding DMSO (dimethyl sulfoxide) at 1% concentration to Buffer 1: a 50 mM Tris-HCl buffer containing 10 mM $MgCl_2$ and 1 mM EGTA (ethylene glycol tetraacetic acid), and the suspension was stored at −80° C. Bovine albumin and DMSO were added to Buffer 1 at 0.1% and 20%, respectively, to make a preparation solution for the test compound. The test compounds (20 μl) diluted at various concentrations with the preparation solution were added to a 96-well multiscreen plate. Next, 80 μl of 25 nM [$^3$H]Ala-(4-fluoro)Phe-Arg-(cyclohexyl)Ala-(homo)Arg-Tyr-$NH_2$ (high affinity TRAP) diluted with Buffer 1 was added and thoroughly mixed therewith. After then adding 100 μl of the previously prepared platelet membrane suspension (0.4 mg/ml) and mixing, incubation was performed at 37° C. for 1 hour. The reaction mixture was suction filtered and then rinsed 3 times with 200 μl of Buffer 1. Next, 30 μl of liquid scintillator was added for measurement of the radioactivity of the plate using a Top Counter (Packard), the value of the radioactivity in the presence of the test compound minus non-specific binding portion was divided by the specific binding value (the value of the binding in the absence of the compound minus the non-specific binding portion) to determine the binding ratio, from which the $IC_{50}$ value was calculated. The non-specific binding was the value obtained with addition of 10 μM of high affinity TRAP. The results are shown in Table 1.

Test Example 2

Inhibitory Effects on Platelet Aggregation Using Platelet Rich Plasma

Blood was sampled from a healthy adult who had taken no drugs for one week, and 3.8% citric acid (a ratio of 1:9 with respect to the blood) was added as an anticoagulant. The mixture was then centrifuged at 100 g for 10 minutes at room temperature to yield platelet rich plasma (PRP). The PRP-removed blood was further centrifuged at 1000 g for 10 minutes to yield platelet poor plasma (PPP). The number of platelet was counted using a multi-parameter automatic hemocyte counter (K4500, Sysmex), and the PRP was diluted to approximately 300,000/μl with the PPP. The platelet aggregation activity was determined in the following manner using an Aggregometer (MC Medical). GPRP-$NH_2$ (final concentration 1 mM, 25 μl) was added as a fibrin polymerization inhibitor to the PRP (175 μl), after which Ca-free Tyrode solution (control) or the test compound suspension (25 μl) at different concentrations was added, incubation was performed at 37° C. for 3 minutes and then 25 μl of thrombin at the minimum concentration required to produce maximum aggregation (final concentration: optimum concentration among 0.5-1.5 units/ml) was added, for initiation of platelet aggregation. PRP and Ca-free Tyrode solution (control) or the preparation solution at various concentrations were pre-incubated at 37° C. for 60 minutes, prior to the platelet aggregation reaction in some experiments. After addition of thrombin, the aggregation reaction was examined for 6 minutes and the areas under the aggregation curves were compared to determine the inhibition ratio, from which the $IC_{50}$ value was calculated. The results are shown in Table 1.

Test Example 3

Rat Smooth Muscle Cell Proliferation Assay

Vascular smooth muscle cells (rSMC) were isolated from male SD rat aorta by the explant method. DMEM medium (Sigma) containing 10% fetal bovine serum (GibcoBRL), streptomycin and penicillin was used as the proliferation medium, and subculture was carried out at 37° C. in the presence of 5% $CO_2$. Culture was initiated after adding 100 μl of rSMC suspension in proliferation medium at a concentration of 1×10$^4$ cells/ml, to a 96-well plate. After 3 days, cells were rinsed twice with 100 μl of DMEM medium, the medium was exchanged with 100 μl of DMEM medium containing 0.1% albumin (starvation medium), and serum starvation was initiated. The medium was exchanged two days after the serum starvation, 80 μl of starvation medium and 10 μl of the test compound diluted to different concentrations with the starvation medium were added, and then 10 μl of thrombin dissolved in the starvation medium (final concentration: 0.1 unit/ml) was added prior to further incubation for 2 days.

Upon adding 20 μl of MTT (3-[4,5-dimethylthiazol-2-yl]-2,5-diphenyltetrazolium bromide) dissolved in DPBS to 7.5 mg/ml, incubation was continued for 4 hours. The medium was removed by suction, 50 μl of a 10% SDS/0.029% ammonia solution was added, and the mixture was allowed to stand for 2 hours in a $CO_2$ incubator for complete lysis of the cells. As an index of cell proliferation, the OD 590 nm was measured using a plate reader (EL340, BIO-TEK Instruments Inc.), and the control OD value (OD value in the absence of the test compound) minus the OD value in the presence of the test compound was divided by the control OD value minus the blank OD value (OD value without thrombin stimulation) to determine the inhibition ratio, from which the value was calculated. The results are shown in Table 1.

result of damage to vascular walls by coronary angioplasty and the like, based on selective inhibition of PAR1.

Thus, in certain embodiments, compounds of the invention and salts thereof are useful as thrombin receptor antagonists (especially PAR1 thrombin receptor antagonists), platelet aggregation inhibitors (antithrombotic agents) and smooth muscle cell proliferation inhibitors, while also being useful as therapeutic or prophylactic agents for restenosis during or following angioplasty, unstable angina, stable angina, myocardial infarction, cerebral infarction, peripheral arterial occlusion and the like, as therapeutic or prophylactic agents for venous thromboses such as deep venous thrombosis, pulmonary embolism and cerebral embolism accompanying atrial fibrillation, glomerulonephritis and the like, as anti-inflammatory agents or as anti-restenosis agents.

The invention claimed is:

1. A compound represented by the formula:

TABLE 1

| Example No. | Compound | Compound name | RBA $IC_{50}$ (μM) | Thr $IC_{50}$ (μM) | Rat SMC $IC_{50}$ (μM) |
| --- | --- | --- | --- | --- | --- |
| Example 3 | | N-{3-tert-Butyl-2-hydroxy-5-[2-((3S,4S)-2-imino-3-phenyl-4-propyl-pyrrolidin-1-yl)-acetyl]-phenyl}-N-methyl-methanesulfonamide hydrobromide | 0.66 | 2.3 | 2.5 |

In certain embodiments, compounds of the present invention and salts thereof exhibited excellent thrombin receptor binding capacity in Test Example 1, and especially selective binding capacity with PAR1 thrombin receptor. In addition, compounds of the invention and salts thereof exhibited excellent platelet aggregation inhibitory action in Test Example 2. Compounds of the invention and salts thereof also exhibited excellent smooth muscle cell proliferation inhibitory action in Test Example 3.

INDUSTRIAL APPLICABILITY

In one aspect, the present invention provides novel cyclic amidine derivatives represented by the formula (I) and salts thereof. In certain embodiments, compounds of the invention represented by the formula (I) and salts thereof exhibit excellent thrombin receptor antagonism and especially selective antagonism for PAR1 thrombin receptors. In certain embodiments, compounds of the invention and salts thereof can therefore inhibit cellular response to thrombin which includes platelet aggregation, without inhibiting the catalytic activity of thrombin which converts fibrinogen to fibrin, and can also inhibit vascular smooth muscle proliferation occurring as a

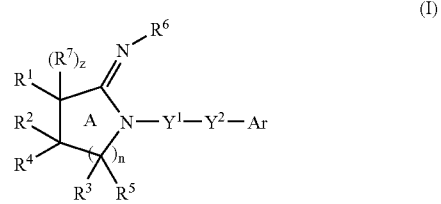

wherein $R^1$, $R^3$, $R^5$ and $R^7$ are the same or different and each independently represents hydrogen, cyano, halogen or a group selected from Substituent Group A, z represents 0 or 1;

$R^2$ and $R^4$ bond together to form a 5- to 6-membered ring optionally having 1 or more heteroatoms selected from O;

$R^6$ represents hydrogen, $C_{1-6}$ alkyl, acyl, carbamoyl, hydroxyl, $C_{1-6}$ alkoxy, $C_{1-6}$ alkyloxycarbonyloxy, $C_{3-8}$ cycloalkyl, $C_{1-6}$ alkyloxycarbonyl optionally substituted with acyloxy or a $C_{6-14}$ aromatic hydrocarbon ring group or a 5- to 14-membered aromatic heterocyclic group, each of the foregoing members being optionally substituted with at least one group selected from Substituent Group E;

n represents 1;

Y¹ represents a single bond, —(CH$_2$)$_m$—, —CR$^8$—, —CR$^8$CR$^9$—, —CH$_2$CO—, —NR$^8$—, —SO—, —SO$_2$—, —CO—, —CONR$^8$— or —SO$_2$NR$^8$—, wherein m represents an integer of 1 to 3, and R$^8$ and R$^9$ are the same or different and each independently represents hydrogen, halogen, C$_{1-6}$ alkyl, carboxyl or C$_{1-6}$ alkoxycarbonyl;

Y² represents a single bond, O, N, —(CH$_2$)$_m$—, —CR$^8$—, CR$^8$R$^9$—, —CO—, —SO—, —SO$_2$— or —C(=N—OR$^8$)—, wherein m represents an integer of 1 to 3, and R$^8$ and R$^9$ are the same or different and each independently represents hydrogen, halogen, C$_{1-6}$ alkyl, carboxyl or C$_{1-6}$ alkoxycarbonyl Ar represents (1) hydrogen, (2) a group represented by the formula:

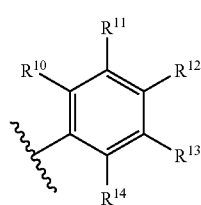

(II)

wherein R$^{10}$, R$^{11}$, R$^{12}$, R$^{13}$ and R$^{14}$ are the same or different and each independently represents hydrogen, cyano, halogen, nitro or a group selected from Substituent Group B, and R$^{11}$ and R$^{12}$ or R$^{12}$ and R$^{13}$ may bond together to form a 5- to 8-membered heterocycle optionally having 1 to 4 hetero atoms selected from N, S and O and optionally substituted with at least one group selected from Substituent Group F, or (3) a 5- to 14-membered aromatic heterocyclic group optionally substituted with at least one group selected from Substituent Group G;

<Substituent Group A> represents moieties selected from the group consisting of C$_{1-6}$ alkyl, alkylidene, C$_{2-6}$ alkenyl, C$_{2-6}$ alkynyl, acyl, carboxyl, carbamoyl, C$_{1-6}$ alkoxycarbonyl, C$_{1-6}$ alkylaminocarbonyl, hydroxyl, C$_{1-6}$ alkoxy, C$_{3-8}$ cycloalkyloxy, amino, C$_{1-6}$ alkylamino, C$_{3-8}$ cycloalkylamino, acylamino, sulfonylamino, sulfonyl, sulfamoyl, C$_{3-8}$ cycloalkyl, a 5- to 14-membered non-aromatic heterocyclic group, a C$_{6-14}$ aromatic hydrocarbon ring group and a 5- to 14-membered aromatic heterocyclic group, each of the foregoing members being optionally substituted with at least one group selected from Substituent Group A';

<Substituent Group A'> represents moieties selected from the group consisting of C$_{1-6}$ alkyl, C$_{2-6}$ alkenyl, C$_{2-6}$ alkynyl, cyano, acyl, carboxyl, carbamoyl, C$_{1-6}$ alkoxycarbonyl, C$_{1-6}$ alkylaminocarbonyl, hydroxyl, C$_{1-6}$ alkoxy, C$_{3-8}$ cycloalkyloxy, amino, C$_{1-6}$ alkylamino, C$_{3-8}$ cycloalkylamino, acylamino, ureido, ureylene, sulfonylamino, sulfonyl, sulfamoyl, halogen, C$_{3-8}$ cycloalkyl, a heterocyclic alkyl group, a 5- to 14-membered non-aromatic heterocyclic group, a C$_{6-14}$ aromatic hydrocarbon ring group and a 5- to 14-membered aromatic heterocyclic group, wherein the C$_{6-14}$ aromatic hydrocarbon ring group and the 5- to 14-membered aromatic heterocyclic group may be substituted with at least one group selected from the group consisting of C$_{1-6}$ alkyl, cyano, acyl, carboxyl, carbamoyl, C$_{1-6}$ alkoxycarbonyl, C$_{1-6}$ alkylaminocarbonyl, hydroxyl, C$_{1-6}$ alkoxy, C$_{3-8}$ cycloalkyloxy, nitro, amino, C$_{1-6}$ alkylamino, C$_{3-8}$ cycloalkylamino, acylamino, ureido, ureylene, sulfonylamino, sulfonyl, sulfamoyl, halogen and C$_{3-8}$ cycloalkyl;

<Substituent Group B> represents moieties selected from the group consisting of C$_{1-6}$ alkyl, C$_{2-6}$ alkenyl, C$_{2-6}$ alkynyl, acyl, carboxyl, carbamoyl, C$_{1-6}$ alkoxycarbonyl, C$_{1-6}$ alkylaminocarbonyl, hydroxyl, C$_{1-6}$ alkoxy, C$_{3-8}$ cycloalkyloxy, amino, C$_{1-6}$ aminoalkyl, C$_{1-6}$ alkylamino, C$_{3-8}$ cycloalkylamino, acylamino, ureido, sulfonylamino, sulfonyl, sulfamoyl, C$_{3-8}$ cycloalkyl, a 5- to 14-membered non-aromatic heterocyclic group, a C$_{6-14}$ aromatic hydrocarbon ring group and a 5- to 14-membered aromatic heterocyclic group, each of the foregoing members being optionally substituted with at least one group selected from Substituent Group B';

<Substituent Group B'> represents moieties selected from the group consisting of C$_{1-6}$ alkyl, C$_{2-6}$ alkenyl, C$_{2-6}$ alkynyl, oxo, cyano, C$_{1-6}$ cyanoacyl, C$_{2-7}$ acyl, C$_{1-6}$ alkanoyl, benzoyl, aralkanoyl, C$_{1-6}$ alkoxyalkylcarbonyl, C$_{1-6}$ hydroxyalkylcarbonyl, carboxyl, C$_{1-6}$ carboxyalkyl, C$_{1-6}$ carboxyalkyloxy, carbamoyl, carbamoylalkyloxy, C$_{1-6}$ alkoxycarbonyl, C$_{1-10}$ alkoxycarbonyl-C$_{1-6}$ alkyl, C$_{1-10}$ alkoxycarbonyl-C$_{1-6}$ alkyloxy, C$_{1-6}$ monoalkylaminocarbonyl, C$_{2-6}$ dialkylaminocarbonyl, hydroxyl, C$_{1-6}$ alkoxy, C$_{1-10}$ alkoxyalkyl, C$_{1-10}$ aralkyloxyalkyl, C$_{1-6}$ hydroxyalkyl, C$_{3-8}$ cycloalkyloxy, amino, C$_{1-6}$ alkylamino, C$_{3-8}$ cycloalkylamino, acylamino, ureido, ureylene, C$_{1-6}$ alkylsulfonylamino, phenylsulfonylamino, C$_{1-6}$ alkylsulfonyl, phenylsulfonyl, C$_{1-6}$ monoalkylaminosulfonyl, C$_{2-6}$ dialkylaminosulfonyl, sulfamoyl, halogeno, C$_{3-8}$ cycloalkyl, a 5- to 14-membered non-aromatic heterocyclic group, a C$_{6-14}$ aromatic hydrocarbon ring group, a 5- to 14-membered aromatic heterocyclic group, a heterocyclic aminocarbonyl group, a heterocyclic aminosulfonyl group and isoxazolinyl, wherein the 5- to 14-membered non-aromatic heterocyclic group, the C$_{6-14}$ aromatic hydrocarbon ring group, the 5- to 14-membered aromatic heterocyclic group and isoxazolinyl may be independently substituted with at least one group selected from the group consisting of C$_{1-6}$ alkyl, oxo, cyano, acyl, carboxyl, carbamoyl, C$_{1-6}$ alkoxycarbonyl, C$_{1-6}$ alkylaminocarbonyl, hydroxyl, C$_{1-6}$ alkoxy, C$_{3-8}$ cycloalkyloxy, nitro, amino, C$_{1-6}$ aminoalkyl, C$_{1-6}$ alkylamino, C$_{1-6}$ dialkylamino, C$_{3-8}$ cycloalkylamino, acylamino, ureido, ureylene, alkylsulfonylamino, alkylsulfonyl, sulfamoyl, halogeno and C$_{3-8}$ cycloalkyl;

<Substituent Group E> represents moieties selected from the group consisting of C$_{1-6}$ alkyl, cyano, acyl, carboxyl, carbamoyl, C$_{1-6}$ alkoxycarbonyl, C$_{1-6}$ alkylaminocarbonyl, hydroxyl, C$_{1-6}$ alkoxy, C$_{3-8}$ cycloalkyloxy, amino, C$_{1-6}$ alkylamino, C$_{3-8}$ cycloalkylamino, acylamino, ureido, ureylene, sulfonylamino, sulfonyl, sulfamoyl, halogen and C$_{3-8}$ cycloalkyl;

<Substituent Group F> represents moieties selected from the group consisting of hydrogen, cyano, halogen, oxo, and C$_{1-6}$ alkyl, alkenyl, alkynyl, acyl, C$_{1-6}$ alkanoyl, carboxyl, carbamoyl, C$_{1-6}$ alkoxycarbonyl, C$_{1-6}$ alkylaminocarbonyl, hydroxyl, C$_{1-6}$ alkoxy, C$_{3-8}$ cycloalkyloxy, amino, imino, C$_{1-6}$ aminoalkyl, C$_{1-6}$ alkylamino, C$_{3-8}$ cycloalkylamino, acylamino, ureido, sulfonylamino, sulfonyl, sulfamoyl, C$_{3-8}$ cycloalkyl, a 5- to 14-membered non-aromatic heterocyclic group, a C$_{6-14}$ aromatic hydrocarbon ring group and a 5- to 14-membered aromatic heterocyclic group, each of the foregoing members being optionally substituted with at least one group selected from Substituent Group F';

<Substituent Group F'> represents moieties selected from the group consisting of $C_{1-6}$ alkyl, oxo, cyano, acyl, carboxyl, carbamoyl, $C_{1-6}$ alkoxycarbonyl, benzyloxycarbonyl, $C_{1-6}$ alkylaminocarbonyl, hydroxyl, $C_{1-6}$ alkoxy, $C_{3-8}$ cycloalkyloxy, amino, $C_{1-6}$ alkylamino, $C_{3-8}$ cycloalkylamino, acylamino, ureido, ureylene, $C_{1-6}$ alkylsulfonylamino, $C_{1-6}$ alkylsulfonyl, sulfamoyl, halogeno, $C_{3-8}$ cycloalkyl, a 5- to 14-membered non-aromatic heterocyclic group, a $C_{6-14}$ aromatic hydrocarbon ring group and a 5- to 14-membered aromatic heterocyclic group; and <Substituent Group G> represents moieties selected from the group consisting of $C_{1-6}$ alkyl, cyano, acyl, carboxyl, carbamoyl, $C_{1-6}$ alkoxycarbonyl, $C_{1-6}$ alkylaminocarbonyl, sulfonyl, sulfamoyl, halogeno and $C_{3-8}$ cycloalkyl; or salt thereof.

2. The compound according to claim 1 or salt thereof, wherein $R^1$ and $R^3$ are the same or different and each independently represents a group selected from the group consisting of hydrogen, $C_{1-6}$ alkyl, $C_{1-6}$ alkoxy, aryl-$C_{1-6}$ alkyl and aryl-$C_{1-6}$ alkylidene;

$R^5$ and $R^7$ are the same or different and each independently represents a group selected from the group consisting of hydrogen, $C_{1-6}$ alkyl and hydroxyl;

$R^6$ represents a group selected from the group consisting of hydrogen, $C_{1-6}$ alkyl and $C_{1-6}$ alkyloxycarbonyl optionally substituted with acyloxy;

$Y^1$ represents a single bond or —$(CH_2)_m$—, wherein m represents an integer of 1 to 3;

$Y^2$ represents a single bond or —CO—;

Ar represents hydrogen or a group represented by the formula:

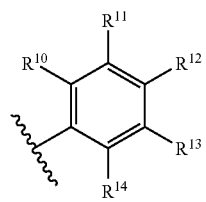

(II)

wherein $R^{10}$, $R^{11}$, $R^{12}$, $R^{13}$ and $R^{14}$ are the same or different and each independently represents a group selected from the group consisting of hydrogen, $C_{1-6}$ alkyl, hydroxyl, $C_{1-6}$ alkoxy, $C_{1-6}$ alkylamino, $C_{3-8}$ cycloalkylamino, acylamino, a 5- to 14-membered non-aromatic heterocyclic group and $C_{1-6}$ alkyloxycarbonyloxy, and $R^{11}$ and $R^{12}$ or $R^{12}$ and $R^{13}$ may bond together to form a 5- to 8-membered heterocycle (i) optionally having 1 to 4 hetero atoms selected from N, S and O and (ii) optionally substituted with at least one group selected from the group consisting of cyano, oxo, and $C_{1-6}$ alkyl, acyl, $C_{1-6}$ alkanoyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, amino, $C_{1-6}$ alkylamino, sulfonyl and a 5- to 14-membered non-aromatic heterocyclic group, each of the foregoing members being optionally substituted with at least one group selected from Substituent Group F''; and <Substituent Group F''> represents moieties selected from the group consisting of $C_{1-6}$ alkyl, oxo, cyano, acyl, carboxyl and $C_{1-6}$ alkoxy.

3. The compound according to claim 1 or a salt thereof, wherein $Y^1$ is —$CH_2$—.

4. The compound according to claim 1 or a salt thereof, wherein $Y^2$ is —CO—.

5. The compound according to claim 1 or a salt thereof, wherein $Y^1$ is —$CH_2$— and $Y^2$ is —CO—.

6. The compound according to claim 1 or a salt thereof, wherein $Y^1$ is a single bond, $Y^2$ is a single bond and Ar is hydrogen.

7. The compound according to claim 1 or a salt thereof, wherein Ar is a group represented by the formula:

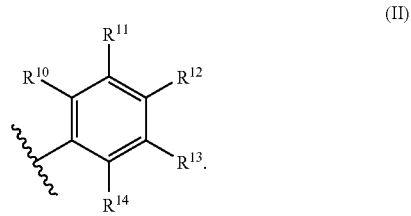

(II)

8. The compound according to claim 7 or a salt thereof, wherein $R^{10}$ and $R^{14}$ are hydrogen.

9. The compound according to claim 1 or a salt thereof, wherein Ar is a group represented by the formula:

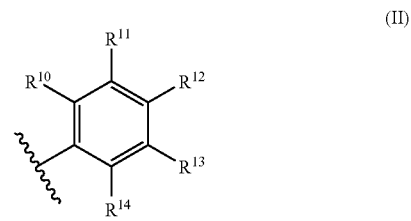

(II)

or a 5- to 14-membered aromatic heterocyclic group optionally substituted with at least one group selected from Substituent Group G.

10. The compound according to claim 9 or a salt thereof, wherein $R^{10}$ and $R^{14}$ are hydrogen.

11. A compound represented by the formula:

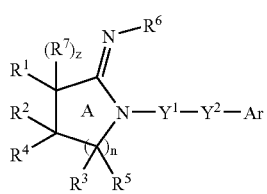

(I)

wherein $R^1$, $R^3$, $R^5$ and $R^7$ are the same or different and each independently represents hydrogen, cyano, halogen or a group selected from Substituent Group A, z represents 0 or 1;

$R^2$ and $R^4$ bond together to form a 5- to 6-membered ring optionally having 1 or more heteroatoms selected from O;

$R^6$ represents hydrogen, $C_{1-6}$ alkyl, acyl, carbamoyl, hydroxyl, $C_{1-6}$ alkoxy, $C_{1-6}$ alkyloxycarbonyloxy, $C_{3-8}$ cycloalkyl, $C_{1-6}$ alkyloxycarbonyl optionally substituted with acyloxy or a $C_{6-14}$ aromatic hydrocarbon ring group or a 5- to 14-membered aromatic heterocyclic group, each of the foregoing members being optionally substituted with at least one group selected from Substituent Group E;

n represents 1;

$Y^1$ represents a single bond, $-(CH_2)_m-$, $-CR^8-$, $-CR^8CR^9-$, $-CH_2CO-$, $-NR^8-$, $-SO-$, $-SO_2-$, $-CO-$, $-CONR^8-$ or $-SO_2NR^8-$, wherein m represents an integer of 1 to 3, and $R^8$ and $R^9$ are the same or different and each independently represents hydrogen, halogen, $C_{1-6}$ alkyl, carboxyl or $C_{1-6}$ alkoxycarbonyl;

$Y^2$ represents a single bond, O, N, $-(CH_2)_m-$, $-CR^8-$, $CR^8R^9-$, $-CO-$, $-SO-$, $-SO_2-$ or $-C(=N-OR^8)-$, wherein m represents an integer of 1 to 3, and $R^8$ and $R^9$ are the same or different and each independently represents hydrogen, halogen, $C_{1-6}$ alkyl, carboxyl or $C_{1-6}$ alkoxycarbonyl wherein Ar is a group represented by the formula:

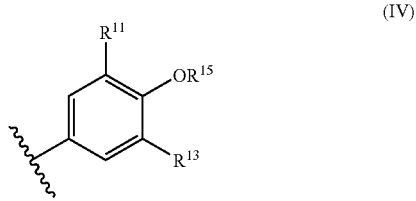

(IV)

wherein $R^{11}$ and $R^{13}$ are the same or different and each independently represents hydrogen, cyano, halogen, nitro or a group selected from Substituent Group B;

$R^{15}$ represents hydrogen or a group selected from Substituent Group H, or $R^{11}$ and $R^{15}$ or $R^{15}$ and $R^{13}$ may bond together to form a 5- to 8-membered heterocycle optionally substituted with at least one group selected from Substituent Group F and optionally having 1 or 2 hetero atoms selected from N, S and O;

<Substituent Group A> represents moieties selected from the group consisting of $C_{1-6}$ alkyl, alkylidene, $C_{2-6}$ alkenyl, $C_{2-6}$ alkynyl, acyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, amino, $C_{1-6}$ alkylamino, $C_{3-8}$ cycloalkylamino, acylamino, sulfonylamino, sulfonyl, sulfamoyl, $C_{3-8}$ cycloalkyl, a 5- to 14-membered non-aromatic heterocyclic group, a $C_{6-14}$ aromatic hydrocarbon ring group and a 5- to 14-membered aromatic heterocyclic group, each of the foregoing members being optionally substituted with at least one group selected from Substituent Group A';

<Substituent Group A'> represents moieties selected from the group consisting of $C_{1-6}$ alkyl, $C_{2-6}$ alkenyl, $C_{2-6}$ alkynyl, cyano, acyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, amino, $C_{1-6}$ alkylamino, $C_{3-8}$ cycloalkylamino, acylamino, ureido, ureylene, sulfonylamino, sulfonyl, sulfamoyl, halogen, $C_{3-8}$ cycloalkyl, a heterocyclic alkyl group, a 5- to 14-membered non-aromatic heterocyclic group, a $C_{6-14}$ aromatic hydrocarbon ring group and a 5- to 14-membered aromatic heterocyclic group, wherein the $C_{6-14}$ aromatic hydrocarbon ring group and the 5- to 14-membered aromatic heterocyclic group may be substituted with at least one group selected from the group consisting of $C_{1-6}$ alkyl, cyano, acyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, nitro, amino $C_{1-6}$ alkylamino, $C_{3-8}$ cycloalkylamino, acylamino, ureido, ureylene, sulfonylamino, sulfonyl, sulfamoyl, halogen and $C_{3-8}$ cycloalkyl;

<Substituent Group B> represents moieties selected from the group consisting of $C_{1-6}$ alkyl, $C_{2-6}$ alkenyl, $C_{2-6}$ alkynyl, acyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, amino, $C_{1-6}$ aminoalkyl, $C_{1-6}$ alkylamino, $C_{3-8}$ cycloalkylamino, acylamino, ureido, sulfonylamino, sulfonyl, sulfamoyl, $C_{3-8}$ cycloalkyl, a 5- to 14-membered non-aromatic heterocyclic group, a $C_{6-14}$ aromatic hydrocarbon ring group and a 5- to 14-membered aromatic heterocyclic group, each of the foregoing members being optionally substituted with at least one group selected from Substituent Group B';

<Substituent Group B'> represents moieties selected from the group consisting of $C_{1-6}$ alkyl, $C_{2-6}$ alkenyl, $C_{2-6}$ alkynyl, oxo, cyano, $C_{1-6}$ cyanoacyl, $C_{2-7}$ acyl, $C_{1-6}$ alkanoyl, benzoyl, aralkanoyl, $C_{1-6}$ alkoxyalkylcarbonyl, $C_{1-6}$ hydroxyalkylcarbonyl, carboxyl, $C_{1-6}$ carboxyalkyl, $C_{1-6}$ carboxyalkyloxy, carbamoyl, carbamoylalkyloxy, $C_{1-6}$ alkoxycarbonyl, $C_{1-10}$ alkoxycarbonyl-$C_{1-6}$ alkyl, $C_{1-10}$ alkoxycarbonyl-$C_{1-6}$ alkyloxy, $C_{1-6}$ monoalkylaminocarbonyl, $C_{2-6}$ dialkylaminocarbonyl, hydroxyl, $C_{1-6}$ alkoxy, $C_{1-10}$ alkoxyalkyl, $C_{1-10}$ aralkyloxyalkyl, $C_{1-6}$ hydroxyalkyl, $C_{3-8}$ cycloalkyloxy, amino, $C_{1-6}$ alkylamino, $C_{3-8}$ cycloalkylamino, acylamino, ureido, ureylene, $C_{1-6}$ alkylsulfonylamino, phenylsulfonylamino, $C_{1-6}$ alkylsulfonyl, phenylsulfonyl, $C_{1-6}$ monoalkylaminosulfonyl, $C_{2-6}$ dialkylaminosulfonyl, sulfamoyl, halogeno, $C_{3-8}$ cycloalkyl, a 5- to 14-membered non-aromatic heterocyclic group, a $C_{6-14}$ aromatic hydrocarbon ring group, a 5- to 14-membered aromatic heterocyclic group, a heterocyclic aminocarbonyl group, a heterocyclic aminosulfonyl group and isoxazolinyl, wherein the 5- to 14-membered non-aromatic heterocyclic group, the $C_{6-14}$ aromatic hydrocarbon ring group, the 5- to 14-membered aromatic heterocyclic group and isoxazolinyl may be independently substituted with at least one group selected from the group consisting of $C_{1-6}$ alkyl, oxo, cyano, acyl, carboxyl, carbamoyl, $C_{1-6}$ alkoxycarbonyl, $C_{1-6}$ alkylaminocarbonyl, hydroxyl $C_{1-6}$ alkoxy, $C_{3-8}$ cycloalkyloxy, nitro, amino, $C_{1-6}$ aminoalkyl, $C_{1-6}$ alkylamino, $C_{1-6}$ dialkylamino, $C_{3-8}$ cycloalkylamino, acylamino, ureido, ureylene, alkylsulfonylamino, alkylsulfonyl, sulfamoyl, halogeno and $C_{3-8}$ cycloalkyl;

<Substituent Group E> represents moieties selected from the group consisting of $C_{1-6}$ alkyl, cyano, acyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, amino, $C_{1-6}$ alkylamino, $C_{3-8}$ cycloalkylamino, acylamino, ureido, ureylene, sulfonylamino, sulfonyl, sulfamoyl, halogen and $C_{3-8}$ cycloalkyl;

<Substituent Group F> represents moieties selected from the group consisting of hydrogen, cyano, halogen, oxo, $C_{1-6}$ alkyl, alkenyl, alkynyl, acyl, $C_{1-6}$ alkanoyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, amino, imino, $C_{1-6}$ aminoalkyl, $C_{1-6}$ alkylamino, $C_{3-8}$ cycloalkylamino, acylamino, ureido, sulfonylamino, sulfonyl, sulfamoyl, $C_{3-8}$ cycloalkyl, a 5- to 14-membered non-aromatic heterocyclic group, a $C_{6-14}$ aromatic hydrocarbon ring group and a 5- to 14-membered aromatic heterocyclic group (each of the foregoing members being optionally substituted with at least one group selected from Substituent Group F' below);

<Substituent Group F'> represents moieties selected from the group consisting of $C_{1-6}$ alkyl, oxo, cyano, acyl, carboxyl, carbamoyl, $C_{1-6}$ alkoxycarbonyl, benzyloxycarbonyl $C_{1-6}$ alkylaminocarbonyl, hydroxyl $C_{1-6}$ alkoxy, $C_{3-8}$ cycloalkyloxy, amino, $C_{1-6}$ alkylamino, $C_{3-8}$ cycloalkylamino, acylamino, ureido, ureylene, $C_{1-6}$ alkylsulfonylamino, $C_{1-6}$ alkylsulfonyl, sulfamoyl, halogeno, $C_{3-8}$ cycloalkyl, a 5- to 14-membered non-aromatic heterocyclic group, a $C_{6-14}$ aromatic hydrocarbon ring group and a 5- to 14-membered aromatic heterocyclic group;

<Substituent Group H> represents moieties selected from the group consisting of $C_{1-6}$ alkyl, $C_{2-6}$ alkenyl, $C_{2-6}$ alkynyl, acyl, $C_{1-6}$ alkoxycarbonyl, aminocarbonyl, $C_{1-6}$ alkylaminocarbonyl, $C_{3-8}$ cycloalkyl, $C_{1-6}$ aminoalkyl, sulfonyl, $C_{3-8}$ cycloalkylamino, a 5- to 14-membered non-aromatic heterocyclic group, a $C_{6-14}$ aromatic hydrocarbon ring group and a 5- to 14-membered aromatic heterocyclic group, each of the foregoing members being optionally substituted with at least one group selected from Substituent Group H'; and <Substituent Group H'> represents moieties selected from the group consisting of $C_{1-6}$ alkyl, $C_{2-6}$ alkenyl, $C_{2-6}$ alkynyl, oxo, cyano, $C_{1-6}$ cyanoalkyl, $C_{2-7}$ acyl, $C_{1-6}$ alkanoyl, benzoyl, aralkanoyl, $C_{1-6}$ alkoxyalkylcarbonyl, $C_{1-6}$ hydroxyalkylcarbonyl, carboxyl, $C_{1-6}$ carboxyalkyl, $C_{1-6}$ carboxyalkyloxy, carbamoyl, carbamoylalkyloxy, $C_{1-6}$ alkoxycarbonyl, $C_{1-10}$ alkoxycarbonyl-$C_{1-6}$ alkyl, $C_{1-10}$ alkoxycarbonyl-$C_{1-6}$ alkyloxy, $C_{1-6}$ monoalkylaminocarbonyl, $C_{2-6}$ dialkylaminocarbonyl, hydroxyl, $C_{1-6}$ alkoxy, $C_{1-10}$ alkoxyalkyl, $C_{1-10}$ aralkyloxyalkyl, $C_{1-6}$ hydroxyalkyl, $C_{3-8}$ cycloalkyloxy, amino, $C_{1-6}$ alkylamino, $C_{3-8}$ cycloalkylamino, acylamino, ureido, ureylene, $C_{1-6}$ alkylsulfonylamino, phenylsulfonylamino, $C_{1-6}$ alkylsulfonyl, phenylsulfonyl, $C_{1-6}$ monoalkylaminosulfonyl, $C_{2-6}$ dialkylaminosulfonyl, sulfamoyl, halogeno, $C_{3-8}$ cycloalkyl, a 5- to 14-membered non-aromatic heterocyclic group, a $C_{6-14}$ aromatic hydrocarbon ring group, a 5- to 14-membered aromatic heterocyclic group, a heterocyclic aminocarbonyl group, a heterocyclic aminosulfonyl group and isoxazolinyl, wherein the 5- to 14-membered non-aromatic heterocyclic group, the $C_{6-14}$ aromatic hydrocarbon ring group, the 5- to 14-membered aromatic heterocyclic group and isoxazolinyl may be independently substituted with at least one group selected from the group consisting of $C_{1-6}$ alkyl, oxo, cyano, acyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, nitro, amino, $C_{1-6}$ aminoalkyl, $C_{1-6}$ alkylamino, $C_{1-6}$ dialkylamino, $C_{3-8}$ cycloalkylamino, acylamino, ureido, ureylene, alkylsulfonylamino, alkylsulfonyl, sulfamoyl, halogeno and $C_{3-8}$ cycloalkyl;

or salt thereof.

12. The compound according to claim 11 or a salt thereof, wherein Ar is a group represented by the formula:

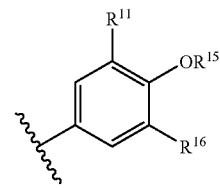

(V)

wherein $R^{11}$ represents hydrogen, cyano, halogen, nitro or a group selected from Substituent Group B;

$R^{15}$ represents hydrogen or a group selected from Substituent Group H;

$R^{16}$ represents hydrogen or a group selected from Substituent Group H, or $R^{11}$ and $R^{15}$ or $R^{15}$ and $R^{16}$ may bond together to form a 5- to 6-membered heterocycle optionally substituted with at least one group selected from Substituent Group F and optionally having 1 or 2 hetero atoms selected from N, S and O;

<Substituent Group F> represents moieties selected from the group consisting of hydrogen, cyano, halogen, oxo, $C_{1-6}$ alkyl, alkenyl, alkynyl, acyl $C_{1-6}$ alkanoyl, carboxyl, carbamoyl, $C_{1-6}$ alkoxycarbonyl, $C_{1-6}$ alkylaminocarbonyl, hydroxyl, $C_{1-6}$ alkoxy $C_{3-8}$ cycloalkyloxy, amino, imino, $C_{1-6}$ aminoalkyl, $C_{1-6}$ alkylamino, $C_{3-8}$ cycloalkylamino, acylamino, ureido, sulfonylamino, sulfonyl, sulfamoyl, $C_{3-8}$ cycloalkyl, a 5- to 14-membered non-aromatic heterocyclic group, a $C_{6-14}$ aromatic hydrocarbon ring group and a 5- to 14-membered aromatic heterocyclic group, each of the foregoing members being optionally substituted with at least one group selected from Substituent Group F';

<Substituent Group F'> represents moieties selected from the group consisting of $C_{1-6}$ alkyl, oxo, cyano, acyl, carboxyl, carbamoyl, $C_{1-6}$ alkoxycarbonyl, benzyloxycarbonyl, $C_{1-6}$ alkylaminocarbonyl, hydroxyl, $C_{1-6}$ alkoxy $C_{3-8}$ cycloalkyloxy, amino, $C_{1-6}$ alkylamino, $C_{3-8}$ cycloalkylamino, acylamino, ureido, ureylene, $C_{1-6}$ alkylsulfonylamino, $C_{1-6}$ alkylsulfonyl, sulfamoyl, halogeno, $C_{3-8}$ cycloalkyl, a 5- to 14-membered non-aromatic heterocyclic group, a $C_{6-14}$ aromatic hydrocarbon ring group and a 5- to 14-membered aromatic heterocyclic group;

<Substituent Group H> represents moieties selected from the group consisting of $C_{1-6}$ alkyl, $C_{2-6}$ alkenyl, $C_{2-6}$ alkynyl, acyl, $C_{1-6}$ alkoxycarbonyl, aminocarbonyl, $C_{1-6}$ alkylaminocarbonyl, $C_{3-8}$ cycloalkyl, $C_{1-6}$ aminoalkyl, sulfonyl, $C_{3-8}$ cycloalkylamino, a 5- to 14-membered non-aromatic heterocyclic group, a $C_{6-14}$ aromatic hydrocarbon ring group and a 5- to 14-membered aromatic heterocyclic group, each of the foregoing members being optionally substituted with at least one group selected from Substituent Group H'; and <Substituent Group H'> represents moieties selected from the group consisting of $C_{1-6}$ alkyl, $C_{2-6}$ alkenyl, $C_{2-6}$ alkynyl, oxo, cyano, $C_{1-6}$ cyanoalkyl, $C_{2-7}$ acyl, $C_{1-6}$ alkanoyl, benzoyl, aralkanoyl, $C_{1-6}$ alkoxyalkylcarbonyl, $C_{1-6}$ hydroxyalkylcarbonyl, carboxyl, $C_{1-6}$ carboxyalkyl, $C_{1-6}$ carboxyalkyloxy, carbamoyl, carbamoylalkyloxy, $C_{1-6}$ alkoxycarbonyl, $C_{1-10}$ alkoxycarbonyl-$C_{1-6}$ alkyl, $C_{1-10}$ alkoxycarbonyl-$C_{1-6}$ alkyloxy, $C_{1-6}$ monoalkylaminocarbonyl, $C_{2-6}$ dialkylaminocarbonyl, hydroxyl, $C_{1-6}$ alkoxy, $C_{1-10}$ alkoxyalkyl, $C_{1-10}$ aralkyloxyalkyl, $C_{1-6}$ hydroxyalkyl, $C_{3-8}$ cycloalkyloxy, amino, $C_{1-6}$ alkylamino, $C_{3-8}$ cycloalkylamino, acylamino, ureido, ureylene, $C_{1-6}$ alkylsulfonylamino, phenylsulfonylamino, $C_{1-6}$ alkylsulfonyl, phenylsulfonyl, $C_{1-6}$ monoalkylaminosulfonyl, $C_{2-6}$ dialkylaminosulfonyl, sulfamoyl, halogeno, $C_{3-8}$ cycloalkyl, a 5- to 14-membered non-aromatic heterocyclic group, a $C_{6-14}$ aromatic hydrocarbon ring group, a 5- to 14-membered aromatic heterocyclic group, a heterocyclic aminocarbonyl group, a heterocyclic aminosulfonyl group and isoxazolinyl, wherein the 5- to 14-membered non-aromatic heterocyclic group, the $C_{6-14}$ aromatic hydrocarbon ring group, the 5- to 14-membered aromatic heterocyclic group and isoxazolinyl may be independently substituted with at least one group selected from the group consisting of $C_{1-6}$ alkyl, oxo, cyano, acyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, nitro, amino, $C_{1-6}$ aminoalkyl, $C_{1-6}$ alkylamino, $C_{1-6}$ dialkylamino, $C_{3-8}$ cycloalkylamino, acylamino, ureido, ureylene, alkylsulfonylamino, alkylsulfonyl, sulfamoyl, halogeno and $C_{3-8}$ cycloalkyl.

13. The compound according to claim 11 or a salt thereof, wherein Ar is a group represented by the formula:

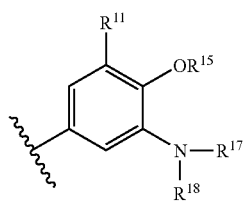

(VI)

wherein $R^{11}$ represents hydrogen cyano, halogen, nitro or a group selected from Substituent Group B;

$R^{15}$ represents hydrogen or a group selected from Substituent Group H;

$R^{17}$ and $R^{18}$ are the same or different and each independently represents hydrogen or a group selected from Substituent Group I, or $R^{11}$ and $R^{15}$, $R^{15}$ and $R^{17}$, $R^{15}$ and $R^{18}$, or $R^{17}$ and $R^{18}$ may bond together to form a 5- to 8-membered heterocycle optionally substituted with at least one group selected from Substituent Group F and optionally having 1 or 2 hetero atoms selected from N, S and O;

<Substituent Group F> represents moieties selected from the group consisting of hydrogen, cyano, halogen, oxo, $C_{1-6}$ alkyl, alkenyl, alkynyl, acyl, $C_{1-6}$ alkanoyl, carboxyl, carbamoyl, $C_{1-6}$ alkoxycarbonyl, $C_{1-6}$ alkylaminocarbonyl, hydroxyl, $C_{1-6}$ alkoxy $C_{3-8}$ cycloalkyloxy, amino, imino, $C_{1-6}$ aminoalkyl, $C_{1-6}$ alkylamino, $C_{3-8}$ cycloalkylamino, acylamino, ureido, sulfonylamino, sulfonyl, sulfamoyl, $C_{3-8}$ cycloalkyl, a 5- to 14-membered non-aromatic heterocyclic group, a $C_{6-14}$ aromatic hydrocarbon ring group and a 5- to 14-membered aromatic heterocyclic group, each of the foregoing members being optionally substituted with at least one group selected from Substituent Group F';

<Substituent Group F'> represents moieties selected from the group consisting of $C_{1-6}$ alkyl, oxo, cyano, acyl, carboxyl, carbamoyl, $C_{1-6}$ alkoxycarbonyl, benzyloxycarbonyl $C_{1-6}$ alkylaminocarbonyl, hydroxyl, $C_{1-6}$ alkoxy, $C_{3-8}$ cycloalkyloxy, amino, $C_{1-6}$ alkylamino $C_{3-8}$ cycloalkylamino, acylamino, ureido, ureylene, $C_{1-6}$ alkylsulfonylamino, $C_{1-6}$ alkylsulfonyl, sulfamoyl, halogeno, $C_{3-8}$ cycloalkyl, a 5- to 14-membered non-aromatic heterocyclic group, a $C_{6-14}$ aromatic hydrocarbon ring group and a 5- to 14-membered aromatic heterocyclic group;

<Substituent Group H> represents moieties selected from the group consisting of $C_{1-6}$ alkyl, $C_{2-6}$ alkenyl, $C_{2-6}$ alkynyl, acyl, $C_{1-6}$ alkoxycarbonyl, aminocarbonyl, $C_{1-6}$ alkylaminocarbonyl, $C_{3-8}$ cycloalkyl, $C_{1-6}$ aminoalkyl, sulfonyl, $C_{3-8}$ cycloalkylamino, a 5- to 14-membered non-aromatic heterocyclic group, a $C_{6-14}$ aromatic hydrocarbon ring group and a 5- to 14-membered aromatic heterocyclic group, each of the foregoing members being optionally substituted with at least one group selected from Substituent Group H';

<Substituent Group H'> represents moieties selected from the group consisting of $C_{1-6}$ alkyl, $C_{2-6}$ alkenyl, $C_{2-6}$ alkynyl, oxo, cyano, $C_{1-6}$ cyanoalkyl, $C_{2-7}$ acyl, $C_{1-6}$ alkanoyl, benzoyl, aralkanoyl, $C_{1-6}$ alkoxyalkylcarbonyl, $C_{1-6}$ hydroxyalkylcarbonyl, carboxyl, $C_{1-6}$ carboxyalkyl, $C_{1-6}$ carboxyalkyloxy, carbamoyl, carbamoylalkyloxy, $C_{1-6}$ alkoxycarbonyl, $C_{1-10}$ alkoxycarbonyl-$C_{1-6}$ alkyl, $C_{1-10}$ alkoxycarbonyl-$C_{1-6}$ alkyloxy, $C_{1-6}$ monoalkylaminocarbonyl, $C_{2-6}$ dialkylaminocarbonyl, hydroxyl, $C_{1-6}$ alkoxy, $C_{1-10}$ alkoxyalkyl, $C_{1-10}$ aralkyloxyalkyl $C_{1-6}$ hydroxyalkyl, $C_{3-8}$ cycloalkyloxy, amino, $C_{1-6}$ alkylamino, $C_{3-8}$ cycloalkylamino, acylamino, ureido, ureylene, $C_{1-6}$ alkylsulfonylamino, phenylsulfonylamino, $C_{1-6}$ alkylsulfonyl, phenylsulfonyl, $C_{1-6}$ monoalkylaminosulfonyl, $C_{2-6}$ dialkylaminosulfonyl, sulfamoyl, halogeno, $C_{3-8}$ cycloalkyl, a 5- to 14-membered non-aromatic heterocyclic group, a $C_{6-14}$ aromatic hydrocarbon ring group, a 5- to 14-membered aromatic heterocyclic group, a heterocyclic aminocarbonyl group, a heterocyclic aminosulfonyl group and isoxazolinyl, wherein the 5- to 14-membered non-aromatic heterocyclic group, the $C_{6-14}$ aromatic hydrocarbon ring group, the 5- to 14-membered aromatic heterocyclic group and isoxazolinyl may be independently substituted with at least one group selected from the group consisting of $C_{1-6}$ alkyl, oxo, cyano, acyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, nitro, amino, $C_{1-6}$ aminoalkyl, $C_{1-6}$ alkylamino, $C_{1-6}$ dialkylamino, $C_{3-8}$ cycloalkylamino, acylamino, ureido, ureylene, alkylsulfonylamino, alkylsulfonyl, sulfamoyl, halogeno and $C_{3-8}$ cycloalkyl;

<Substituent Group I> represents moieties selected from the group consisting of $C_{1-6}$ alkyl, $C_{2-6}$ alkenyl, $C_{2-6}$ alkynyl, acyl, carbamoyl, $C_{1-6}$ alkoxycarbonyl, $C_{1-6}$ alkylaminocarbonyl, $C_{1-6}$ aminoalkyl, sulfonyl, sulfamoyl, $C_{3-8}$ cycloalkyl, a 5- to 14-membered non-aromatic heterocyclic group, a $C_{6-14}$ aromatic hydrocarbon ring group and a 5- to 14-membered aromatic heterocyclic group, each of the foregoing members being optionally substituted with at least one group selected from Substituent Group I'; and <Substituent Group I'> represents moieties selected from the group consisting of $C_{1-6}$ alkyl, $C_{2-6}$ alkenyl, $C_{2-6}$ alkynyl, oxo, cyano, $C_{1-6}$ cyanoalkyl, $C_{2-7}$ acyl, $C_{1-6}$ alkanoyl, benzoyl, aralkanoyl, $C_{1-6}$ alkoxyalkylcarbonyl, $C_{1-6}$ hydroxyalkylcarbonyl, carboxyl, $C_{1-6}$ carboxyalkyl, $C_{1-6}$ carboxyalkyloxy, carbamoyl, carbamoylalkyloxy, $C_{1-6}$ alkoxycarbonyl, $C_{1-10}$ alkoxycarbonyl-$C_{1-6}$ alkyl, $C_{1-10}$ alkoxycarbonyl-$C_{1-6}$ alkyloxy, $C_{1-6}$ monoalkylaminocarbonyl, $C_{2-6}$ dialkylaminocarbonyl, hydroxyl, $C_{1-6}$ alkoxy, $C_{1-10}$ alkoxyalkyl, $C_{1-10}$ aralkyloxyalkyl, $C_{1-6}$ hydroxyalkyl, $C_{3-8}$ cycloalkyloxy, amino, $C_{1-6}$ alkylamino, $C_{3-8}$ cycloalkylamino, acylamino, ureido, ureylene, $C_{1-6}$ alkylsulfonylamino, phenylsulfonylamino, $C_{1-6}$ alkylsulfonyl, phenylsulfonyl, $C_{1-6}$ monoalkylaminosulfonyl, $C_{2-6}$ dialkylaminosulfonyl, sulfamoyl, halogeno, $C_{3-8}$ cycloalkyl, a 5- to 14-membered non-aromatic heterocyclic group, a $C_{6-14}$ aromatic hydrocarbon ring group, a 5- to 14-membered aromatic heterocyclic group, a heterocyclic aminocarbonyl group, a heterocyclic aminosulfonyl group and isoxazolinyl, wherein the 5- to 14-membered non-aromatic heterocyclic group, the $C_{6-14}$ aromatic hydrocarbon ring group, the 5- to 14-membered aromatic heterocyclic group and isoxazolinyl may be independently substituted with at least one group selected from the group consisting of $C_{1-6}$ alkyl, oxo, cyano, acyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, nitro, amino, $C_{1-6}$ aminoalkyl, $C_{1-6}$ alkylamino, $C_{1-6}$ dialkylamino, $C_{3-8}$ cycloalkylamino, acylamino, ureido, ureylene, alkylsulfonylamino, alkylsulfonyl, sulfamoyl, halogeno and $C_{3-8}$ cycloalkyl.

14. The compound according to claim 1 or claim 11, or salt thereof, wherein $R^2$ and $R^4$ bond together to form a 5- to 6-membered cycloalkyl ring.

15. The compound according to claim 14, or salt thereof, wherein $R^2$ and $R^4$ bond together to form a cyclopentyl ring.

16. The compound according to claim 15, or salt thereof, having the structure:

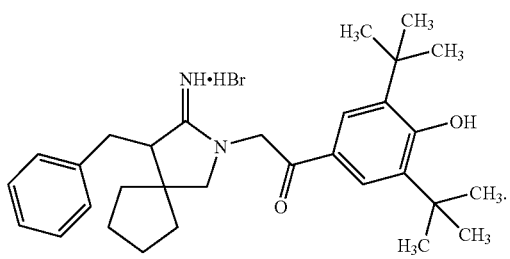

17. The compound according to claim 14, or salt thereof, wherein $R^2$ and $R^4$ bond together to form a cyclohexyl ring.

18. The compound according to claim 17, or salt thereof, having the structure:

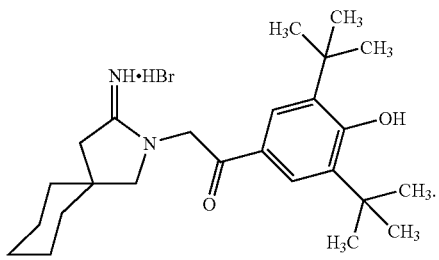

19. The compound according to claim 1 or claim 11, or salt thereof, wherein $R^2$ and $R^4$ bond together to form a 5- to 6-membered ring having 1 or more heteroatoms selected from O.

20. The compound according to claim 19, or salt thereof, wherein $R^2$ and $R^4$ bond together to form a tetrahydropyranyl ring.

21. The compound according to claim 20, or salt thereof, having the structure:

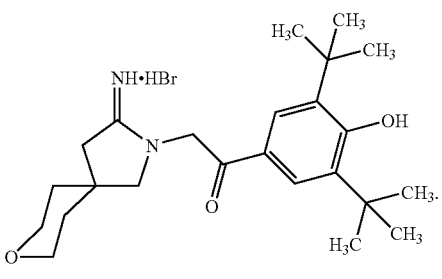

22. A pharmaceutical composition comprising a compound according to claim 1 or claim 11 or a salt thereof.

23. The composition according to claim 22, wherein the composition is useful as a thrombin receptor antagonist.

24. The composition according to claim 22, wherein the composition is useful as a thrombin receptor PAR1 antagonist.

25. The composition according to claim 22, wherein the composition is useful as a platelet aggregation inhibitor.

26. The composition according to claim 22, wherein the composition is useful as a proliferation inhibitor for smooth muscle cells.

27. The composition according to claim 22, wherein the composition is useful as a proliferation inhibitor for endothelial cells, fibroblasts, nephrocytes, osteosarcoma cells, muscle cells, cancer cells and/or glia cells.

28. The composition according to claim 22, wherein the composition is useful as a therapeutic or prophylactic agent for thrombosis, vascular restenosis, deep venous thrombosis, pulmonary embolism, cerebral infarction, heart disease, disseminated intravascular coagulation, hypertension, inflammatory disease, rheumatism, asthma, glomerulonephritis, osteoporosis, neurological disease and/or malignant tumor.

* * * * *

UNITED STATES PATENT AND TRADEMARK OFFICE
CERTIFICATE OF CORRECTION

| | | |
|---|---|---|
| PATENT NO. | : 7,476,688 B2 | Page 1 of 1 |
| APPLICATION NO. | : 10/475060 | |
| DATED | : January 13, 2009 | |
| INVENTOR(S) | : Suzuki et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1049 days.

Signed and Sealed this

Twenty-sixth Day of October, 2010

David J. Kappos
*Director of the United States Patent and Trademark Office*